(12) United States Patent
Morrison et al.

(10) Patent No.: US 11,465,969 B2
(45) Date of Patent: Oct. 11, 2022

(54) SALTS AND CRYSTAL FORMS OF OMECAMTIV MECARBIL

(71) Applicants: AMGEN INC., Thousand Oaks, CA (US); CYTOKINETICS, INC., South San Francisco, CA (US)

(72) Inventors: Henry Morrison, Thousand Oaks, CA (US); Sheng Cui, Thousand Oaks, CA (US); Kyle Quasdorf, Thousand Oaks, CA (US); Evelyn Yanez, Thousand Oaks, CA (US); Bin Peter Quan, Thousand Oaks, CA (US); Ron C. Kelly, Thousand Oaks, CA (US); Sebastien Caille, Thousand Oaks, CA (US); Lingyun Xiao, Thousand Oaks, CA (US); David Pearson, Berwickshire (GB); Jaclyn Raeburn, Milton Bridge (GB); Ailsa Golightly, Tranent (GB); Bradley Morgan, Moraga, CA (US); Matthew Peterson, San Diego, CA (US); Alex Eberlin, South San Francisco, CA (US); Alexander Oblezov, South San Francisco, CA (US)

(73) Assignees: CYTOKINETICS, INC., South San Francisco, CA (US); AMGEN INC., Thousand Oaks, CA (US)

( * ) Notice: Subject to any disclaimer, the term of this patent is extended or adjusted under 35 U.S.C. 154(b) by 0 days.

(21) Appl. No.: 17/263,224

(22) PCT Filed: Aug. 16, 2019

(86) PCT No.: PCT/US2019/046726
§ 371 (c)(1),
(2) Date: Jan. 26, 2021

(87) PCT Pub. No.: WO2020/037164
PCT Pub. Date: Feb. 20, 2020

(65) Prior Publication Data
US 2021/0221771 A1    Jul. 22, 2021

Related U.S. Application Data

(60) Provisional application No. 62/765,090, filed on Aug. 17, 2018.

(51) Int. Cl.
*C07D 213/75* (2006.01)

(52) U.S. Cl.
CPC ........ *C07D 213/75* (2013.01); *C07B 2200/13* (2013.01)

(58) Field of Classification Search
CPC .................................................... C07D 213/75
USPC .................................................. 514/253.01
See application file for complete search history.

(56) References Cited

U.S. PATENT DOCUMENTS

| | | | |
|---|---|---|---|
| 4,522,811 A | 6/1985 | Eppstein et al. | |
| 7,507,735 B2 | 3/2009 | Morgan et al. | |
| 8,101,617 B2 | 1/2012 | Morgan et al. | |
| 8,110,595 B2 | 2/2012 | Morgan et al. | |
| 8,445,495 B2 | 5/2013 | Morgan et al. | |
| 8,513,257 B2 | 8/2013 | Morgan et al. | |
| 8,871,768 B2 | 10/2014 | Morgan et al. | |
| 8,871,769 B2 | 10/2014 | Morgan et al. | |
| 9,150,564 B2 | 10/2015 | Morgan et al. | |
| 9,643,925 B2 | 5/2017 | Morgan et al. | |
| 9,895,308 B2 | 2/2018 | Caldwell | |
| 9,951,015 B2* | 4/2018 | Bi .............................. | A61P 9/04 |
| 9,988,354 B2 | 6/2018 | Cui et al. | |
| 10,035,770 B2 | 7/2018 | Morgan et al. | |
| 10,385,023 B2 | 8/2019 | Morgan et al. | |
| 10,421,726 B2 | 9/2019 | Bi et al. | |
| 10,543,215 B2 | 1/2020 | Scott et al. | |
| 10,975,034 B2 | 4/2021 | Morgan et al. | |
| 11,040,956 B2 | 6/2021 | Caille et al. | |
| 2006/0014761 A1 | 1/2006 | Morgan et al. | |
| 2007/0161617 A1 | 7/2007 | Morgan et al. | |
| 2009/0036447 A1 | 2/2009 | Morgan et al. | |
| 2009/0099198 A1 | 4/2009 | Morgan et al. | |
| 2009/0192168 A1 | 7/2009 | Muci et al. | |
| 2010/0029680 A1 | 2/2010 | Morgan et al. | |
| 2012/0172372 A1 | 7/2012 | Morgan et al. | |
| 2013/0324549 A1 | 12/2013 | Morgan et al. | |
| 2014/0038983 A1 | 2/2014 | Morgan et al. | |
| 2014/0309235 A1 | 10/2014 | Bi et al. | |
| 2015/0005296 A1 | 1/2015 | Morgan et al. | |
| 2016/0015628 A1 | 1/2016 | Caldwell | |
| 2016/0016906 A1 | 1/2016 | Cui et al. | |
| 2016/0115133 A1 | 4/2016 | Morgan et al. | |

(Continued)

FOREIGN PATENT DOCUMENTS

| WO | WO-2006/009726 A2 | 1/2006 |
|---|---|---|
| WO | WO-2014/152236 A1 | 9/2014 |

(Continued)

OTHER PUBLICATIONS

International Preliminary Report on Patentability dated Feb. 23, 2021, for Patent Application No. PCT/US2019/046726, filed Aug. 16, 2019, 9 pages.
U.S. Appl. No. 15/898,303, filed Feb. 16, 2018, by William Brett Caldwell et al. (A copy of the U.S. Patent Application is not submitted herewith pursuant to the waiver of 37 C.F.R. § 1.98(a)(2)(iii) issued by the Office on Sep. 21, 2004.).
U.S. Appl. No. 17/176,003, filed Feb. 15, 2021, by Sheng Cui et al. (A copy of the U.S. Patent Application is not submitted herewith pursuant to the waiver of 37 C.F.R. § 1.98(a)(2)(iii) issued by the Office on Sep. 21, 2004.).

(Continued)

*Primary Examiner* — Niloofar Rahmani
(74) *Attorney, Agent, or Firm* — Morrison & Foerster LLP

(57) ABSTRACT

Provided herein are free base crystalline forms, crystalline salts, and an amorphous salts of omecamtiv mecarbil.

32 Claims, 75 Drawing Sheets

(56) References Cited

U.S. PATENT DOCUMENTS

| | | |
|---|---|---|
| 2017/0267638 A1 | 9/2017 | Morgan et al. |
| 2018/0140611 A1 | 5/2018 | Scott et al. |
| 2018/0273479 A1 | 9/2018 | Bi et al. |
| 2018/0305316 A1 | 10/2018 | Morgan et al. |
| 2018/0312469 A1 | 11/2018 | Cui et al. |
| 2019/0352267 A1 | 11/2019 | Morgan et al. |
| 2020/0079736 A1 | 3/2020 | Cui et al. |
| 2020/0108076 A1 | 4/2020 | Scott et al. |
| 2020/0155547 A1 | 5/2020 | Honarpour et al. |
| 2020/0277261 A1 | 9/2020 | Bi et al. |
| 2020/0308143 A1 | 10/2020 | Caille et al. |
| 2020/0331859 A1 | 10/2020 | Cui et al. |
| 2020/0399221 A1 | 12/2020 | Cui et al. |
| 2021/0198203 A1 | 7/2021 | Morgan et al. |
| 2021/0292271 A1 | 9/2021 | Brasola et al. |
| 2021/0371397 A1 | 12/2021 | Caille et al. |
| 2022/0042055 A1 | 2/2022 | Bisagni et al. |

FOREIGN PATENT DOCUMENTS

| | | |
|---|---|---|
| WO | WO-2014/152270 A1 | 9/2014 |
| WO | WO-2016/210240 A1 | 12/2016 |
| WO | 2020011626 A1 | 1/2020 |
| WO | WO-2020/014406 A1 | 1/2020 |
| WO | 2021053175 A1 | 3/2021 |
| WO | 2021053189 A1 | 3/2021 |
| WO | 2021070123 A1 | 4/2021 |
| WO | 2021070124 A1 | 4/2021 |
| WO | 2021136477 A1 | 7/2021 |

OTHER PUBLICATIONS

U.S. Appl. No. 17/258,385, filed Jan. 6, 2021, by Elena Brasola et al. (A copy of the U.S. Patent Application is not submitted herewith pursuant to the waiver of 37 C.F.R. § 1.98(a)(2)(iii) issued by the Office on Sep. 21, 2004.).

U.S. Appl. No. 17/263,224, filed Jan. 26, 2021, by Henry Morrison et al. (A copy of the U.S. Patent Application is not submitted herewith pursuant to the waiver of 37 C.F.R. § 1.98(a)(2)(iii) issued by the Office on Sep. 21, 2004.).

U.S. Appl. No. 17/309,727, filed Jun. 16, 2021, by Serena Bisagni et al. (A copy of the U.S. Patent Application is not submitted herewith pursuant to the waiver of 37 C.F.R. § 1.98(a)(2)(iii) issued by the Office on Sep. 21, 2004.).

U.S. Appl. No. 17/324,867, filed May 19, 2021, by Sebastien Caille et al. (A copy of the U.S. Patent Application is not submitted herewith pursuant to the waiver of 37 C.F.R. § 1.98(a)(2)(iii) issued by the Office on Sep. 21, 2004.).

Caira et al., Crystalline Polymorphism of Organic Compounds, Topics in Current Chemistry, vol. 198, pp. 163-208 (Jan. 1998).

International Application No. PCT/US2019/046726, International Search Report and Written Opinion, dated Jan. 14, 2020.

Morrison et al., Appearance of a New Hydrated Form during Development: A Case Study in Process and Solid-State Optimization, Org. Process Res. Dev., 19(12):1842-8 (2015).

U.S. Appl. No. 17/448,833, filed Sep. 24, 2021, by Sheng Cui et al. (A copy of the U.S. Patent Application is not submitted herewith pursuant to the waiver of 37 C.F.R. § 1,98(a)(2)(iii) issued by the Office on Sep. 21, 2004.).

U.S. Appl. No. 17/452,025, filed Oct. 22, 2021, by Bradley Paul Morgan et al. (A copy of the U.S. Patent Application is not submitted herewith pursuant to the waiver of 37 C.F.R. § 1.98(a)(2)(iii) issued by the Office on Sep. 21, 2004.).

U.S. Appl. No. 17/454,592, filed Nov. 11, 2021, by Narimon Honarpour et al.(A copy of the U.S. Patent Application is not submitted herewith pursuant to the waiver of 37 C.F.R. § 1.98(a)(2)(iii) issued by the Office on Sep. 21, 2004.).

\* cited by examiner

SALTS AND CRYSTAL FORMS OF OMECAMTIV MECARBIL

TECHNICAL FIELD OF INVENTION

The present disclosure relates to salts and crystal forms of omecamtiv mecarbil, pharmaceutical compositions thereof and methods of using the same.

BACKGROUND

The cardiac sarcomere is the basic unit of muscle contraction in the heart. The cardiac sarcomere is a highly ordered cytoskeletal structure composed of cardiac muscle myosin, actin and a set of regulatory proteins. The discovery and development of small molecule cardiac muscle myosin activators would lead to promising treatments for acute and chronic heart failure and dilated cardiomyopathy (DCM) and conditions associated with left and/or right ventricular systolic dysfunction or systolic reserve. Cardiac muscle myosin is the cytoskeletal motor protein in the cardiac muscle cell. It is directly responsible for converting chemical energy into the mechanical force, resulting in cardiac muscle contraction.

Current positive inotropic agents, such as beta-adrenergic receptor agonists or inhibitors of phosphodiesterase activity, increase the concentration of intracellular calcium, thereby increasing cardiac sarcomere contractility. However, the increase in calcium levels increase the velocity of cardiac muscle contraction and shortens systolic ejection time, which has been linked to potentially life-threatening side effects. In contrast, cardiac muscle myosin activators work by a mechanism that directly stimulates the activity of the cardiac muscle myosin motor protein, without increasing the intracellular calcium concentration. They accelerate the rate-limiting step of the myosin enzymatic cycle and shift it in favor of the force-producing state. Rather than increasing the velocity of cardiac contraction, this mechanism instead lengthens the systolic ejection time, which results in increased cardiac muscle contractility and cardiac output in a potentially more oxygen-efficient manner.

Omecamtiv mecarbil is a first in class direct activator of cardiac myosin, the motor protein that causes cardiac contraction. It is being evaluated as a potential treatment of heart failure in both intravenous and oral formulations with the goal of establishing a new continuum of care for patients in both the in-hospital and outpatient settings. Omecamtiv mecarbil has a structure of

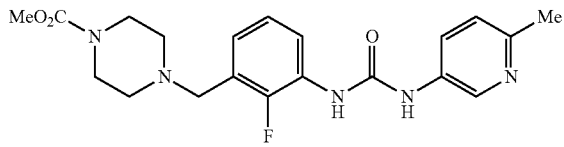 [SMILES: COC(=O)N1CCN(Cc2cccc(NC(=O)Nc3ccc(C)nc3)c2F)CC1]

(see, e.g., U.S. Pat. No. 7,507,735), and has alternatively been referred to as methyl 4-(2-fluoro-3-(3-(6-methylpyridin-3-yl)ureido)benzyl)piperazine-1-carboxylate, AMG 423, and CK 1827452.

There is a need for various new salt and crystalline forms of omecamtiv mecarbil with different chemical and physical stabilities, and formulations and uses of the same.

SUMMARY

Provided herein are salts and crystal forms of omecamtiv mecarbil, including free base crystalline forms, crystalline salts and amorphous salt forms of omecamtiv mecarbil. In some embodiments, provided herein is the omecamtiv mecarbil free base crystalline form III. In some embodiments, provided herein is the omecamtiv mecarbil free base crystalline form IV. In some embodiments, provided herein is the omecamtiv mecarbil free base crystalline form V. In some embodiments, provided herein is the omecamtiv mecarbil free base crystalline form VI. In some embodiments, provided herein is the omecamtiv mecarbil free base crystalline form VII. In some embodiments, provided herein is the omecamtiv mecarbil amorphous hydrochloride salt. In some embodiments, provided herein is the omecamtiv mecarbil ethane sulfonate crystalline salt. In some embodiments, provided herein is the omecamtiv mecarbil bis-fumarate crystalline salt form A. In some embodiments, provided herein is the omecamtiv mecarbil bis-fumarate crystalline salt form B. In some embodiments, provided herein is the omecamtiv mecarbil bis-fumarate crystalline salt form C. In some embodiments, provided herein is the omecamtiv mecarbil mono-fumarate crystalline salt form D. In some embodiments, provided herein is the omecamtiv mecarbil bis-maleate crystalline salt. In some embodiments, provided herein is the omecamtiv mecarbil bis-malonate crystalline salt. In some embodiments, provided herein is the omecamtiv mecarbil mesylate crystalline salt form A. In some embodiments, provided herein is the omecamtiv mecarbil bis-mesylate crystalline salt form B. In some embodiments, provided herein is the omecamtiv mecarbil bis-naphthalate-2-sulfonate crystalline salt. In some embodiments, provided herein is the omecamtiv mecarbil mono-napadisylate crystalline salt. In some embodiments, provided herein is the omecamtiv mecarbil nicotinate crystalline salt. In some embodiments, provided herein is the omecamtiv mecarbil oxalate crystalline salt form A. In some embodiments, provided herein is the omecamtiv mecarbil oxalate crystalline salt form B. In some embodiments, provided herein is the omecamtiv mecarbil salicylate crystalline salt. In some embodiments, provided herein is the omecamtiv mecarbil hemi-succinate crystalline salt. In some embodiments, provided herein is the omecamtiv mecarbil bis-sulfate crystalline salt form A. In some embodiments, provided herein is the omecamtiv mecarbil bis-sulfate crystalline salt form B. In some embodiments, provided herein is the omecamtiv mecarbil bis-sulfate crystalline salt form C. In some embodiments, provided herein is the omecamtiv mecarbil sulfate crystalline salt form D. In some embodiments, provided herein is the omecamtiv mecarbil 2-hydroxyethane sulfonate crystalline salt. In some embodiments, provided herein is the omecamtiv mecarbil bis-tartrate crystalline salt form A. In some embodiments, provided herein is the omecamtiv mecarbil bis-tartrate crystalline salt form B. In some embodiments, provided herein is the omecamtiv mecarbil bis-tartrate crystalline salt form C. In some embodiments, provided herein is the omecamtiv mecarbil mono-tartrate crystalline salt form D.

Also provided are pharmaceutical compositions comprising a salt or crystal form of omecamtiv mecarbil as disclosed herein and a pharmaceutically acceptable excipient.

Further provided are methods of treating heart failure in a subject in need thereof comprising administering to the subject a salt or crystal form of omecamtiv mecarbil as disclosed herein in an amount effective to treat heart failure.

DETAILED DESCRIPTION

The present disclosure provides salts and crystal forms of omecamtiv mecarbil.

Embodiments of the free base crystalline forms, crystalline salts and amorphous salt of omecamtiv mecarbil can be characterized by one or more of the parameters described in further detail below.

Free Base Crystalline Forms of Omecamtiv Mecarbil

Figure 13:
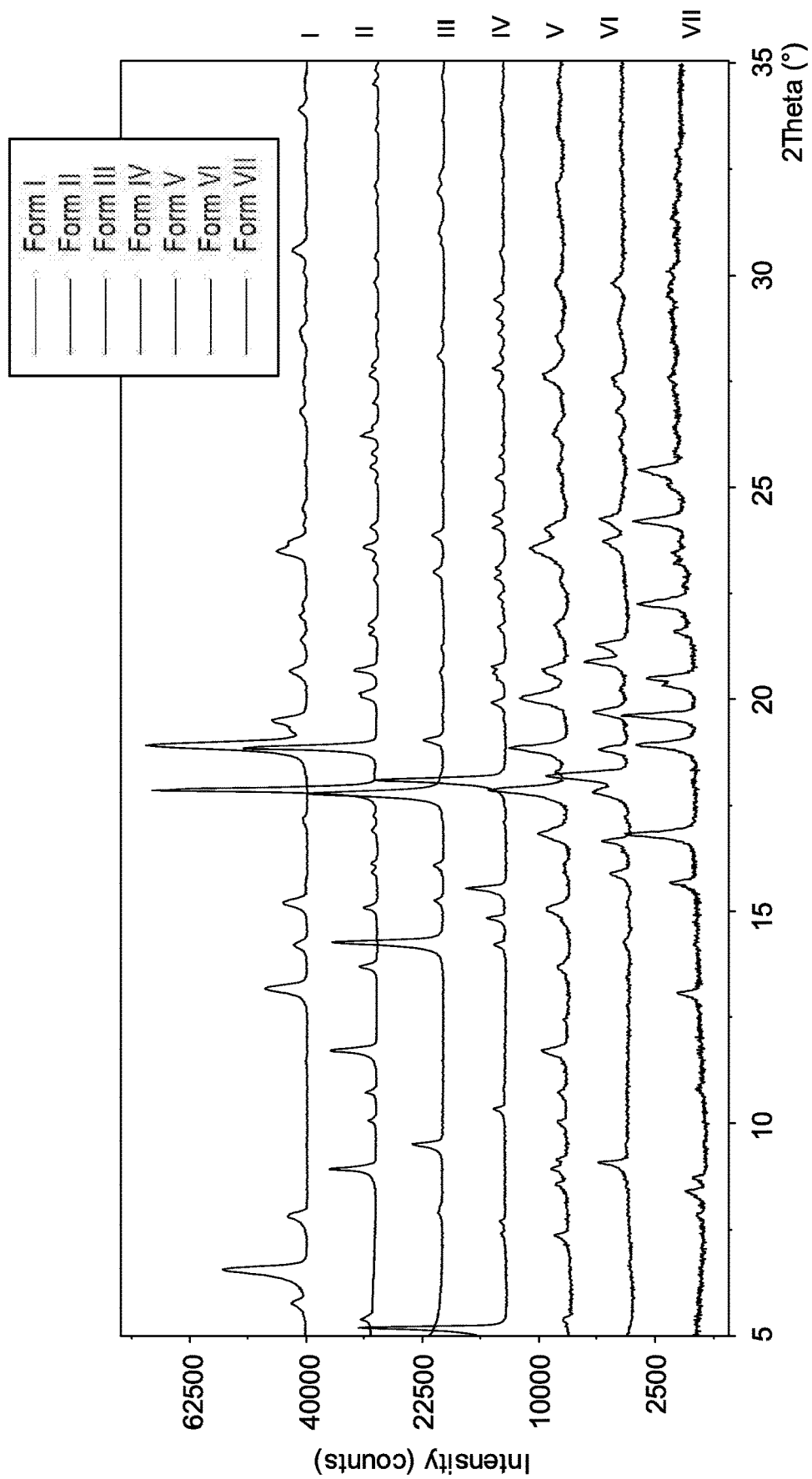
FIG. 13 depicts an XRPD pattern overlay of the free base crystalline forms I-VII.

Provided herein are free base crystalline forms of omecamtiv mecarbil. In some embodiments, the free base crystalline forms of omecamtiv mecarbil can be nonionic forms of omecamtiv mecarbil. In some embodiments, the free base crystalline forms III-VII of omecamtiv mecarbil can be anhydrous. The free base crystalline forms I and II of omecamtiv mecarbil depicted in FIG. 13 are prepared and discussed in detail in Morrison et. al, *Organic Process Research & Development*, 2015, 19, 1842-1848.

Free Base Crystalline Form III

Figure 1:
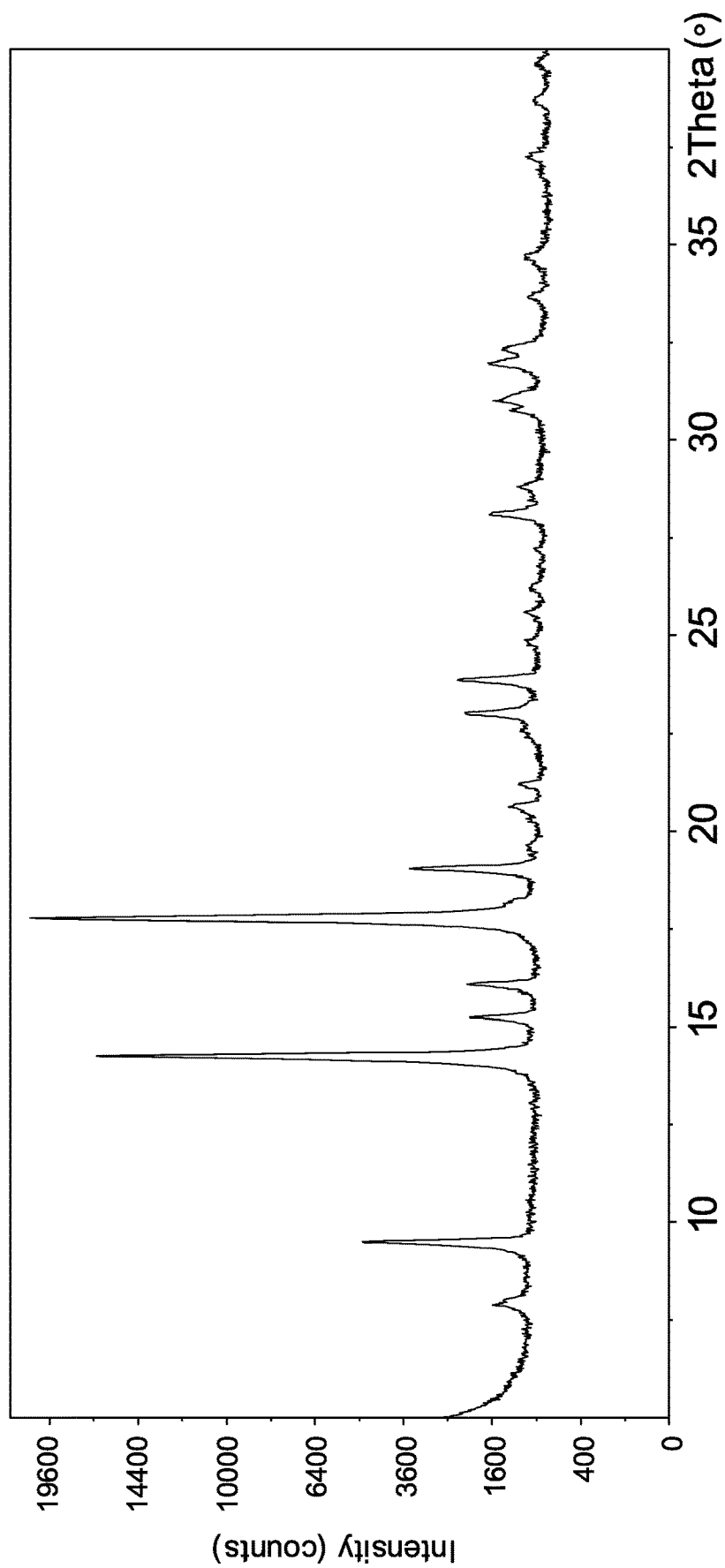
FIG. 1 depicts an X-ray powder diffraction ("XRPD") pattern of the free base crystalline form III.

Free base crystalline form III of omecamtiv mecarbil can be characterized by an X-ray powder diffraction pattern, obtained as set forth in the Examples, having peaks at about 9.50, 19.06, and 23.01±0.2° 2θ using Cu Kα radiation. Free base crystalline form III optionally can be further characterized by an X-ray powder diffraction pattern having additional peaks at about 14.27, 15.25, 16.10, 17.78, and 23.87±0.2° 2θ using Cu Kα radiation. Free base crystalline form III optionally can be further characterized by an X-ray powder diffraction pattern having additional peaks at about 7.91, 20.65, 28.11, 31.01, 31.95, and 32.34±0.2° 2θ using Cu Kα radiation. Free base crystalline form III optionally can be characterized by an X-ray powder diffraction pattern having peaks shown in Table 1 set forth in the Examples. In some embodiments, free base crystalline form III has an X-ray powder diffraction pattern substantially as shown in FIG. 1, wherein by "substantially" is meant that the reported peaks can vary by about ±0.2°. It is well known in the field of XRPD that while relative peak heights in spectra are dependent on a number of factors, such as sample preparation and instrument geometry, peak positions are relatively insensitive to experimental details.

Figure 2:
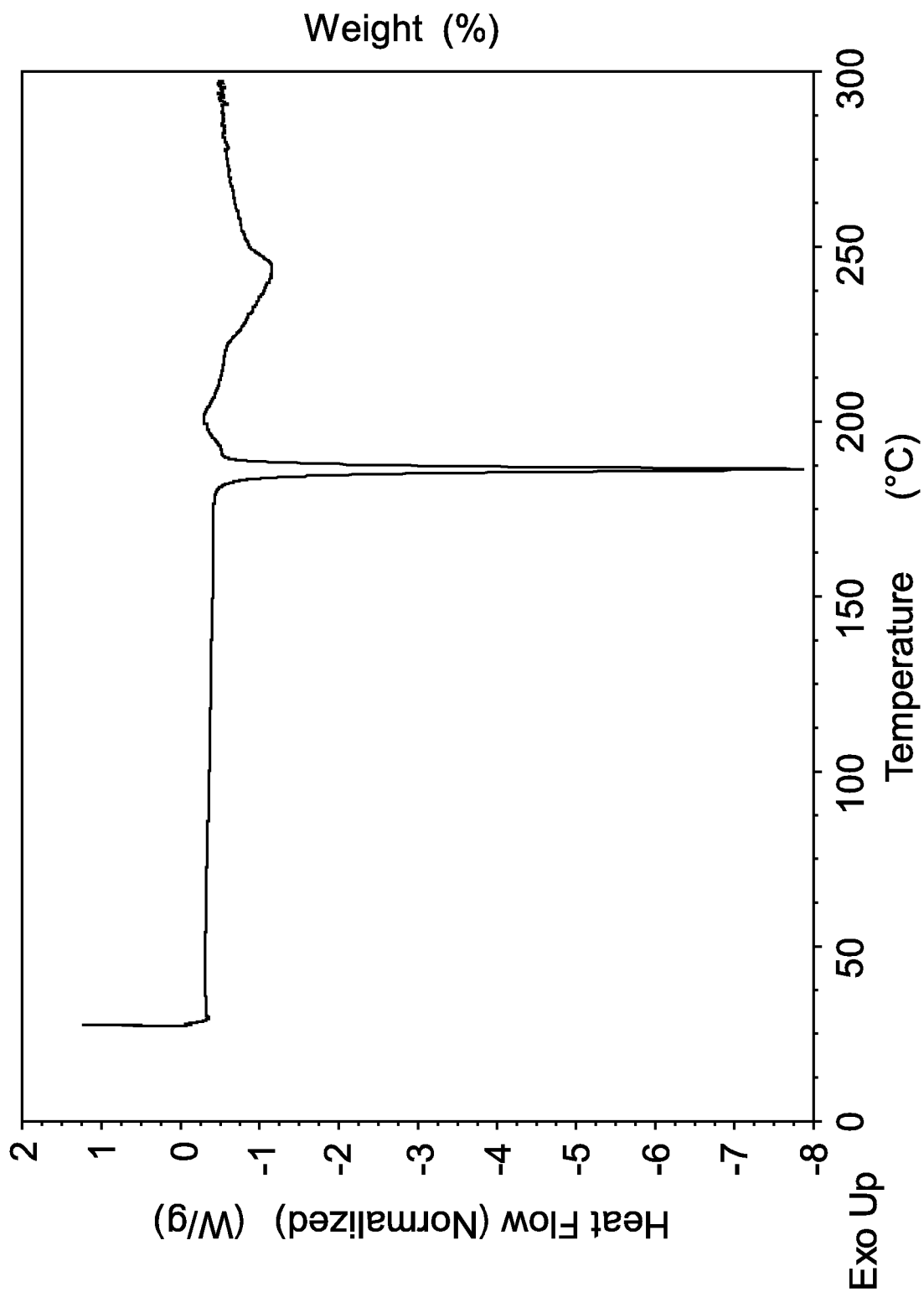
FIG. 2 depicts a differential scanning calorimetry ("DSC") thermograph of the free crystalline form III.

Differential scanning calorimetry (DSC) thermographs were obtained, as set forth in the Examples, for free base crystalline form III. The DSC curve indicates an endothermic transition at about 186° C.±3° C. Thus, in some embodiments, free base crystalline form III can be characterized by a DSC thermograph having a decomposition endotherm with an onset in a range of about 175° C. to about 190° C. For example, in some embodiments free base crystalline form III is characterized by DSC, as shown in FIG. 2.

Figure 3:
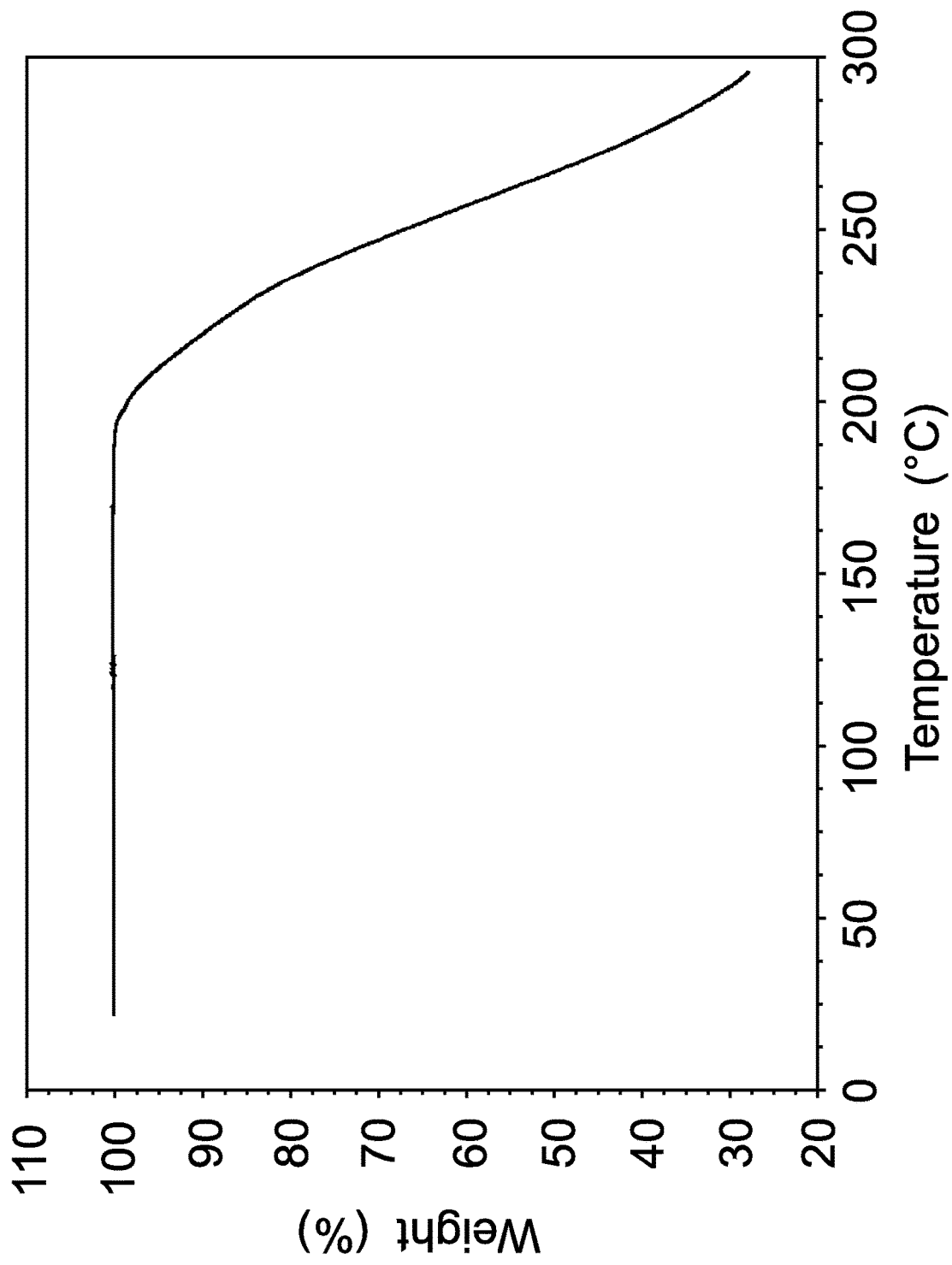
FIG. 3 depicts a thermogravimetric analysis ("TGA") trace of the free base crystalline form III.

Free base crystalline form III also can be characterized by thermogravimetric analysis (TGA). Thus, free base crystalline form III can be characterized by a weight loss in a range of about 0% to about 1% with an onset temperature in a range of about 25° C. to about 100° C. For example, free base crystalline form III can be characterized by a weight loss of about 0%, up to about 150° C. In some embodiments, free base crystalline form III has a thermogravimetric analysis substantially as depicted in FIG. 3, wherein by "substantially" is meant that the reported TGA features can vary by about ±5° C.

Free Base Crystalline Form IV

Figure 4:
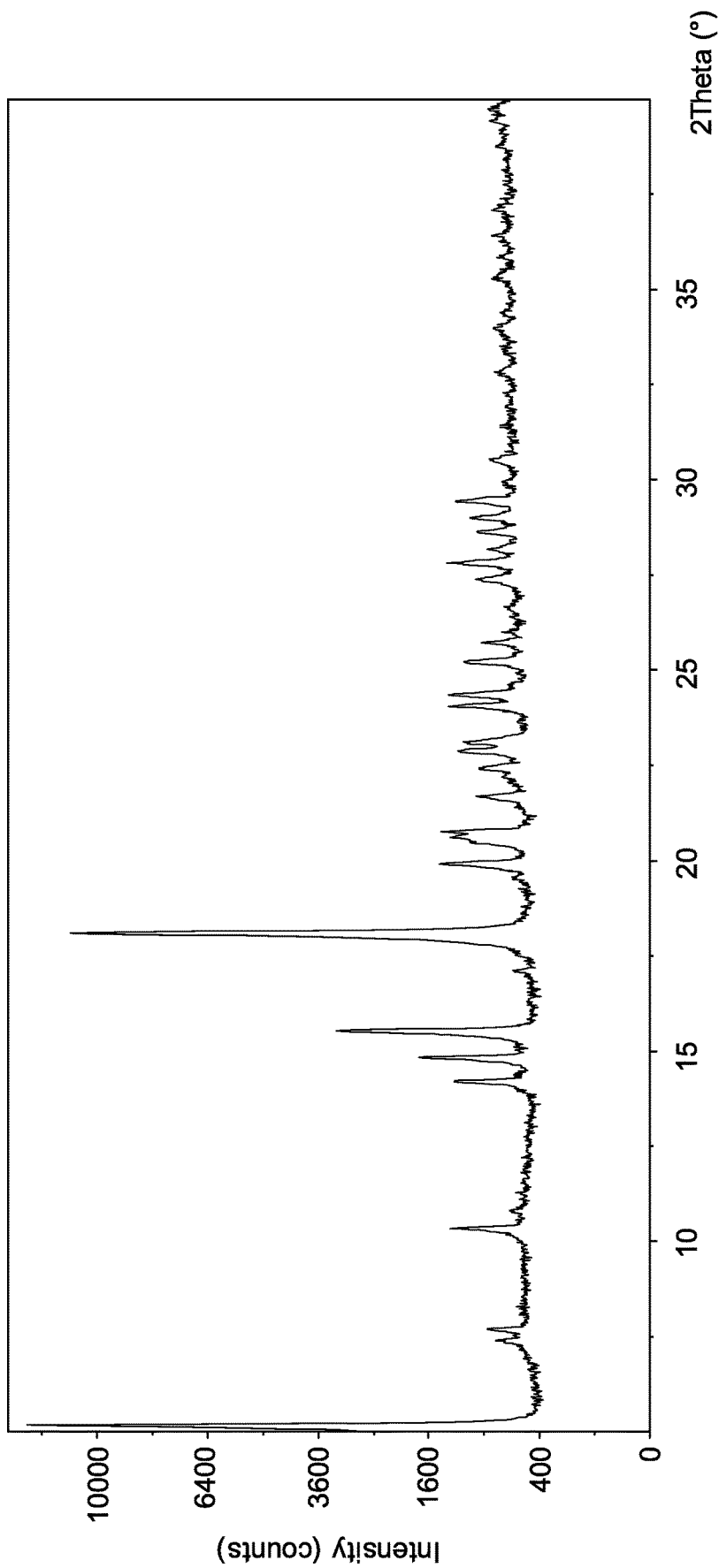
FIG. 4 depicts an XRPD pattern of the free base crystalline form IV.

Free base crystalline form IV of omecamtiv mecarbil can be characterized by an X-ray powder diffraction pattern, obtained as set forth in the Examples, having peaks at about 5.18, 10.35, 14.84, 15.54, 18.10, and 19.92±0.2° 2θ using Cu Kα radiation. Free base crystalline form IV optionally can be further characterized by an X-ray powder diffraction pattern having additional peaks at about 14.21, 20.62, 20.77, 22.86, 24.05, 24.36, 27.81, and 29.42±0.2° 2θ using Cu Kα radiation. Free base crystalline form IV optionally can be further characterized by an X-ray powder diffraction pattern having additional peaks at about 7.42, 7.70, 21.70, 22.40, 23.09, 25.20, 25.72, 27.40, 28.18, 28.63, 28.98, and 30.51±0.2° 2θ using Cu Kα radiation. Free base crystalline form IV can be characterized by an X-ray powder diffraction pattern having peaks shown in Table 2 set forth in the Examples. In some embodiments, free base crystalline form IV has an X-ray powder diffraction pattern substantially as shown in FIG. 4, wherein by "substantially" is meant that the reported peaks can vary by about ±0.2°.

Figure 5:
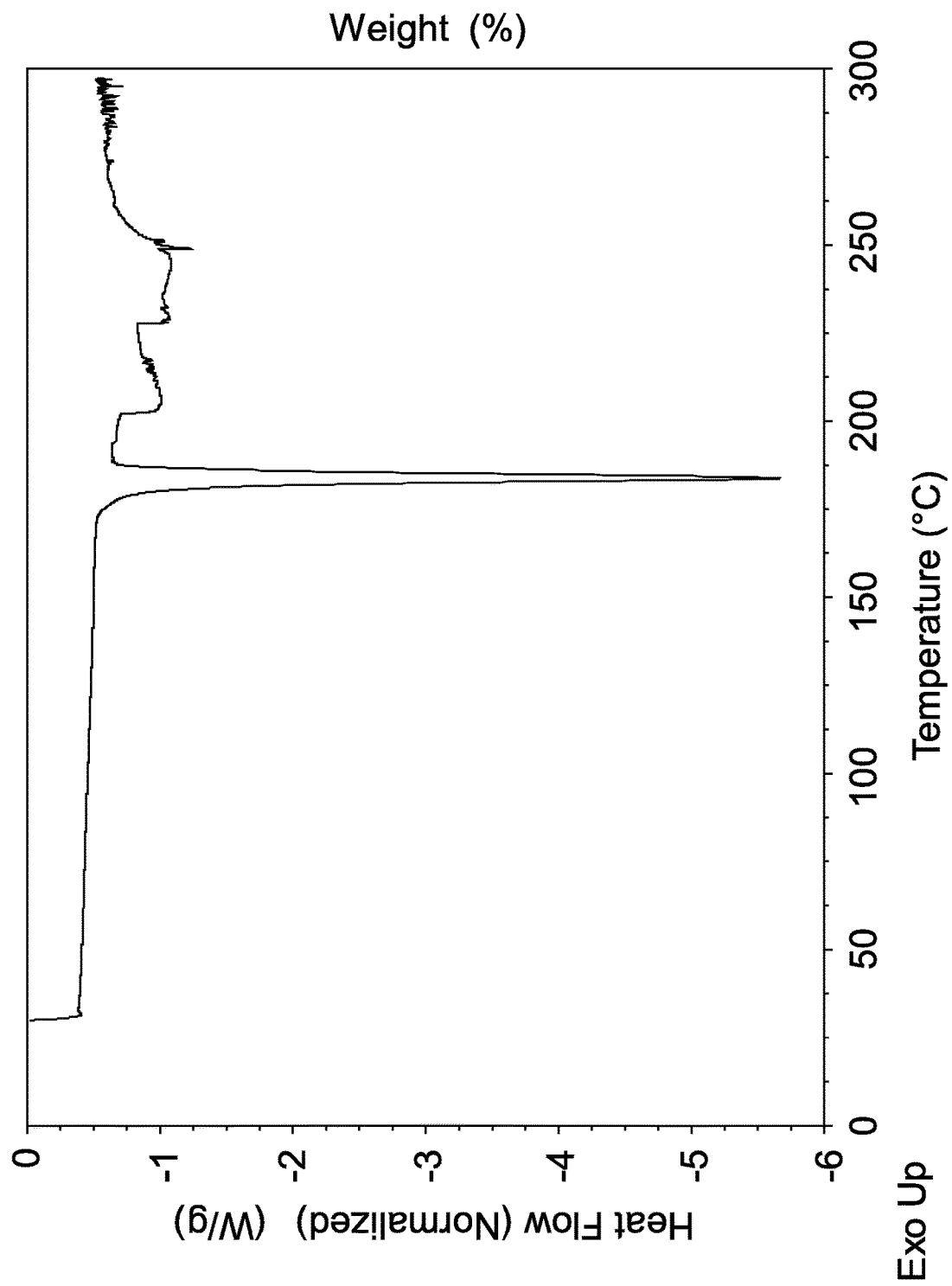
FIG. 5 depicts a DSC thermograph of the free base crystalline form IV.

Differential scanning calorimetry (DSC) thermographs were obtained, as set forth in the Examples, for free base crystalline form IV. The DSC curve indicates an endothermic transition at about 185° C.±3° C. Thus, in some embodiments, free base crystalline form IV can be characterized by a DSC thermograph having a decomposition endotherm with an onset in a range of about 175° C. to about 190° C. For example, in some embodiments free base crystalline form IV is characterized by DSC, as shown in FIG. 5.

Figure 6:
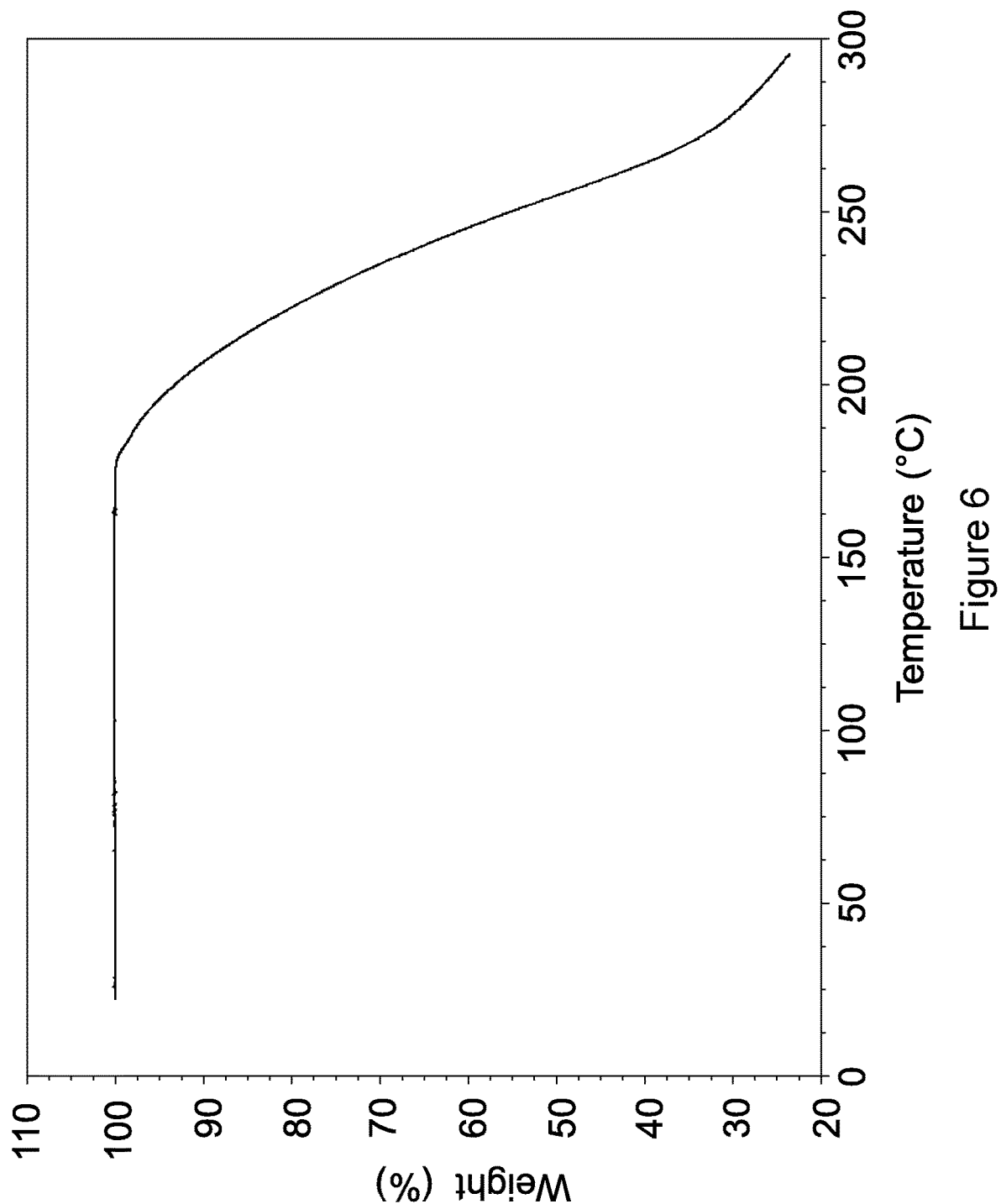
FIG. 6 depicts a TGA trace of the free base crystalline form IV.

Free base crystalline form IV also can be characterized by thermogravimetric analysis (TGA). Thus, free base crystalline form IV can be characterized by a weight loss in a range of about 0% to about 1% with an onset temperature in a range of about 25° C. to about 100° C. For example, free base crystalline form IV can be characterized by a weight loss of about 0%, up to about 150° C. In some embodiments, free base crystalline form IV has a thermogravimetric analysis substantially as depicted in FIG. 6, wherein by "substantially" is meant that the reported TGA features can vary by about ±5° C.

Free Base Crystalline Form V

Figure 7:
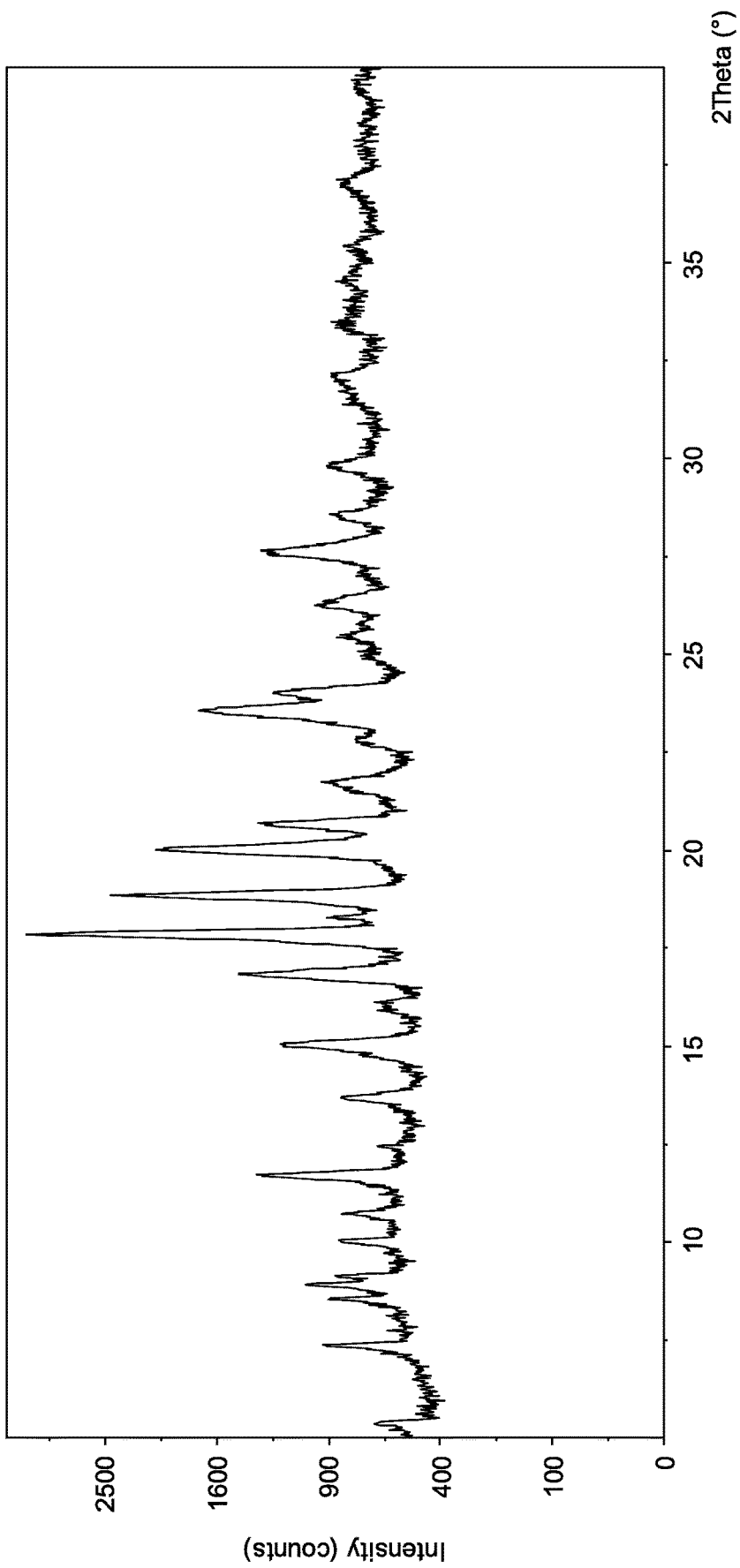
FIG. 7 depicts an XRPD pattern of the free base crystalline form V.

Free base crystalline form V of omecamtiv mecarbil can be characterized by an X-ray powder diffraction pattern, obtained as set forth in the Examples, having peaks at about 7.38, 8.56, 9.14, and 18.28±0.2° 2θ using Cu Kα radiation. Free base crystalline form V optionally can be further characterized by an X-ray powder diffraction pattern having additional peaks at about 8.93, 10.03, 10.73, 11.71, 13.69, 15.08, 16.85, 17.85, 18.86, 20.05, 20.72, 21.74, 23.56, 24.03, 26.23, and 27.62±0.2° 2θ using Cu Kα radiation. Free base crystalline form V optionally can be further characterized by an X-ray powder diffraction pattern having additional peaks at about 5.40, 16.04, 22.83, 25.45, 26.23, 27.62, 28.58, 29.85, 32.10, and 33.37±0.2° 2θ using Cu Kα radiation. Free base crystalline form V can be characterized by an X-ray powder diffraction pattern having peaks shown in Table 3 set forth in the Examples. In some embodiments, free base crystalline form V has an X-ray powder diffraction pattern substantially as shown in FIG. 7, wherein by "substantially" is meant that the reported peaks can vary by about ±0.2°.

Figure 8:
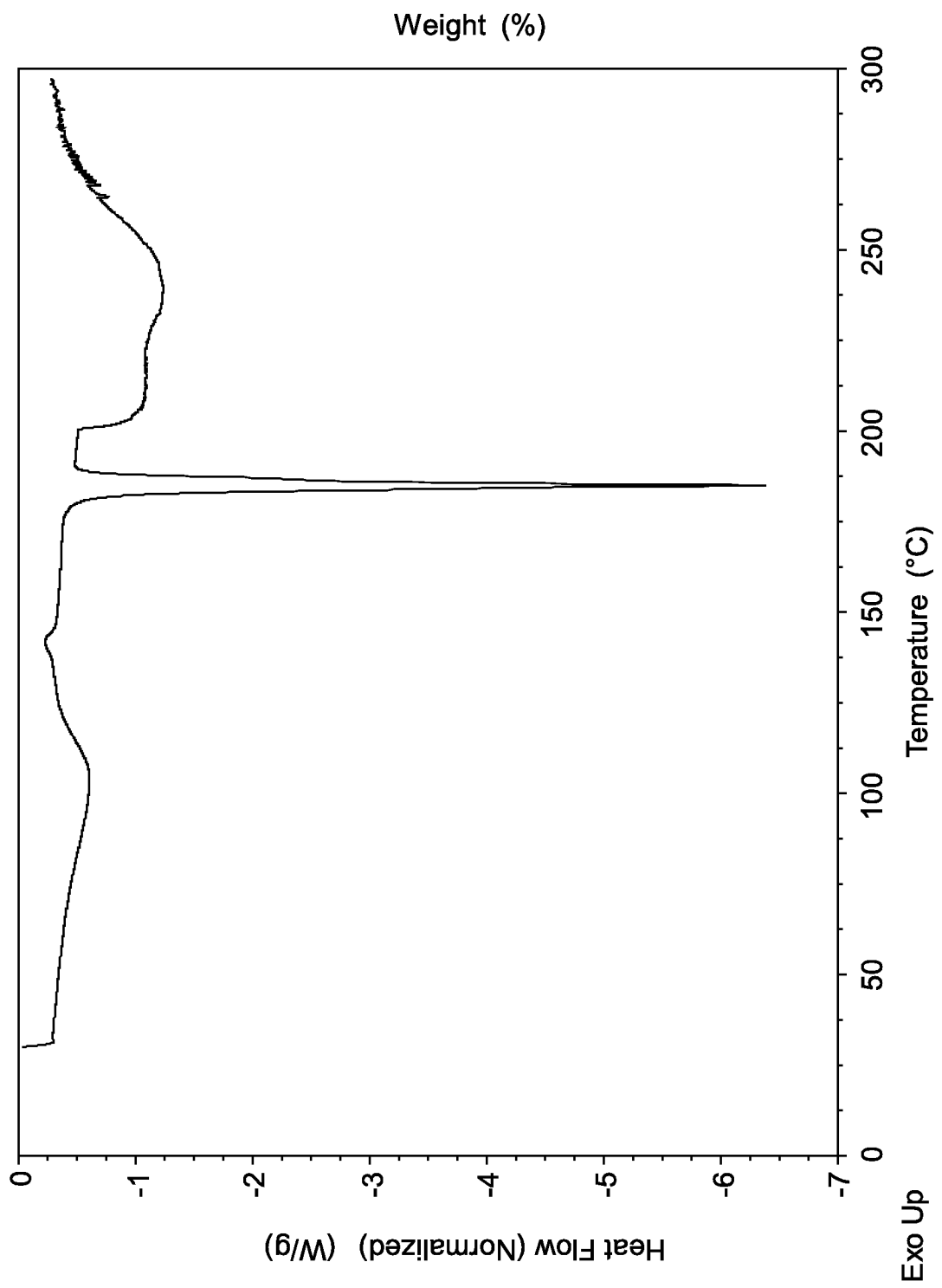
FIG. 8 depicts a DSC thermograph of the free base crystalline form V.

Differential scanning calorimetry (DSC) thermographs were obtained, as set forth in the Examples, for Form V. The DSC curve indicates an endothermic transition at about 185° C.±3° C. Thus, in some embodiments, free base crystalline form V can be characterized by a DSC thermograph having a decomposition endotherm with an onset in a range of about 175° C. to about 190° C. For example, in some embodiments free base crystalline form V is characterized by DSC, as shown in FIG. 8.

Figure 9:
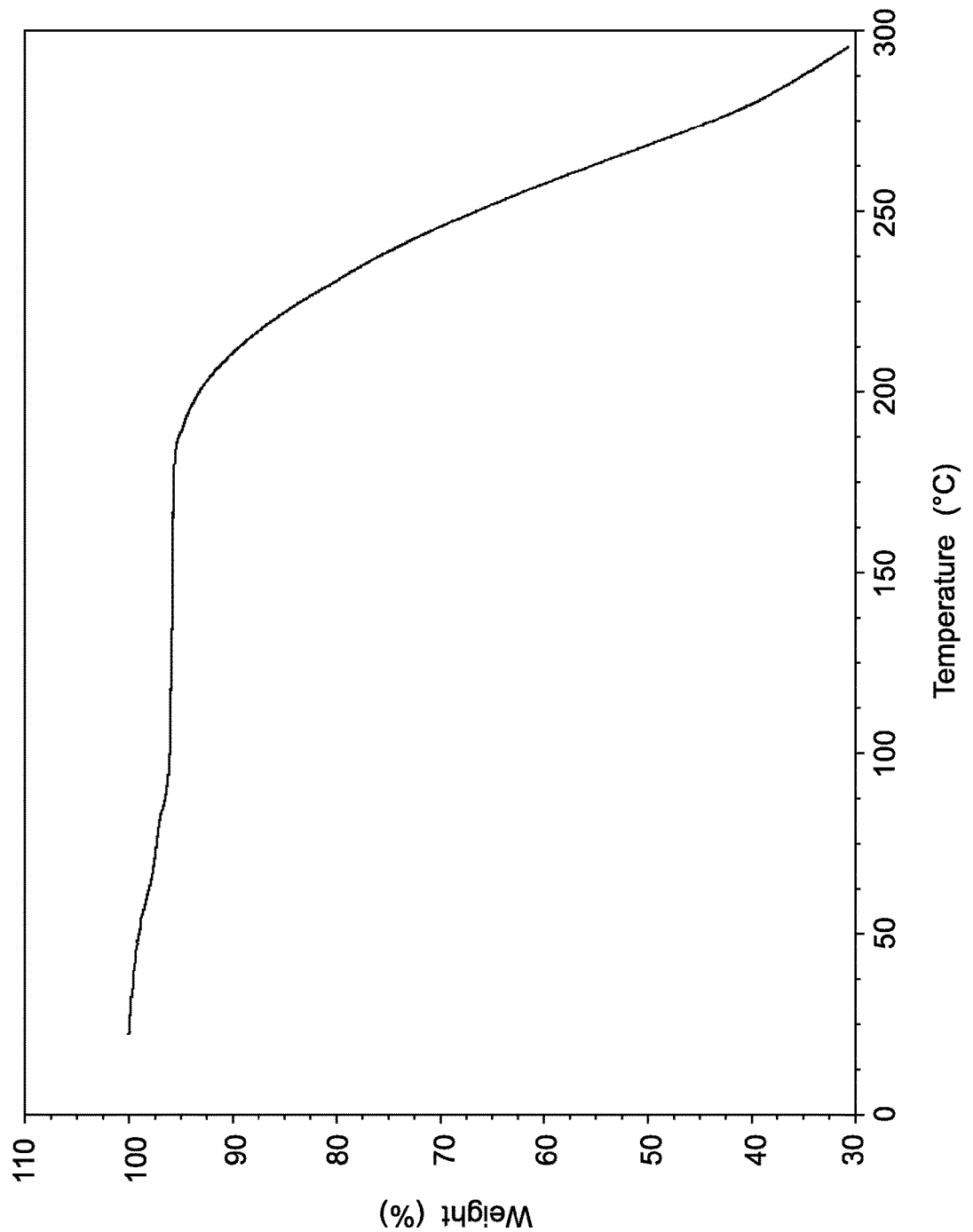
FIG. 9 depicts a TGA trace of the free base crystalline form V.

Free base crystalline form V also can be characterized by thermogravimetric analysis (TGA). Thus, free base crystalline form V can be characterized by a weight loss in a range of about 2% to about 6% with an onset temperature in a range of about 25° C. to about 100° C. For example, free base crystalline form V can be characterized by a weight loss of about 4.2%, up to about 150° C. In some embodiments, free base crystalline form V has a thermogravimetric analysis substantially as depicted in FIG. 9, wherein by "substantially" is meant that the reported TGA features can vary by about ±5° C.

Free Base Crystalline Form VI

Figure 10:
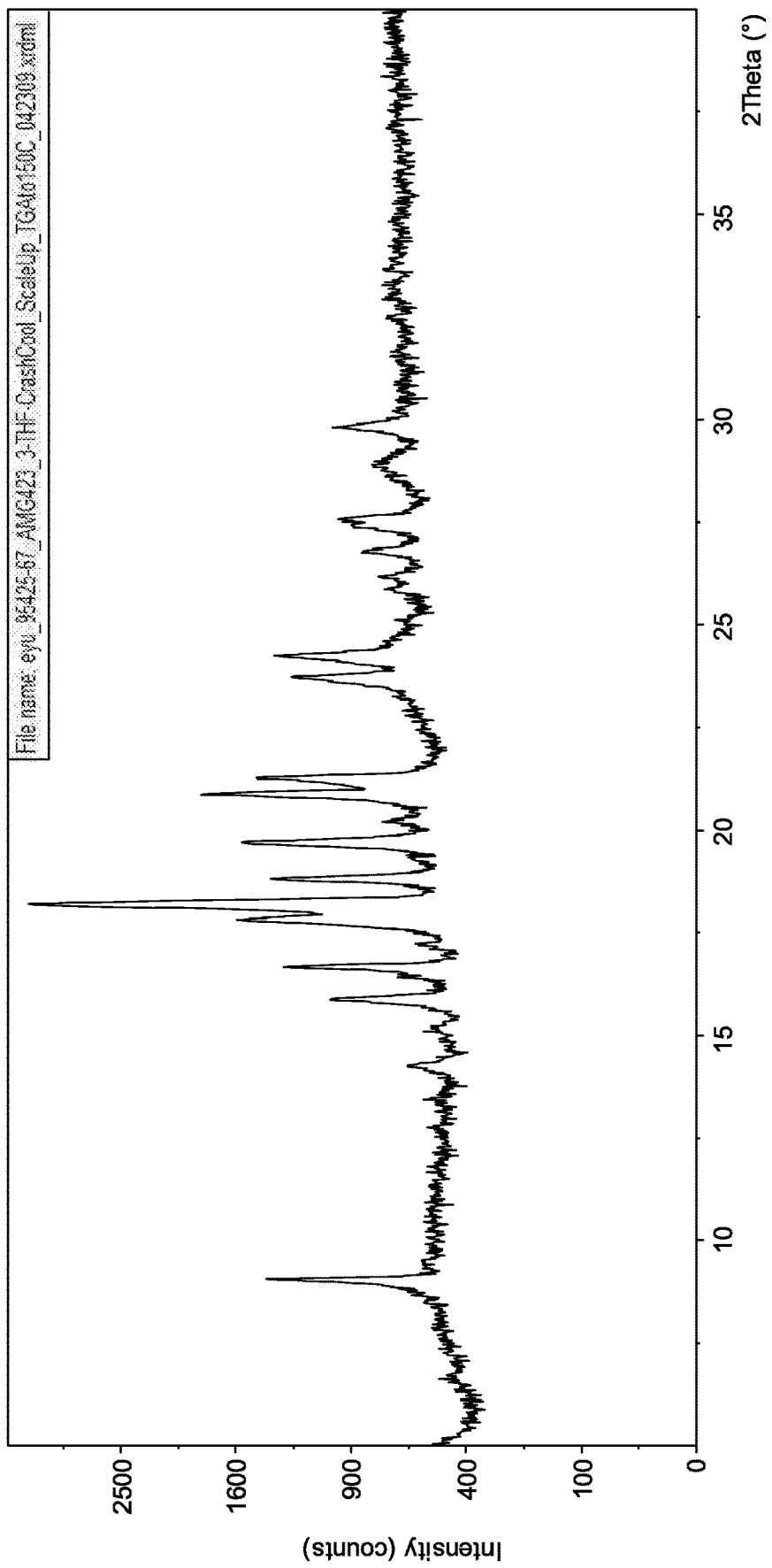
FIG. 10 depicts an XRPD pattern of the free base crystalline form VI.

Free base crystalline form VI of omecamtiv mecarbil can be characterized by an X-ray powder diffraction pattern, obtained as set forth in the Examples, having peaks at about 9.07, 16.67, 18.18, 19.70, 20.89, and 21.28±0.2° 2θ using Cu Kα radiation. Free base crystalline form VI optionally can be further characterized by an X-ray powder diffraction pattern having additional peaks at about 15.88, 17.81, 18.80, 23.72, 24.26, 26.80, 27.59, and 29.82±0.2° 2θ using Cu Kα radiation. Free base crystalline form VI optionally can be further characterized by an X-ray powder diffraction pattern having additional peaks at about 14.28, 20.23, 26.19, and 28.90±0.2° 2θ using Cu Kα radiation. Free base crystalline form VI can be characterized by an X-ray powder diffraction pattern having peaks shown in Table 4 set forth in the Examples. In some embodiments, free base crystalline form VI has an X-ray powder diffraction pattern substantially as shown in FIG. 10, wherein by "substantially" is meant that the reported peaks can vary by about ±0.2°.

Figure 11:
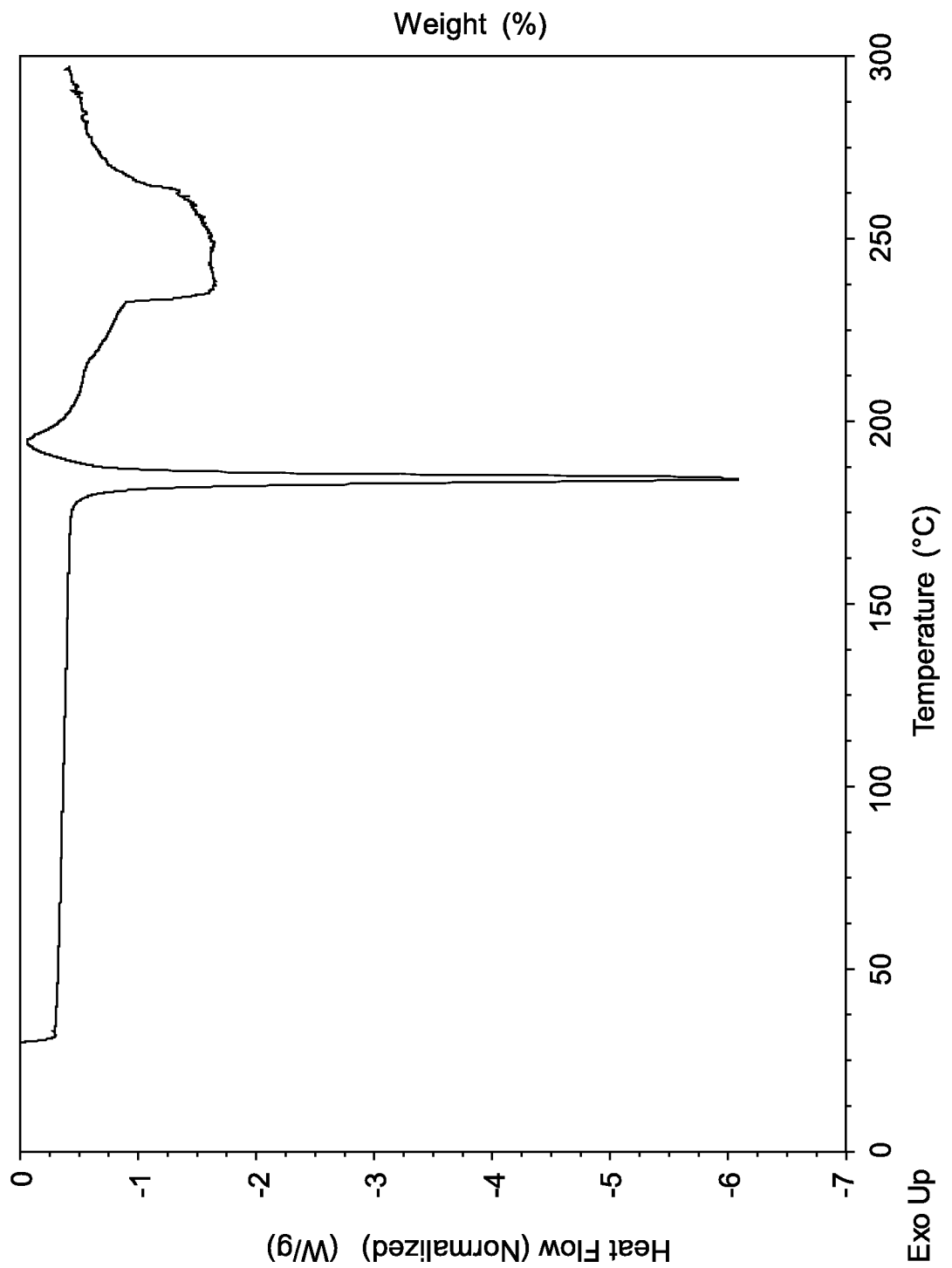
FIG. 11 depicts a DSC thermograph of the free base crystalline form VI.

Differential scanning calorimetry (DSC) thermographs were obtained, as set forth in the Examples, for Form VI. The DSC curve indicates an endothermic transition at about 185° C.±3° C. Thus, in some embodiments, free base crystalline form VI can be characterized by a DSC thermograph having a decomposition endotherm with an onset in a range of about 175° C. to about 190° C. For example, in some embodiments free base crystalline form VI is characterized by DSC, as shown in FIG. 11.

Free Base Crystalline Form VII

Figure 12:
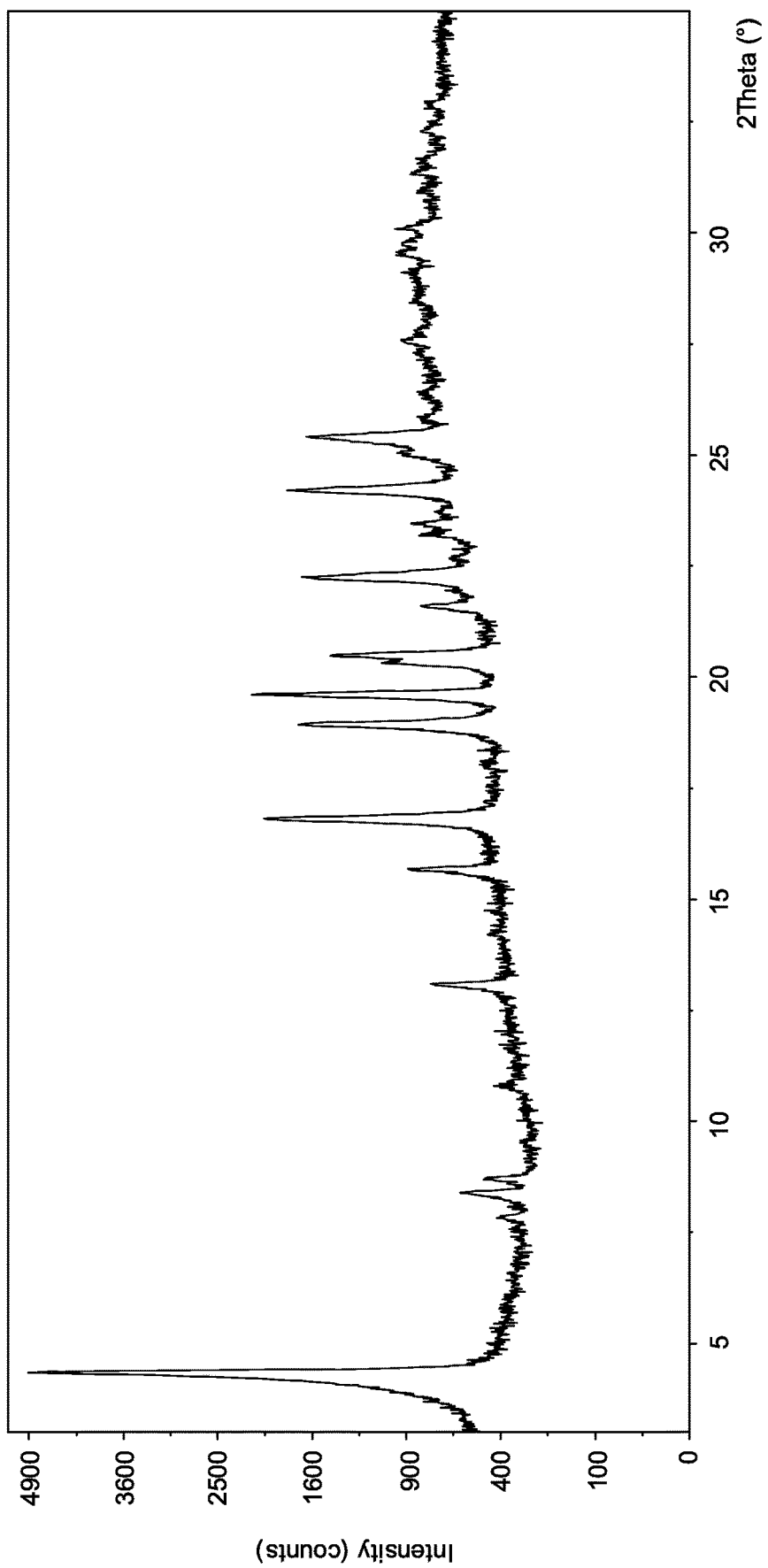
FIG. 12 depicts an XRPD pattern of the free base crystalline form VII.

Free base crystalline form VII of omecamtiv mecarbil can be characterized by an X-ray powder diffraction pattern, obtained as set forth in the Examples, having peaks at about 8.40, 8.71, 13.08, 15.66, and 19.61±0.2° 2θ using Cu Kα radiation. Free base crystalline form VII optionally can be further characterized by an X-ray powder diffraction pattern having additional peaks at about 4.37, 16.83, 18.92, 20.32, 20.49, 22.26, 24.21, and 25.41±0.2° 2θ using Cu Kα radiation. Free base crystalline form VII optionally can be further characterized by an X-ray powder diffraction pattern having additional peaks at about 7.84, 10.81, 21.61, 23.22, 23.46, 27.58, 29.53, 30.13, and 31.32±0.2° 2θ using Cu Kα radiation. Free base crystalline form VII can be characterized by an X-ray powder diffraction pattern having peaks shown in Table 5 set forth in the Examples. In some embodiments, the free base crystalline form VII has an X-ray powder diffraction pattern substantially as shown in FIG. 12, wherein by "substantially" is meant that the reported peaks can vary by about ±0.2°.

Crystalline Salts of Omecamtiv Mecarbil

Provided herein are various crystalline salts of omecamtiv mecarbil. Specifically provided are crystalline salts of omecamtiv mecarbil, wherein the salt is an ethane sulfonate salt, a fumarate salt, a maleate salt, a malonate salt, a mesylate salt, a naphthalate-2-sulfonate salt, a napadisylate salt, a nicotinate salt, an oxalate salt, a salicylate salt, a succinate salt, a sulfate salt, a hydroxyethane sulfonate salt, or a tartrate salt.

Ethane Sulfonate Crystalline Salt

Figure 18:
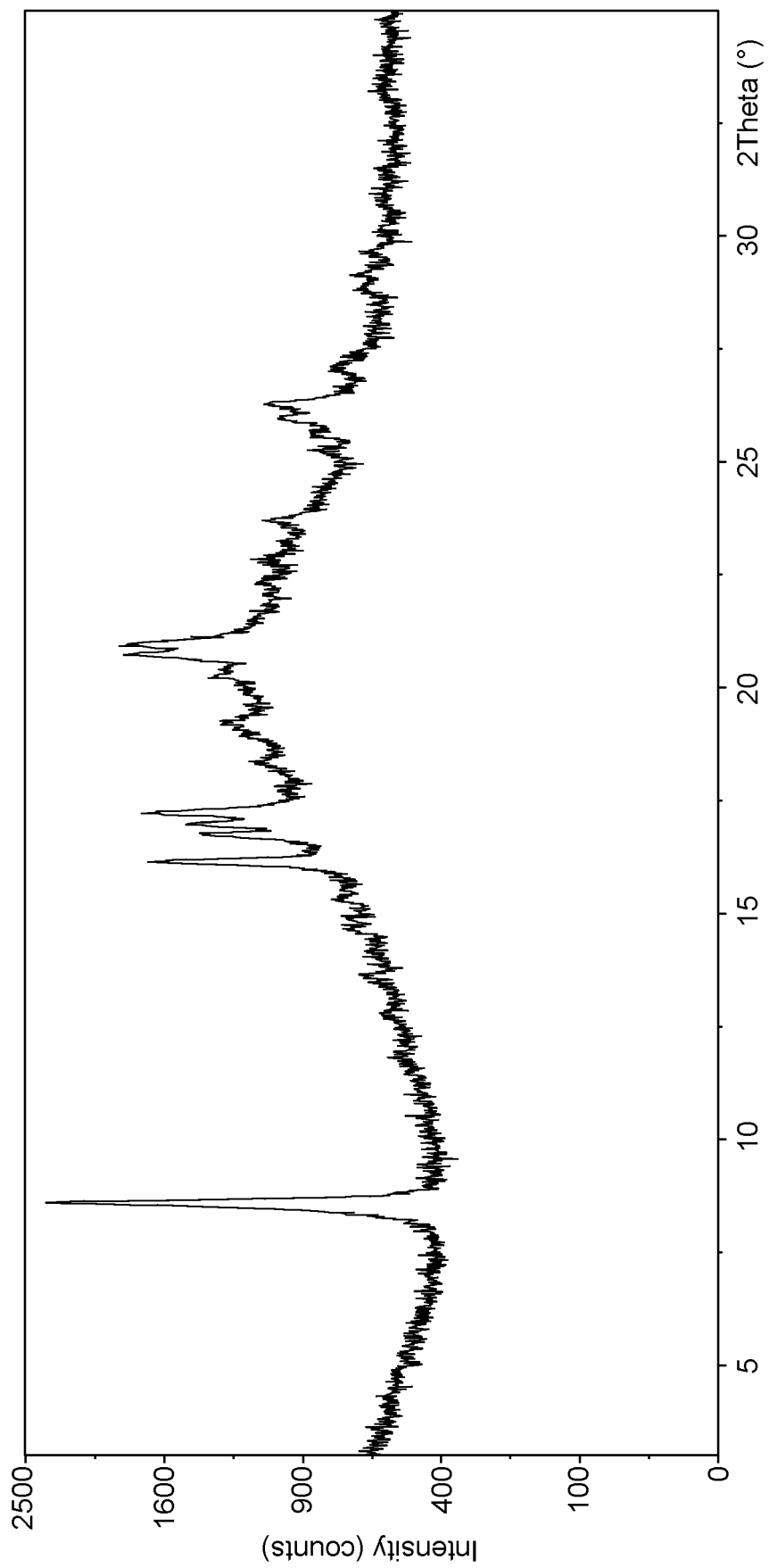
FIG. 18 depicts an XRPD pattern of the ethane sulfonate crystalline salt.
Figure 19:
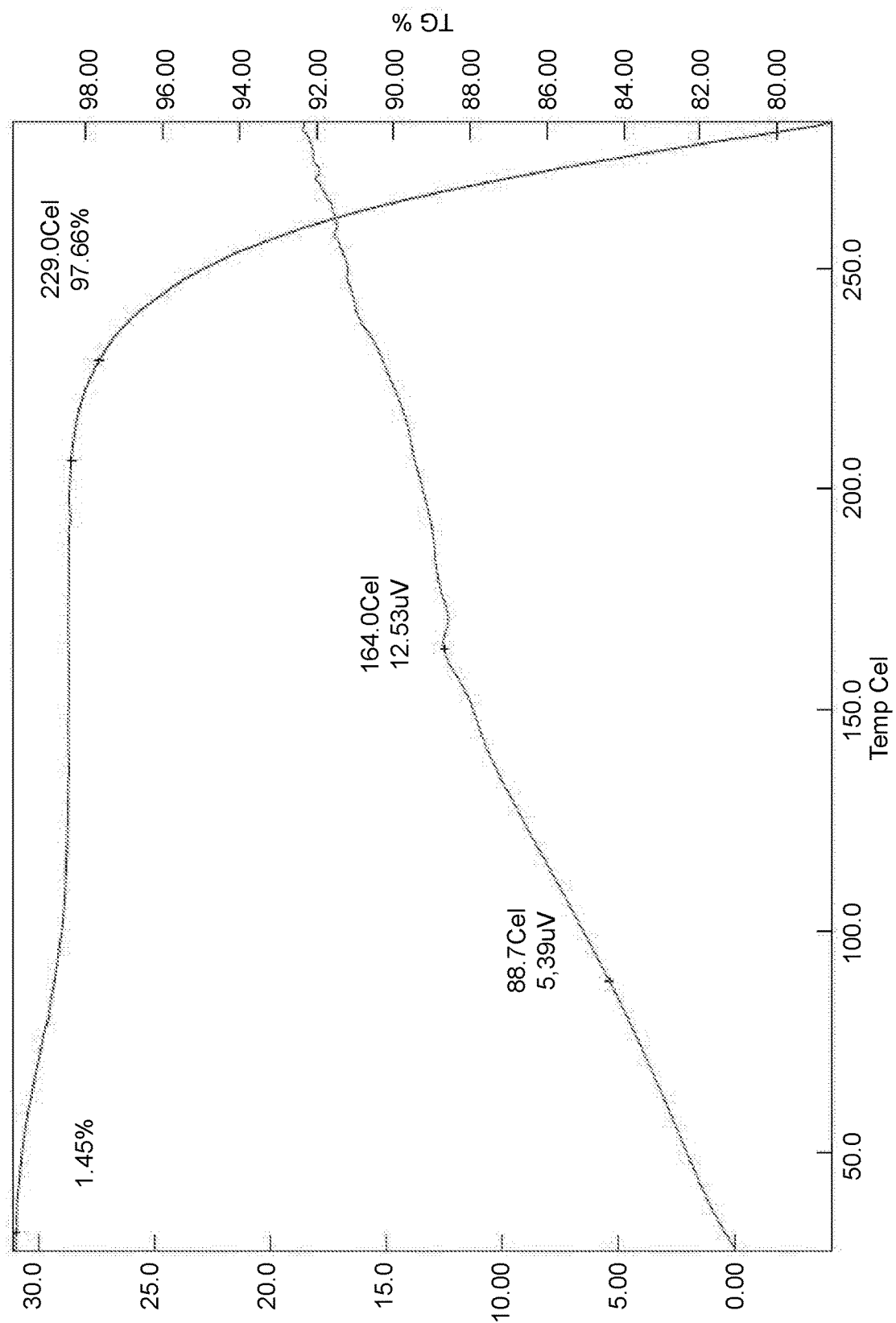
FIG. 19 depicts a thermal gravimetric/differential thermal analysis ("TG/DTA") thermograph of the ethane sulfonate crystalline salt.

The ethane sulfonate crystalline salt of omecamtiv mecarbil can be characterized by an X-ray powder diffraction pattern, obtained as set forth in the Examples, having peaks at about 8.61, 16.14, 16.76, 16.97 20.73, 20.96, 25.95, and 26.30±0.2° 2θ using Cu Kα radiation. The ethane sulfonate crystalline salt optionally can be further characterized by an X-ray powder diffraction pattern having additional peaks at about 17.23, 18.35, 19.20, 20.27, 23.73, 25.24, and 27.09±0.2° 2θ using Cu Kα radiation. The ethane sulfonate crystalline salt can be characterized by an X-ray powder diffraction pattern having peaks shown in Table 7 set forth in the Examples. In some embodiments, the ethane sulfonate crystalline salt has an X-ray powder diffraction pattern substantially as shown in FIG. 18, wherein by "substantially" is meant that the reported peaks can vary by about ±0.2°. In some embodiments, ethane sulfonate crystalline salt has an TG/DTA substantially as shown in FIG. 19.

Bis-Fumarate Crystalline Salt Form A

Figure 20:
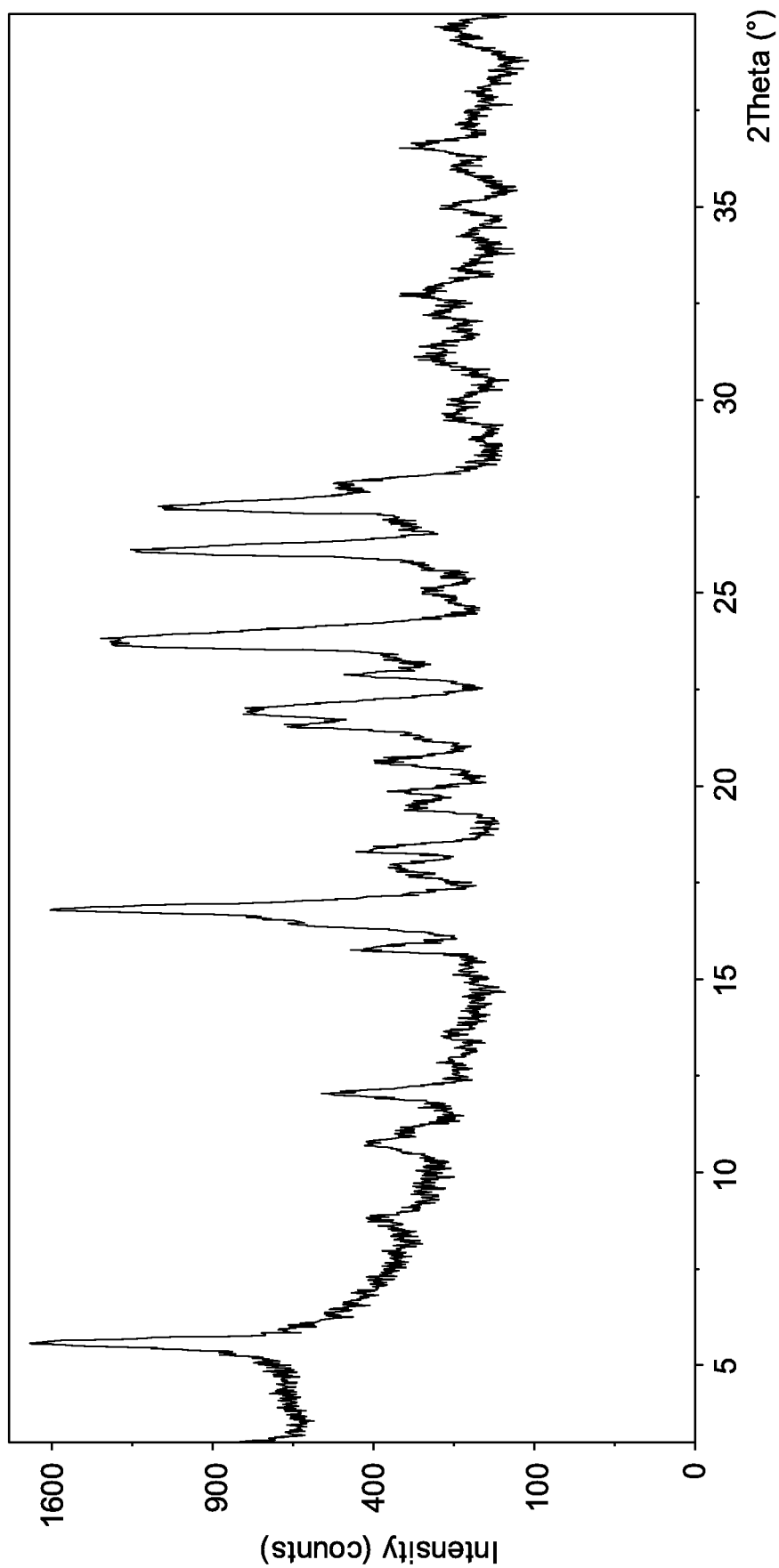
FIG. 20 depicts an XRPD pattern of the bis-fumarate crystalline salt form A.

Bis-fumarate crystalline salt form A of omecamtiv mecarbil can be characterized by an X-ray powder diffraction pattern, obtained as set forth in the Examples, having peaks at about 5.64, 15.76, 22.03, and 23.87±0.2° 2θ using Cu Kα radiation. Bis-fumarate crystalline salt form A optionally can be further characterized by an X-ray powder diffraction pattern having additional peaks at about 16.80, 21.55, 21.87, 23.61, 23.87, 26.01, and 27.20±0.2° 2θ using Cu Kα radiation. Bis-fumarate crystalline salt form A optionally can be further characterized by an X-ray powder diffraction pattern having additional peaks at about 10.80, 12.04, 15.76, 16.40, 17.94, 18.32, 19.87, 20.61, 22.88, 27.86, 32.73, and 36.54±0.2° 2θ using Cu Kα radiation. Bis-fumarate crystalline salt form A can be characterized by an X-ray powder diffraction pattern having peaks shown in Table 8 set forth in the Examples. In some embodiments, the bis-fumarate crystalline salt form A has an X-ray powder diffraction pattern substantially as shown in FIG. 20, wherein by "substantially" is meant that the reported peaks can vary by about ±0.2°.

Figure 21:
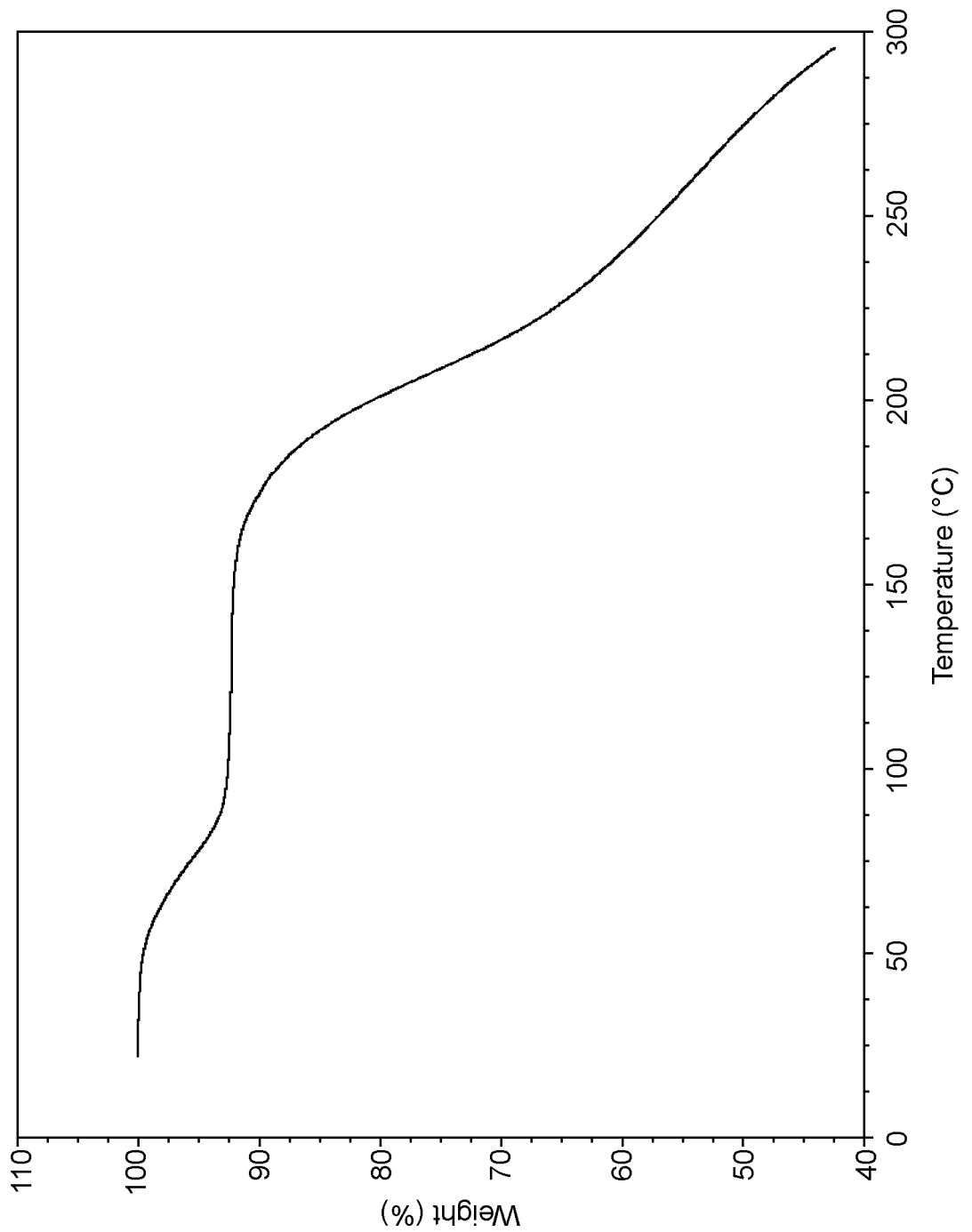
FIG. 21 depicts a TGA trace of the bis-fumarate crystalline salt form A.

Bis-fumarate crystalline salt form A also can be characterized by thermogravimetric analysis (TGA). Thus, bis-fumarate crystalline salt form A can be characterized by a weight loss in a range of about 6% to about 10% with an onset temperature in a range of about 25° C. to about 100° C. For example, bis-fumarate crystalline salt form A can be characterized by a weight loss of about 7.9%, up to about 150° C. In some embodiments, bis-fumarate crystalline salt form A has a thermogravimetric analysis substantially as depicted in FIG. 21, wherein by "substantially" is meant that the reported TGA features can vary by about ±5° C.

Bis-Fumarate Crystalline Salt Form B

Figure 22:
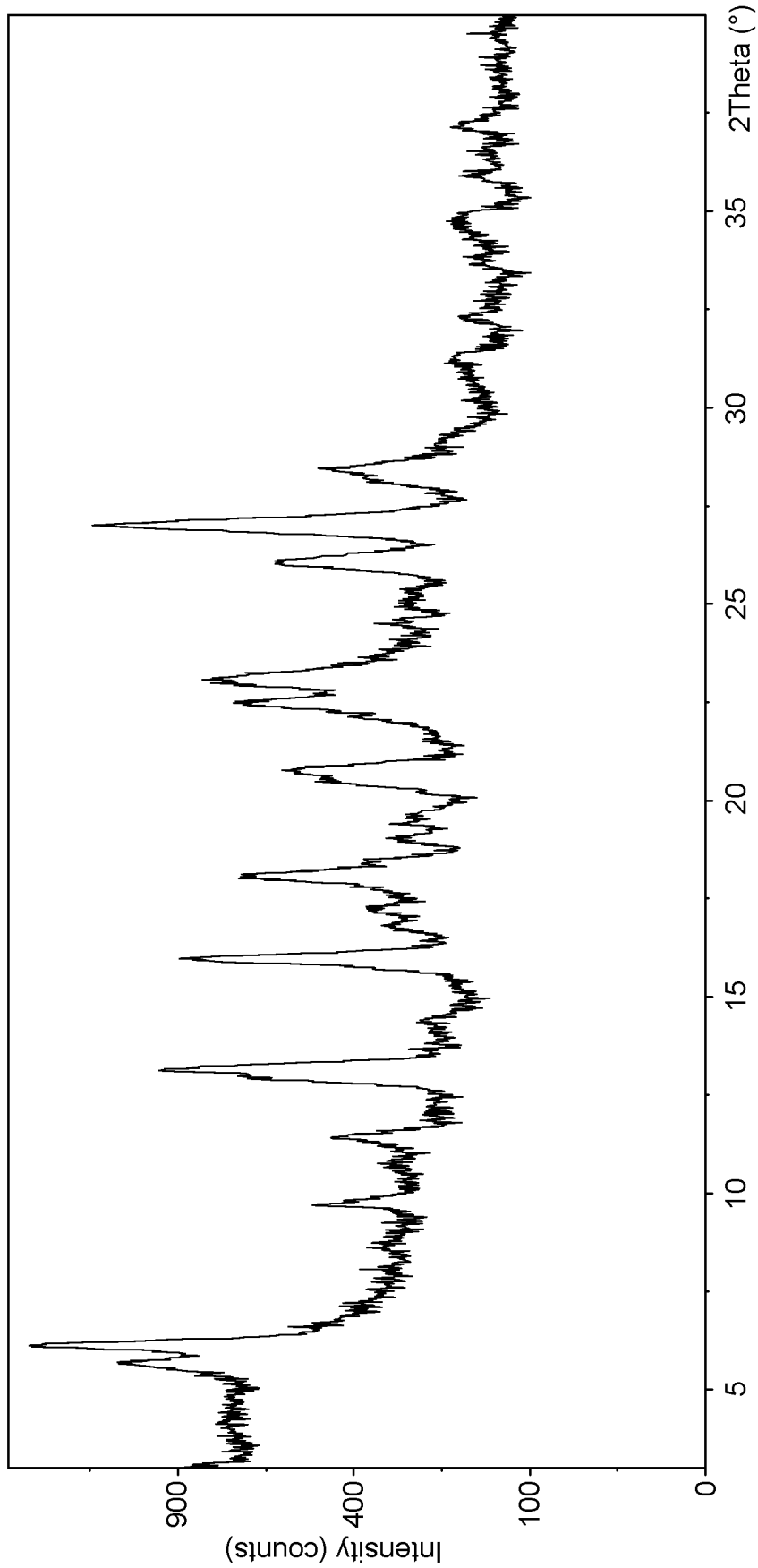
FIG. 22 depicts an XRPD pattern of the bis-fumarate crystalline salt form B.

Bis-fumarate crystalline salt form B of omecamtiv mecarbil can be characterized by an X-ray powder diffraction pattern, obtained as set forth in the Examples, having peaks at about 5.68, 6.11, 13.13, 18.08, and 22.47±0.2° 2θ using Cu Kα radiation. Bis-fumarate crystalline salt form B optionally can be further characterized by an X-ray powder diffraction pattern having additional peaks at about 9.69, 11.43, 12.92, 15.95, 20.81, 22.95, 26.04, 27.01, and 28.43±0.2° 2θ using Cu Kα radiation. Bis-fumarate crystalline salt form B optionally can be further characterized by an X-ray powder diffraction pattern having additional peaks at about 19.52, 24.53, 31.37, 32.32, 34.89, 35.89, and 37.16±0.2° 2θ using Cu Kα radiation. Bis-fumarate crystalline salt form B optionally can be characterized by an X-ray powder diffraction pattern having peaks shown in Table 9 set forth in the Examples. In some embodiments, the bis-fumarate crystalline salt form B has an X-ray powder diffraction pattern substantially as shown in FIG. 22, wherein by "substantially" is meant that the reported peaks can vary by about ±0.2°.

Figure 23:
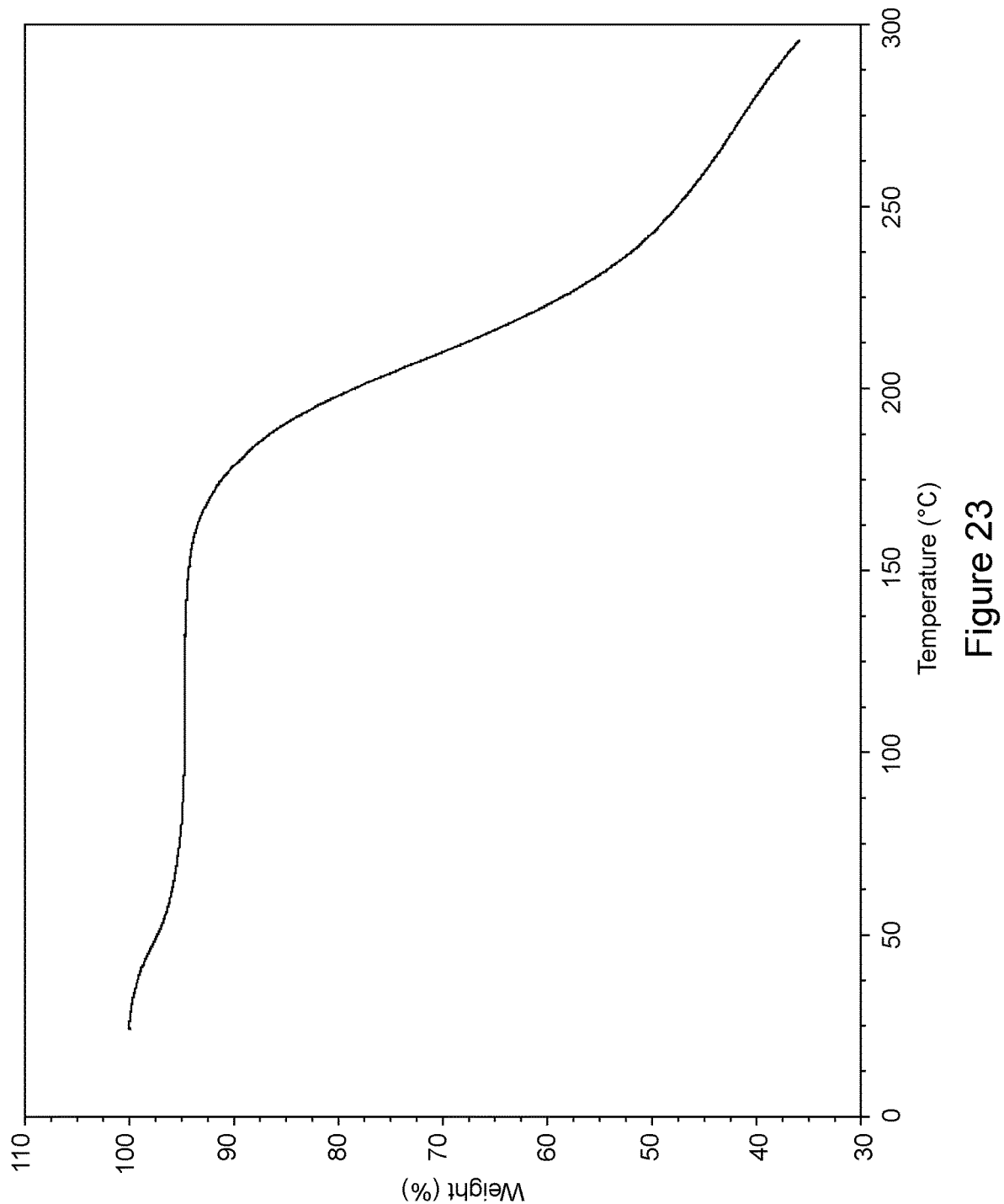
FIG. 23 depicts a TGA trace of the bis-fumarate crystalline salt form B.

Bis-fumarate crystalline salt form B also can be characterized by thermogravimetric analysis (TGA). Thus, bis-fumarate crystalline salt form B can be characterized by a weight loss in a range of about 4% to about 8% with an onset temperature in a range of about 25° C. to about 100° C. For example, bis-fumarate crystalline salt form B can be characterized by a weight loss of about 5.6%, up to about 150° C. In some embodiments, bis-fumarate crystalline salt form B has a thermogravimetric analysis substantially as depicted in FIG. 23, wherein by "substantially" is meant that the reported TGA features can vary by about ±5° C.

Bis-Fumarate Crystalline Salt Form C

Figure 24:
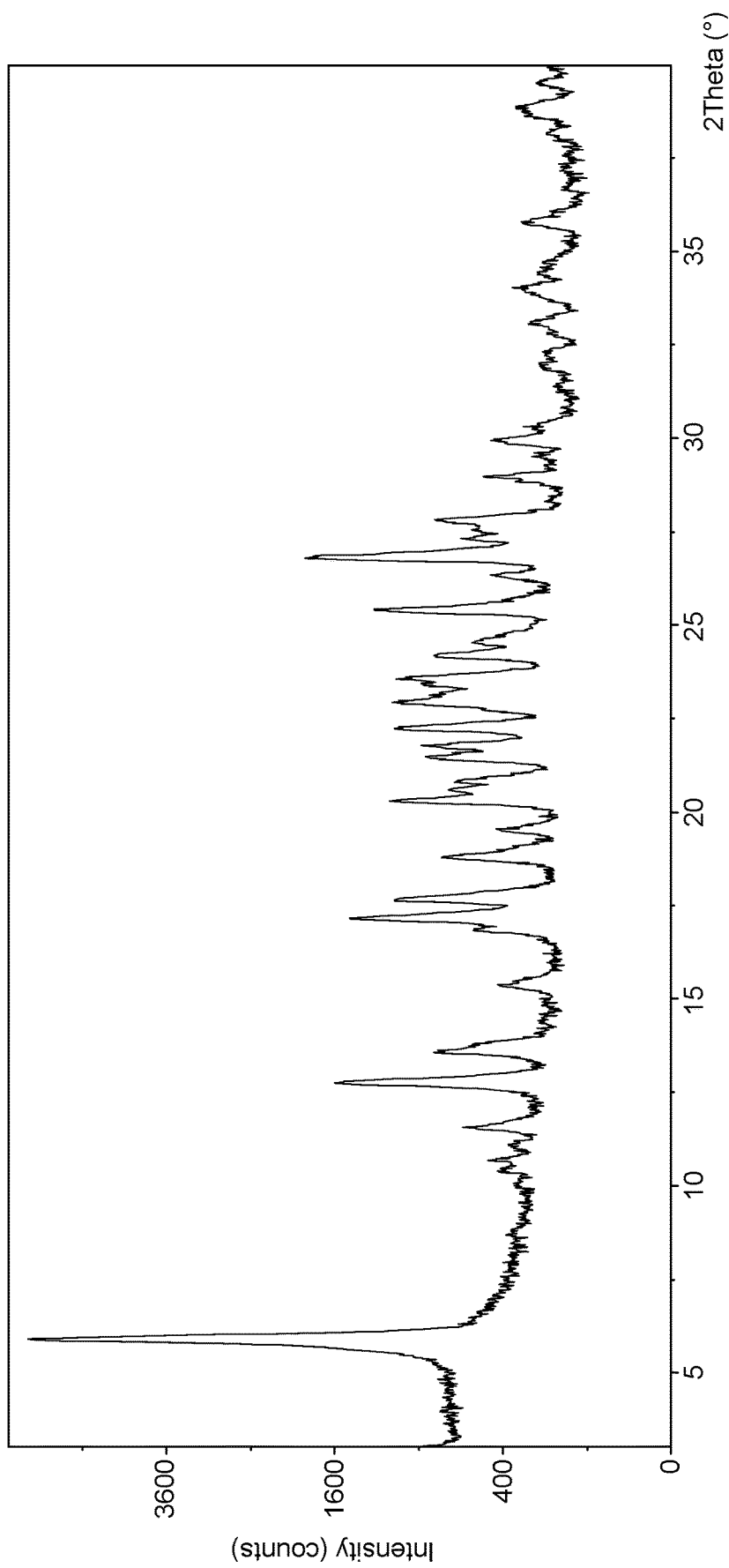
FIG. 24 depicts an XRPD pattern of the bis-fumarate crystalline salt form C.

Bis-fumarate crystalline salt form C of omecamtiv mecarbil can be characterized by an X-ray powder diffraction pattern, obtained as set forth in the Examples, having peaks at about 5.88, 18.79, 25.41, and 26.86±0.2° 2θ using Cu Kα radiation. Bis-fumarate crystalline salt form C optionally can be further characterized by an X-ray powder diffraction pattern having additional peaks at about 12.74, 13.56, 17.15, 17.63, 20.29, 21.47, 21.77, 22.21, 22.92, 23.58, 24.15, 25.41, 26.78, and 27.83±0.2° 2θ using Cu Kα radiation. Bis-fumarate crystalline salt form C can be characterized by an X-ray powder diffraction pattern having peaks shown in Table 10 set forth in the Examples. In some embodiments, the bis-fumarate crystalline salt form C has an X-ray powder diffraction pattern substantially as shown in FIG. 24, wherein by "substantially" is meant that the reported peaks can vary by about ±0.2°.

Figure 25:
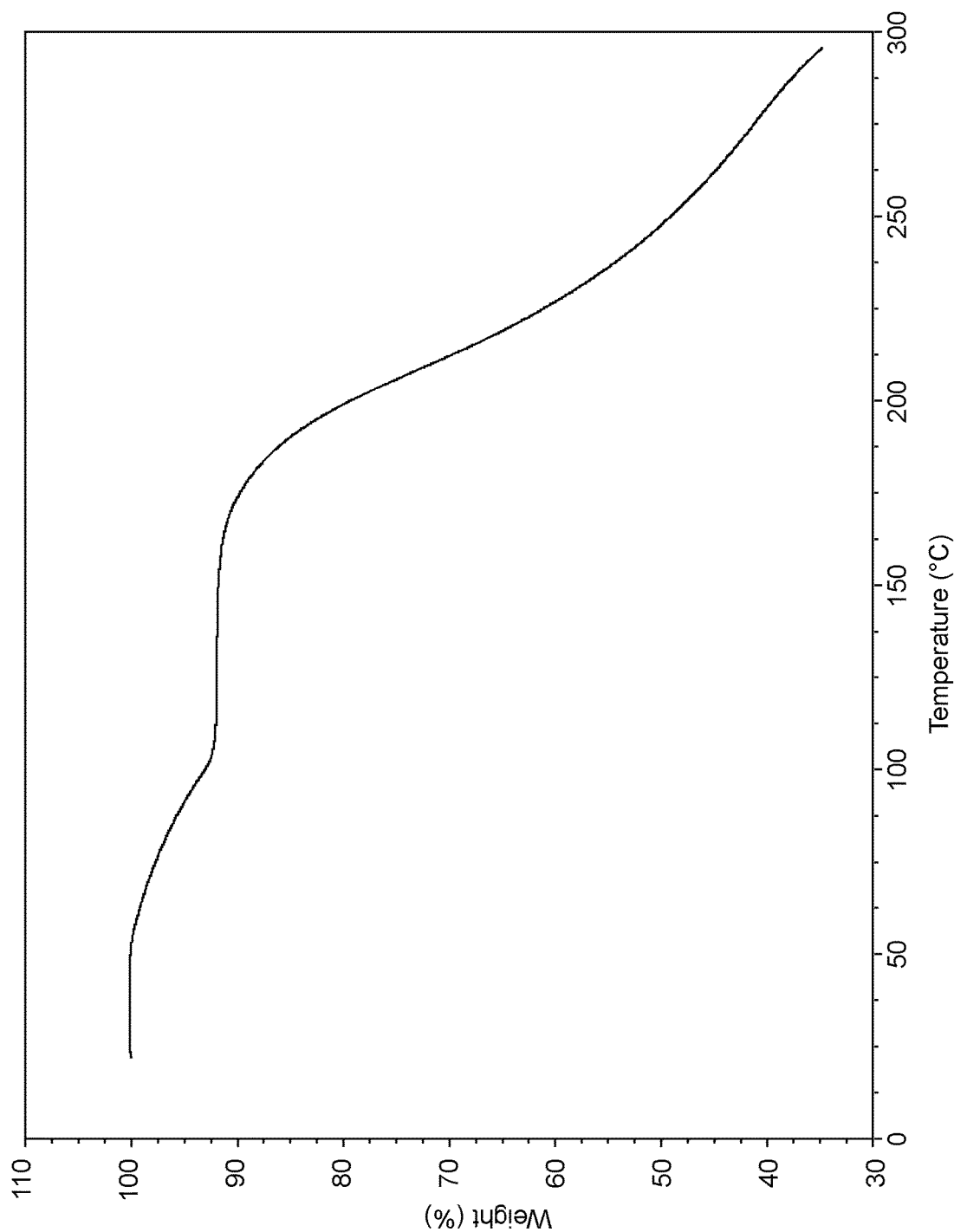
FIG. 25 depicts a TGA trace of the bis-fumarate crystalline salt form C.

Bis-fumarate crystalline salt form C also can be characterized by thermogravimetric analysis (TGA). Thus, bis-fumarate crystalline salt form C can be characterized by a weight loss in a range of about 6% to about 10% with an onset temperature in a range of about 25° C. to about 100° C. For example, bis-fumarate crystalline salt form C can be characterized by a weight loss of about 8.4%, up to about 150° C. In some embodiments, bis-fumarate crystalline salt form C has a thermogravimetric analysis substantially as depicted in FIG. 25, wherein by "substantially" is meant that the reported TGA features can vary by about ±5° C. This weight loss was determined to be water via Karl Fischer (KF) analysis. KF analysis shows that the water content of bis-fumarate crystalline salt form C can be about 8.4%, corresponding to a trihydrate.

Mono-Fumarate Crystalline Salt Form D

Figure 26:
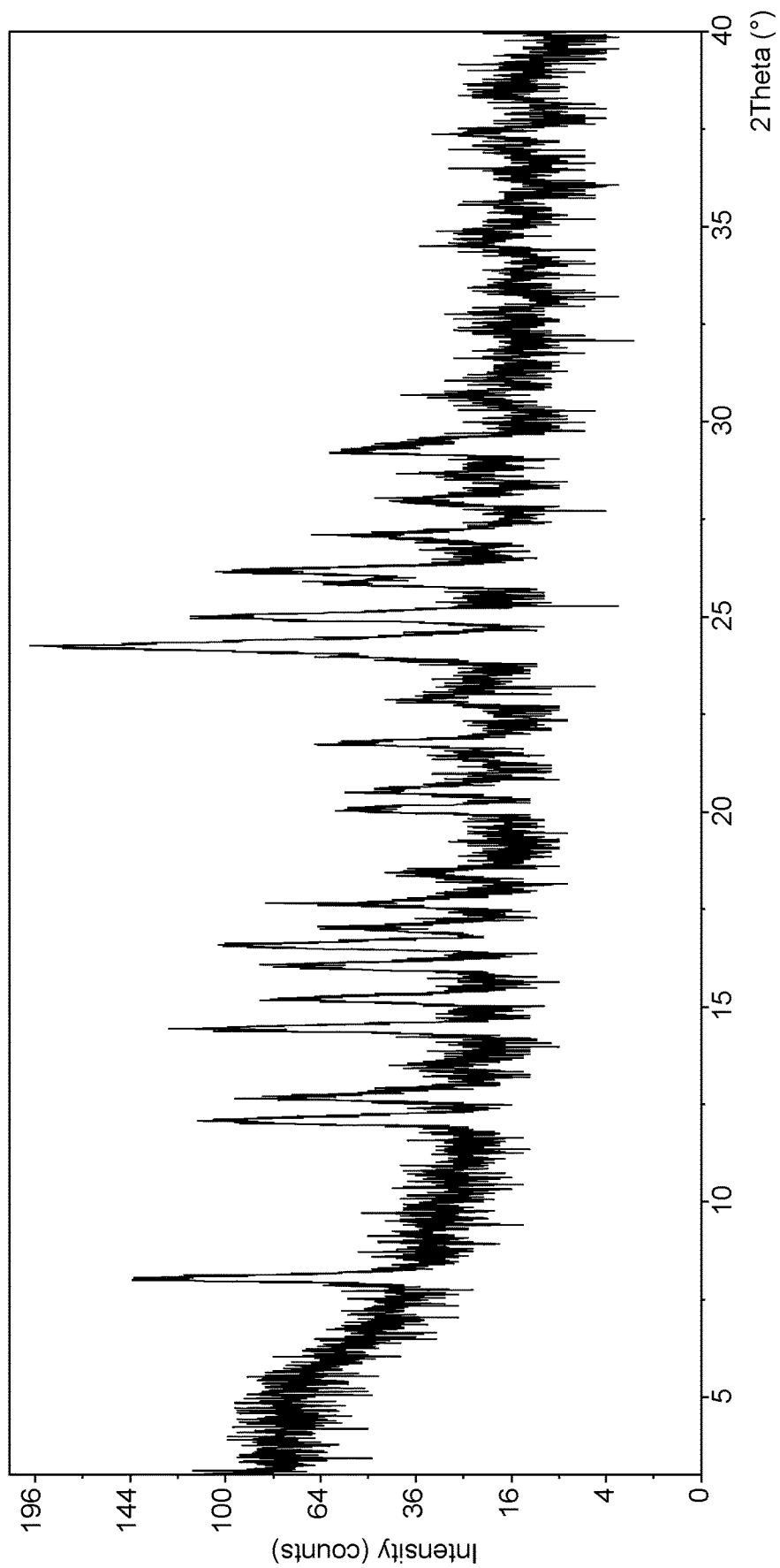
FIG. 26 depicts an XRPD pattern of the mono-fumarate crystalline salt form D.

Mono-fumarate crystalline salt form D of omecamtiv mecarbil can be characterized by an X-ray powder diffraction pattern, obtained as set forth in the Examples, having peaks at about 8.01, 15.20, and 20.02±0.2° 2θ using Cu Kα radiation. Mono-fumarate crystalline salt form D optionally can be further characterized by an X-ray powder diffraction pattern having additional peaks at about 12.11, 12.67, 14.46, 16.01, 16.57, 17.04, 17.63, 20.51, 21.75, 22.86, 24.25, 24.97, 25.84, 26.17, 27.10, 27.97, and 29.21±0.2° 2θ using Cu Kα radiation. Mono-fumarate crystalline salt form D can be characterized by an X-ray powder diffraction pattern having peaks shown in Table 11 set forth in the Examples. In some embodiments, mono-fumarate crystalline salt form D has an X-ray powder diffraction pattern substantially as shown in FIG. 26, wherein by "substantially" is meant that the reported peaks can vary by about ±0.2°.

Figure 27:
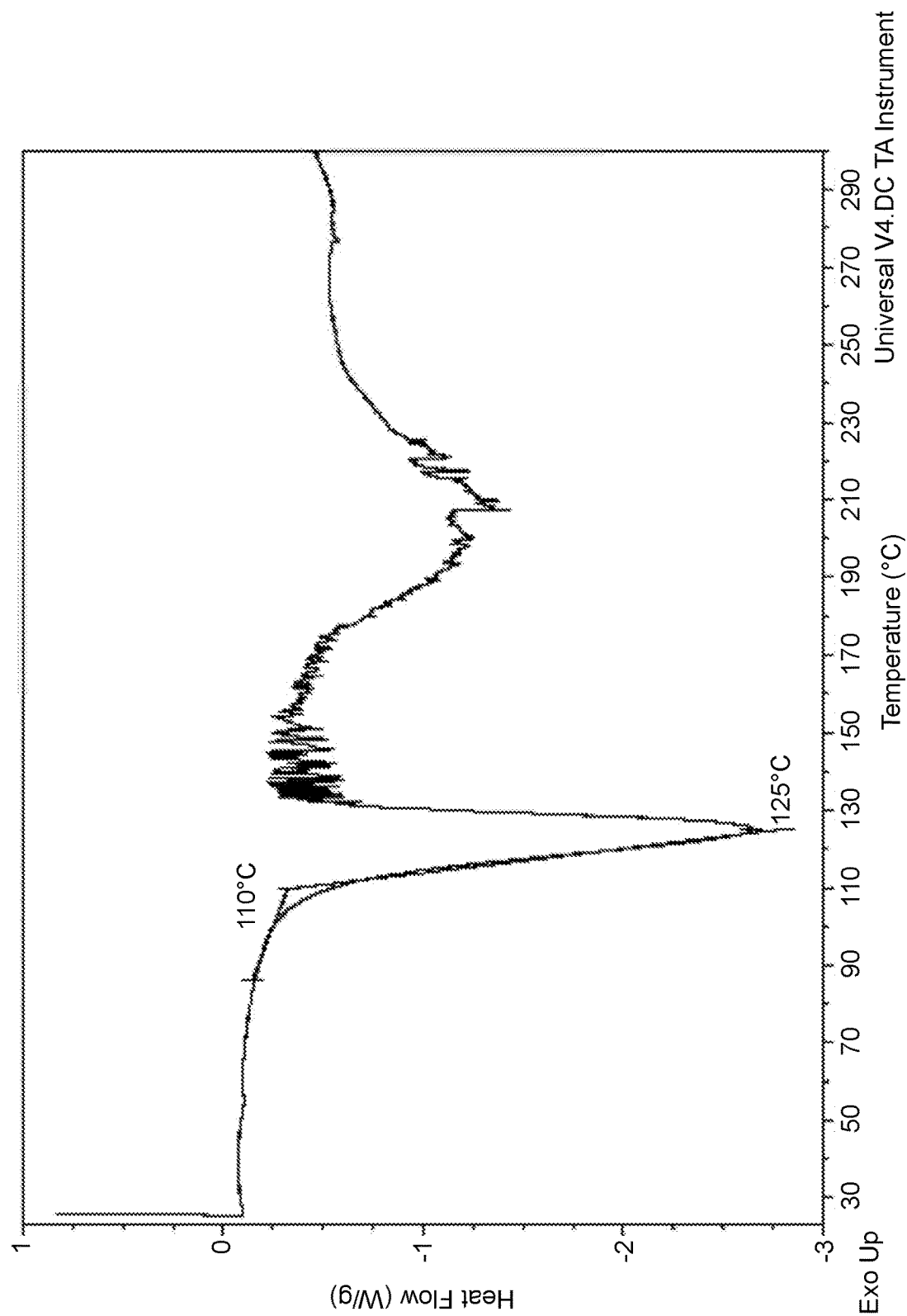
FIG. 27 depicts a DSC thermograph of the mono-fumarate crystalline salt form D.

Differential scanning calorimetry (DSC) thermographs were obtained, as set forth in the Examples, for mono-fumarate crystalline salt form D. The DSC curve indicates an endothermic transition at about 125° C.±3° C. Thus, in some embodiments, mono-fumarate crystalline salt form D can be characterized by a DSC thermograph having a decomposition endotherm with an onset in a range of about 110° C. to about 130° C. For example, in some embodiments mono-fumarate crystalline salt form D is characterized by DSC, as shown in FIG. 27.

Figure 28:
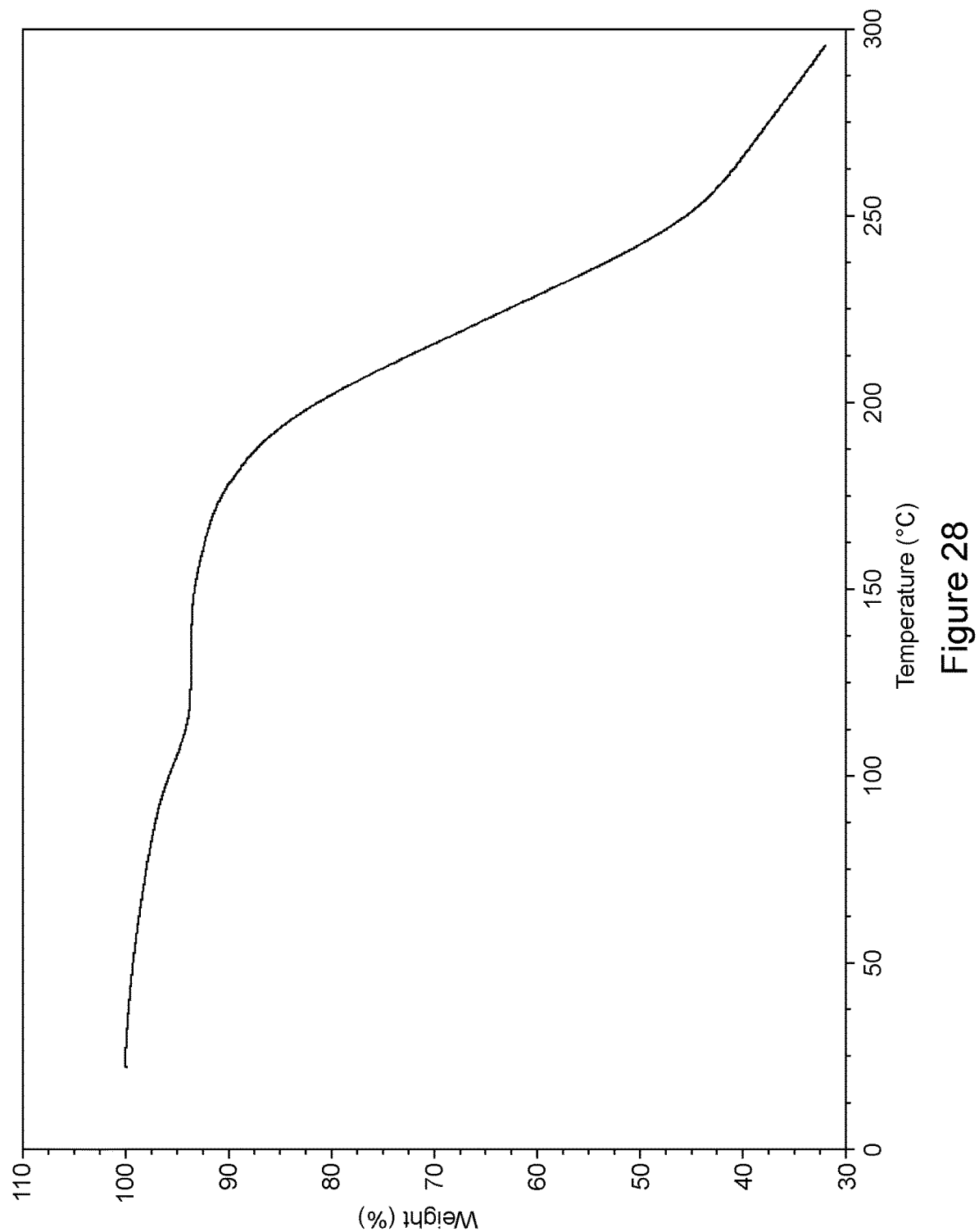
FIG. 28 depicts a TGA trace of the mono-fumarate crystalline salt form D.
Figure 29:
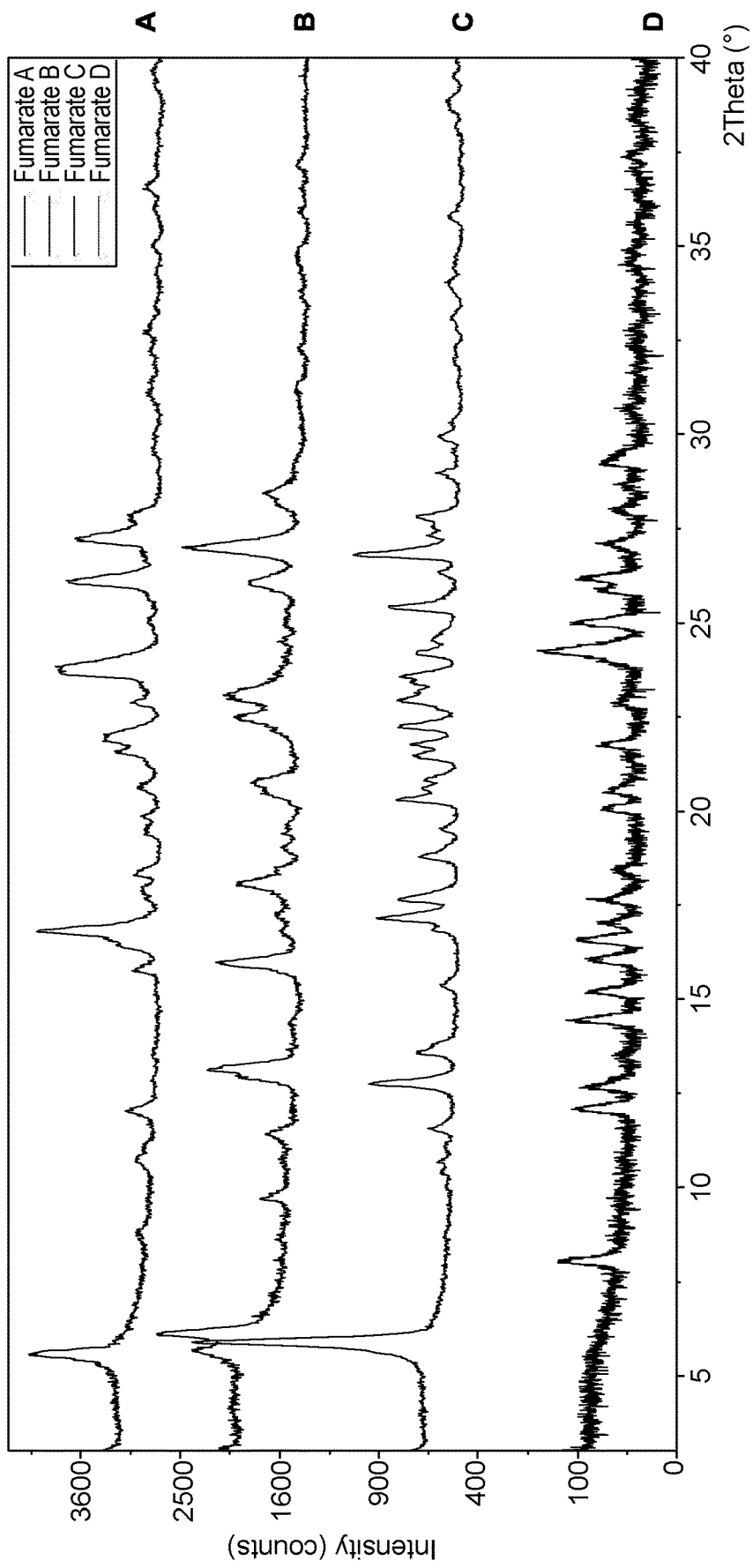
FIG. 29 depicts an XRPD pattern overlay of the fumarate crystalline salts A-D.

Mono-fumarate crystalline salt form D also can be characterized by thermogravimetric analysis (TGA). Thus, mono-fumarate crystalline salt form D can be characterized by a weight loss in a range of about 5% to about 9% with an onset temperature in a range of about 25° C. to about 100° C. For example, mono-fumarate crystalline salt form D can be characterized by a weight loss of about 6.7%, up to about 150° C. In some embodiments, mono-fumarate crystalline salt form D has a thermogravimetric analysis substantially as depicted in FIG. 28, wherein by "substantially" is meant that the reported TGA features can vary by about ±5° C.

Bis-Maleate Crystalline Salt

Figure 30:
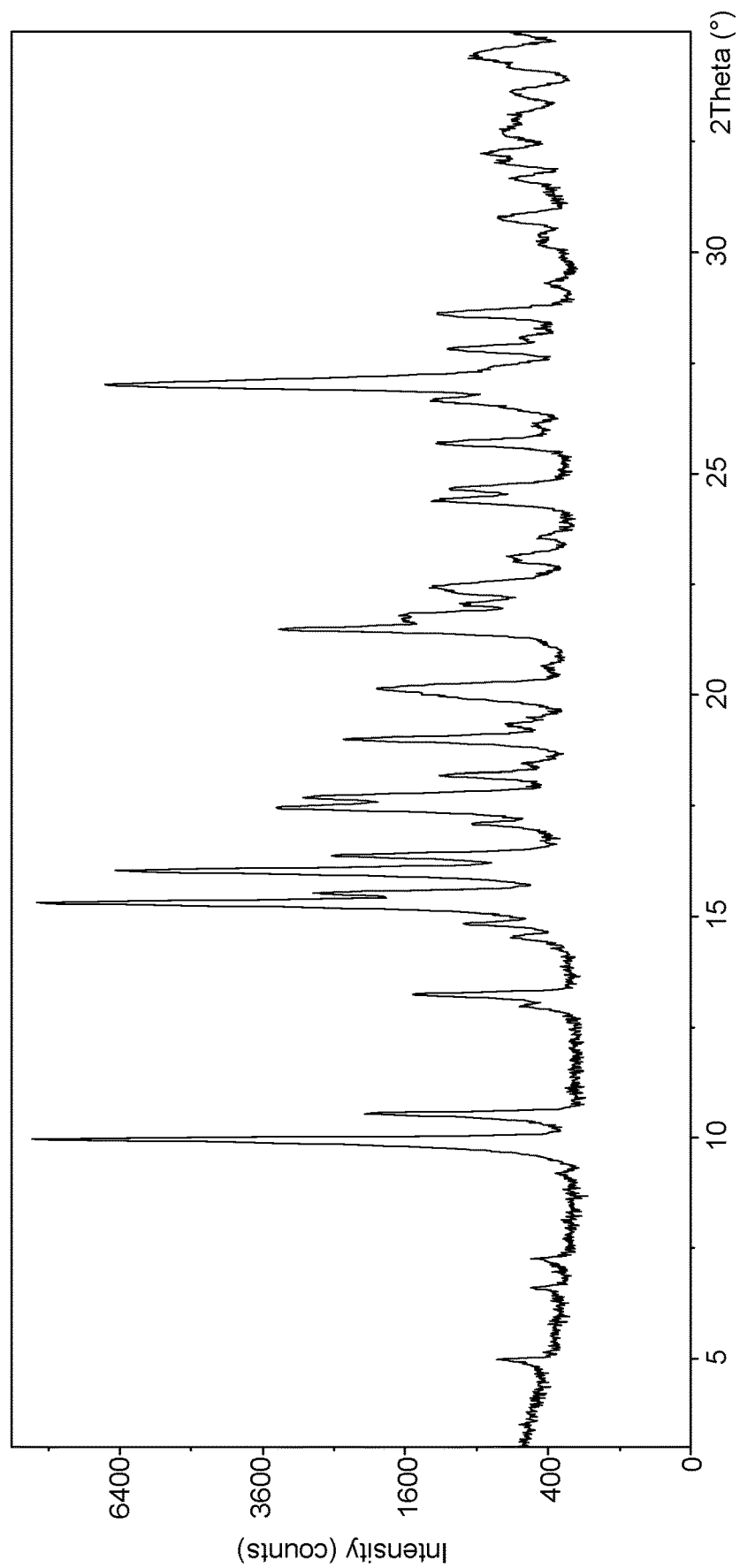
FIG. 30 depicts an XRPD pattern of the bis-maleate crystalline salt.
Figure 31:
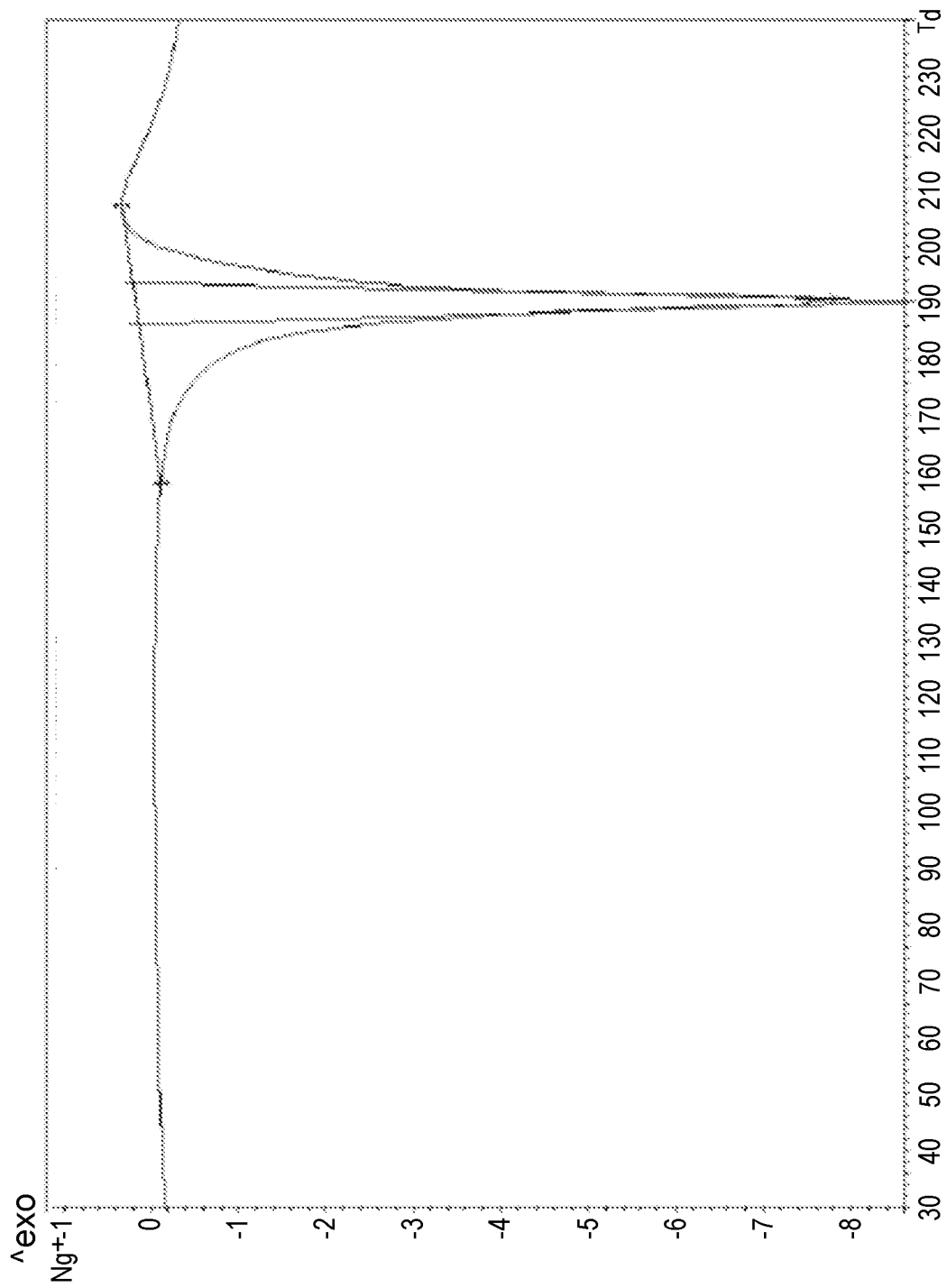
FIG. 31 depicts a DSC thermograph of the bis-maleate crystalline salt.

The bis-maleate crystalline salt of omecamtiv mecarbil can be characterized by an X-ray powder diffraction pattern, obtained as set forth in the Examples, having peaks at about 9.97, 15.31, 16.04, and 26.96±0.2° 2θ using Cu Kα radiation. The bis-maleate crystalline salt optionally can be further characterized by an X-ray powder diffraction pattern having additional peaks at about 10.56, 13.25, 15.53, 16.38, 17.44, 17.70, 18.17, 19.00, 20.13, 21.47, 22.31, 22.44, 24.38, 24.64, 25.66, 26.66, and 27.83±0.2° 2θ using Cu Kα radiation. The bis-maleate crystalline salt optionally can be further characterized by an X-ray powder diffraction pattern having additional peaks at 4.99, 14.83, 17.10, 22.02, 28.55, 30.76, 32.01, 34.39, and 34.51±0.2° 2θ using Cu Kα radiation. The bis-maleate crystalline salt can be characterized by an X-ray powder diffraction pattern having peaks shown in Table 13 set forth in the Examples. In some embodiments, the bis-maleate crystalline salt has an X-ray powder diffraction pattern substantially as shown in FIG. 30, wherein by "substantially" is meant that the reported peaks can vary by about ±0.2°.

Figure 32:
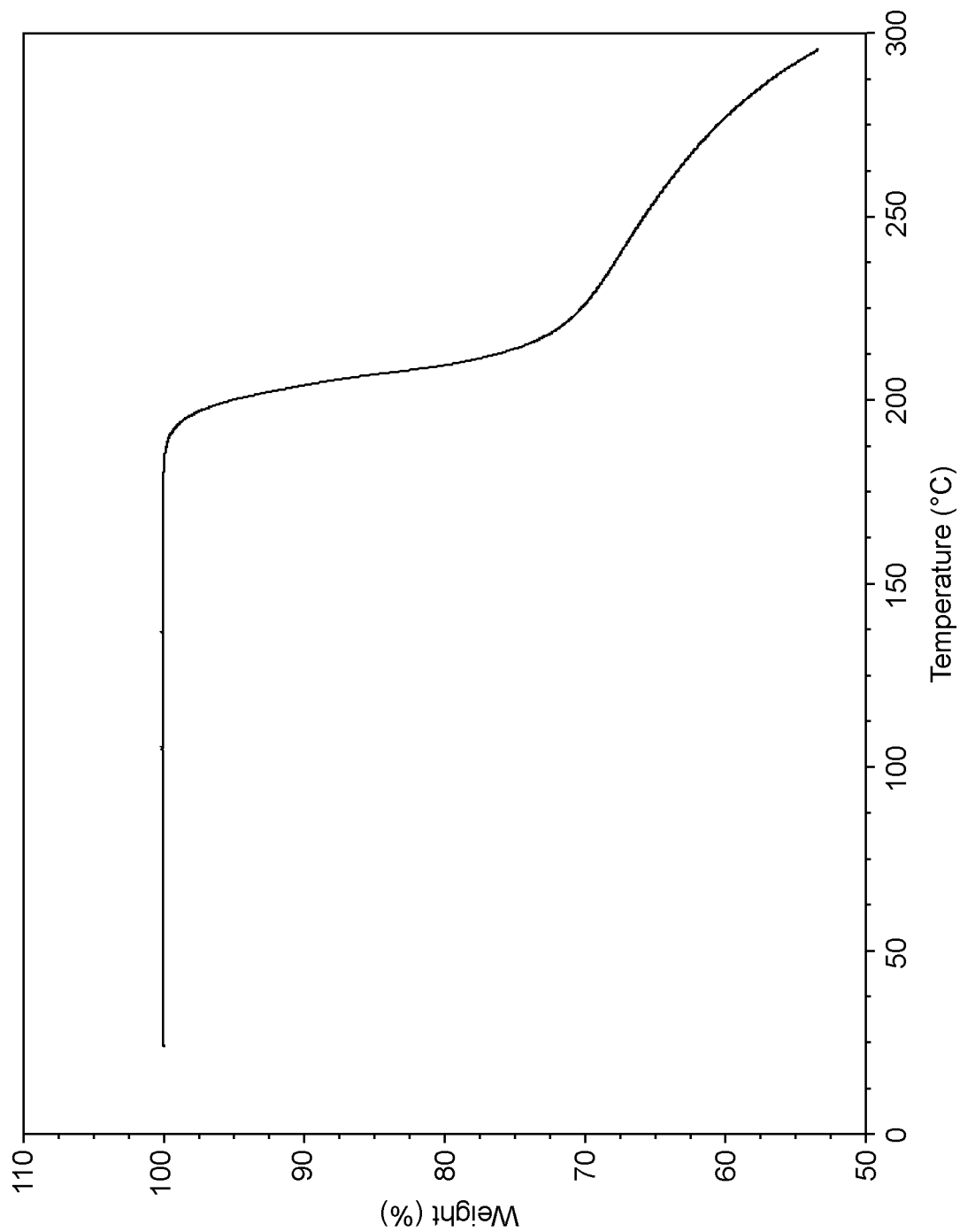
FIG. 32 depicts a TGA trace of the bis-maleate crystalline salt.

Differential scanning calorimetry (DSC) thermographs were obtained, as set forth in the Examples, for the bis-maleate crystalline salt. The DSC curve indicates an endothermic transition at about 190° C.±3° C. Thus, in some embodiments, the bis-maleate crystalline salt can be characterized by a DSC thermograph having a decomposition endotherm with an onset in a range of about 160° C. to about 210° C. For example, in some embodiments the bis-maleate crystalline salt is characterized by DSC, as shown in Figure The bis-maleate crystalline salt also can be characterized by thermogravimetric analysis (TGA). Thus, the bis-maleate crystalline salt can be characterized by a weight loss in a range of about 0% to about 1% with an onset temperature in a range of about 25° C. to about 150° C. For example, the bis-maleate crystalline salt can be characterized by a weight loss of about 0%, up to about 150° C. In some embodiments, the bis-maleate crystalline salt has a thermogravimetric analysis substantially as depicted in FIG. 32, wherein by "substantially" is meant that the reported TGA features can vary by about ±5° C.

Bis-Malonate Crystalline Salt

Figure 33:
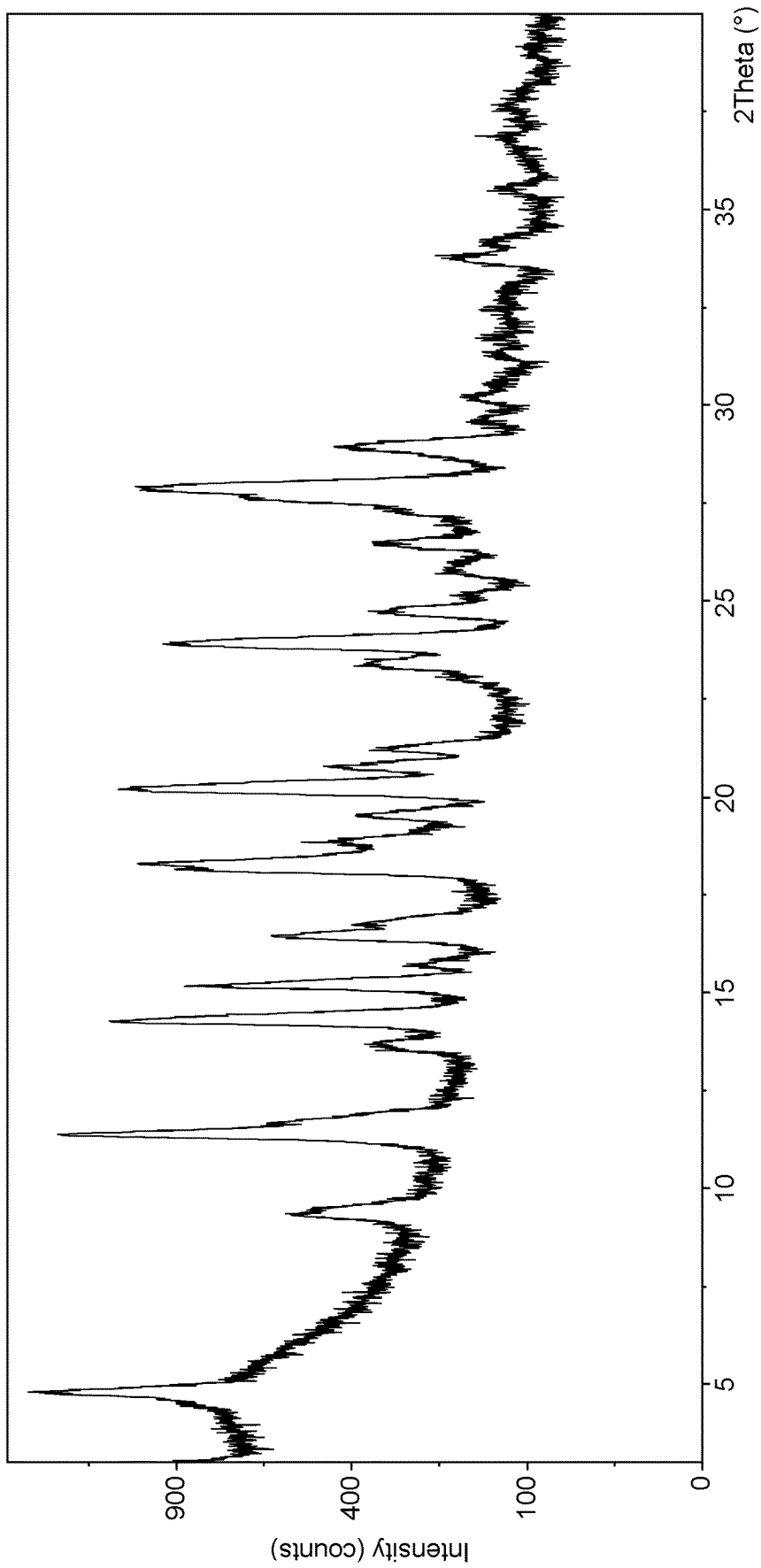
FIG. 33 depicts an XRPD pattern of the bis-malonate crystalline salt.

The bis-malonate crystalline salt of omecamtiv mecarbil can be characterized by an X-ray powder diffraction pattern, obtained as set forth in the Examples, having peaks at about 4.74, 11.37, 14.25, 15.13, 18.29, 20.14, 23.87, 27.78, and 28.01±0.2° 2θ using Cu Kα radiation. The bis-malonate crystalline salt optionally can be further characterized by an X-ray powder diffraction pattern having additional peaks at about 9.30, 13.73, 16.45, 16.83, 18.08, 18.88, 19.54, 20.77, 21.21, 23.32, 24.67, 26.51, 27.59, and 28.90±0.2° 2θ using Cu Kα radiation. The bis-malonate crystalline salt optionally can be further characterized by an X-ray powder diffraction pattern having additional peaks at about 15.69, 25.72, 30.18, 33.70, 34.19±0.2° 2θ using Cu Kα radiation. The bis-malonate crystalline salt can be characterized by an X-ray powder diffraction pattern having peaks shown in Table 14 set forth in the Examples. In some embodiments, the bis-malonate crystalline salt has an X-ray powder diffraction pattern substantially as shown in FIG. 33, wherein by "substantially" is meant that the reported peaks can vary by about ±0.2°.

Figure 34:
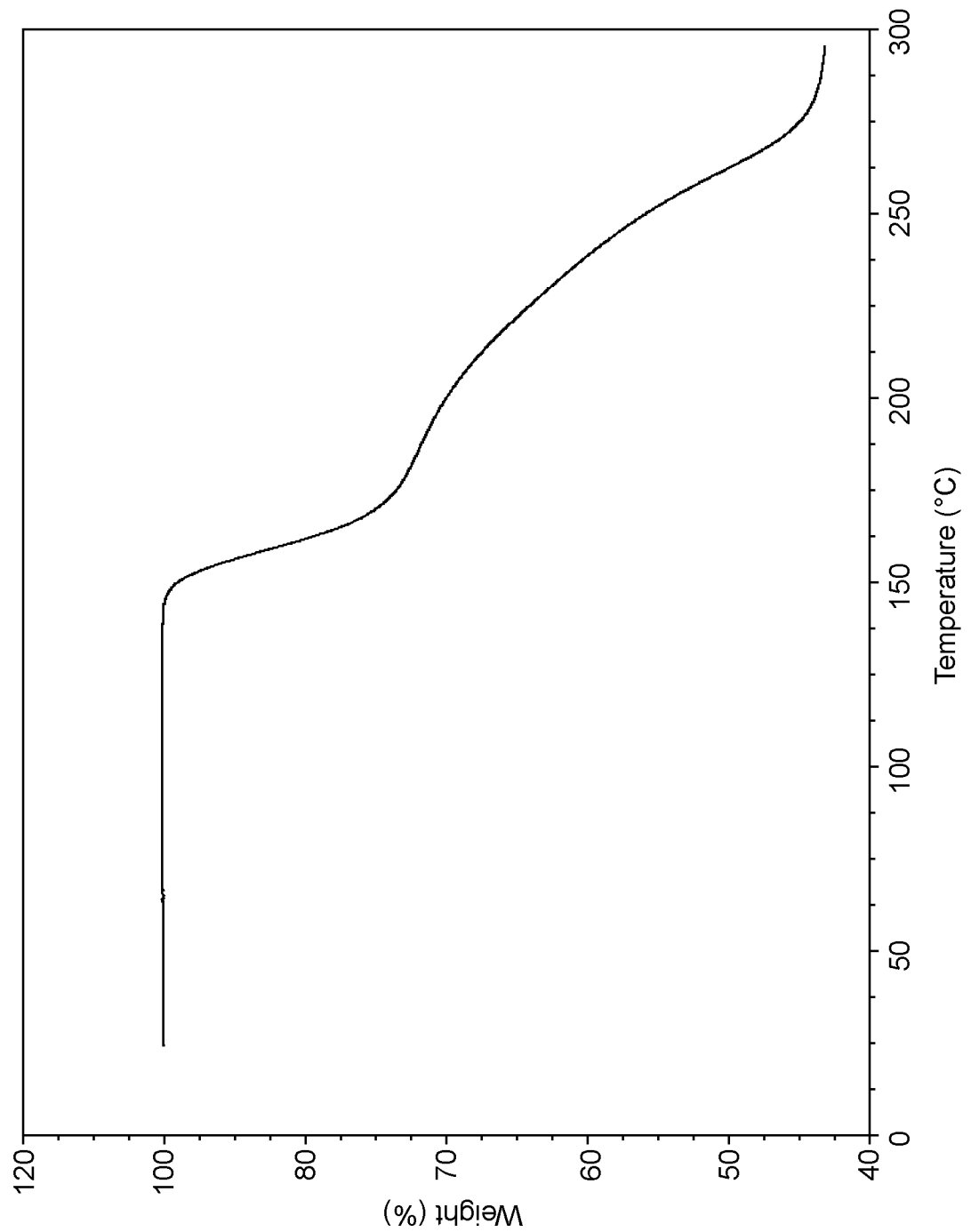
FIG. 34 depicts a TGA trace of the bis-malonate crystalline salt.

The bis-malonate crystalline salt also can be characterized by thermogravimetric analysis (TGA). Thus, the bis-malonate crystalline salt can be characterized by a weight loss in a range of about 0% to about 1% with an onset temperature in a range of about 25° C. to about 140° C. For example, the bis-malonate crystalline salt can be characterized by a weight loss of about 0%, up to about 140° C. In some embodiments, the bis-malonate crystalline salt has a thermogravimetric analysis substantially as depicted in FIG. 34, wherein by "substantially" is meant that the reported TGA features can vary by about ±5° C.

Mesylate Crystalline Salt Form A

Figure 35:
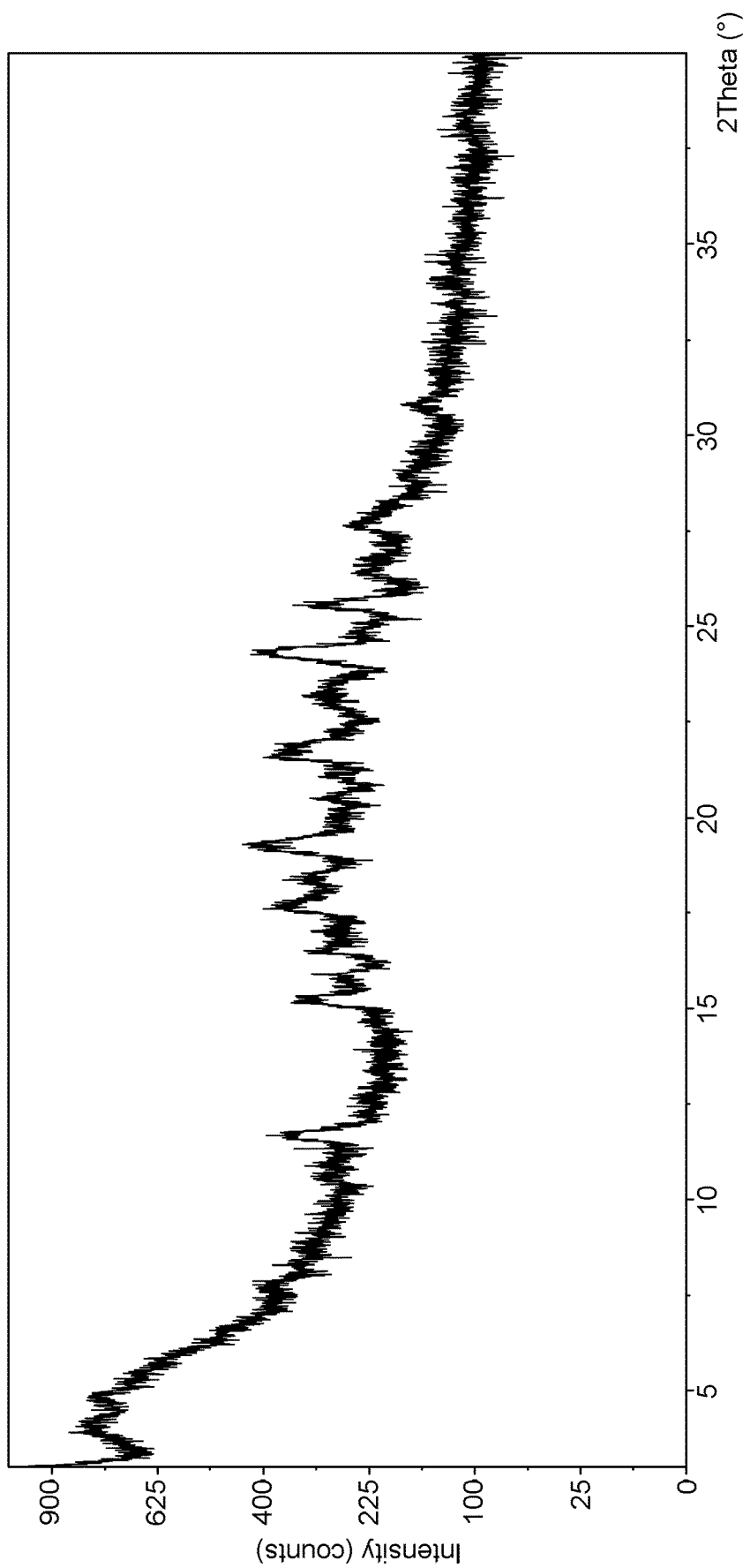
FIG. 35 depicts an XRPD pattern of the mesylate crystalline salt form A.

Mesylate crystalline salt form A of omecamtiv mecarbil can be characterized by an X-ray powder diffraction pattern, obtained as set forth in the Examples, having peaks at about 4.02, 4.87, 15.21, 15.86, 20.53, and 24.39±0.2° 2θ using Cu Kα radiation. Mesylate crystalline salt form A optionally can be further characterized by an X-ray powder diffraction pattern having additional peaks at about 7.79, 11.61, 16.51, 17.57, 18.42, 19.26, 21.55, 23.17, 25.51, 26.38, and 27.63±0.2° 2θ using Cu Kα radiation. Mesylate crystalline salt form A can be characterized by an X-ray powder diffraction pattern having peaks shown in Table 15 set forth in the Examples. In some embodiments, mesylate crystalline salt form A has an X-ray powder diffraction pattern substantially as shown in FIG. 35, wherein by "substantially" is meant that the reported peaks can vary by about ±0.2°.

Figure 36:
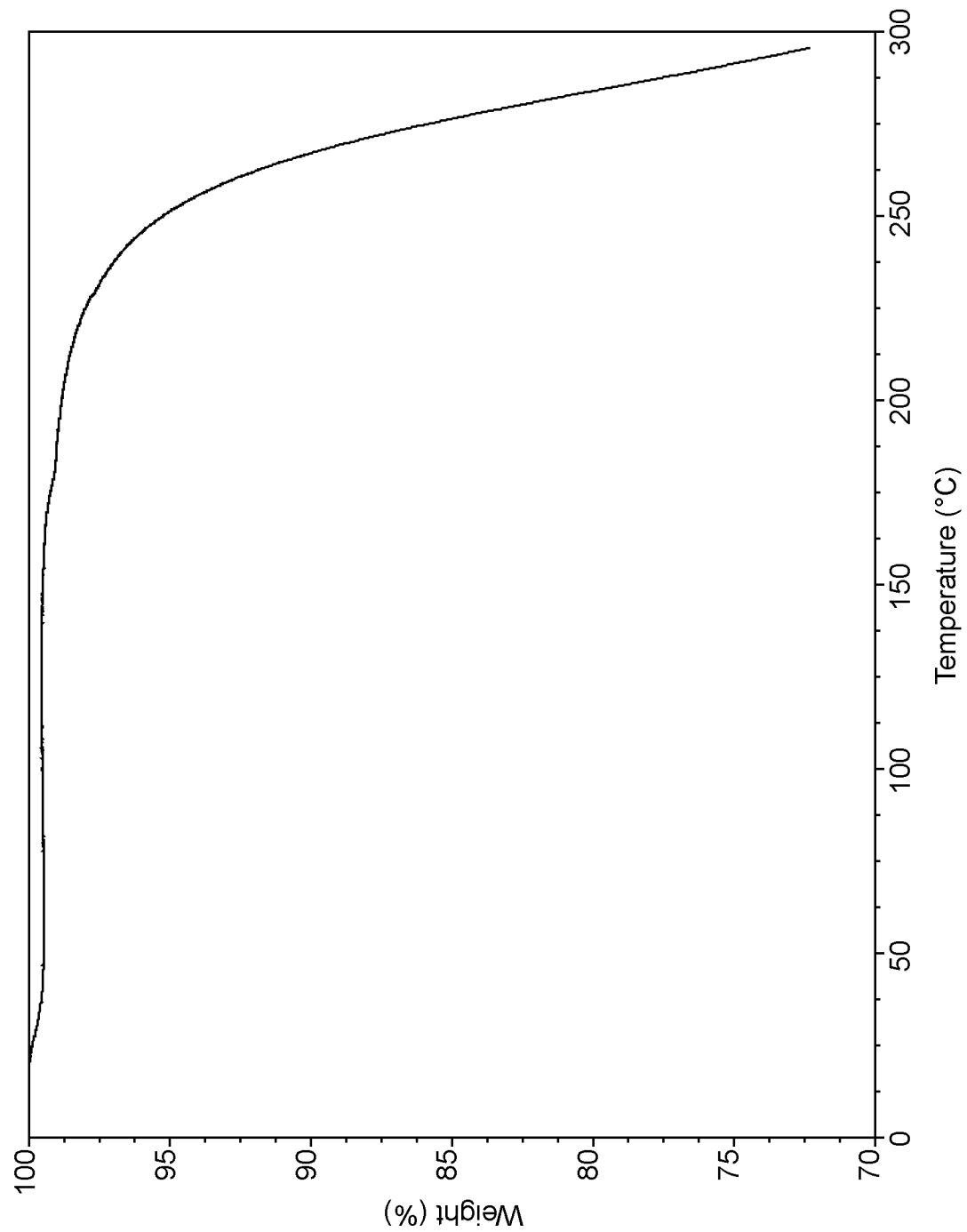
FIG. 36 depicts a TGA trace of the mesylate crystalline salt form A.

Mesylate crystalline salt form A also can be characterized by thermogravimetric analysis (TGA). Thus, mesylate crystalline salt form A can be characterized by a weight loss in a range of about 0% to about 2% with an onset temperature in a range of about 25° C. to about 175° C. For example, mesylate crystalline salt form A can be characterized by a weight loss of about 1.0%, up to about 200° C. In some embodiments, mesylate crystalline salt form A has a thermogravimetric analysis substantially as depicted in FIG. 36, wherein by "substantially" is meant that the reported TGA features can vary by about ±5° C.

Bis-Mesylate Crystalline Salt Form B

Figure 37:
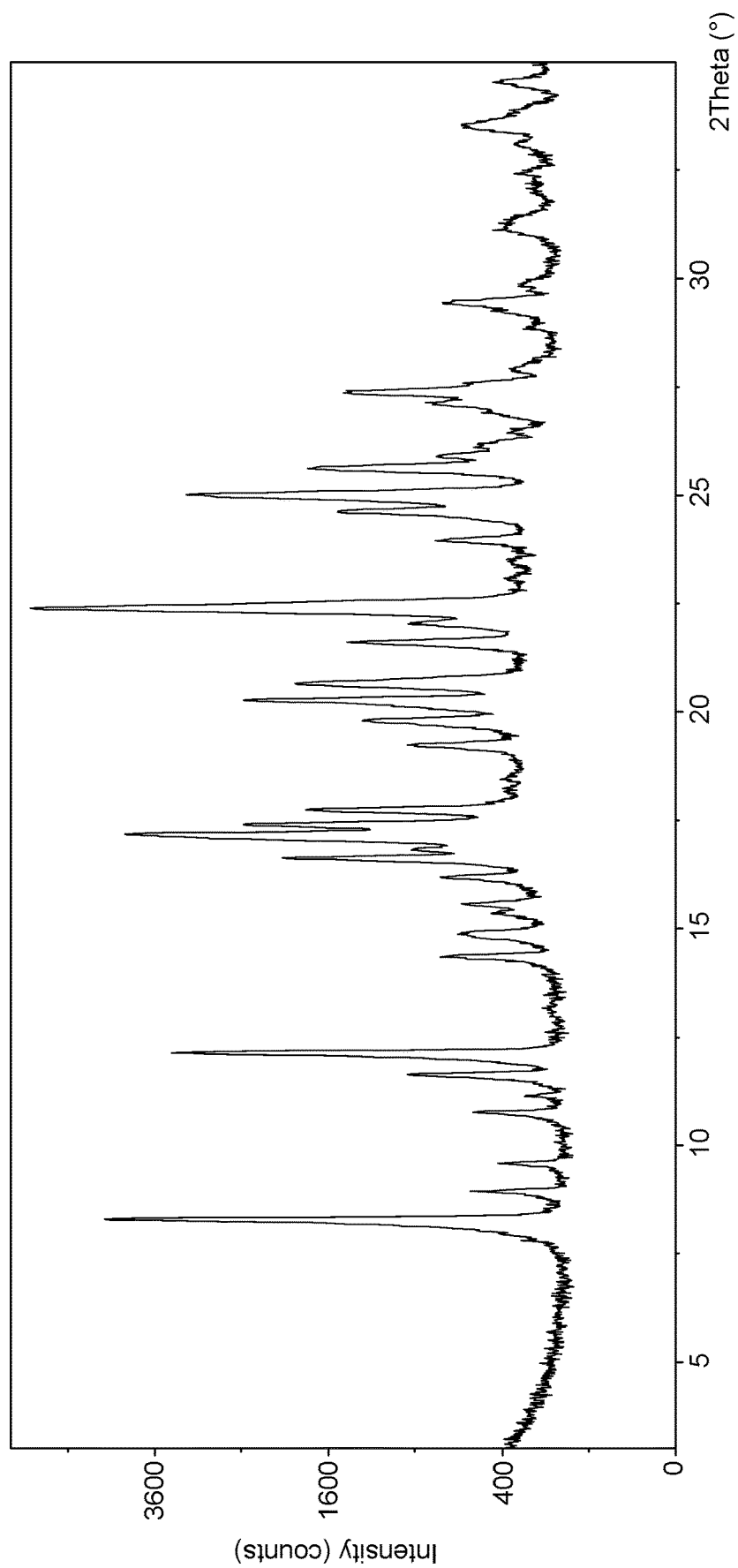
FIG. 37 depicts an XRPD of the bis-mesylate crystalline salt form B.
Figure 38:
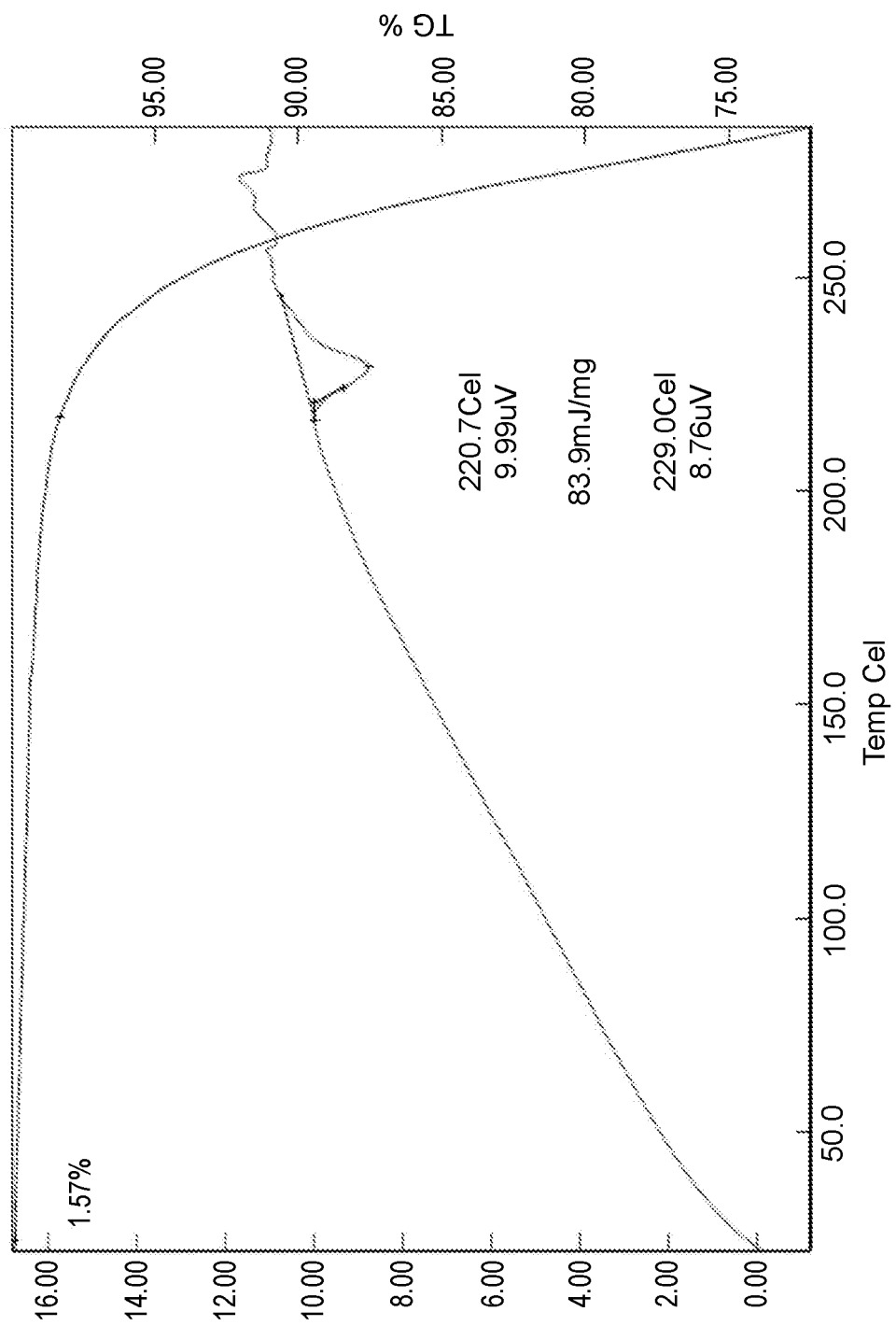
FIG. 38 depicts a thermal gravimetric/differential thermal analysis ("TG/DTA") of the bis-mesylate crystalline salt form B.
Figure 39:
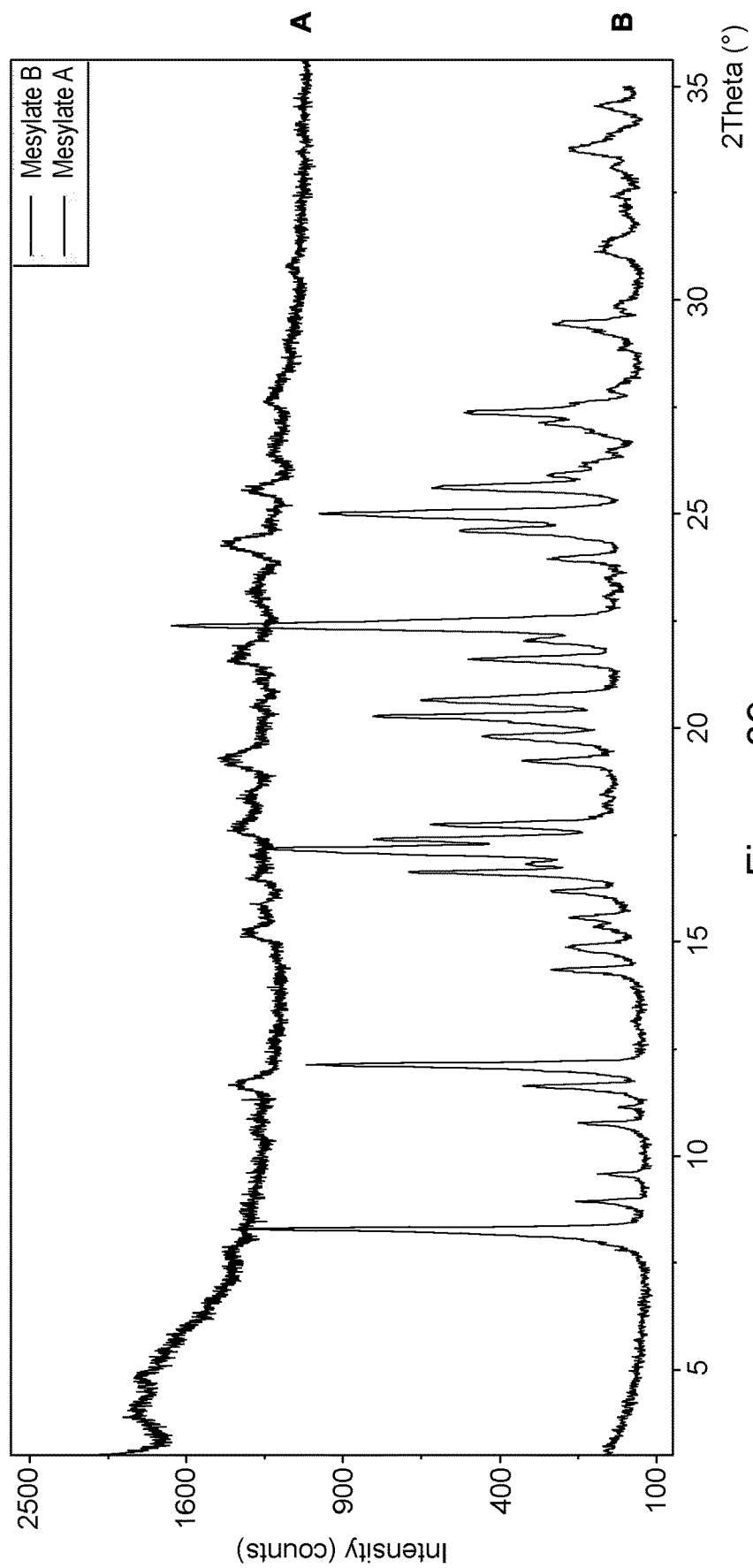
FIG. 39 depicts an XRPD pattern overlay of the mesylate crystalline salt form A and B.

Bis-mesylate crystalline salt form B of omecamtiv mecarbil can be characterized by an X-ray powder diffraction pattern, obtained as set forth in the Examples, having peaks at about 8.30, 8.94, 9.59, 12.15, 14.37, 19.82, 20.29, 22.04, and 25.02±0.2° 2θ using Cu Kα radiation. Bis-mesylate crystalline salt form B optionally can be further characterized by an X-ray powder diffraction pattern having additional peaks at about 11.66, 16.18, 16.64, 16.81, 17.07, 17.19, 17.41, 17.76, 19.24, 20.66, 21.62, 22.39, 23.95, 24.60, 25.59, 25.89, 27.14, 27.35, 27.41, and 29.45±0.2° 2θ using Cu Kα radiation. Bis-mesylate crystalline salt form B optionally can be further characterized by an X-ray powder diffraction pattern having additional peaks at about 10.78, 11.15, 14.93, 15.36, 15.57, 23.54, 26.14, 26.49, 27.89, 28.86, 29.89, 31.11, 32.47, 33.10, 33.51, 34.56±0.2° 2θ using Cu Kα radiation. Bis-mesylate crystalline salt form B can be characterized by an X-ray powder diffraction pattern having peaks shown in Table 16 set forth in the Examples. In some embodiments, bis-mesylate crystalline salt form B has an X-ray powder diffraction pattern substantially as shown in FIG. 37, wherein by "substantially" is meant that the reported peaks can vary by about ±0.2°. In some embodiments, bis-mesylate crystalline salt form B has a TG/DTA substantially as shown in FIG. 38.

Bis-Naphthalate-2-Sulfonate Crystalline Salt

Figure 40:
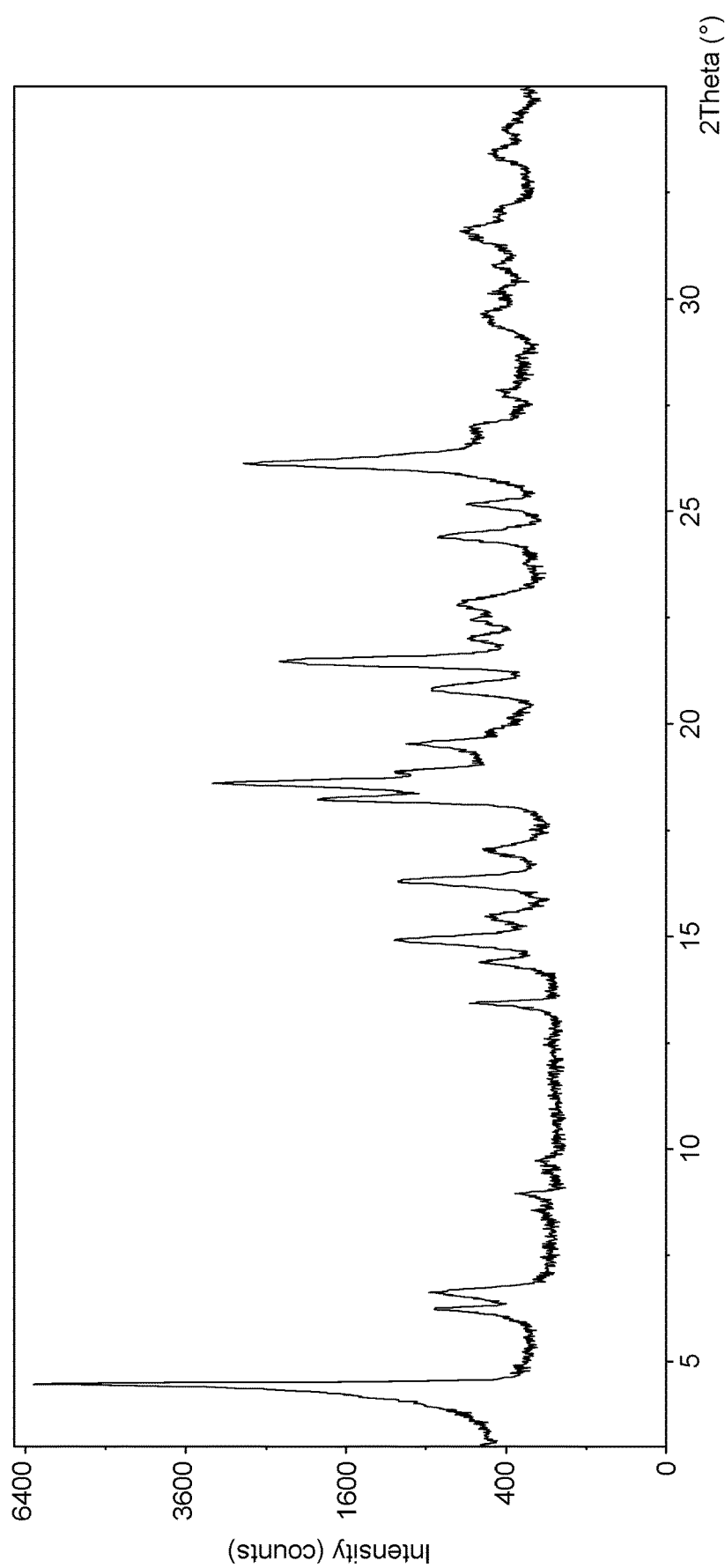
FIG. 40 depicts an XRPD pattern of the bis-naphthalate-2-sulfonate crystalline salt.
Figure 41:
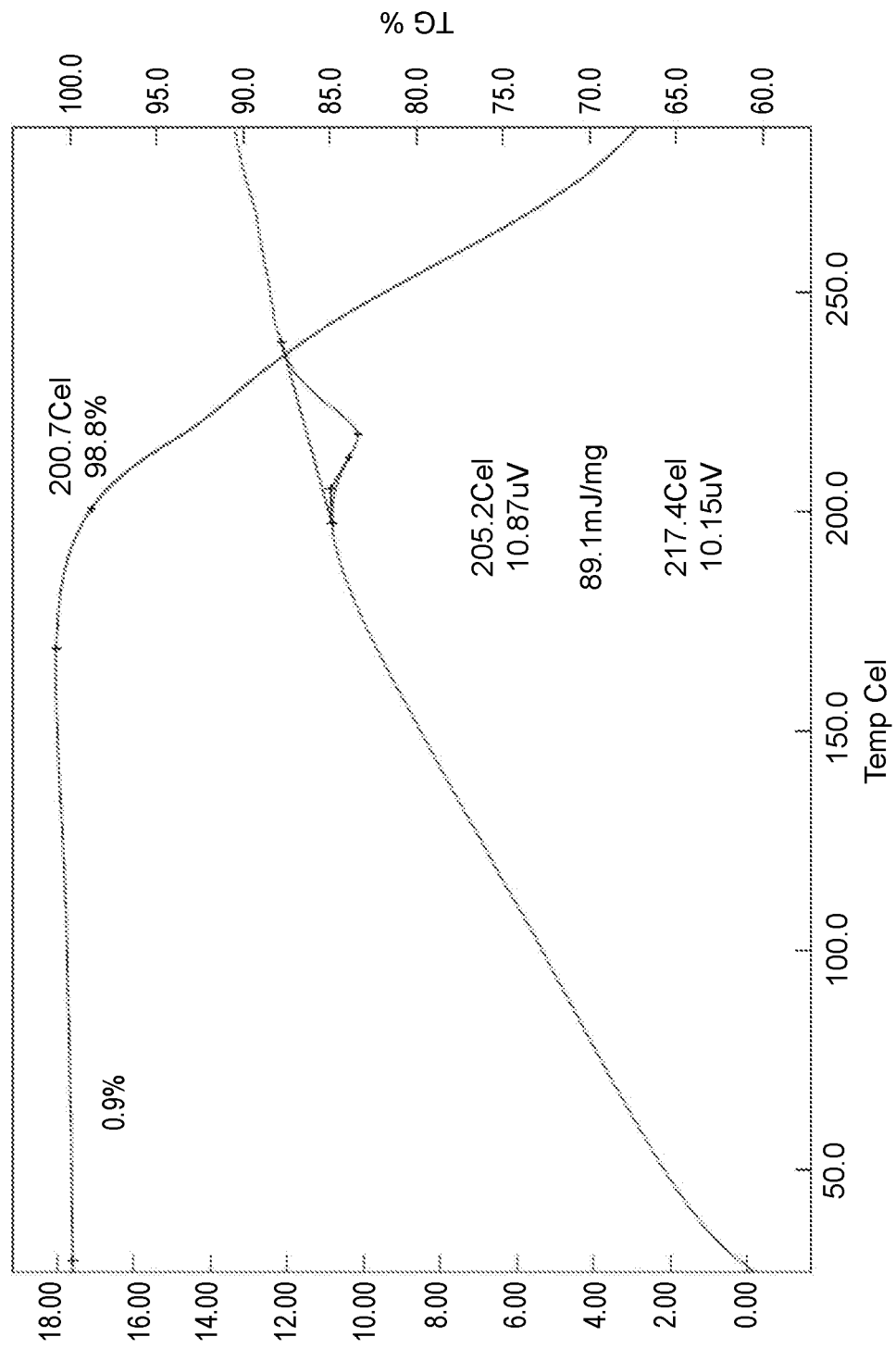
FIG. 41 depicts a TG/DTA of the bis-naphthalate-2-sulfonate crystalline salt.

The bis-naphthalate-2-sulfonate crystalline salt can be characterized by an X-ray powder diffraction pattern, obtained as set forth in the Examples, having peaks at about 4.49, 18.20, 18.62, 21.38, 21.52, and 26.11±0.2° 2θ using Cu Kα radiation. The bis-naphthalate-2-sulfonate crystalline salt optionally can be further characterized by an X-ray powder diffraction pattern having additional peaks at about 6.25, 6.65, 13.44, 14.39, 14.92, 16.28, 18.90, 19.53, 20.82, 22.02, 22.43, 22.80, 24.40, 25.16, 27.01, 29.67, 31.63, and 33.42±0.2° 2θ using Cu Kα radiation. The bis-naphthalate-2-sulfonate crystalline salt can be characterized by an X-ray powder diffraction pattern having peaks shown in Table 18 set forth in the Examples. In some embodiments, the bis-naphthalate-2-sulfonate crystalline salt has an X-ray powder diffraction pattern substantially as shown in FIG. 40, wherein by "substantially" is meant that the reported peaks can vary by about ±0.2°. In some embodiments, bis-naphthalate-2-sulfonate crystalline salt has a TG/DTA substantially as shown in FIG. 41.

Mono-Napadisylate Crystalline Salt

Figure 42:
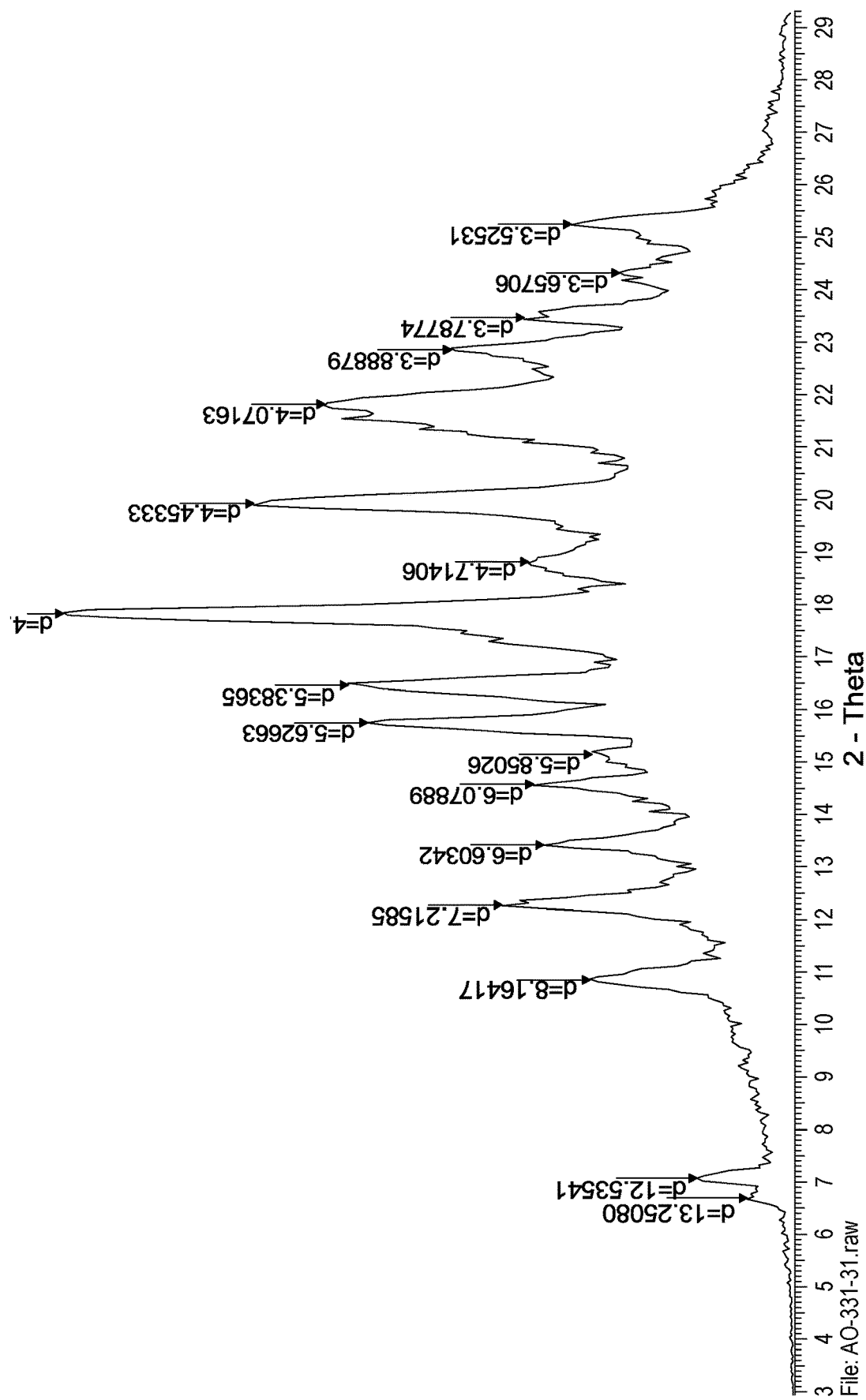
FIG. 42 depicts an XRPD pattern of the mono-napadisylate crystalline salt.

The mono-napadisylate crystalline salt of omecamtiv mecarbil can be characterized by an X-ray powder diffraction pattern, obtained as set forth in the Examples, having peaks at about 12.27, 15.75, 16.5, 17.83, 19.94, 21.83, and 22.87±0.2° 2θ using Cu Kα radiation. The mono-napadisylate crystalline salt optionally can be further characterized by an X-ray powder diffraction pattern having additional peaks at about 13.41, 14.57, 15.14, 18.82, 23.49, 24.34, and 25.26±0.2° 2θ using Cu Kα radiation. The mono-napadisylate crystalline salt can be characterized by an X-ray powder diffraction pattern having peaks shown in Table 19 set forth in the Examples. In some embodiments, the mono-napadisylate crystalline salt has an X-ray powder diffraction pattern substantially as shown in FIG. 42, wherein by "substantially" is meant that the reported peaks can vary by about ±0.2°.

Figure 43:
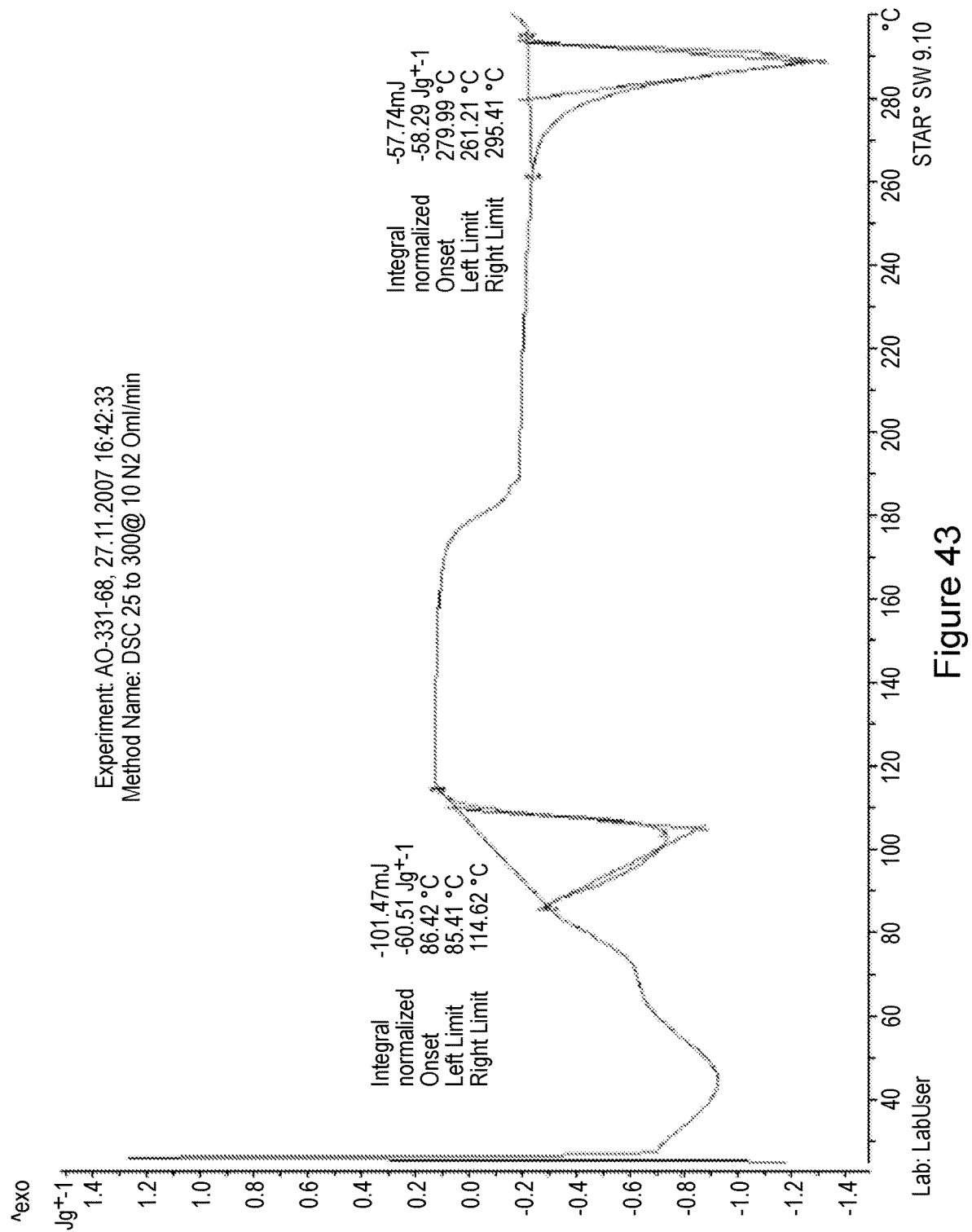
FIG. 43 depicts a DSC thermograph of the mono-napadisylate crystalline salt.

Differential scanning calorimetry (DSC) thermographs were obtained, as set forth in the Examples, for the mono-napadisylate crystalline salt. The DSC curve indicates an endothermic transition at about 100° C.±3° C. Thus, in some embodiments, the mono-napadisylate crystalline salt can be characterized by a DSC thermograph having a decomposition endotherm with an onset in a range of about 80° C. to about 115° C. For example, in some embodiments the mono-napadisylate crystalline salt is characterized by DSC, as shown in FIG. 43.

Figure 44:
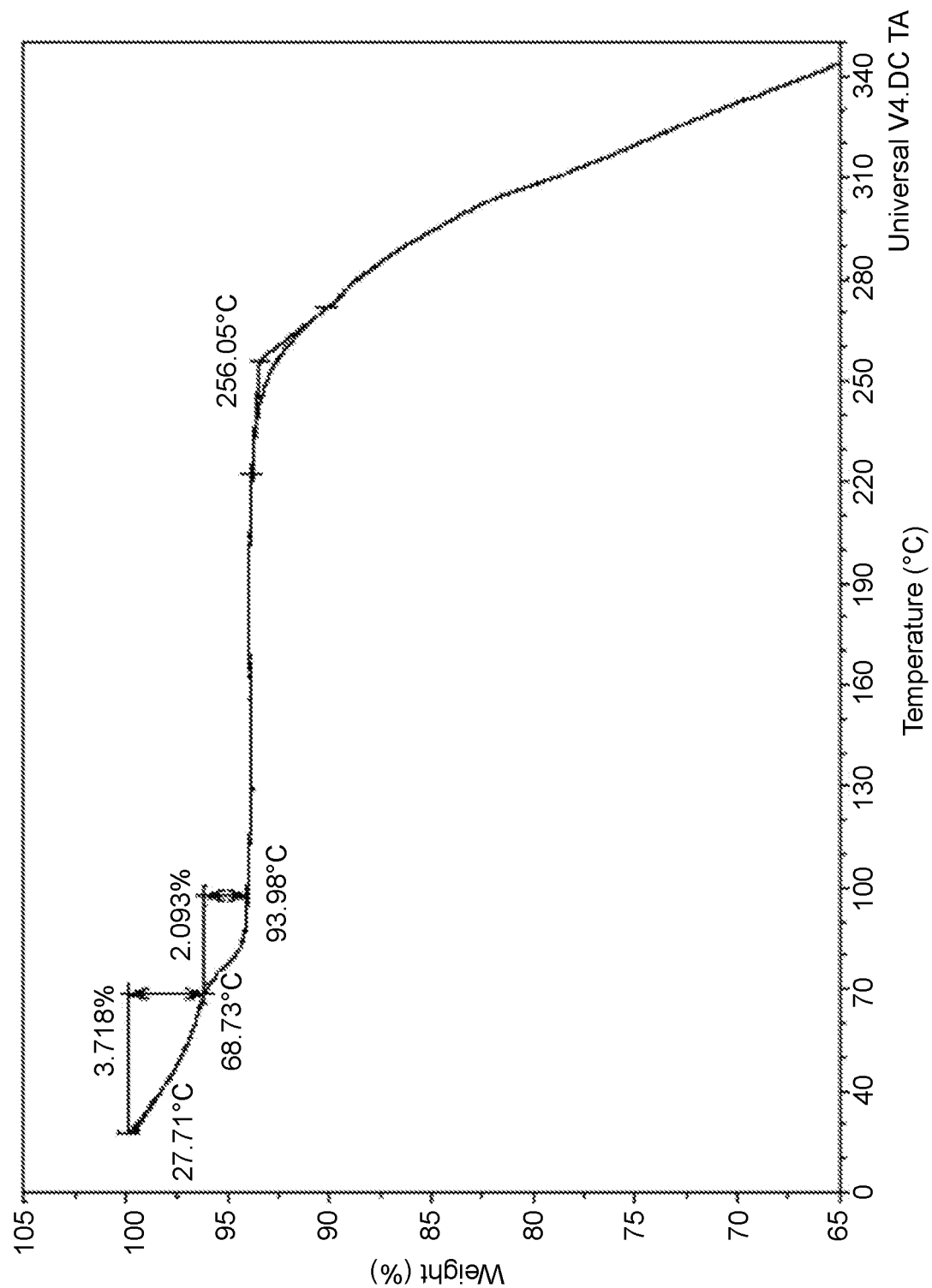
FIG. 44 depicts a TGA trace of the mono-napadisylate crystalline salt.

The mono-napadisylate crystalline salt also can be characterized by thermogravimetric analysis (TGA). Thus, the mono-napadisylate crystalline salt can be characterized by a weight loss in a range of about 4% to about 8% with an onset temperature in a range of about 20° C. to about 100° C. For example, the mono-napadisylate crystalline salt can be characterized by a weight loss of about 5.8%, up to about 100° C. In some embodiments, the mono-napadisylate crystalline salt has a thermogravimetric analysis substantially as depicted in FIG. 44, wherein by "substantially" is meant that the reported TGA features can vary by about ±5° C.

Nicotinate Crystalline Salt

Figure 45:
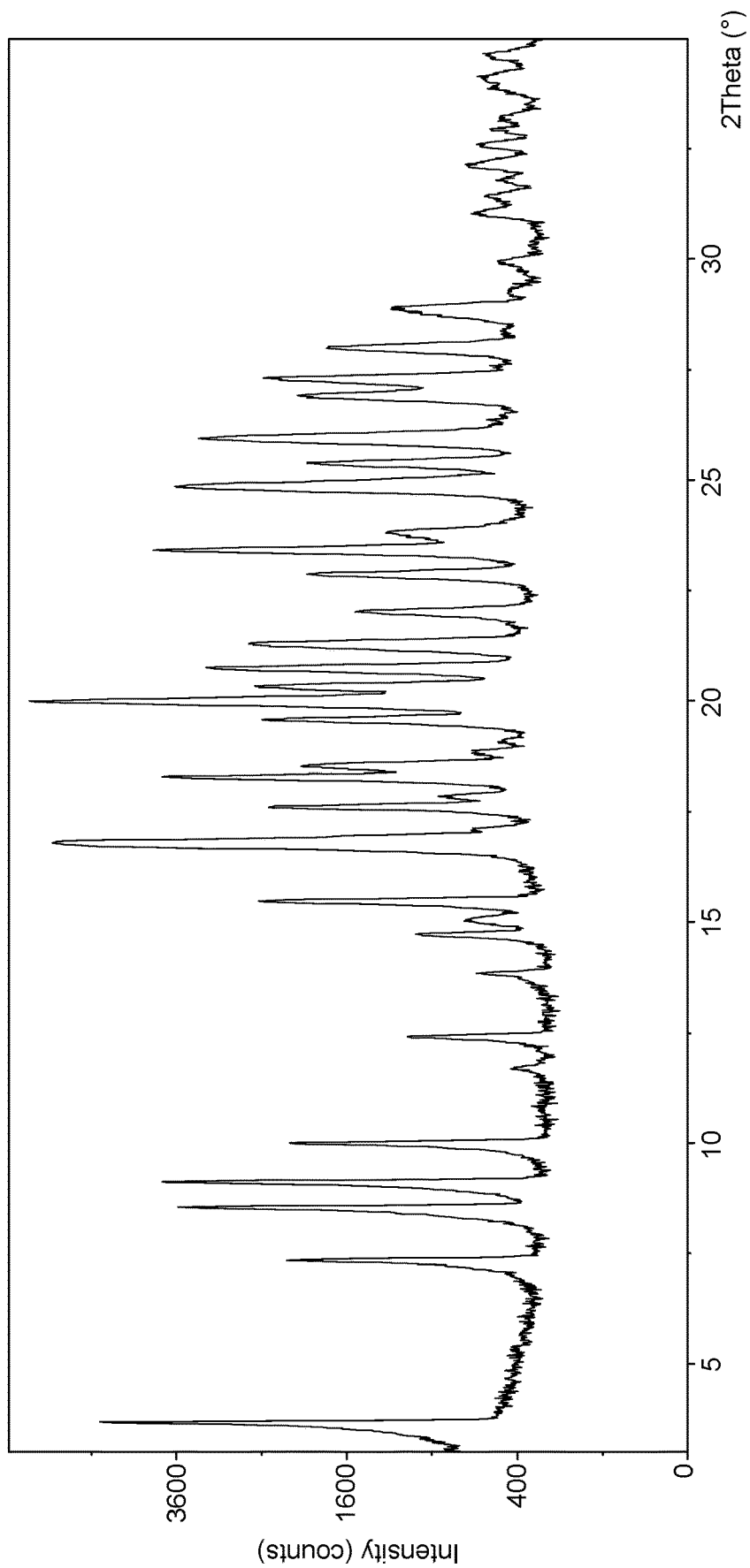
FIG. 45 depicts an XRPD pattern of the nicotinate crystalline salt.
Figure 46:
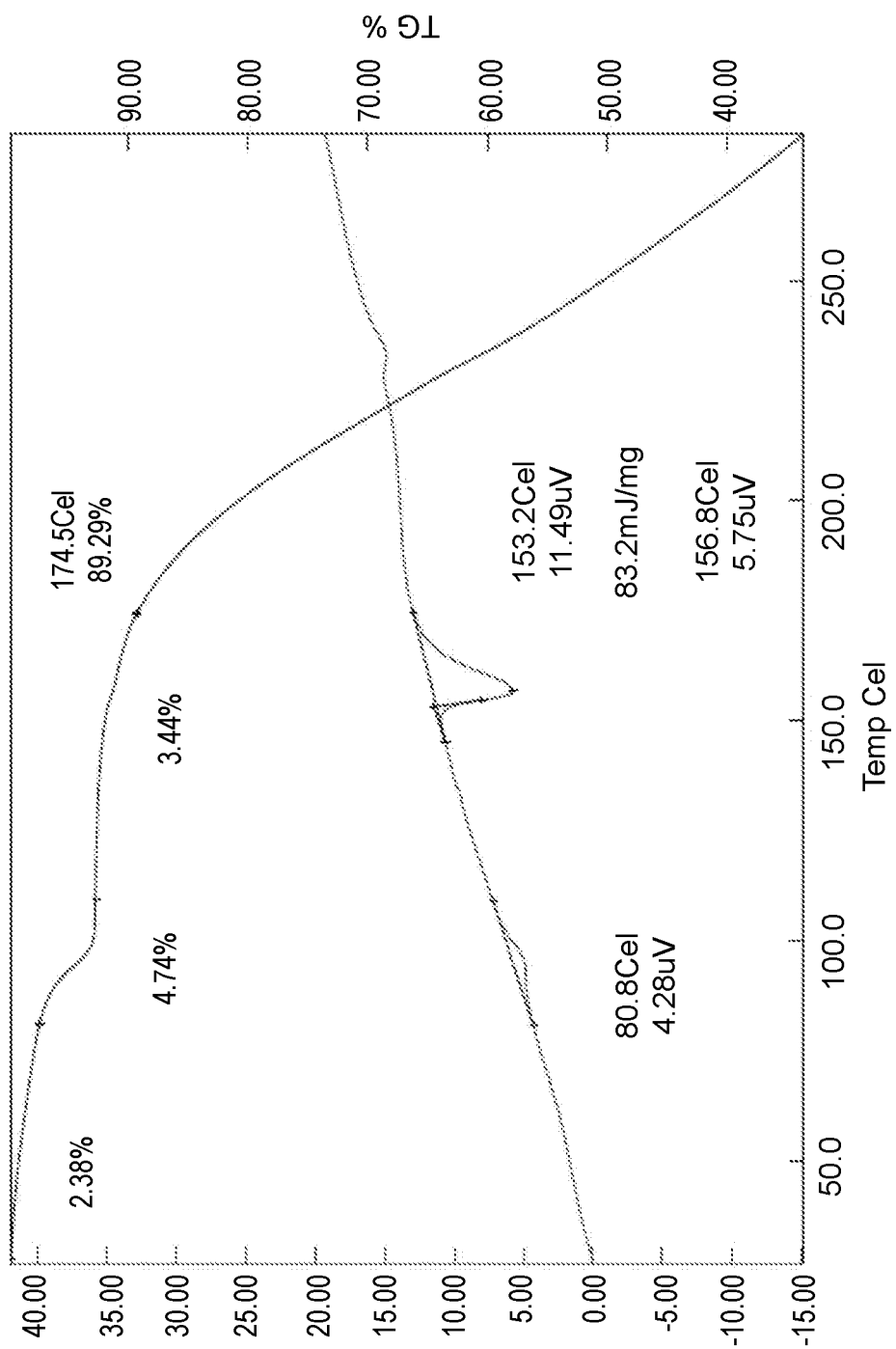
FIG. 46 depicts a TG/DTA of the nicotinate crystalline salt.

The nicotinate crystalline salt of omecamtiv mecarbil can be characterized by an X-ray powder diffraction pattern, obtained as set forth in the Examples, having peaks at about 3.69, 8.55, 9.13, 16.70, 16.84, 18.30, 19.99, 20.76, 23.43 24.83, and 25.95±0.2° 2θ using Cu Kα radiation. The nicotinate crystalline salt optionally can be further characterized by an X-ray powder diffraction pattern having additional peaks at about 7.36, 10.01, 12.43, 14.74, 15.50, 17.62, 18.58, 19.59, 20.34, 21.32, 22.03, 22.91, 23.87, 24.92, 25.40, 26.85, 26.94, 27.32, 28.01, and 28.94±0.2° 2θ using Cu Kα radiation. The nicotinate crystalline salt can be characterized by an X-ray powder diffraction pattern having peaks shown in Table 20 set forth in the Examples. In some embodiments, the nicotinate crystalline salt has an X-ray powder diffraction pattern substantially as shown in FIG. 45, wherein by "substantially" is meant that the reported peaks can vary by about ±0.2°. In some embodiments, the nicotinate crystalline salt form D has an TG/DTA substantially as shown in FIG. 46.

Oxalate Crystalline Salt Form A

Figure 47:
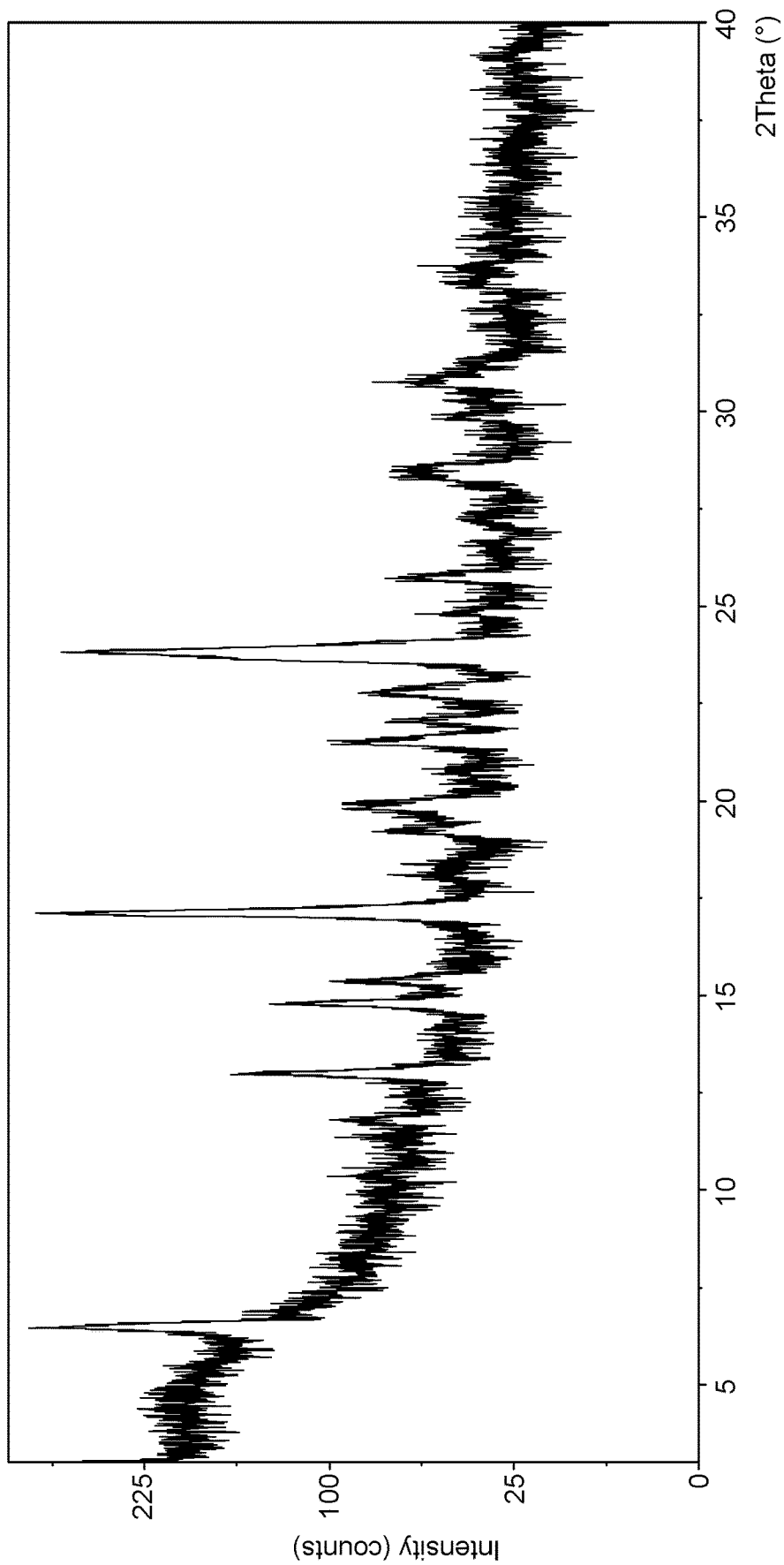
FIG. 47 depicts an XRPD pattern of the oxalate crystalline salt form A.

Oxalate crystalline salt form A of omecamtiv mecarbil can be characterized by an X-ray powder diffraction pattern, obtained as set forth in the Examples, having peaks at about 6.48, 13.01, and 23.82±0.2° 2θ using Cu Kα radiation. Oxalate crystalline salt form A optionally can be further characterized by an X-ray powder diffraction pattern having additional peaks at about 10.36, 11.85, 14.79, 15.35, 17.11, 19.23, 19.91, 21.48, 22.07, 22.75, 25.70, 28.55, and 30.71±0.2° 2θ using Cu Kα radiation. Oxalate crystalline salt form A can be characterized by an X-ray powder diffraction pattern having peaks shown in Table 21 set forth in the Examples. In some embodiments, oxalate crystalline salt form A has an X-ray powder diffraction pattern substantially as shown in FIG. 47, wherein by "substantially" is meant that the reported peaks can vary by about ±0.2°.

Figure 48:
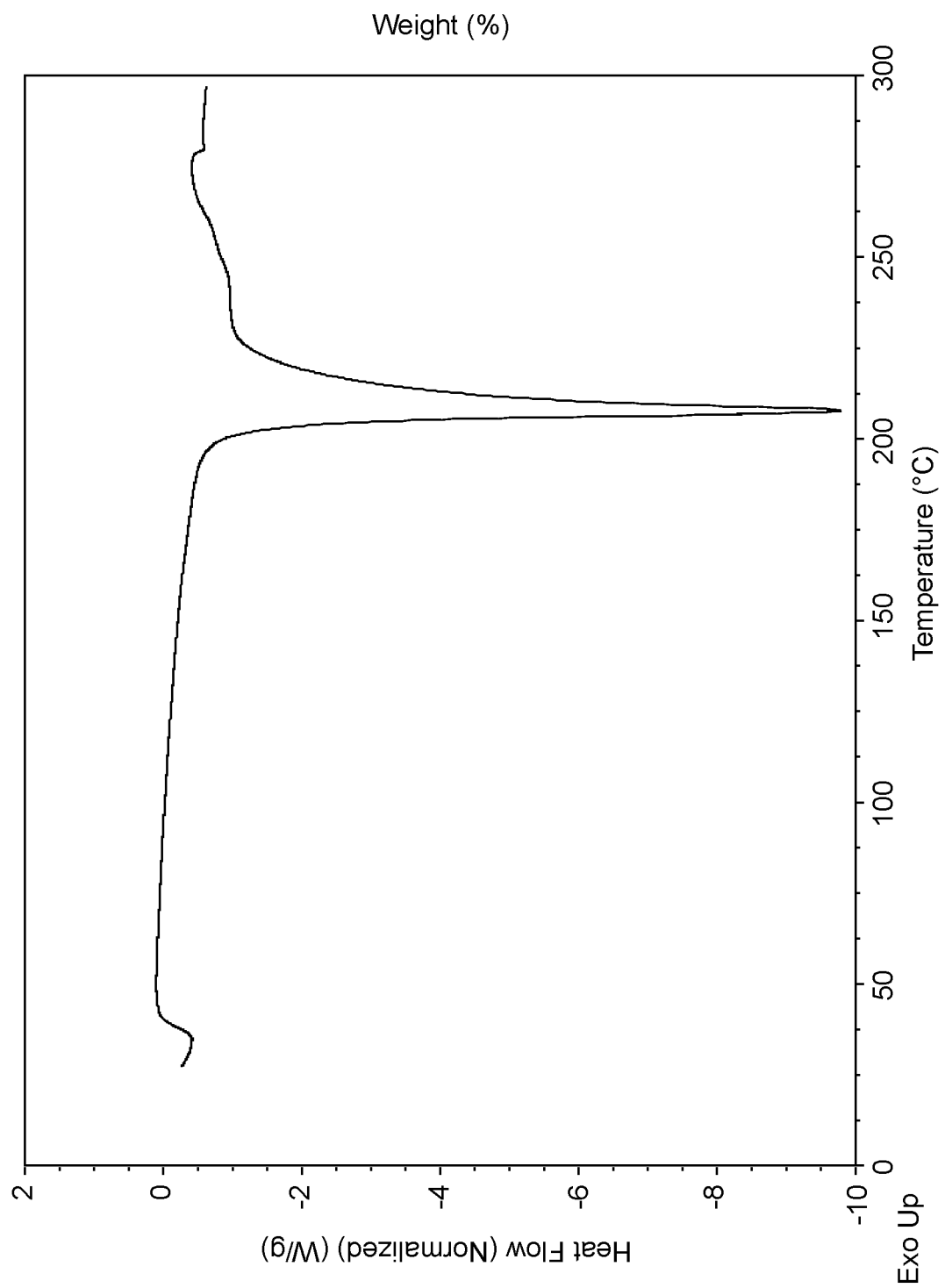
FIG. 48 depicts a DSC thermograph of the oxalate crystalline salt form A.

Differential scanning calorimetry (DSC) thermographs were obtained, as set forth in the Examples, for oxalate crystalline salt form A. The DSC curve indicates an endothermic transition at about 209° C.±3° C. Thus, in some embodiments, oxalate crystalline salt form A can be characterized by a DSC thermograph having a decomposition endotherm with an onset in a range of about 190° C. to about 230° C. For example, in some embodiments oxalate crystalline salt form A is characterized by DSC, as shown in FIG. 48.

Figure 49:
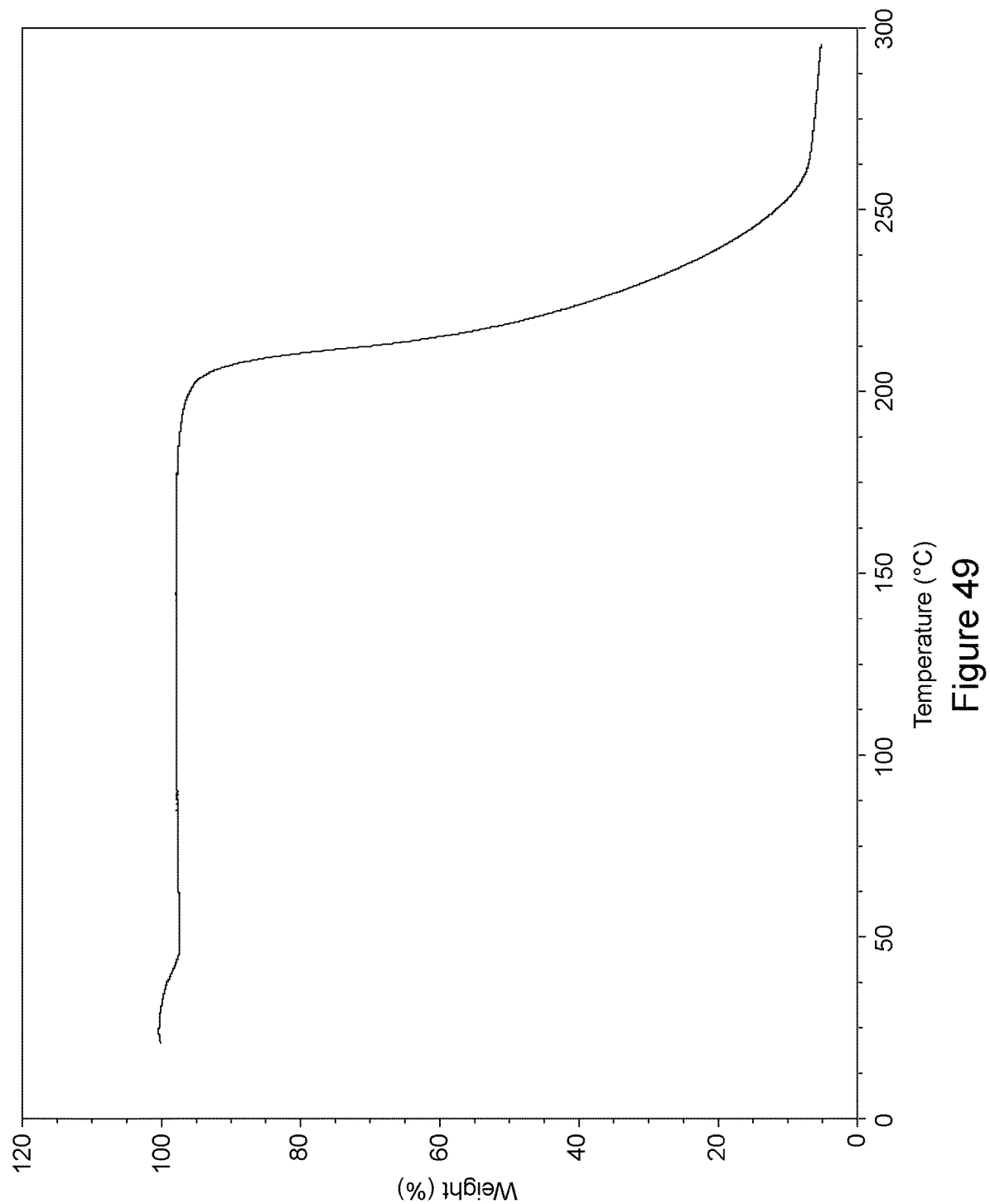
FIG. 49 depicts a TGA trace of the oxalate crystalline salt form A.

Oxalate crystalline salt form A also can be characterized by thermogravimetric analysis (TGA). Thus, oxalate crystalline salt form A can be characterized by a weight loss in a range of about 0.5% to about 4.5% with an onset temperature in a range of about 25° C. to about 100° C. For example, oxalate crystalline salt form A can be characterized by a weight loss of about 2.5%, up to about 150° C. In some embodiments, oxalate crystalline salt form A has a thermogravimetric analysis substantially as depicted in FIG. 49, wherein by "substantially" is meant that the reported TGA features can vary by about ±5° C.

Oxalate Crystalline Salt Form B

Figure 50:
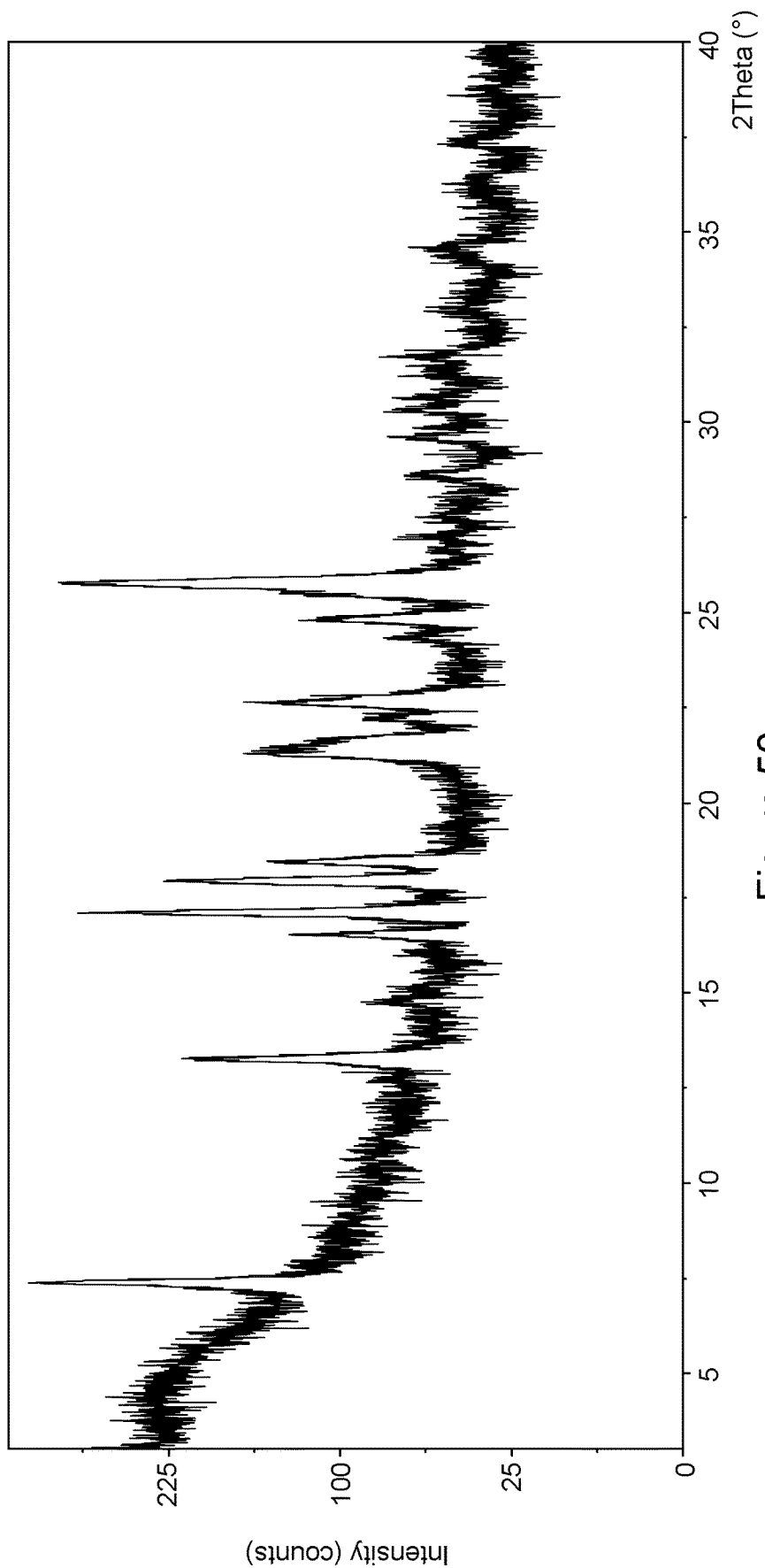
FIG. 50 depicts an XRPD pattern of the oxalate crystalline salt form B.

Oxalate crystalline salt form B of omecamtiv mecarbil can be characterized by an X-ray powder diffraction pattern, obtained as set forth in the Examples, having peaks at about 7.38, 13.30, and 16.54±0.2° 2θ using Cu Kα radiation. Oxalate crystalline salt form B optionally can be further characterized by an X-ray powder diffraction pattern having additional peaks at about 17.11, 17.95, 18.45, 21.25, 22.63, 24.82, and 25.77±0.2° 2θ using Cu Kα radiation. Oxalate crystalline salt form B optionally can be further characterized by an X-ray powder diffraction pattern having additional peaks at about 14.76, 24.35, 28.61, 29.58, 30.49, 31.76, 34.46, and 37.35±0.2° 2θ using Cu Kα radiation. Oxalate crystalline salt form B can be characterized by an X-ray powder diffraction pattern having peaks shown in Table 22 set forth in the Examples. In some embodiments, oxalate crystalline salt form B has an X-ray powder diffraction pattern substantially as shown in FIG. 50, wherein by "substantially" is meant that the reported peaks can vary by about ±0.2°.

Figure 51:
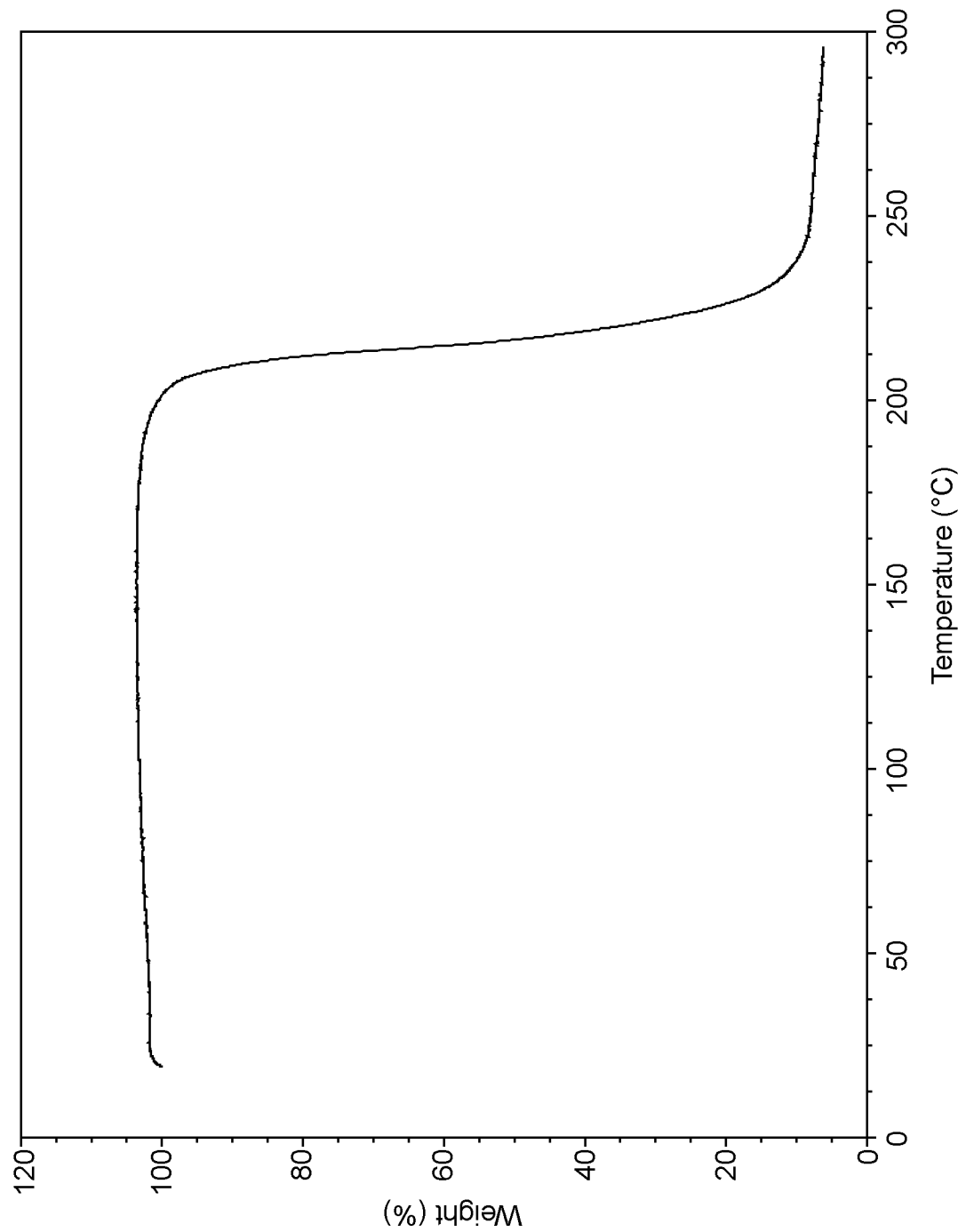
FIG. 51 depicts a TGA trace of the oxalate crystalline salt form B.
Figure 52:
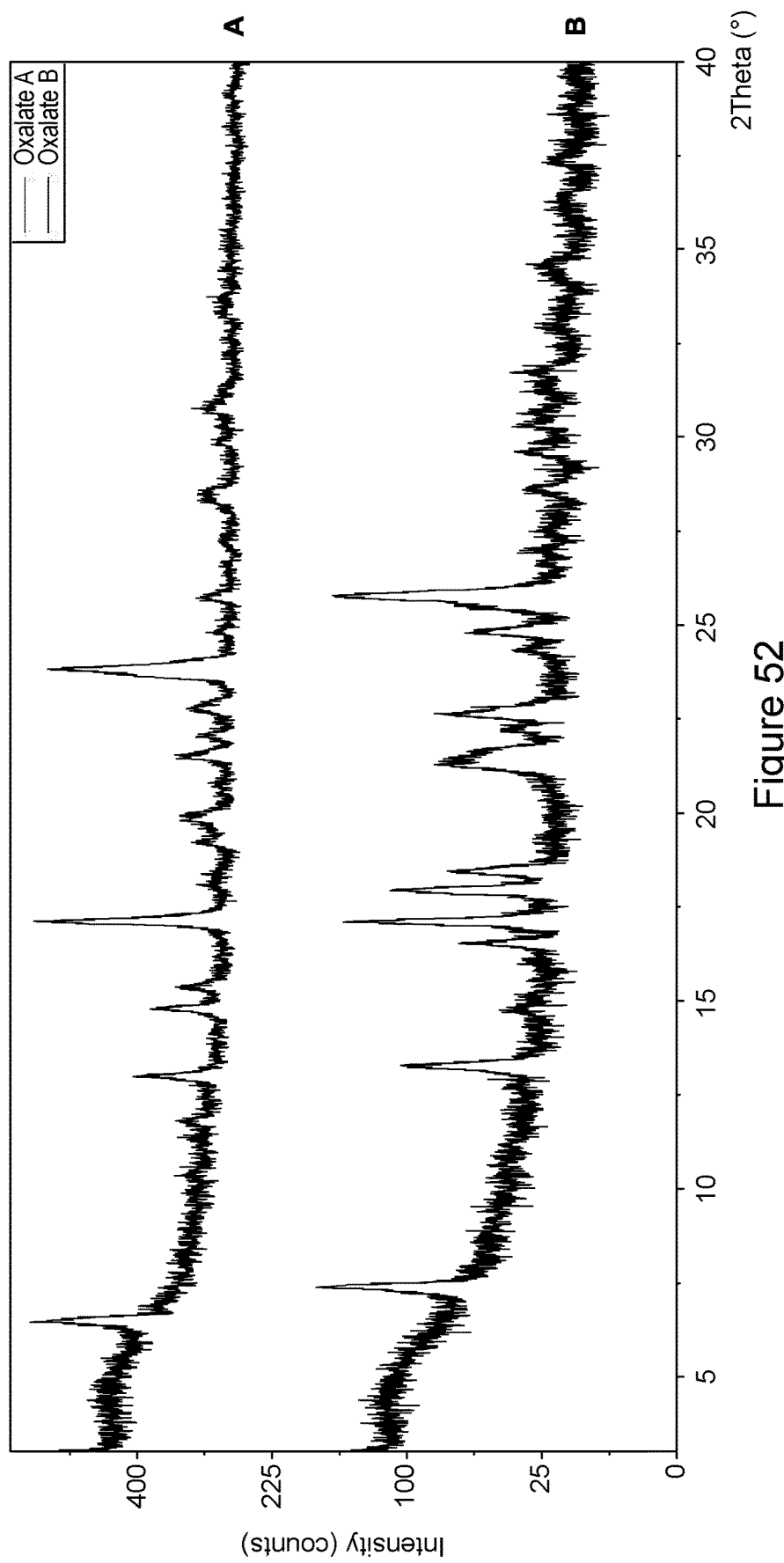
FIG. 52 depicts an XRPD overlay of the oxalate crystalline salt forms A and B.

Oxalate crystalline salt form B also can be characterized by thermogravimetric analysis (TGA). Thus, oxalate crystalline salt form B can be characterized by a weight loss in a range of about 0% to about 1% with an onset temperature in a range of about 25° C. to about 100° C. For example, oxalate crystalline salt form B can be characterized by a weight loss of about 0%, up to about 150° C. In some embodiments, oxalate crystalline salt form B has a thermogravimetric analysis substantially as depicted in FIG. 51, wherein by "substantially" is meant that the reported TGA features can vary by about ±5° C.

Salicylate Crystalline Salt

Figure 53:
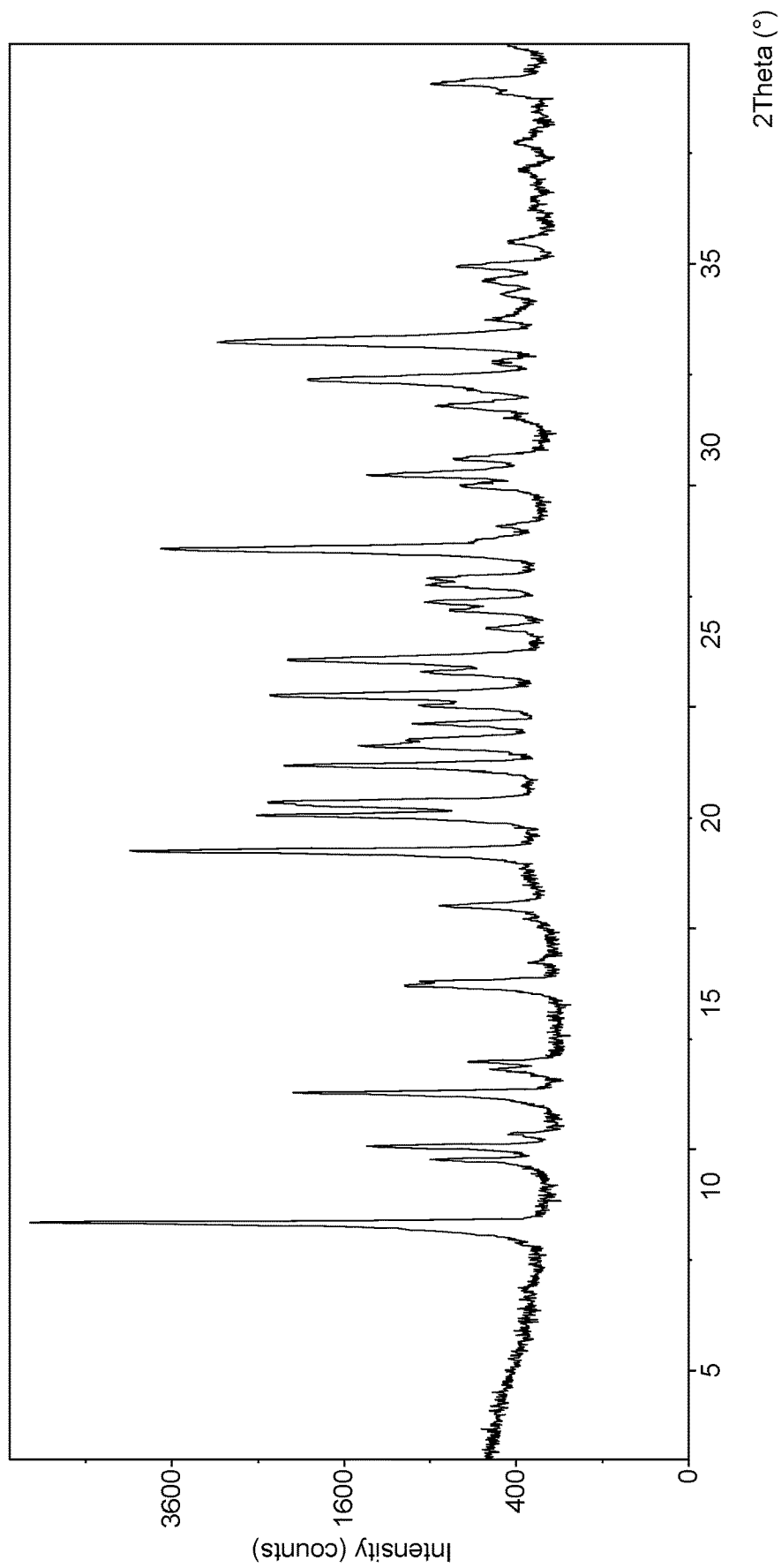
FIG. 53 depicts an XRPD pattern of the salicylate crystalline salt.
Figure 54:
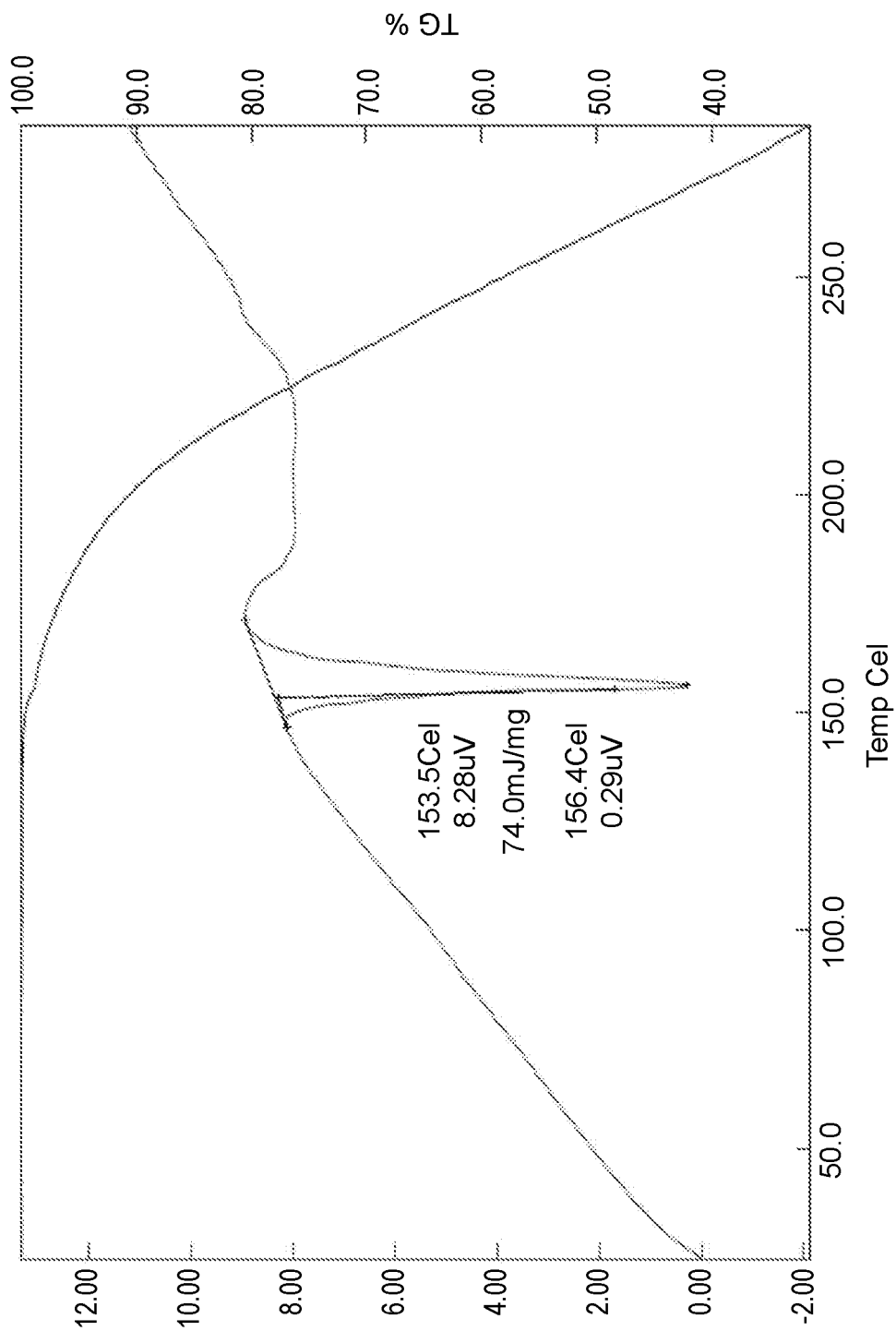
FIG. 54 depicts a TG/DTA of the salicylate crystalline salt.

The salicylate crystalline salt of omecamtiv mecarbil can be characterized by an X-ray powder diffraction pattern, obtained as set forth in the Examples, having peaks at about 8.36, 16.75, 17.56, 23.58, and 28.21±0.2° 2θ using Cu Kα radiation. The salicylate crystalline salt optionally can be further characterized by an X-ray powder diffraction pattern having additional peaks at about 10.08, 11.30, 13.69, 17.77, 17.86, 18.67, 19.11, 20.22, 21.07, 25.23, and 27.40±0.2° 2θ using Cu Kα radiation. The salicylate crystalline salt optionally can be further characterized by an X-ray powder diffraction pattern having additional peaks at about 9.78, 12.00, 13.80, 15.51, 19.27, 19.62, 20.02, 20.79, 22.19, 22.39, 22.75, 22.92, 24.99, 25.59, 26.79, 29.94, and 34.07±0.2° 2θ using Cu Kα radiation. The salicylate crystalline salt can be characterized by an X-ray powder diffraction pattern having peaks shown in Table 24 set forth in the Examples. In some embodiments, the salicylate crystalline salt has an X-ray powder diffraction pattern substantially as shown in FIG. 53, wherein by "substantially" is meant that the reported peaks can vary by about ±0.2°. In some embodiments, the salicylate crystalline salt has an TG/DTA substantially as shown in FIG. 54.

Hemi-Succinate Crystalline Salt

Figure 55:
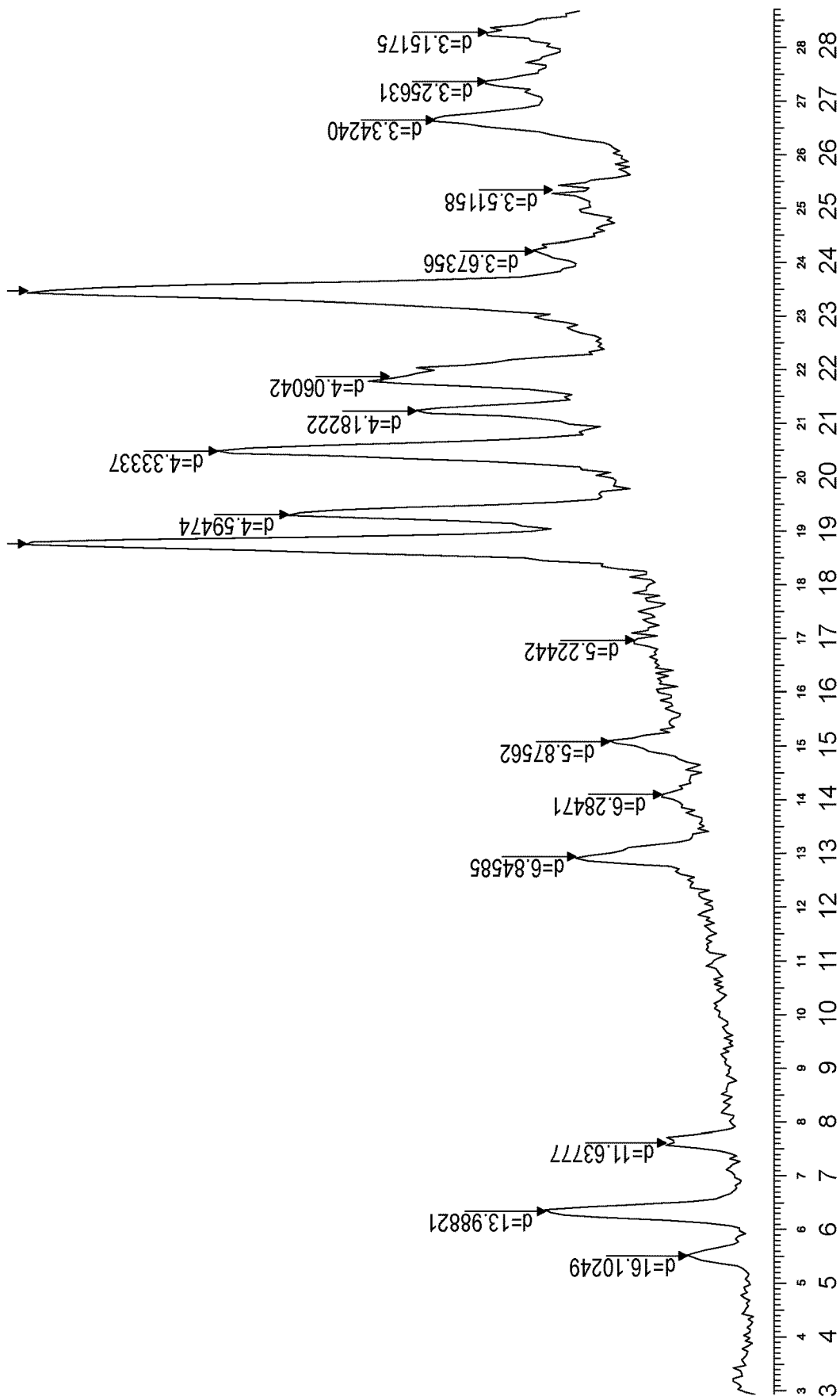
FIG. 55 depicts XRPD patterns of the hemi-succinate crystalline salts overlaid.

The hemi-succinate crystalline salt of omecamtiv mecarbil can be characterized by an X-ray powder diffraction pattern, obtained as set forth in the Examples, having peaks at about 6.32, 18.87, 19.32, 20.5, 21.24, 21.89, 23.49, 24.23, and 26.71±0.2° 2θ using Cu Kα radiation. The hemi-succinate crystalline salt optionally can be further characterized by an X-ray powder diffraction pattern having additional peaks at about 12.93, 15.08, 16.97, 25.36, 27.39, and 28.32±0.2° 2θ using Cu Kα radiation. The hemi-succinate crystalline salt can be characterized by an X-ray powder diffraction pattern having peaks shown in Table 25 set forth in the Examples. In some embodiments, the hemi-succinate crystalline salt has an X-ray powder diffraction pattern substantially as shown in FIG. 55, wherein by "substantially" is meant that the reported peaks can vary by about ±0.2°.

Figure 56:
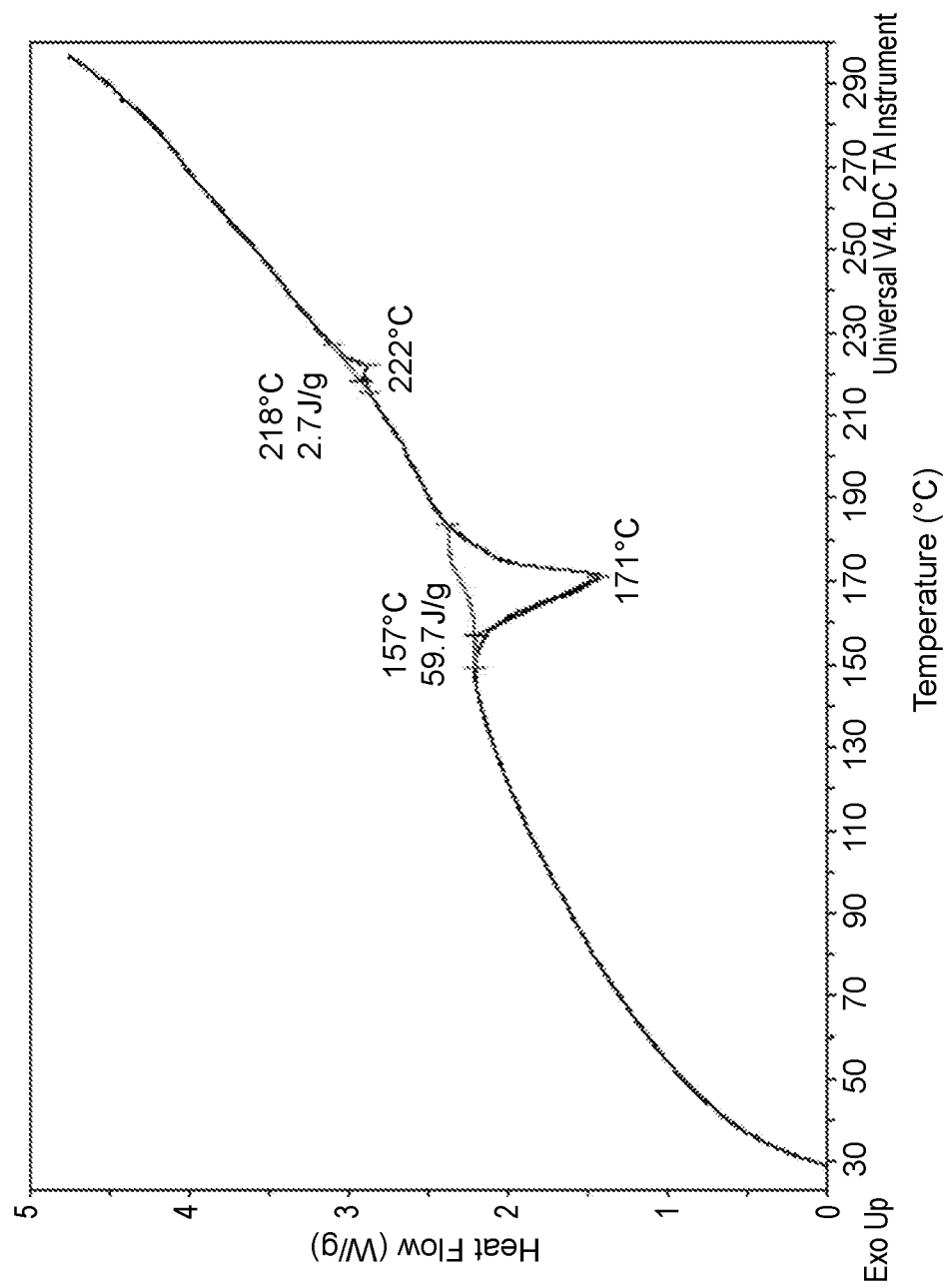
FIG. 56 depicts a DSC thermograph of the hemi-succinate crystalline salt.

Differential scanning calorimetry (DSC) thermographs were obtained, as set forth in the Examples, for the hemi-succinate crystalline salt. The DSC curve indicates an endothermic transition at about 171° C.±3° C. Thus, in some embodiments, the hemi-succinate crystalline salt can be characterized by a DSC thermograph having a decomposition endotherm with an onset in a range of about 155° C. to about 190° C. For example, in some embodiments the hemi-succinate crystalline salt is characterized by DSC, as shown in FIG. 56.

Bis-Sulfate Crystalline Salt Form A

Figure 57:
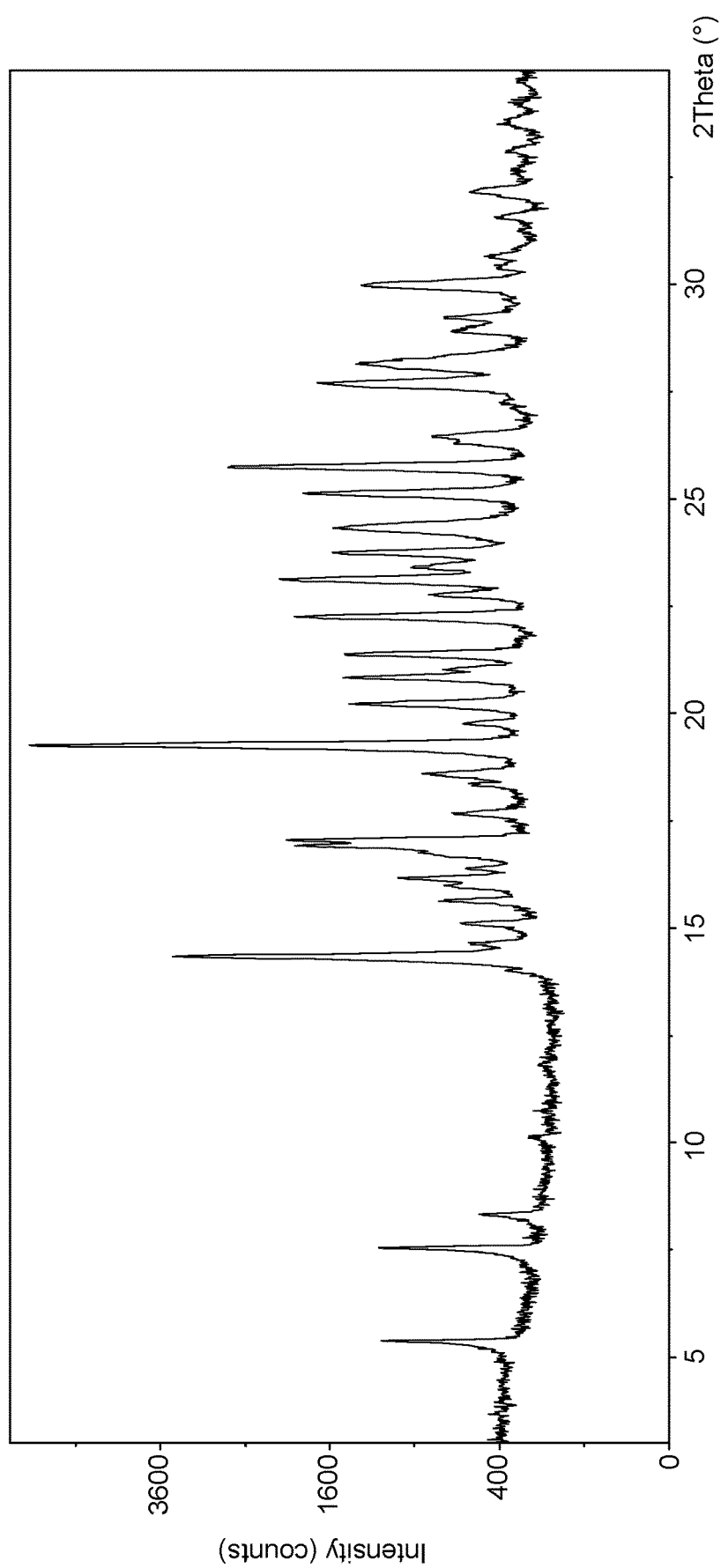
FIG. 57 depicts an XRPD patter of the bis-sulfate crystalline salt form A.

Bis-sulfate crystalline salt form A of omecamtiv mecarbil can be characterized by an X-ray powder diffraction pattern, obtained as set forth in the Examples, having peaks at about 5.39, 7.55, 14.35, 19.26, and 20.22±0.2° 2θ using Cu Kα radiation. Bis-sulfate crystalline salt form A optionally can be further characterized by an X-ray powder diffraction pattern having additional peaks at about 16.17, 16.71, 16.92, 17.07, 18.60, 20.83, 21.38, 22.27, 22.77, 23.14, 23.42, 23.76, 24.32, 25.11, 25.74, 26.46, 27.71, 28.15, and 29.92±0.2° 2θ using Cu Kα radiation. Bis-sulfate crystalline salt form A can be characterized by an X-ray powder diffraction pattern having peaks shown in Table 26 set forth in the Examples. In some embodiments, bis-sulfate crystalline salt form A has an X-ray powder diffraction pattern substantially as shown in FIG. 57, wherein by "substantially" is meant that the reported peaks can vary by about ±0.2°.

Bis-Sulfate Crystalline Salt Form B

Figure 58:
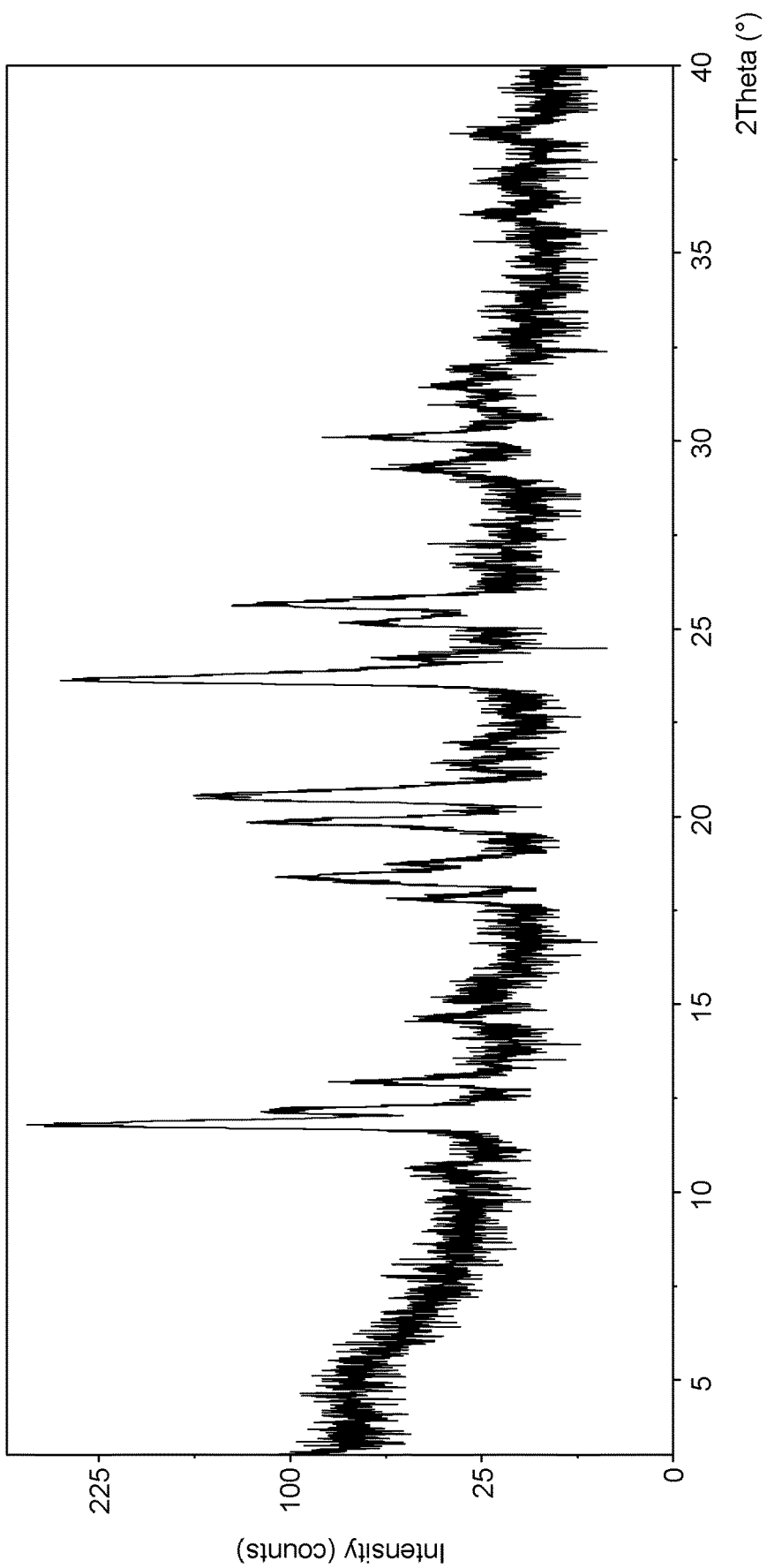
FIG. 58 depicts an XRPD pattern of the bis-sulfate crystalline salt form B.

Bis-sulfate crystalline salt form B of omecamtiv mecarbil can be characterized by an X-ray powder diffraction pattern, obtained as set forth in the Examples, having peaks at about 11.72 and 20.48±0.2° 2θ using Cu Kα radiation. Bis-sulfate crystalline salt form B optionally can be further characterized by an X-ray powder diffraction pattern having additional peaks at about 12.17, 12.93, 17.79, 18.39, 18.76, 19.84, 23.60, 25.13, 25.63, and 30.12±0.2° 2θ using Cu Kα radiation. Bis-sulfate crystalline salt form B can be characterized by an X-ray powder diffraction pattern having peaks shown in Table 27 set forth in the Examples. In some embodiments, bis-sulfate crystalline salt form B has an X-ray powder diffraction pattern substantially as shown in FIG. 58, wherein by "substantially" is meant that the reported peaks can vary by about ±0.2°.

Figure 59:
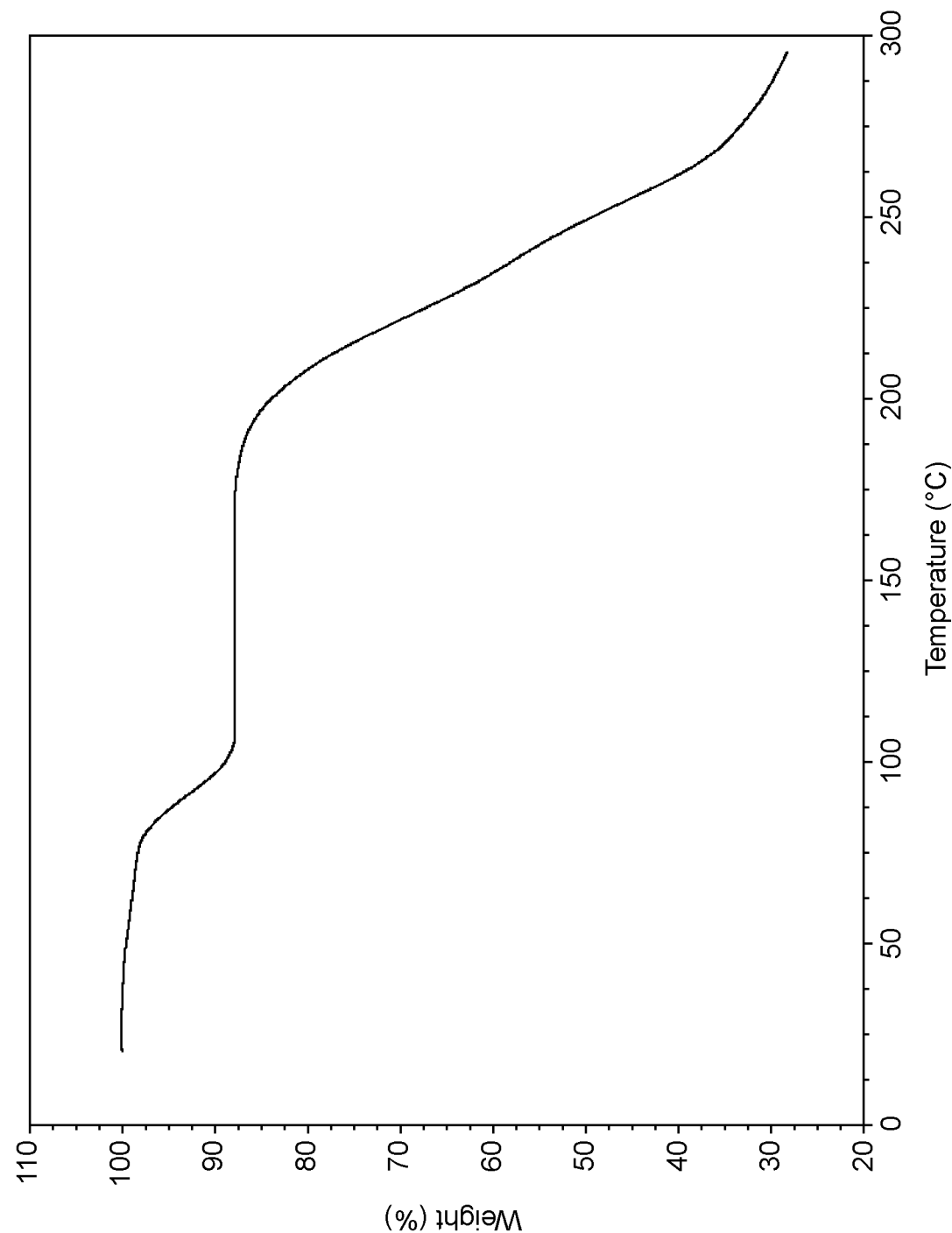
FIG. 59 depicts a TGA trace of the bis-sulfate crystalline salt form B.

Bis-sulfate crystalline salt form B also can be characterized by thermogravimetric analysis (TGA). Thus, bis-sulfate crystalline salt form B can be characterized by a weight loss in a range of about 10% to about 14% with an onset temperature in a range of about 25° C. to about 100° C. For example, bis-sulfate crystalline salt form B can be characterized by a weight loss of about 12.2%, up to about 150° C. In some embodiments, bis-sulfate crystalline salt form B has a thermogravimetric analysis as depicted in FIG. 59, wherein by "substantially" is meant that the reported TGA features can vary by about ±5° C. This weight loss was determined to be water via Karl Fischer (KF) analysis. KF analysis shows that the water content of bis-sulfate crystalline salt form B can be about 12%, corresponding to a pentahydrate.

Bis-Sulfate Crystalline Salt Form C

Figure 60:
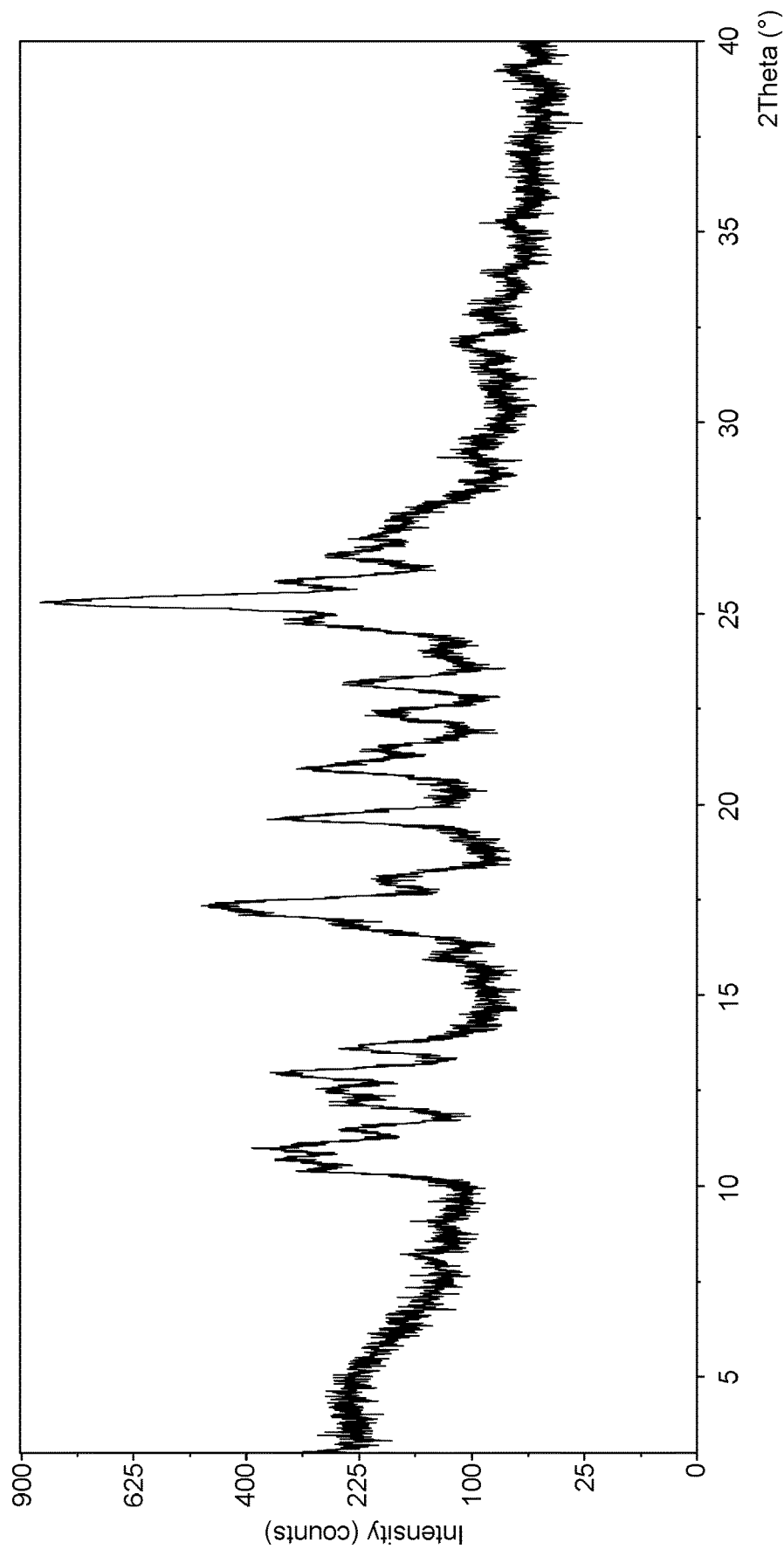
FIG. 60 depicts an XRPD pattern of the bis-sulfate crystalline salt form C.

Bis-sulfate crystalline salt form C of omecamtiv mecarbil can be characterized by an X-ray powder diffraction pattern, obtained as set forth in the Examples, having peaks at about 10.98, 11.49, 18.04, and 19.60±0.2° 2θ using Cu Kα radiation. Bis-sulfate crystalline salt form C optionally can be further characterized by an X-ray powder diffraction pattern having additional peaks at about 10.39, 10.72, 12.52, 12.99, 17.11, 17.43, 20.94, 24.76, 25.25, 25.87, and 26.51±0.2° 2θ using Cu Kα radiation. Bis-sulfate crystalline salt form C can be characterized by an X-ray powder diffraction pattern having peaks shown in Table 28 set forth in the Examples. In some embodiments, bis-sulfate crystalline salt form C has an X-ray powder diffraction pattern substantially as shown in FIG. 60, wherein by "substantially" is meant that the reported peaks can vary by about ±0.2°.

Figure 61:
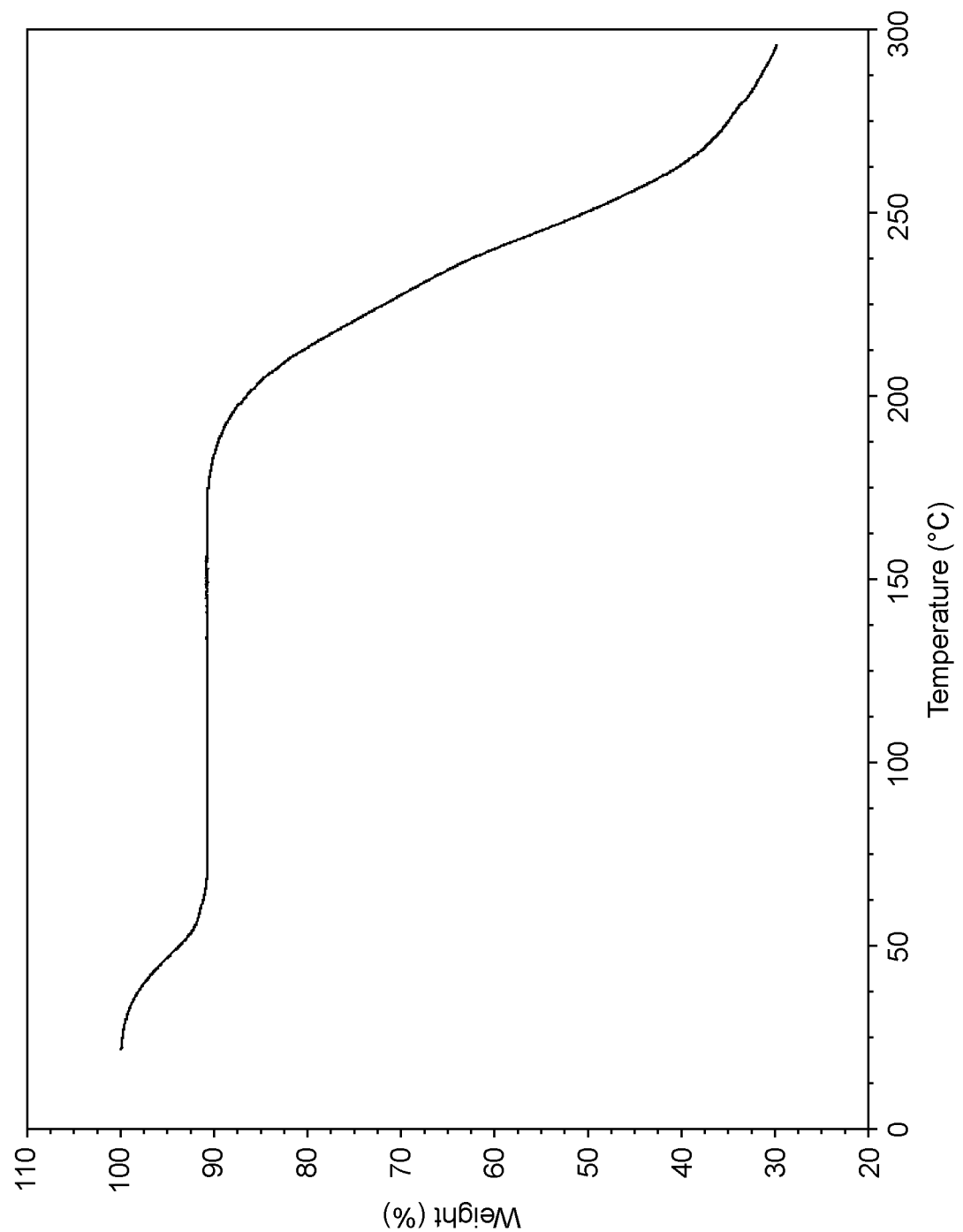
FIG. 61 depicts a TGA trace of the bis-sulfate crystalline salt form C.

Bis-sulfate crystalline salt form C also can be characterized by thermogravimetric analysis (TGA). Thus, bis-sulfate crystalline salt form C can be characterized by a weight loss in a range of about 7% to about 11% with an onset temperature in a range of about 25° C. to about 60° C. For example, bis-sulfate crystalline salt form C can be characterized by a weight loss of about 9.0%, up to about 150° C. In some embodiments, bis-sulfate crystalline salt form C has a thermogravimetric analysis substantially as depicted in FIG. 61, wherein by "substantially" is meant that the reported TGA features can vary by about ±5° C.

Sulfate Crystalline Salt Form D

Figure 62:
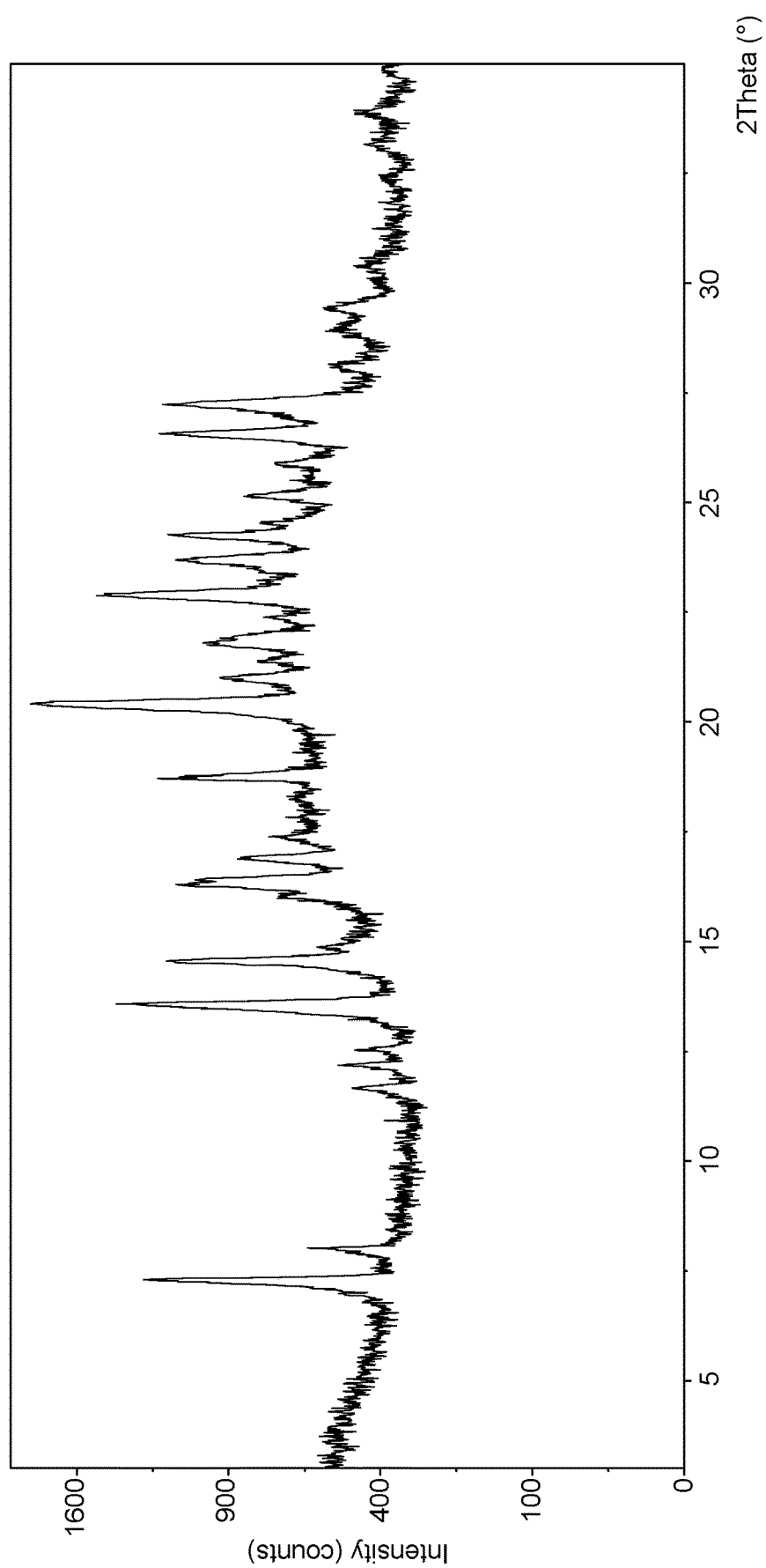
FIG. 62 depicts an XRPD pattern of the sulfate crystalline salt form D.
Figure 63:
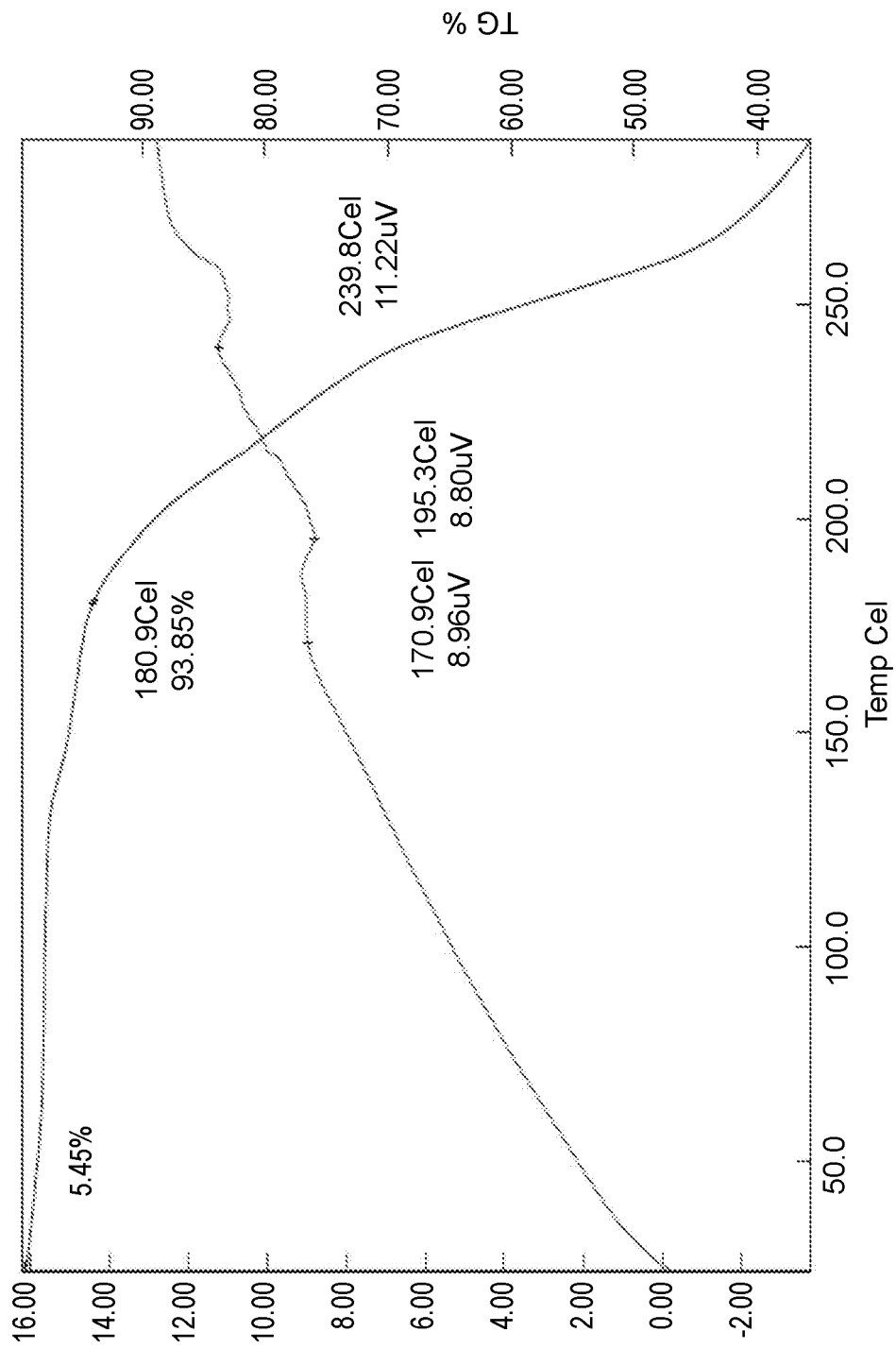
FIG. 63 depicts a TG/DTA of the sulfate crystalline salt form D.
Figure 64:
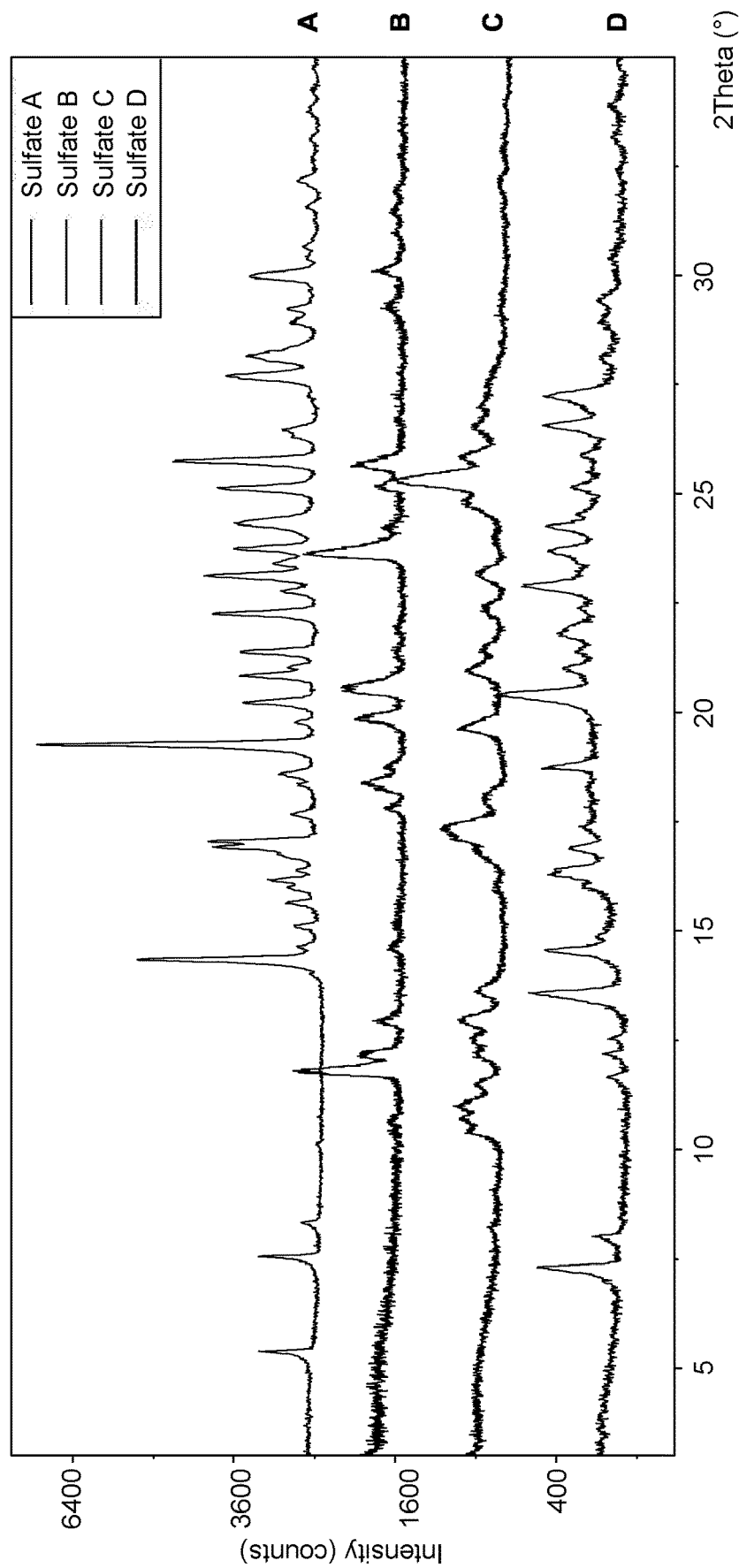
FIG. 64 depicts an XRPD pattern overlay of the sulfate crystalline salt forms A-D.

Sulfate crystalline salt form D of omecamtiv mecarbil can be characterized by an X-ray powder diffraction pattern, obtained as set forth in the Examples, having peaks at about 7.32, 8.02, and 20.44±0.2° 2θ using Cu Kα radiation. Sulfate crystalline salt form D optionally can be further characterized by an X-ray powder diffraction pattern having additional peaks at about 13.57, 14.54, 16.29, 16.41, 16.91, 17.36, 18.70, 21.02, 21.77, 22.37, 22.90, 23.72, 24.28, 25.14, 25.88, 26.58, 27.25, 28.10, and 29.43±0.2° 2θ using Cu Kα radiation. Sulfate crystalline salt form D can be characterized by an X-ray powder diffraction pattern having peaks shown in Table 29 set forth in the Examples. In some embodiments, sulfate crystalline salt form D has an X-ray powder diffraction pattern substantially as shown in FIG. 62, wherein by "substantially" is meant that the reported peaks can vary by about ±0.2°. In embodiments, sulfate crystalline salt form D has a TG/DTA substantially as shown in FIG. 63.

2-Hydroxyethane Sulfonate Crystalline Salt

Figure 65:
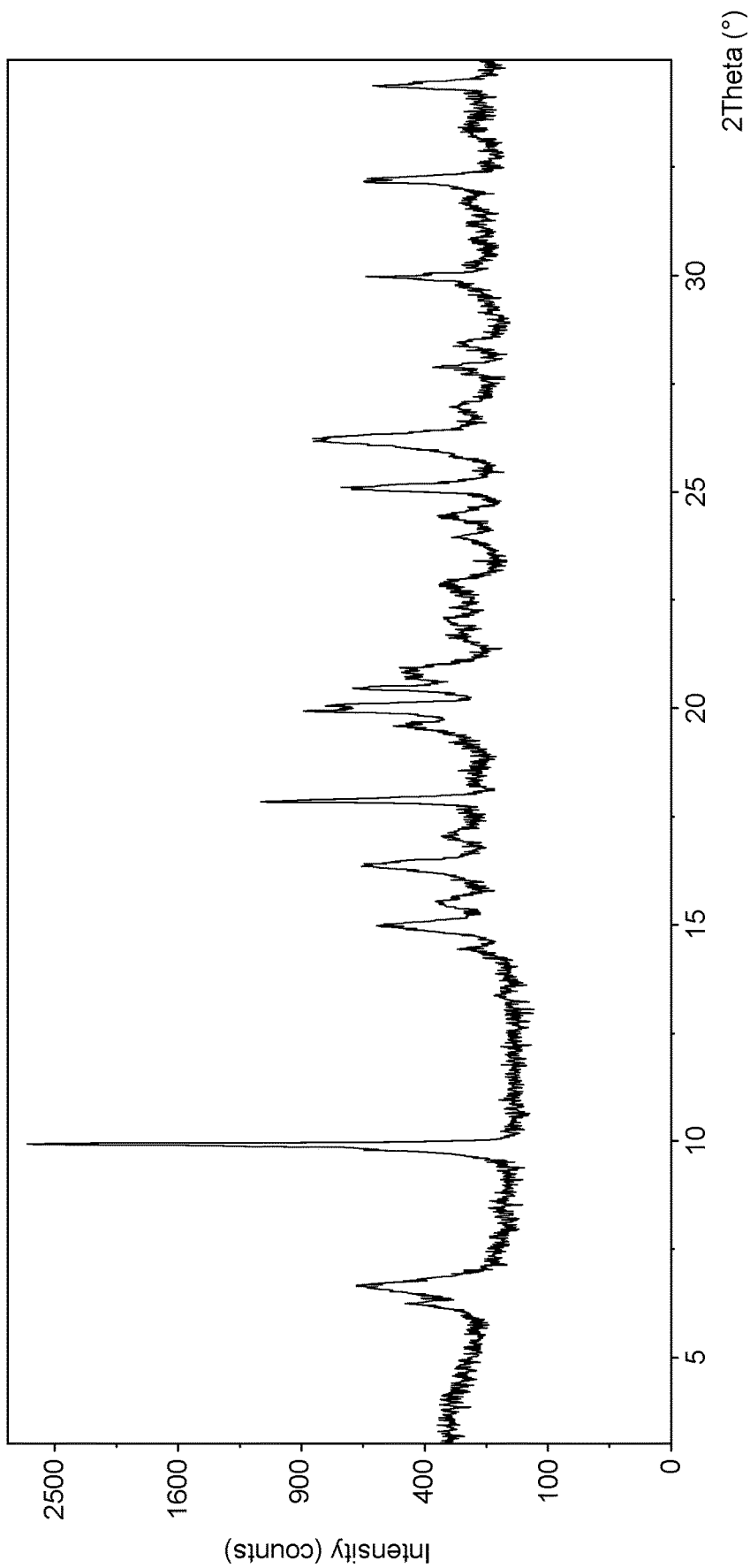
FIG. 65 depicts an XRPD pattern of the 2-hydroxyethane sulfonate crystalline salt.
Figure 66:
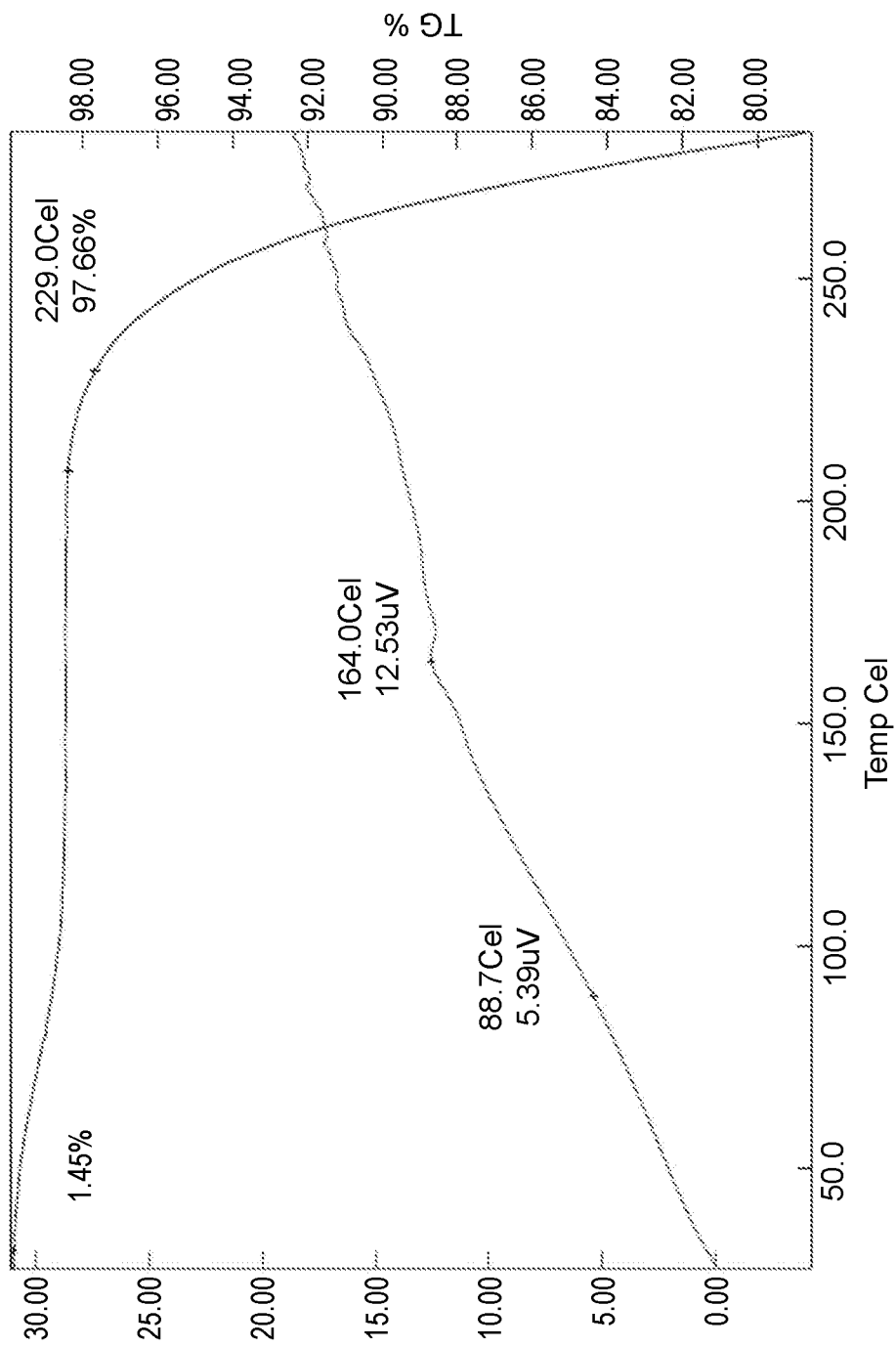
FIG. 66 depicts a TG/DTA of the 2-hydroxyethane sulfonate crystalline salt.

The 2-hydroxyethane sulfonate crystalline salt of omecamtiv mecarbil can be characterized by an X-ray powder diffraction pattern, obtained as set forth in the Examples, having peaks at about 9.95, 17.85, 19.93, 20.07, 20.46, 25.06, and 26.20±0.2° 2θ using Cu Kα radiation. The 2-hydroxyethane sulfonate crystalline salt optionally can be further characterized by an X-ray powder diffraction pattern having additional peaks at about 6.26, 6.69, 14.99, 16.37, 19.61, 20.95, 29.98, 32.16, and 34.39±0.2° 2θ using Cu Kα radiation. The 2-hydroxyethane sulfonate crystalline salt can be characterized by an X-ray powder diffraction pattern having peaks shown in Table 31 set forth in the Examples. In some embodiments, the 2-hydroxyethane sulfonate crystalline salt has an X-ray powder diffraction pattern substantially as shown in FIG. 65, wherein by "substantially" is meant that the reported peaks can vary by about ±0.2°. In some embodiments, the 2-hydroxyethane sulfonate crystalline salt has a TG/DTA substantially as shown in FIG. 66.

Bis-Tartrate Crystalline Salt Form A

Figure 67:
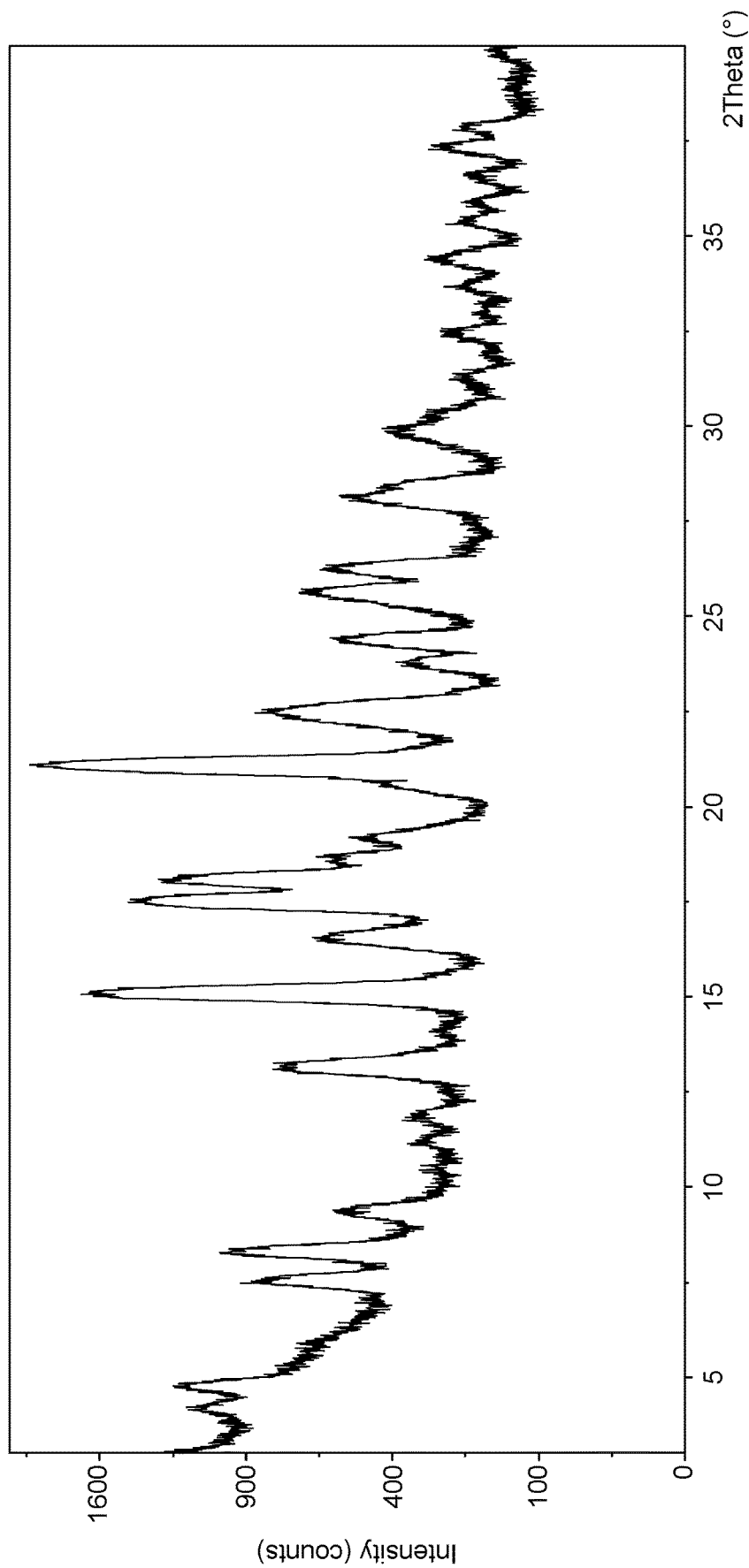
FIG. 67 depicts an XRPD pattern of the bis-tartrate crystalline salt form A.

Bis-tartrate crystalline salt form A of omecamtiv mecarbil can be characterized by an X-ray powder diffraction pattern, obtained as set forth in the Examples, having peaks at about 4.20, 7.49, 8.22, 11.88, 16.42, and 21.19±0.2° 2θ using Cu Kα radiation. Bis-tartrate crystalline salt form A optionally can be further characterized by an X-ray powder diffraction pattern having additional peaks at about 4.77, 7.67, 8.43, 9.49, 13.05, 13.26, 14.98, 15.14, 17.34, 17.47, 18.02, 18.23, 18.72, 19.20, 22.50, 24.53, 25.67, 26.30, and 28.14±0.2° 2θ using Cu Kα radiation. Bis-tartrate crystalline salt form A can be characterized by an X-ray powder diffraction pattern having peaks shown in Table 32 set forth in the Examples. In some embodiments, bis-tartrate crystalline salt form A has an X-ray powder diffraction pattern substantially as shown in FIG. 67, wherein by "substantially" is meant that the reported peaks can vary by about ±0.2°.

Figure 68:
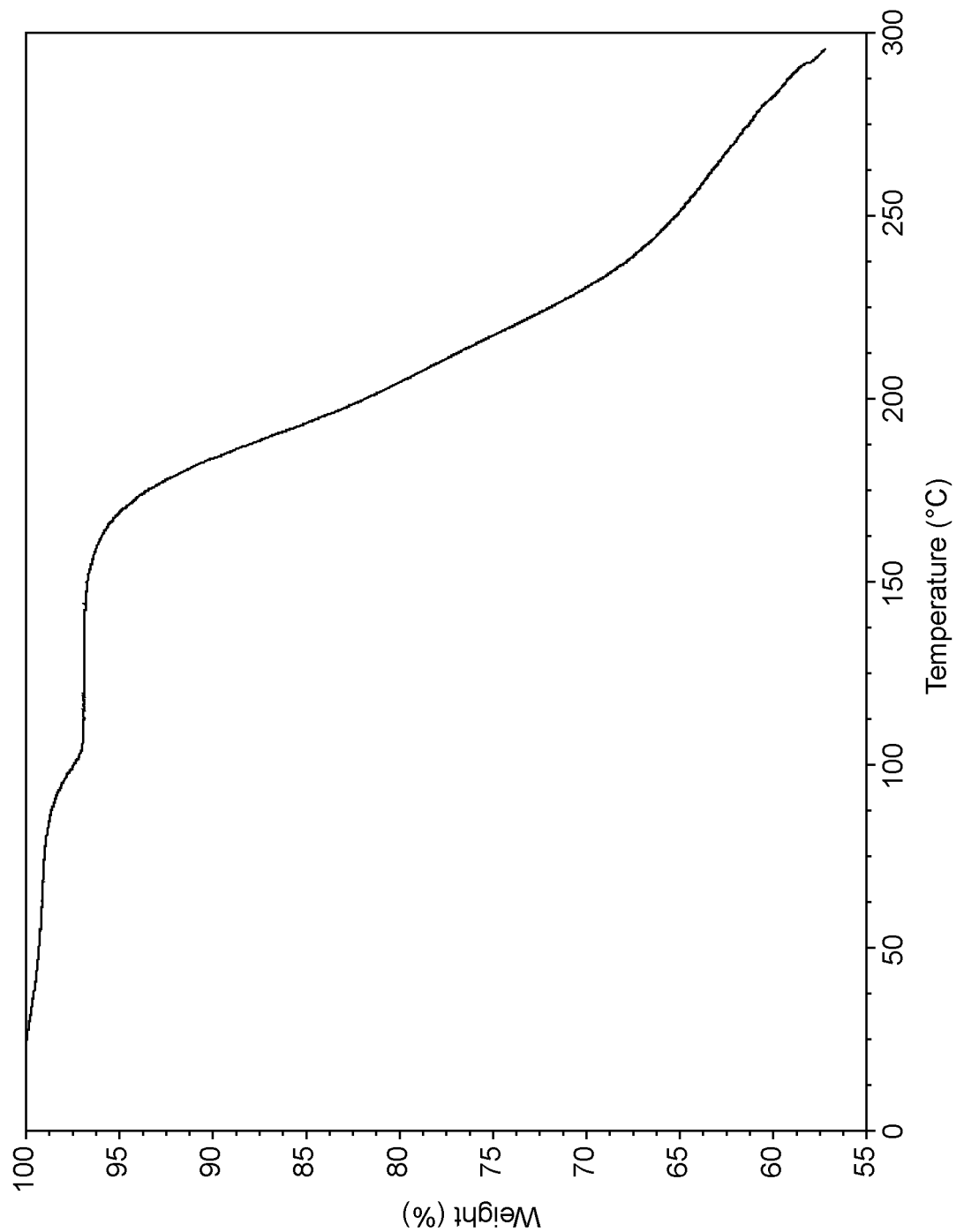
FIG. 68 depicts a TGA trace of the bis-tartrate crystalline salt form A.

Bis-tartrate crystalline salt form A also can be characterized by thermogravimetric analysis (TGA). Thus, bis-tartrate crystalline salt form A can be characterized by a weight loss in a range of about 1% to about 5% with an onset temperature in a range of about 25° C. to about 120° C. For example, bis-tartrate crystalline salt form A can be characterized by a weight loss of about 3.2%, up to about 150° C. In some embodiments, bis-tartrate crystalline salt form A has a thermogravimetric analysis substantially as depicted in FIG. 68, wherein by "substantially" is meant that the reported TGA features can vary by about ±5° C.

Bis-Tartrate Crystalline Salt Form B

Figure 69:
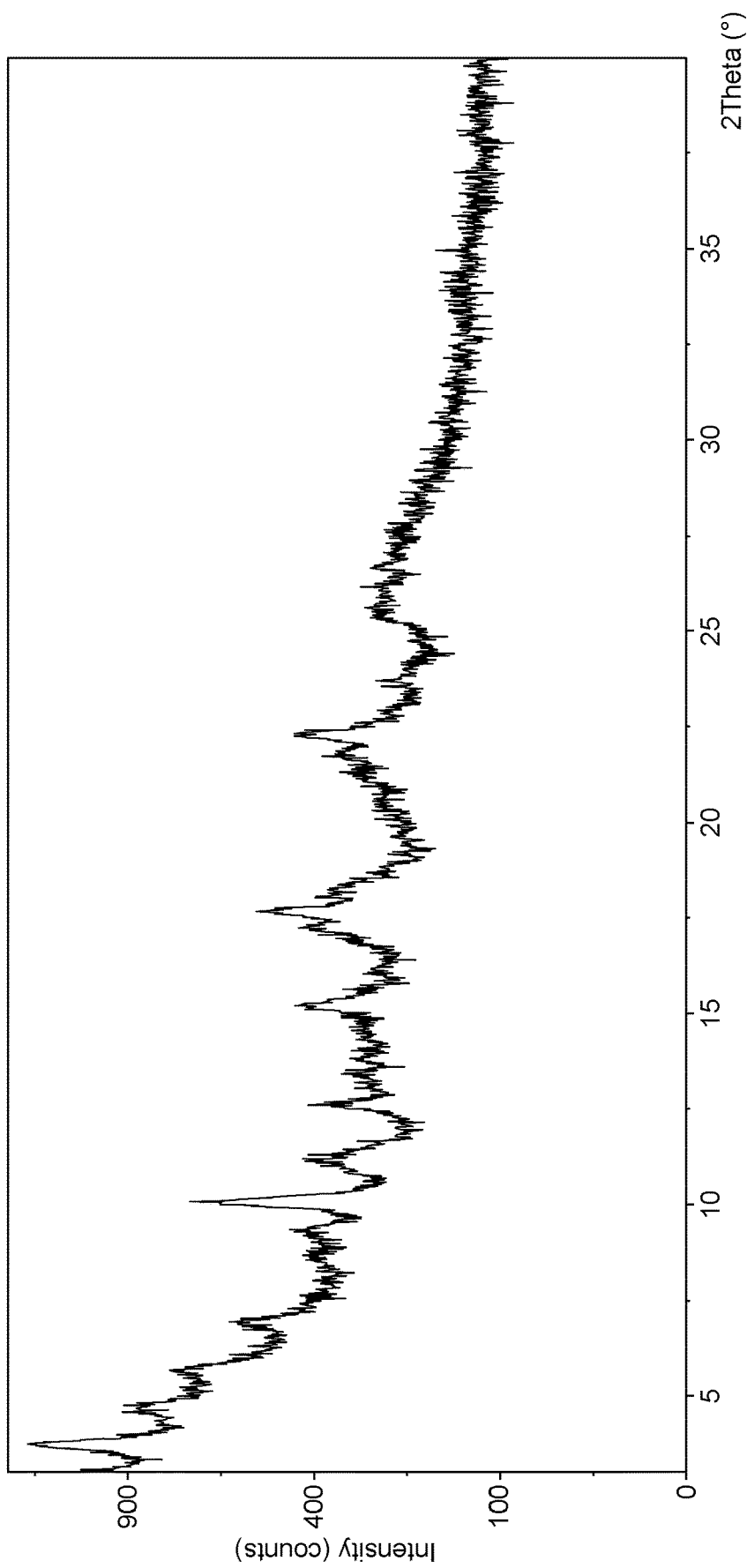
FIG. 69 depicts an XRPD pattern of the bis-tartrate crystalline salt form B.

Bis-tartrate crystalline salt form B of omecamtiv mecarbil can be characterized by an X-ray powder diffraction pattern, obtained as set forth in the Examples, having peaks at about 3.77, 5.69, and 10.07±0.2° 2θ using Cu Kα radiation. Bis-tartrate crystalline salt form B optionally can be further characterized by an X-ray powder diffraction pattern having additional peaks at about 4.72, 6.95, 9.34, 11.18, 12.63, 15.18, 17.69, 22.35, and 25.46±0.2° 2θ using Cu Kα radiation. Bis-tartrate crystalline salt form B can be characterized by an X-ray powder diffraction pattern having peaks shown in Table 33 set forth in the Examples. In some embodiments, bis-tartrate crystalline salt form B has an X-ray powder diffraction pattern substantially as shown in FIG. 69, wherein by "substantially" is meant that the reported peaks can vary by about ±0.2°.

Figure 70:
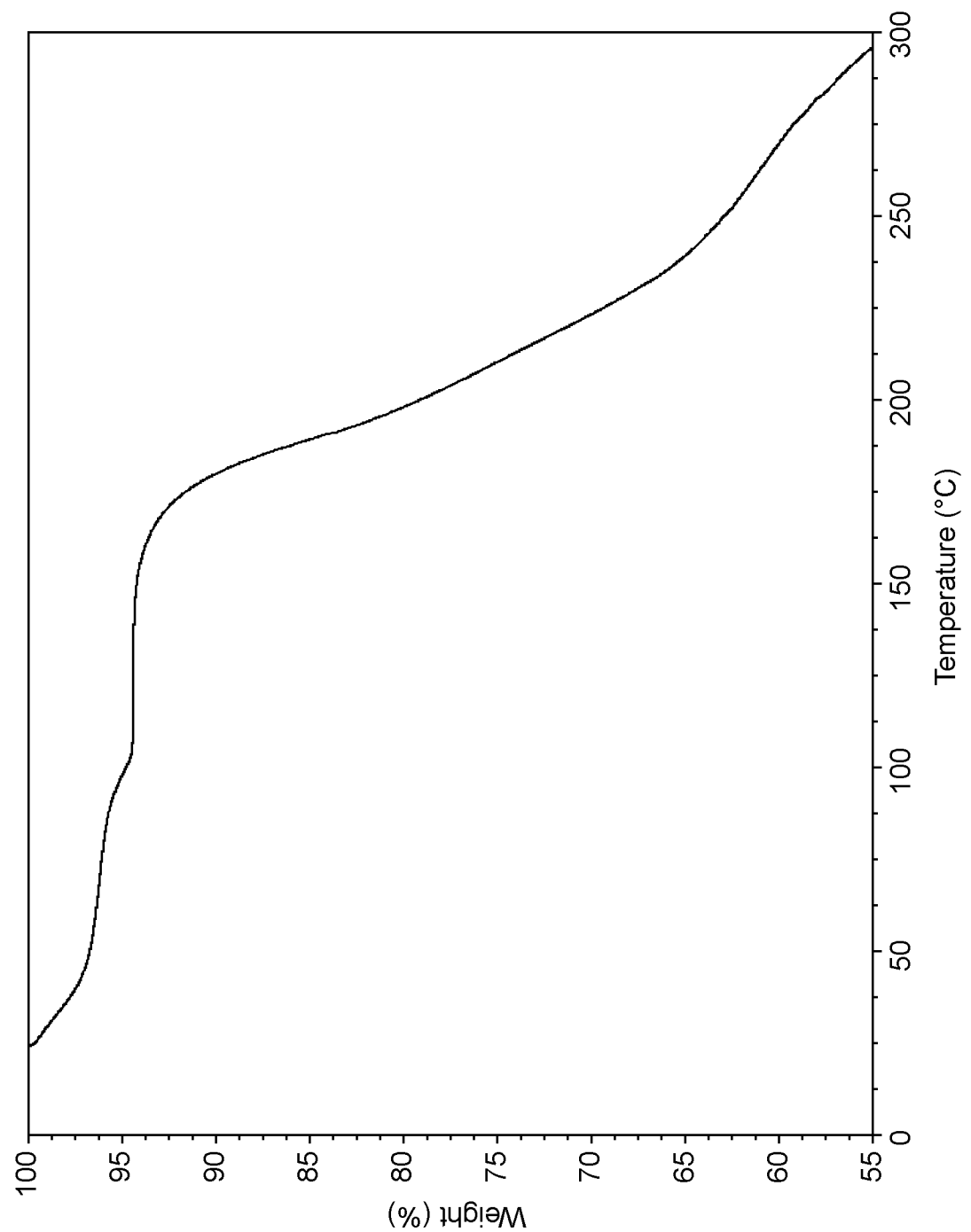
FIG. 70 depicts a TGA trace of the bis-tartrate crystalline salt form B.

Bis-tartrate crystalline salt form B also can be characterized by thermogravimetric analysis (TGA). Thus, bis-tartrate crystalline salt form B can be characterized by a weight loss in a range of about 3% to about 7% with an onset temperature in a range of about 20° C. to about 100° C. For example, bis-tartrate crystalline salt form B can be characterized by a weight loss of about 5.4%, up to about 150° C. In some embodiments, bis-tartrate crystalline salt form B has a thermogravimetric analysis substantially as depicted in FIG. 70, wherein by "substantially" is meant that the reported TGA features can vary by about ±5° C.

Bis-Tartrate Crystalline Salt Form C

Figure 71:
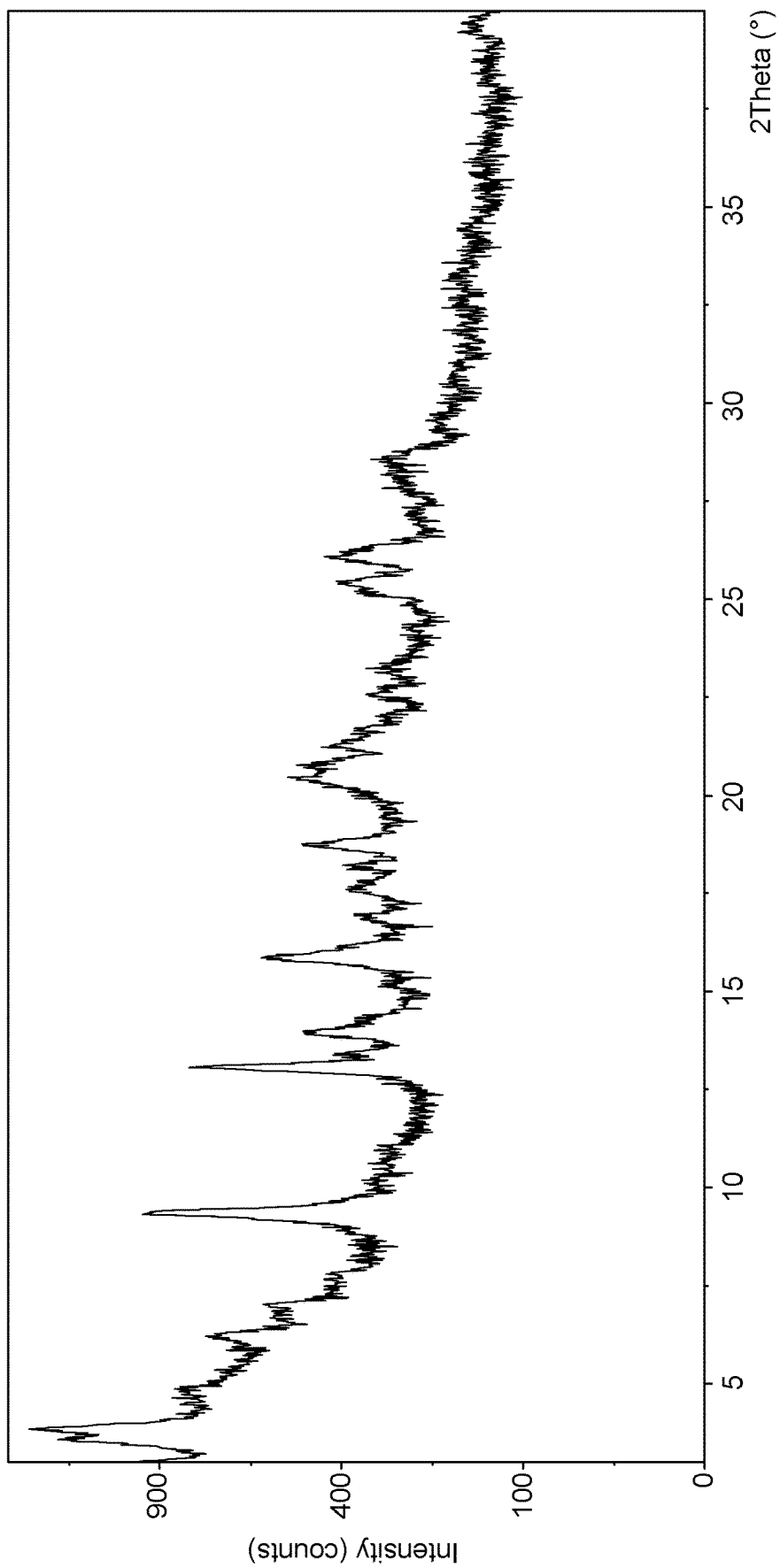
FIG. 71 depicts an XRPD pattern of the bis-tartrate crystalline salt form C.

Bis-tartrate crystalline salt form C of omecamtiv mecarbil can be characterized by an X-ray powder diffraction pattern, obtained as set forth in the Examples, having peaks at about 3.57, 6.23, and 15.84±0.2° 2θ using Cu Kα radiation. Bis-tartrate crystalline salt form C optionally can be further characterized by an X-ray powder diffraction pattern having additional peaks at about 3.86, 4.78, 7.04, 9.36, 13.08, 13.96, 16.88, 17.60, 18.20, 18.73, 20.40, 22.58, 25.44, 26.06, and 28.61±0.2° 2θ using Cu Kα radiation. Bis-tartrate crystalline salt form C can be characterized by an X-ray powder diffraction pattern having peaks shown in Table 34 set forth in the Examples. In some embodiments, bis-tartrate crystalline salt form C has an X-ray powder diffraction pattern substantially as shown in FIG. 71, wherein by "substantially" is meant that the reported peaks can vary by about ±0.2°.

Figure 72:
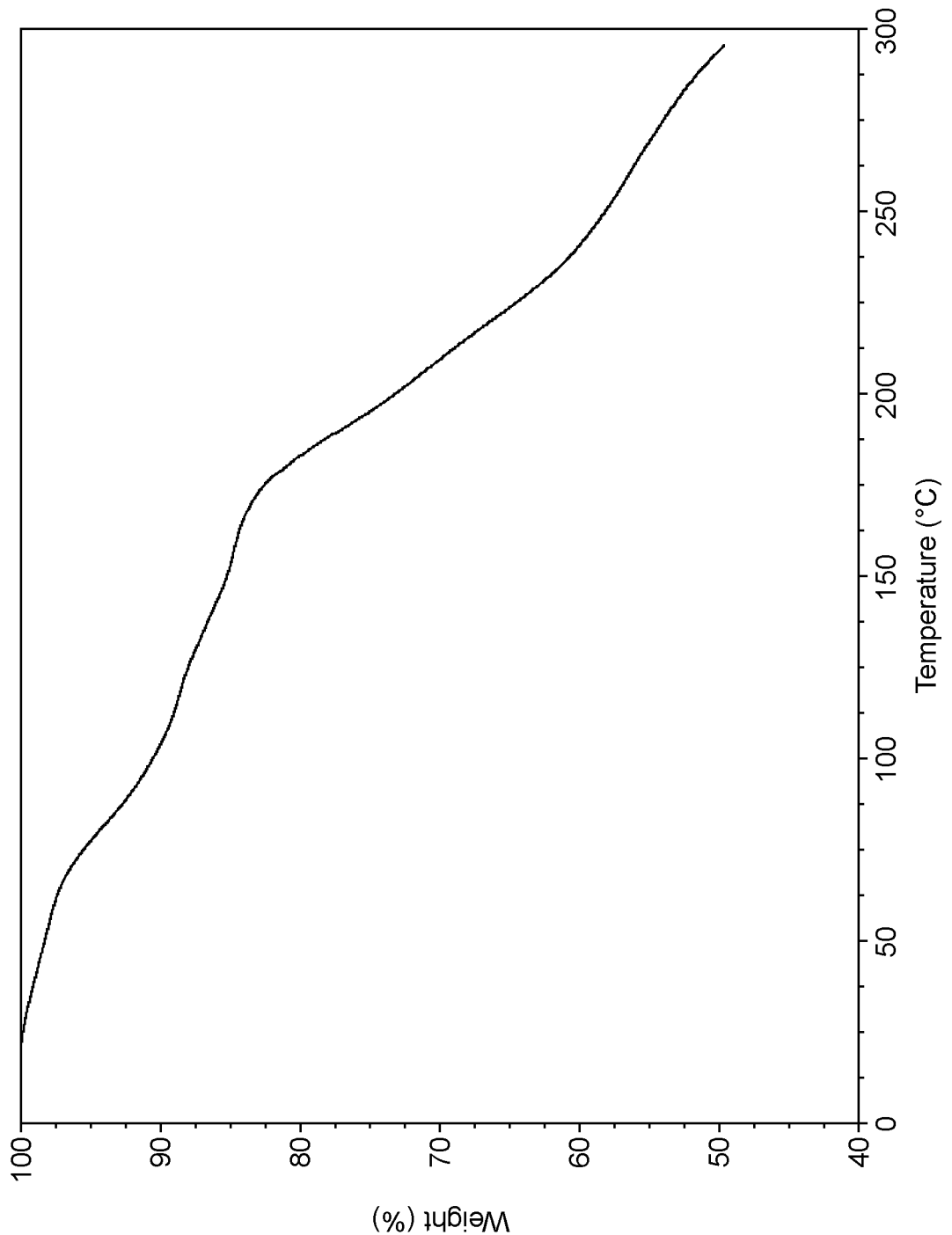
FIG. 72 depicts a TGA trace of the bis-tartrate crystalline salt form C.

Bis-tartrate crystalline salt form C also can be characterized by thermogravimetric analysis (TGA). Thus, bis-tartrate crystalline salt form C can be characterized by a weight loss in a range of about 12% to about 17% with an onset temperature in a range of about 20° C. to about 100° C. For example, bis-tartrate crystalline salt form C can be characterized by a weight loss of about 14.6%, up to about 150° C. In some embodiments, bis-tartrate crystalline salt form C has a thermogravimetric analysis substantially as depicted in FIG. 72, wherein by "substantially" is meant that the reported TGA features can vary by about ±5° C.

Mono-Tartrate Crystalline Salt Form D

Figure 73:
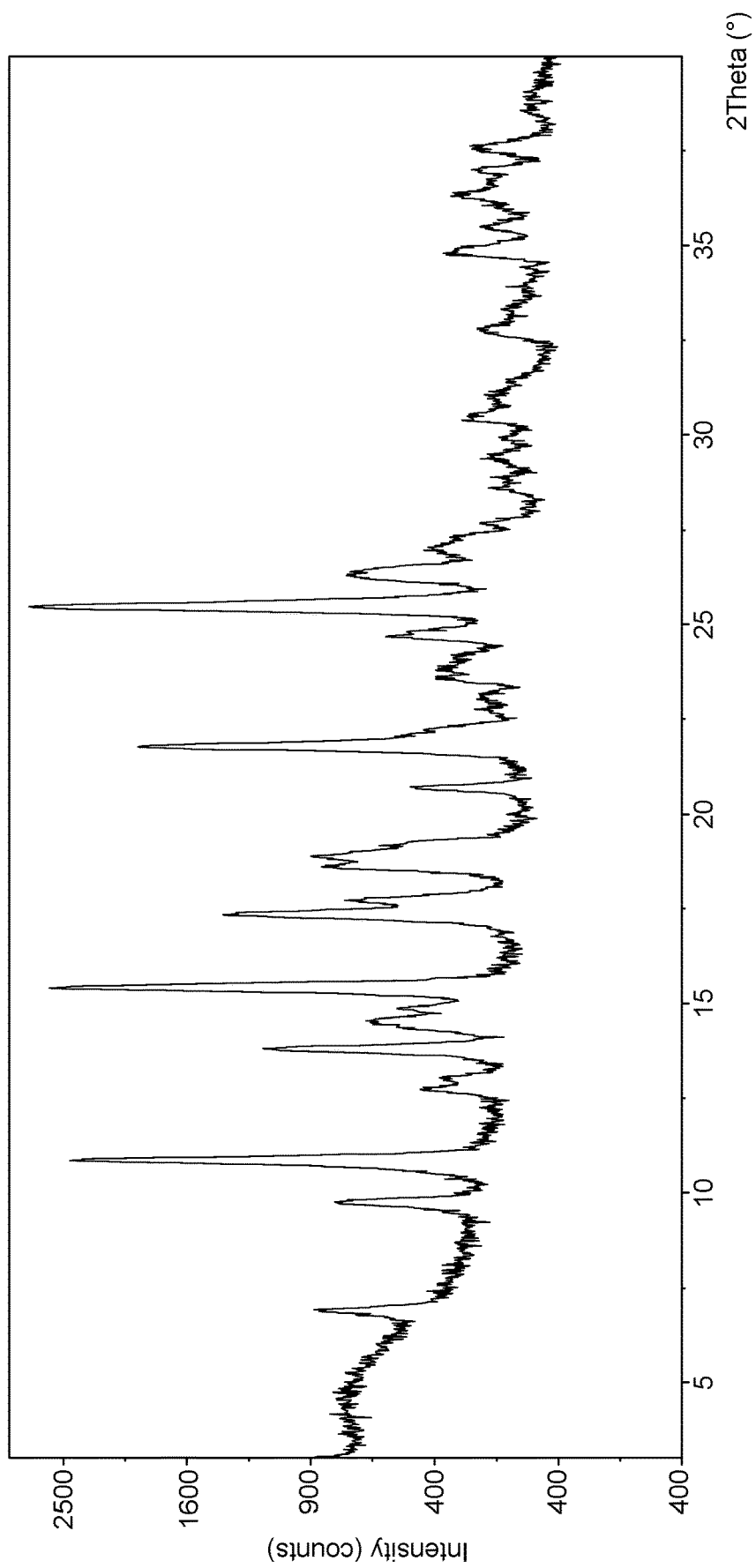
FIG. 73 depicts an XRPD pattern of the mono-tartrate crystalline salt form D.

Mono-tartrate crystalline salt form D of omecamtiv mecarbil can be characterized by an X-ray powder diffraction pattern, obtained as set forth in the Examples, having peaks at about 9.77 and 15.40±0.2° 2θ using Cu Kα radiation. Mono-tartrate crystalline salt form D optionally can be further characterized by an X-ray powder diffraction pattern having additional peaks at about 10.87, 13.79, 17.36, 17.74, 18.58, 18.87, 21.78, 25.43, and 26.24±0.2° 2θ using Cu Kα radiation. Mono-tartrate crystalline salt form D can be characterized by an X-ray powder diffraction pattern having peaks shown in Table 35 set forth in the Examples. In some embodiments, mono-tartrate crystalline salt form D has an X-ray powder diffraction pattern substantially as shown in FIG. 73, wherein by "substantially" is meant that the reported peaks can vary by about ±0.2°.

Figure 74:
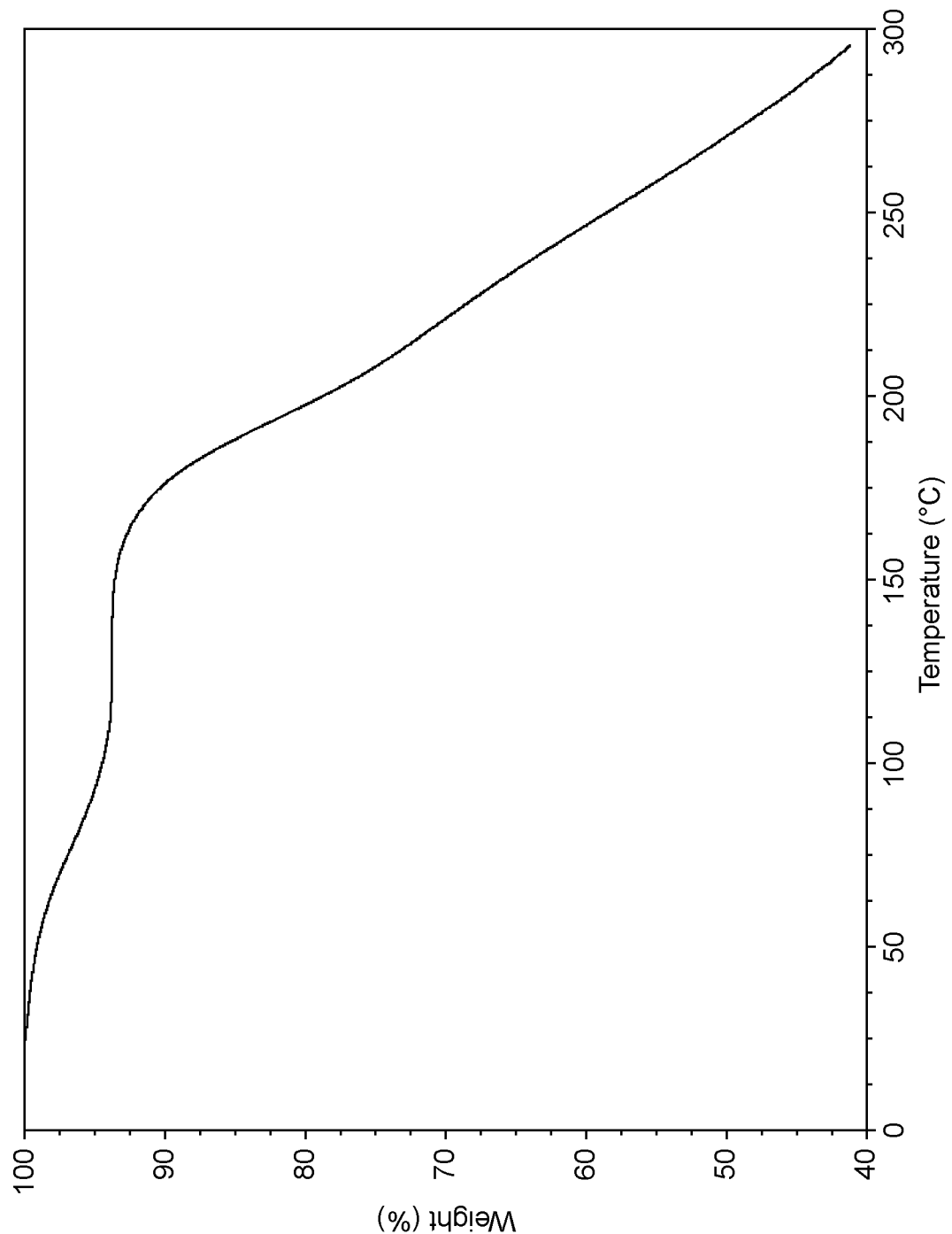
FIG. 74 depicts a TGA trace of the mono-tartrate crystalline salt form D.
Figure 75:
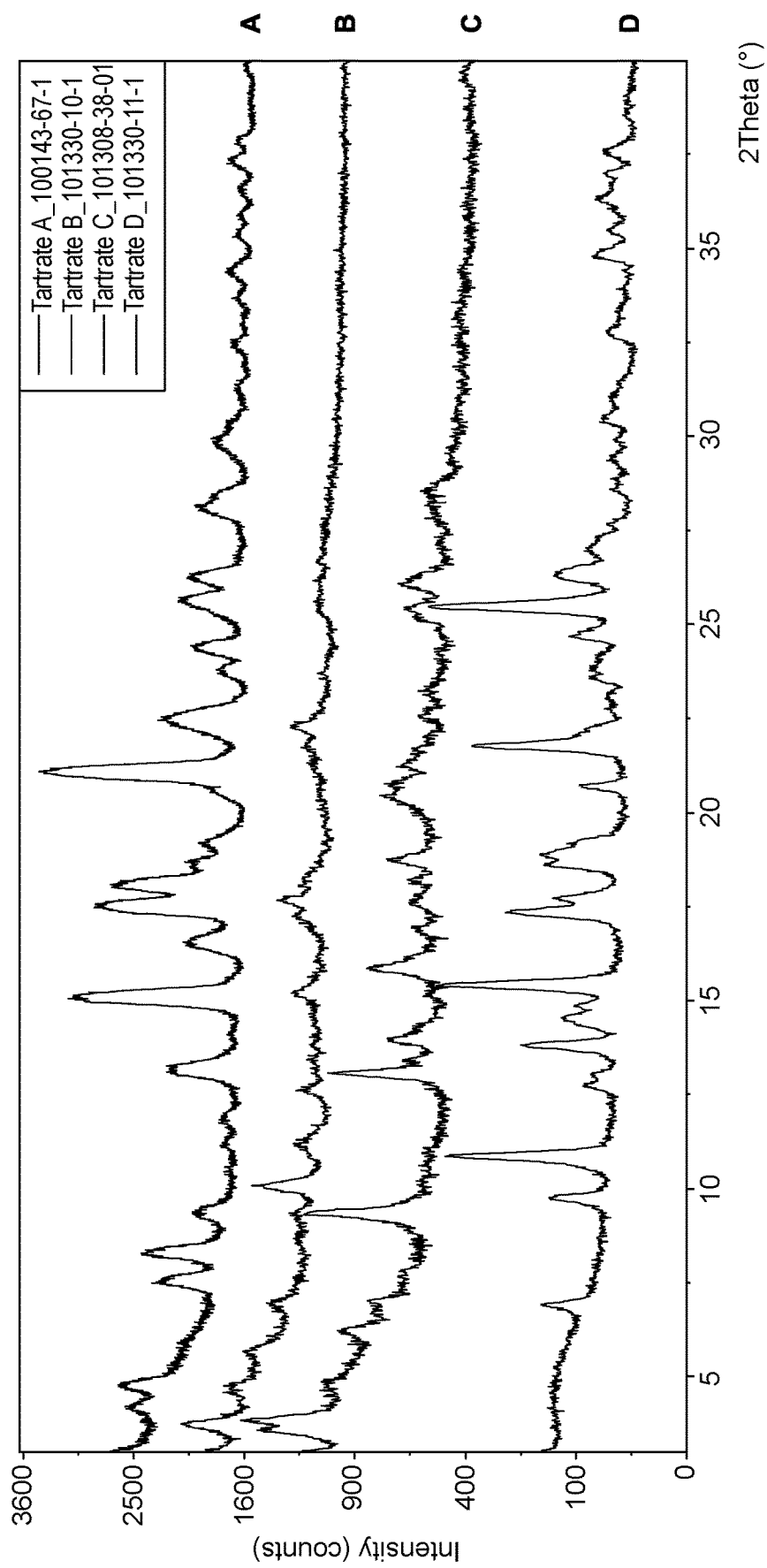
FIG. 75 depicts an XRPD pattern overlay of the tartrate crystalline salt form A-D.

Mono-tartrate crystalline salt form D also can be characterized by thermogravimetric analysis (TGA). Thus, mono-tartrate crystalline salt form D can be characterized by a weight loss in a range of about 4% to about 8% with an onset temperature in a range of about 20° C. to about 75° C. For example, mono-tartrate crystalline salt form D can be characterized by a weight loss of about 6.4%, up to about 150° C. In some embodiments, mono-tartrate crystalline salt form D has a thermogravimetric analysis substantially as depicted in FIG. 74, wherein by "substantially" is meant that the reported TGA features can vary by about ±5° C. This weight loss was determined to be water via Karl Fischer (KF) analysis. KF analysis shows that the water content of mono-tartrate crystalline salt form D can be about 6.9%, corresponding to a dihydrate.

Amorphous Hydrochloride Salt

Figure 14:
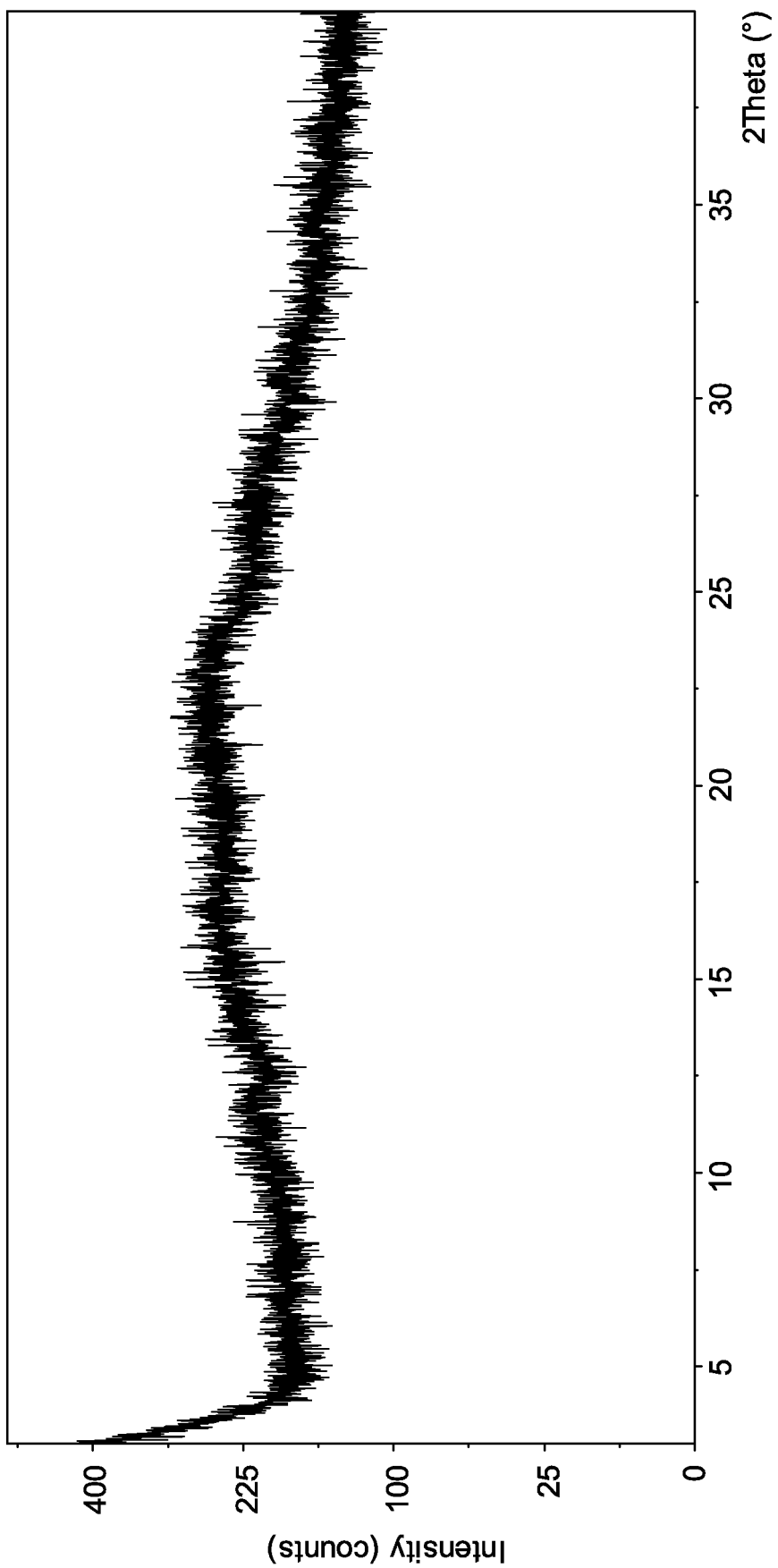
FIG. 14 depicts an XRPD pattern of the amorphous hydrochloride salt.

Also provided herein is an amorphous hydrochloride salt of omecamtiv mecarbil, and confirmation of its amorphous nature is provided by its X-ray powder diffraction pattern as shown in FIG. 14.

Figure 15:
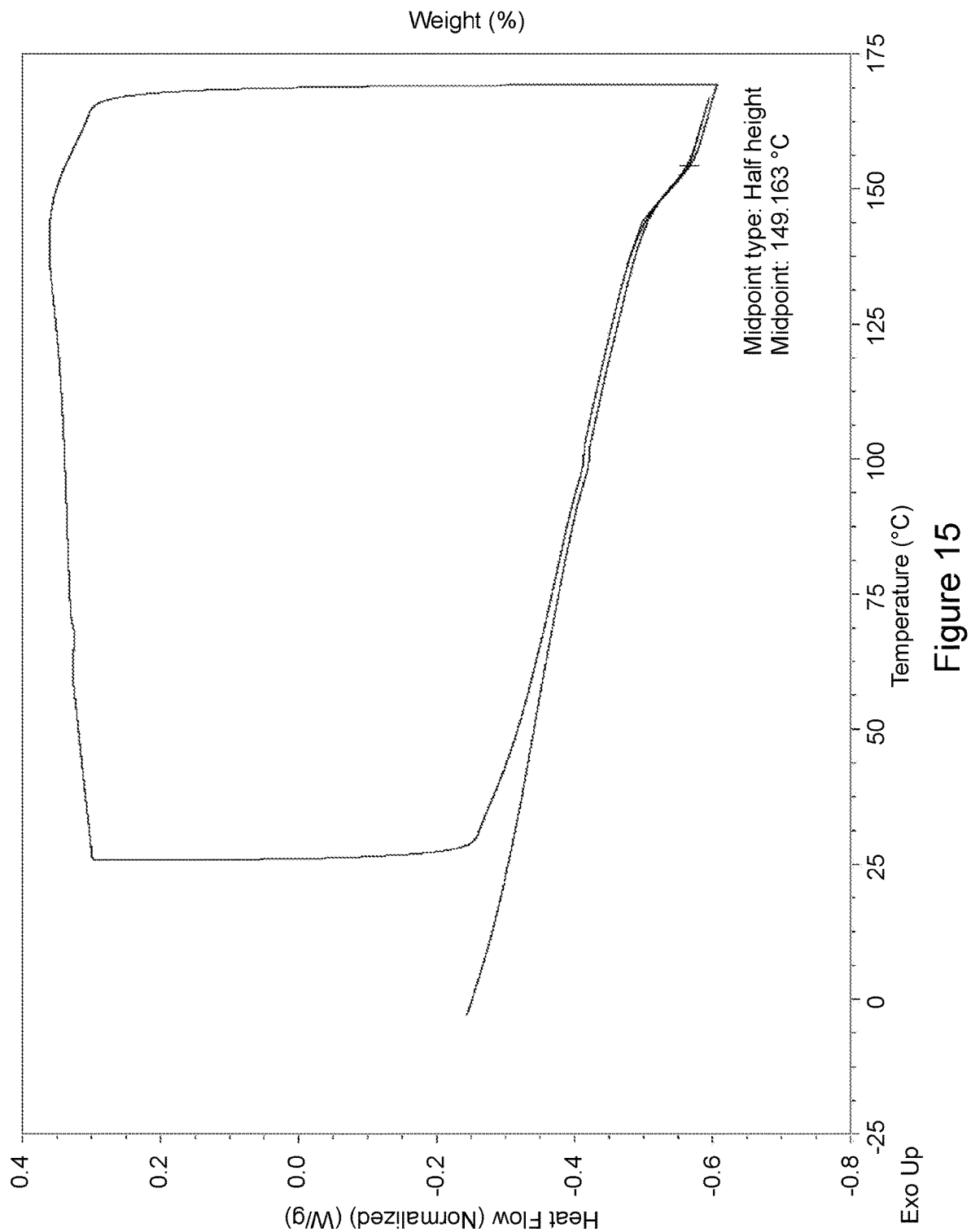
FIG. 15 depicts a DSC thermograph of the amorphous hydrochloride salt indicating a Tg of ~149.16° C.

Differential scanning calorimetry (DSC) thermographs were obtained, as set forth in the Examples, for the amorphous hydrochloride salt. The DSC curve indicates an endothermic transition at about 171° C.±3° C. Thus, in some embodiments, the amorphous hydrochloride salt can be characterized by a DSC thermograph having a decomposition endotherm with an onset in a range of about 155° C. to about 190° C. For example, in some embodiments the amorphous hydrochloride salt is characterized by DSC, as shown in FIG. 15.

Figure 16:
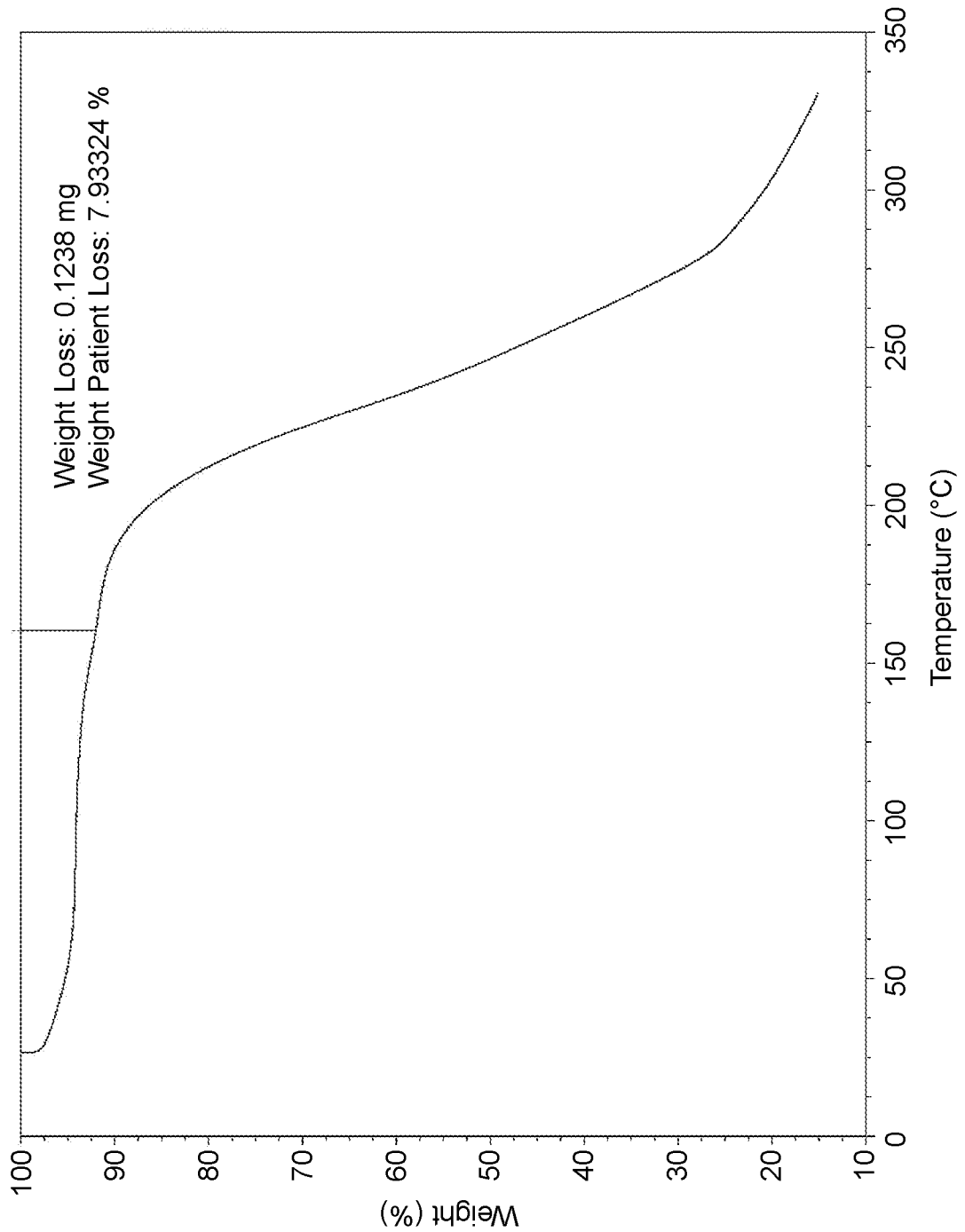
FIG. 16 depicts a TGA trace of the amorphous hydrochloride salt indicating a weight loss of ~7.9% from ~26° C. to 160° C.
Figure 17:
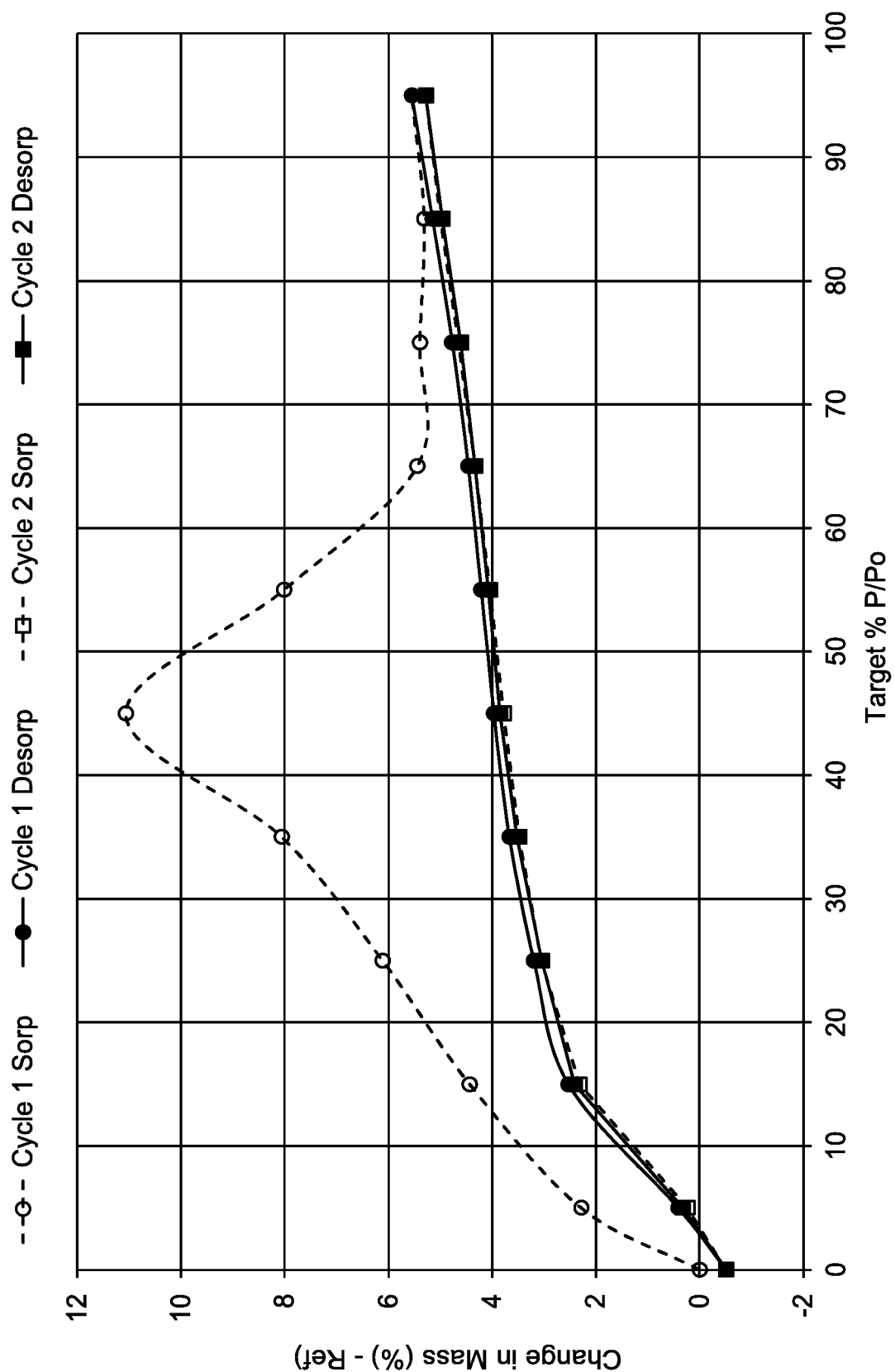
FIG. 17 depicts a moisture sorption profile of the amorphous hydrochloride salt indicating a weight gain of ~11% by 50% RH then weight loss due to crystallization to Form A up to 95% RH.

The amorphous hydrochloride salt also can be characterized by thermogravimetric analysis (TGA). Thus, the amorphous hydrochloride salt can be characterized by a weight loss in a range of about 6% to about 10% with an onset temperature in a range of about 20° C. to about 60° C. For example, the amorphous hydrochloride salt can be characterized by a weight loss of about 7.9%, up to about 150° C. In some embodiments, the amorphous hydrochloride salt has a thermogravimetric analysis substantially as depicted in FIG. 16, wherein by "substantially" is meant that the reported TGA features can vary by about ±5° C. In some embodiments, the amorphous hydrochloride salt has a moisture sorption profile substantially as depicted in FIG. 17.

Pharmaceutical Compositions

Also provided herein are pharmaceutical compositions comprising a salt or crystalline form of omecamtiv mecarbil described herein; and a pharmaceutically acceptable excipient.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The compositions described herein can be formulated for any form of administration. In various cases, the composition is for oral administration. In various cases, the composition is in tablet form.

In some embodiments, the pharmaceutical compositions can include a pharmaceutically acceptable carrier. The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffers, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions as excipients.

Examples of pharmaceutically acceptable antioxidants as excipient include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A pharmaceutical composition may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

In some cases, in order to prolong the effect of one or more compounds provided herein, it is desirable to slow the absorption of the compound from subcutaneous or intramuscular injection. For example, delayed absorption of a parenterally administered compound can be accomplished by dissolving or suspending the compound in an oil vehicle.

The composition should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the methods of preparation are freeze-drying (lyophilization), which yields a powder of the active ingredient plus any additional desired ingredient from a previously sterile-filtered solution thereof.

Injectable depot forms can be made by forming microencapsule or nanoencapsule matrices of a compound provided herein in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes, microemulsions or nanoemulsions, which are compatible with body tissue.

In one embodiment, the therapeutic crystalline salts are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811, which is incorporated herein by reference in its entirety.

The pharmaceutical compositions can be included in a container, pack, or dispenser together with instructions for administration.

Controlled Release Compositions

In various cases, the pharmaceutical formulations described herein are capable of releasing omecamtiv mecarbil evenly at a pace controlled by the diffusion of omecamtiv mecarbil through a gel layer formed by the hydration of the control release agents in the tablets. In some embodiments, in conjunction with other above or below embodiments, the present modified release matrix tablets demonstrate a minimal pH-dependent release in-vitro. In some embodiments, in conjunction with other above or below embodiments, complete release of omecamtiv mecarbil is achieved in both pH 2 and 6.8 dissolution medium within 24 hours, possibly resulting in less inter- and intra-subject variability and food effect. It is found that the present modified release matrix tablet dosage form is superior to the former immediate release dosage form in minimizing the plasma peak-trough ratio. As a result, the present modified release matrix tablets reduce plasma concentration fluctuation, leading to reduced side effects, and improved safety and efficacy. It is also expected that the present modified release matrix tablets will improve patient compliance by reducing the dosing frequency. Additionally, the present modified release matrix tablets are physicochemically stable—resulting in no physical attribute, assay, impurity, or dissolution profile changes after storage at 40° C./75% RH for 6 months.

Provided are pharmaceutical formulations comprising the salt or crystalline omecamtiv mecarbil as disclosed herein; a control release agent; a pH modifying agent; a filler; and a lubricant.

As used herein, the term "control release agents" refer to agents that facilitate the release of the active ingredient from the present composition in a controlled fashion. In some embodiments, in conjunction with other above or below embodiments, the control release agents form a gel upon hydration. Control release agents include pullulan, dextrin, sodium and calcium acid, polyacrylic acid, polymethacrylic acid, polymethylvinylether co-maleic anhydride, polyvinylpyrrolidone, polyethylene oxide, polyethylene glycol, hydroxypropylcellulose, hydroxypropylmethylcellulose, hydroxyethylcellulose, hydroxymethyl methacrylate, sodium carboxymethylcellulose, calcium carboxymethylcellulose, methylcellulose, maltodextrin, xanthan gum, tragacanth gum, agar, gellan gum, kayara gum, alginic acids, pectins, pre-gelatinized starch, polyvinyl alcohol, carboxymethylethylcellulose, cellulose acetate phthalate, cellulose acetate succinate, methylcellulose phthate, hydroxymethylethylcellulosephthate, hydroxypropylmethylcellulose phthalate, hydroxypropylmethylcellulose acetate succinate, polyvinyl alcohol phthalate, polyvinyl butylate phthalate, polyvinyl actal phthalate, a copolymer of vinyl acetate/maleic anhydride, a copolymer of styrene/maleic acid monoester, a copolymer of methyl acryl-ate/methacrylic acid, a copolymer of styrene/acrylic acid, a copolymer of methyl acrylate/methacrylic acid/octyl acrylate, a copolymer of methacrylic acid/methyl methacrylate, benzylaminomethylcellulose, diethylaminomethylcellulose, piperidylethylhydroxyethylcellulose, cellulose acetate di methylaminoacetate, a copolymer of vinyl diethylamine/vinyl acetate, a copolymer of vinyl benzylamine/vinyl acetate, polyvinyl acetaldiethylamino acetate, a copolymer of vinylpiperidylacetoacetal/vinyl acetate, polydiethylaminomethylstyrene, a copolymer of methyl methacrylate/butyl methacrylate/dimethylaminoethyl methacrylate and polydimethylaminoethylmethacrylate, a copolymer of 2-methyl-5-vinylpyridine/methylmethacrylate/methacrylic acid, a copolymer of 2-methyl-5-vinylpyridine/methyl acrylate/methacrylic acid, a copolymer of 2-vinyl-5-ethylpyridine/methacrylic acid/methy acrylate, a copolymer of 2-vinylpyrid-ine/methacrylic acid/acrylonitrile, carboxymethylpiperidyl starch, carboxy-methylbenzylaminocellulose, a copolymer of N-vinylglycine/styrene, chitosan, poly(vinyl alcohol), maleic anhydride copolymer, poly (vinyl pyrolidone), starch and starch-based polymers, poly (2-ehtyl-2-oxazoline), poly(ethyleneimine), polyurethane hydrogels, welan gum, rhamsan gum, polyvinyl acetates, ethylcellulose, eudragit RL, RS, NE 30D, Kollicoat EMM 30D, or combinations thereof.

In some embodiments, in conjunction with other above or below embodiments, the control release agent is a polymer.

In some embodiments, in conjunction with other above or below embodiments, the control release agent is selected from pullulan, dextrin, sodium and calcium acid, polyacrylic acid, polymethacrylic acid, polymethylvinylether co-maleic anhydride, polyvinylpyrrolidone, polyethylene oxide, polyethylene glycol, hydroxypropylcellulose, hydroxypropylmethylcellulose, hydroxyethylcellulose, hydroxymethyl methacrylate, sodium carboxymethylcellulose, calcium carboxymethylcellulose, methylcellulose, maltodextrin, xanthan gum, tragacanth gum, agar, gellan gum, kayara gum, alginic acids, pectins, pre-gelatinized starch, polyvinyl alcohol, carboxymethylethylcellulose, cellulose acetate phthalate, cellulose acetate succinate, methylcellulose phthate, hydroxymethylethylcellulosephthate, hydroxypropylmethylcellulose phthalate, hydroxypropylmethylcellulose acetate succinate, polyvinyl alcohol phthalate, polyvinyl butylate phthalate, polyvinyl actal phthalate, a copolymer of vinyl acetate/maleic anhydride, a copolymer of styrene/maleic acid monoester, a copolymer of methyl acryl-ate/methacrylic acid, a copolymer of styrene/acrylic acid, a copolymer of methyl acrylate/methacrylic acid/octyl acrylate, a copolymer of methacrylic acid/methyl methacrylate, benzylaminomethylcellulose, diethylaminomethylcellulose, piperidylethylhydroxyethylcellulose, cellulose acetate dimethylaminoacetate, a copolymer of vinyl diethylamine/vinyl acetate, a copolymer of vinyl benzylamine/vinyl acetate, polyvinyl acetaldiethylamino acetate, a copolymer of vinylpiperidylacetoacetal/vinyl acetate, polydiethylaminomethylstyrene, a copolymer of methyl methacrylate/butyl methacrylate/dimethylaminoethyl methacrylate and polydimethylaminoethyl methacrylate, a copolymer of 2-methy-5vinylpyrid-ine/methylmethacryl-ate/methacrylic acid, a copolymer of 2-methyl-5-vinylpyridine/methyl acrylate/methacrylic acid, a copolymer of 2-vinyl-5-ethylpyridine/methacrylic acid/methy acrylate, a copolymer of 2-vinylpyrid-ine/methacrylic acid/acrylonitrile, carboxymethylpiperidyl starch, carboxy-methylbenzylaminocellulose, a copolymer of N-vinylglycine/styrene, chitosan, poly(vinyl alcohol), maleic anhydride copolymer, poly (vinyl pyrolidone), starch and starch-based polymers, poly (2-ehtyl-2-oxazoline), poly(ethyleneimine), polyurethane hydrogels, welan gum, rhamsan gum, polyvinyl acetates, ethylcellulose, eudragit RL, RS, NE 30D, and Kollicoat EMM 30D, or any combination thereof.

As used herein, the term "pH modifying agent" refers to an agent capable of modulating the pH to a desired range. In some embodiments, in conjunction with other above or below embodiments, the pH modifying agent is an acidifying agent. In some embodiments, in conjunction with other above or below embodiments, the pH modifying agent is present in an amount sufficient to lower the pH. pH modifying agents include maleic acid, citric acid, tartaric acid, pamoic acid, fumaric acid, salicylic acid, 2,6-diaminohexanoic acid, camphorsulfonic acid, glycerophosphoric acid, 2-hydroxyethanesulfonic acid, isethionic acid, succinic acid, carbonic acid, p-toluenesulfonic acid, aspartic acid, 8-chloro-itheophylline, benezenesulfonic acid, malic acid, orotic acid, oxalic acid, benzoic acid, 2-naphthalenesulfonic acid, stearic acid, adipic acid, p-amino-isalicylic acid, 5-aminoslicylic acid, ascorbic acid, sulfuric acid, cyclamic acid, sodium lauryl sulfate, glucoheptonic acid, glucuronic acid, glycine, sulfuric acid, mandelic acid, 1,5-naphthalenedisulfonic acid, nicotinic acid, oleic acid, 2-oxoglutaric acid, pyridoxal 5-phosphate, undecanoic acid, p-acetamidobenzoic acid, o-acetamido-benzoic acid, m-acetamidobenzoic acid, N-acetyl-L-aspartic acid, camphoric acid, dehydrocholic acid, malonic acid, edetic acid, ethylenediainetetraacetic acid, ethylsulf uric acid, hydroxyphenylbenzoylbenzoic acid, glutamic acid, glycyrrhizic acid, 4-hexylresorcinol, hippuric acid, p-phenolsulfonic acid, 4-hydroxybenzoic acid, 3-hydroxybenzoic acid, 3-hydroxy-2-naphthoic acid, 1-hydroxy-2naphthoic acid, lactobionic acid, 3'-adenylic acid, 5'-adenylic acid, mucic acid, galactaric acid, pantothenic acid, pectic acid, polygalacturonic acid, 5-sulfosalicylic acid, 1,2,3,6-tetrahydro-1,3-dimethyl-2,6-dioxopurine-7-propanesulfonic acid, terephthalic acid, 1-hydroxy-2naphthoic acid, and combinations thereof. In some embodiments, in conjunction with other above or below embodiments, pH modifying agents include, for example, maleic acid, citric acid, malic acid, fumaric acid, sulfuric acid, tartaric acid, lactoic acid, salicylic acid, aspartic acid, aminosalicylic acid, malonic acid, glutamic acid, and combinations thereof. In some embodiments, in conjunction with other above or below embodiments, the pH modifying agent comprises fumaric acid, tartaric acid, glutamic acid, or a combination thereof.

In some embodiments, in conjunction with other above or below embodiments, pH modifying agent includes maleic acid, citric acid, tartaric acid, pamoic acid, fumaric acid, salicylic acid, 2,6-diaminohexanoic acid, camphorsulfonic acid, glycerophosphoric acid, 2-hydroxyethanesulfonic acid, isethionic acid, succinic acid, carbonic acid, p-toluenesulfonic acid, aspartic acid, 8-chlorotheophylline, benezenesulfonic acid, malic acid, orotic acid, oxalic acid, benzoic acid, 2-naphthalenesulfonic acid, stearic acid, adipic acid, p-amino-salicylic acid, 5-aminoslicylic acid, ascorbic acid, sulfuric acid, cyclamic acid, sodium lauryl sulfate, glucoheptonic acid, glucuronic acid, glycine, sulfuric acid, mandelic acid, 1,5-naphthalenedisulfonic acid, nicotinic acid, oleic acid, 2-oxoglutaric acid, pyridoxal 5-phosphate, undecanoic acid, p-acetamidobenzoic acid, o-acetamidobenzoic acid, m-acetamidobenzoic acid, N-acetyl-L-aspartic acid, camphoric acid, dehydrocholic acid, malonic acid, edetic acid, ethylenediainetetraacetic acid, ethylsulf uric acid, hydroxyphenylbenzoylbenzoic acid, glutamic acid, glycyrrhizic acid, 4-hexylresorcinol, hippuric acid, p-phenolsulfonic acid, 4-hydroxybenzoic acid, 3-hydroxybenzoic acid, 3-hydroxy-2-naphthoic acid, 1-hydroxy-2naphthoic acid, lactobionic acid, 3'-adenylic acid, 5'-adenylic acid, mucic acid, galactaric acid, pantothenic acid, pectic acid, polygalacturonic acid, 5-sulfosalicylic acid, 1,2,3,6-tetrahydro-1,3-dimethyl-2,6-dioxopurine-7-propanesulfonic acid, terephthalic acid, 1-hydroxy-2naphthoic acid, and combinations thereof.

In some embodiments, in conjunction with other above or below embodiments, the pH modifying agent is selected from maleic acid, citric acid, malic acid, fumaric acid, sulfuric acid, tartaric acid, lactoic acid, salicylic acid, aspartic acid, aminosalicylic acid, malonic acid, glutamic acid, and any combination thereof.

In some embodiments, in conjunction with other above or below embodiments, fumaric acid is used as the pH modifying agent as it is less hygroscopic and more compatible with omecamtiv mecarbil dihydrochloride hydrate than citric acid, resulting in less or no active form transformation and no changes in tablet appearance when stored at about 40° C./75% RH for about 6 months, leading to improved final product quality. Additionally, fumaric acid is more acidic (by about 2-fold) than citric acid. Therefore, it is more efficient, i.e., about 1:1 weight ratio to active instead of about 2:1, to use fumaric acid to modulate the microenvironmental pH to enhance omecamtiv mecarbil release at neutral environment. Fumaric acid also has a very slow dissolution rate. As a result, fumaric acid will stay in the tablet longer and maintain the low micro-environmental pH better, resulting in more complete release of omecamtiv mecarbil within about 24 hours.

As used herein, the term "fillers" refers to one or more substances that can be added to components of a pharmaceutical composition to increase bulk weight of the material to be formulated, e.g. tabletted, in order to achieve the desired weight. Fillers include but are not limited to starches, lactose, mannitol (such as Pearlitol™ SD 200), cellulose derivatives, calcium phosphate, sugar and the like.

Different grades of lactose include, but are not limited, to lactose monohydrate, lactose DT (direct tabletting), lactose anhydrous, Flowlac™ (available from Meggle products), Pharmatose™ (available from DMV) and others. Different grades of starches include, but are not limited to, maize starch, potato starch, rice starch, wheat starch, pregelatinized starch (commercially available as PCS PC10 from Signet Chemical Corporation) and Starch 1500, Starch 1500 LM grade (low moisture content grade) from Colorcon, fully pregelatinized starch (commercially available as National 78-1551 from Essex Grain Products) and others. Different cellulose compounds that can be used include crystalline cellulose and powdered cellulose. Examples of crystalline cellulose products include but are not limited to CEOLUS™ KG801, Avicel™ PH 101, PH102, PH301, PH302 and PH-F20, microcrystalline cellulose 114, and microcrystalline cellulose 112. Other useful fillers include, but are not limited to, carmellose, sugar alcohols such as mannitol, sorbitol and xylitol, calcium carbonate, magnesium carbonate, dibasic calcium phosphate, and tribasic calcium phosphate.

In some embodiments, in conjunction with other above or below embodiments, the filler is selected from starch, lactose, mannitol (such as Pearlitol™ SD 200), cellulose derivatives, calcium phosphate, and a sugar.

In some embodiments, in conjunction with other above or below embodiments, the filler is lactose anhydrous or lactose monohydrate. In some embodiments, in conjunction with other above or below embodiments, the filler is lactose DT, Flowlac™, or Pharmatose™'

In some embodiments, in conjunction with other above or below embodiments, the filler is maize starch, potato starch, rice starch, wheat starch, pregelatinized starch (such as Starch 1500 or Starch 1500 LM grade (low moisture content grade)), or fully pregelatinized starch.

In some embodiments, in conjunction with other above or below embodiments, the filler is microcrystalline cellulose, such as CEOLUS™ KG801, Avicel™ PH 101, PH102, PH301, PH302 and PH-F20, microcrystalline cellulose 114, or microcrystalline cellulose 112.

In some embodiments, in conjunction with other above or below embodiments, the filler is carmellose, mannitol, sorbitol, xylitol, calcium carbonate, magnesium carbonate, dibasic calcium phosphate, or tribasic calcium phosphate.

As used herein, the term "lubricants" refers to one or more substances that can be added to components of the present compositions to reduce sticking by a solid formulation to the equipment used for production of a unit doss form. Lubricants include stearic acid, hydrogenated vegetable oils, hydrogenated soybean oil and hydrogenated soybean oil & castor wax, stearyl alcohol, leucine, polyethylene glycol, magnesium stearate, glycerylmonostearate, stearic acid, glycerybehenate, polyethylene glycol, ethylene oxide polymers, sodium lauryl sulfate, magnesium lauryl sulfate, sodium oleate, sodium stearyl fumarate, DL-leucine, colloidal silica, and mixtures thereof.

In some embodiments, in conjunction with other above or below embodiments, the lubricant is stearic acid, hydrogenated vegetable oil, hydrogenated soybean oil, hydrogenated soybean oil, castor wax, stearyl alcohol, leucine, polyethylene glycol, magnesium stearate, glycerylmonostearate, stearic acid, glycerybehenate, polyethylene glycol, ethylene oxide polymers, sodium lauryl sulfate, magnesium lauryl sulfate, sodium oleate, sodium stearyl fumarate, DL-leucine, colloidal silica, or any mixture thereof.

Swellable Core Formulations

Provided herein are pharmaceutical formulations comprising: a drug layer comprising omecamtiv mecarbil as a salt or crystal form as disclosed herein; a sweller layer; and a semi-permeable membrane coating having at least one delivery port.

Further provided are formulations comprising a drug layer comprising:
omecamtiv mecarbil as a salt or crystal form as disclosed herein;
a drug layer polymer; and
a lubricant;
a sweller layer comprising:
a sweller layer polymer;
an osmotic agent;
a diluent; and
a lubricant; and
a semi-permeable membrane coating having at least one delivery port comprising:
an insoluble polymer; and
a pore forming polymer.

In some embodiments, in conjunction with other above or below embodiments, the pharmaceutical formulation comprises:
a drug layer comprising: 10-20 (w/w %) omecamtiv mecarbil salt or crystal form; 40-60 (w/w %) polyethylene oxide; and 0-2% (w/w %) lubricant;
a sweller layer comprising: 12-30 (w/w %) polyethylene oxide; 2-10 (w/w %) an osmotic agent; 1-8 (w/w %) microcrystalline cellulose; and 0.1-2 (w/w %) lubricant; and
a semi-permeable membrane having at least one delivery port comprising: 5-15 (w/w %) cellulose acetate; 0.3-5 (w/w %) polyethylene glycol.

In some embodiments, in conjunction with other above or below embodiments, the pharmaceutical formulation comprises:
a drug layer comprising: 14-17 (w/w %) omecamtiv mecarbil salt or crystal form; 48-55 (w/w %) polyethylene oxide; and 0.1-0.5% (w/w %) lubricant;
a sweller layer comprising: 18-25 (w/w %) polyethylene oxide; 4-9 (w/w %) an osmotic agent; 3-6 (w/w %) microcrystalline cellulose; and 0.1-0.5 (w/w %) lubricant; and
a semi-permeable membrane having at least one delivery port comprising: 8-10 (w/w %) cellulose acetate; 0.5-3 (w/w %) polyethylene glycol.

In some embodiments, in conjunction with other above or below embodiments, the pharmaceutical formulation comprises:
a drug layer comprising: 10-20 (w/w %) omecamtiv mecarbil salt or crystal form; 40-60 (w/w %) polyethylene oxide; and 0-2% (w/w %) magnesium stearate;
a sweller layer comprising: 12-30 (w/w %) polyethylene oxide; 2-10 (w/w %) sodium chloride; 1-8 (w/w %) microcrystalline cellulose; and 0.1-2 (w/w %) magnesium stearate; and
a semi-permeable membrane having at least one delivery port comprising: 5-15 (w/w %) cellulose acetate; 0.3-5 (w/w %) polyethylene glycol 3350.

In some embodiments, in conjunction with other above or below embodiments, the pharmaceutical formulation comprises:
a drug layer comprising: 15-16 (w/w %) omecamtiv mecarbil salt or crystal form; 50-52 (w/w %) PolyOx™ WSR N-80; and 0.1-0.5% (w/w %) magnesium stearate;
a sweller layer comprising: 20-23 (w/w %) PolyOx™ WSR Coagulant; 4-9 (w/w %) sodium chloride; 3-6 (w/w %) Avicel PH 200; and 0.1-0.5 (w/w %) lubricant; and
a semi-permeable membrane having at least one delivery port comprising: 8-10 (w/w %) cellulose acetate; 0.5-3 (w/w %) polyethylene glycol 3350.

In some embodiments, in conjunction with other above or below embodiments, the pharmaceutical formulation comprises:
a drug layer comprising: 15-16 (w/w %) omecamtiv mecarbil salt or crystal form; 50-52 (w/w %) PolyOx™ WSR N-80; and 0.1-0.5% (w/w %) magnesium stearate;
a sweller layer comprising: 20-23 (w/w %) PolyOx™ WSR Coagulant; 4-9 (w/w %) sodium chloride; 3-6 (w/w %) Avicel PH 200; and 0.1-0.5 (w/w %) lubricant; and
a semi-permeable membrane having at least one delivery port comprising: 8-9 (w/w %) cellulose acetate; 2-3 (w/w %) polyethylene glycol 3350.

In some embodiments, in conjunction with other above or below embodiments, the pharmaceutical formulation comprises:
a drug layer comprising: 15-16 (w/w %) omecamtiv mecarbil salt or crystal form; 50-52 (w/w %) PolyOx™ WSR N-80; and 0.1-0.5% (w/w %) magnesium stearate;
a sweller layer comprising: 20-23 (w/w %) PolyOx™ WSR Coagulant; 4-9 (w/w %) sodium chloride; 3-6 (w/w %) Avicel PH 200; and 0.1-0.5 (w/w %) lubricant; and
a semi-permeable membrane having at least one delivery port comprising: 9-10 (w/w %) cellulose acetate; 0.5-2 (w/w %) polyethylene glycol 3350.

Methods of Use

The omecamtiv mecarbil salt or crystal forms disclosed herein, or the pharmaceutical compositions described herein, may be used in the treatment or prevention of heart failure, including but not limited to: acute (or decompensated) congestive heart failure, and chronic congestive heart failure; particularly diseases associated with systolic heart dysfunction.

Also provided herein are methods of treating or preventing heart failure in a subject in need thereof comprising administering to the subject one or more of the omecamtiv mecarbil salt or crystal forms disclosed herein, or one or more of the pharmaceutical compositions described herein in an amount effective to treat or prevent heart failure. Further provided are methods for the use of the disclosed salts and crystal forms of omecamtiv mecarbil, or compositions thereof, for the treatment or prevention of heart failure, including but not limited to: acute (or decompensated) congestive heart failure, and chronic congestive heart failure; particularly diseases associated with systolic heart dysfunction.

Also provided herein is the use of the omecamtiv mecarbil salt or crystal forms disclosed herein, or the pharmaceutical compositions described herein, in the manufacture of a medicament for the treatment or prevention of heart failure. In some embodiments, the present disclosure provides use of the omecamtiv mecarbil salt or crystal forms disclosed herein, or the pharmaceutical compositions described herein, in the manufacture of a medicament for the treatment of acute (or decompensated) congestive heart failure, and chronic congestive heart failure; particularly diseases associated with systolic heart dysfunction.

"Treatment" or "treating" includes one or more of: a) inhibiting a disease or disorder; b) slowing or arresting the development of clinical symptoms of a disease or disorder; and/or c) relieving a disease or disorder, that is, causing the regression of clinical symptoms. The term covers both complete and partial reduction of the condition or disorder, and complete or partial reduction of clinical symptoms of a disease or disorder. Thus, the omecamtiv mecarbil salt or crystal forms described herein, or the pharmaceutical compositions described herein may prevent an existing disease or disorder from worsening, assist in the management of the disease or disorder, or reduce or eliminate the disease or disorder. "Prevention," that is, causing the clinical symptoms of the disease or disorder not to develop, includes the prophylactic administration of a pharmaceutical formulation described herein to a subject (i.e., an animal, preferably a mammal, most preferably a human) believed to be in need of preventative treatment, such as, for example, chronic heart failure.

EXAMPLES

Methods
X-Ray Powder Diffraction
Procedure A: XRPD analysis was carried out on a PANalytical X'pert pro, scanning the samples between 3 and 35° 2θ. The material was gently ground to release any agglomerates and loaded onto a multi-well plate with Kapton or Mylar polymer film to support the sample. The multi-well plate was then placed into the diffractometer and analyzed using Cu K radiation ($\alpha 1 \lambda = 1.54060$ Å; $\alpha 2 = 1.54443$ Å; $\beta = 1.39225$ Å; $\alpha 1:\alpha 2$ ratio=0.5) running in transmission mode (step size 0.0130° 2θ) using 40 kV/40 mA generator settings.

Procedure B: XRPD analysis was carried out on a PANalytical X'pert pro, scanning the samples between 3 and 40° 2θ. The material was loaded onto a zero background sample holder then placed into the diffractometer on a spinning stage at 1 rotation per second and analyzed using Cu K radiation ($\alpha 1 \lambda = 1.54060$ Å; $\alpha 2 = 1.54443$ Å; $\beta = 1.39225$ Å; $\alpha 1:\alpha 2$ ratio=0.5) running in transmission mode (step size 0.0167° 2θ) using 45 kV/40 mA generator settings.

Procedure C: X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single GObel multilayer mirror coupled with a pinhole collimator of 0.3 mm. The beam divergence, i.e. the effective size of the X-ray beam on the sample, was approximately 4 mm. A θ-θ continuous scan mode was employed with a sample—detector distance of 20 cm which gives an effective 2θ range of 3.2°-29.7°. Typically the sample would be exposed to the X-ray beam for 120 seconds. Ambient conditions. Samples run under ambient conditions were prepared as flat plate specimens using powder as received with and without grinding. Approximately 1-2 mg of the sample was lightly pressed on a glass slide to obtain a flat surface.

Differential Scanning Calorimetry (DSC)
Procedure A: Thermal properties were characterized using a DSC Q1000 or DSC Q100 model, TA Instruments, differential scanning calorimetry and a Q500, TA Instruments, thermogravimetric analyzer. Data analysis was performed utilizing Universal Analysis 2000, TA Instruments. Heating rates of 1, 10 and 100° C./min were used over a variety of temperature ranges for differential scanning calorimetry and thermogravimetric analysis. Samples ranging from 1-5 mg were prepared in crimped, hermetic or open aluminum pans for DSC analysis.

Procedure B: DSC data were collected on a TA Instruments Q2000 equipped with a 50 position autosampler. The instrument was calibrated for energy and temperature calibration using certified indium. Typically 0.5-3 mg of each sample, in a pin-holed aluminum pan, was heated at 10° C./min from 25° C. to 350° C. A nitrogen purge at 50 ml/min was maintained over the sample. The instrument control software was Thermal Advantage v4.6.6 and the data were analyzed using Universal Analysis v4.3A.

Thermal Gravimetric/Differential Thermal Analysis (TG/DTA)
Approximately 5 mg of material was weighed into an open aluminum pan and loaded into a simultaneous thermogravimetric/differential thermal analyzer (TG/DTA) and held at room temperature. The sample was then heated at a rate of 10° C./min from 20° C. to 300° C. during which time the change in sample weight was recorded along with any differential thermal events (DTA). Nitrogen was used as the purge gas at a flow rate of 300 cm³/min.

Thermal Gravimetric Analysis
Procedure A: Thermograms were collected on a TA Instruments Q500 thermogravimetric analyzer. Samples were loaded onto a platinum pan, 1-10 mg, and heated at 10° C./min from ambient to 300° C.

Procedure B: TGA data were collected on a TA Instruments Q500 TGA, equipped with a 16 position auto-sampler. The instrument was temperature calibrated using certified Alumel. Typically 5-30 mg of each sample was loaded onto a pre-tared platinum crucible and aluminum DSC pan, and was heated at 10° C./min from ambient temperature to 350° C. A nitrogen purge at 60 ml/min was maintained over the sample. The instrument control software was Thermal Advantage v4.6.6 and the data were analyzed using Universal Analysis v4.3A.

Moisture Sorption

Moisture balance was collected using a dynamic vapor sorption (DVS) analyzer. Relative humidity (RH) was set to 0, 5, 15, 25, 35, 45, 55, 65, 75, 85 and 95% RH for 2 sorption/desorption cycles at 25° C. Equilibration criteria was set at 0.001% weight. Approximately 10 mg of sample was used.

Solubility

An excess of solid was added to water, pH 1.0 or pH 4.5 buffer to produce a suspension and dispersed for at least 24 at room temperature. Suspensions were filtered.

Filtrate was analyzed by HPLC-UV and compared against a standard curve to determine the solution concentration of the crystal form.

Experimental Section

Free base crystalline form III: Procedure A—prepared by adding 429 mg of omecamtiv mecarbil to 20 mL of 2-propanol and 20 mL of water then heating to 50° C. to dissolve then precipitate with 200 mL of water.

Procedure B—prepared during a solubility screen from 7 different solvents (2-BuOAc slurry, Cumene slurry, Isopropyl acetate slurry, MTBE slurry, heptane slurry, tBuOAc slurry or toluene slurry). 10 mg of free base was placed in a vial and 50 µL aliquots for the first 300 µL, 100 µL thereafter (up to 1 mL), of the solvents were added to the vial. Between each addition the mixture was checked for dissolution and if no dissolution was apparent the mixture was heated to ca. 50° C. and checked again. This procedure was continued until dissolution was observed or until 100 volumes of solvent had been added. If no dissolution occurred the solid was filtered and an XRPD collected. If dissolution occurred, the cap was removed to allow evaporation of the solvent and an XRPD of the remaining solid was collected. Free base crystalline form III was then reproduced from a slurry in cumene, isopropyl acetate, MTBE or tBuOAc by adding 60 mg of lyophilized free base to the solvent and gently heating to about 40° C.

The omecamtiv mecarbil free base crystalline form III was characterized by an XRPD pattern comprising peaks in Table 1.

TABLE 1

| Pos. [°2 Th.] | FWHM [°2 Th.] | d-spacing [Å] | Height [cts] | Rel. Int. [%] |
|---|---|---|---|---|
| 7.91 | 0.07 | 11.17 | 533.03 | 2.67 |
| 9.50 | 0.08 | 9.31 | 3776.76 | 18.91 |
| 14.27 | 0.10 | 6.21 | 15559.92 | 77.89 |
| 15.25 | 0.08 | 5.81 | 1095.46 | 5.48 |
| 16.10 | 0.10 | 5.51 | 1128.03 | 5.65 |
| 17.78 | 0.10 | 4.99 | 19975.52 | 100.00 |
| 19.06 | 0.10 | 4.66 | 2511.63 | 12.57 |
| 19.64 | 0.20 | 4.52 | 143.81 | 0.72 |
| 20.65 | 0.13 | 4.30 | 421.10 | 2.11 |
| 21.24 | 0.15 | 4.18 | 293.88 | 1.47 |
| 23.01 | 0.10 | 3.87 | 1285.85 | 6.44 |
| 23.87 | 0.10 | 3.73 | 1434.94 | 7.18 |
| 24.83 | 0.13 | 3.59 | 201.27 | 1.01 |
| 25.59 | 0.10 | 3.48 | 226.37 | 1.13 |
| 26.23 | 0.20 | 3.40 | 166.45 | 0.83 |
| 27.23 | 0.20 | 3.28 | 89.66 | 0.45 |
| 28.11 | 0.15 | 3.17 | 805.44 | 4.03 |
| 28.80 | 0.13 | 3.10 | 362.99 | 1.82 |
| 31.01 | 0.17 | 2.88 | 701.54 | 3.51 |
| 31.95 | 0.12 | 2.80 | 844.68 | 4.23 |
| 32.34 | 0.20 | 2.77 | 605.43 | 3.03 |
| 33.67 | 0.13 | 2.66 | 248.53 | 1.24 |
| 34.69 | 0.13 | 2.59 | 293.11 | 1.47 |
| 37.26 | 0.13 | 2.41 | 245.07 | 1.23 |
| 38.73 | 0.23 | 2.33 | 152.34 | 0.76 |

Free base crystalline form IV: was prepared by precipitation of 46 mg of omecamtiv mecarbil from 2 mL THF with 2 mL n-butyl ether.

The omecamtiv mecarbil free base crystalline form IV was characterized by an XRPD pattern comprising peaks in Table 2.

TABLE 2

| Pos. [°2 Th.] | FWHM [°2 Th.] | d-spacing [Å] | Height [cts] | Rel. Int. [%] |
|---|---|---|---|---|
| 5.18 | 0.07 | 17.04 | 12067.81 | 100.00 |
| 7.42 | 0.10 | 11.91 | 322.11 | 2.67 |
| 7.70 | 0.08 | 11.48 | 416.99 | 3.46 |
| 10.35 | 0.07 | 8.55 | 814.51 | 6.75 |
| 10.81 | 0.10 | 8.19 | 170.45 | 1.41 |
| 14.21 | 0.08 | 6.23 | 789.68 | 6.54 |
| 14.84 | 0.07 | 5.97 | 1276.45 | 10.58 |
| 15.54 | 0.08 | 5.70 | 2686.48 | 22.26 |
| 17.10 | 0.10 | 5.18 | 122.93 | 1.02 |
| 18.10 | 0.10 | 4.90 | 10344.17 | 85.72 |
| 19.92 | 0.08 | 4.46 | 939.94 | 7.79 |
| 20.62 | 0.07 | 4.31 | 802.71 | 6.65 |
| 20.77 | 0.07 | 4.28 | 931.21 | 7.72 |
| 21.70 | 0.08 | 4.10 | 481.64 | 3.99 |
| 22.40 | 0.12 | 3.97 | 418.41 | 3.47 |
| 22.86 | 0.10 | 3.89 | 673.49 | 5.58 |
| 23.09 | 0.08 | 3.85 | 571.53 | 4.74 |
| 24.05 | 0.08 | 3.70 | 774.58 | 6.42 |
| 24.36 | 0.12 | 3.65 | 752.02 | 6.23 |
| 25.20 | 0.10 | 3.53 | 582.91 | 4.83 |
| 25.72 | 0.07 | 3.46 | 378.21 | 3.13 |
| 26.00 | 0.10 | 3.43 | 138.03 | 1.14 |
| 26.68 | 0.27 | 3.34 | 93.44 | 0.77 |
| 27.40 | 0.10 | 3.26 | 400.49 | 3.32 |
| 27.81 | 0.12 | 3.21 | 724.88 | 6.01 |
| 28.18 | 0.10 | 3.17 | 278.71 | 2.31 |
| 28.63 | 0.08 | 3.12 | 399.78 | 3.31 |
| 28.98 | 0.08 | 3.08 | 480.22 | 3.98 |
| 29.42 | 0.10 | 3.04 | 644.30 | 5.34 |
| 30.51 | 0.13 | 2.93 | 247.42 | 2.05 |
| 32.80 | 0.13 | 2.73 | 137.46 | 1.14 |
| 33.98 | 0.20 | 2.64 | 155.02 | 1.28 |
| 35.34 | 0.20 | 2.54 | 147.52 | 1.22 |
| 36.38 | 0.20 | 2.47 | 110.92 | 0.92 |
| 37.12 | 0.20 | 2.42 | 126.42 | 1.05 |

Free base crystalline form V: Procedure A—was prepared by adding 50 mg of omecamtiv mecarbil to 2 mL of THF at 60 C, filtering, then crash cooling by placing sample into an acetone/dry ice bath.

Procedure B—Free base crystalline form V was prepared during a solubility screen from 1,4-dioxane slurry. 10 mg of free base was placed in a Vial and 50 µL aliquots for the first 300 µL, 100 µL thereafter (up to 1 mL), of the solvent was added to the vial. Between each addition the mixture was checked for dissolution and if no dissolution was apparent the mixture was heated to ca. 50° C. and checked again. This procedure was continued until dissolution was observed or until 100 volumes of solvent had been added. If no dissolution occurred the solid was filtered and an XRPD collected. If dissolution occurred, the cap was removed to allow evaporation of the solvent and an XRPD of the remaining solid was collected.

The omecamtiv mecarbil free base crystalline form V was characterized by an XRPD pattern comprising peaks in Table 3.

TABLE 3

| Pos. [°2 Th.] | FWHM [°2 Th.] | d-spacing [Å] | Height [cts] | Rel. Int. [%] |
|---|---|---|---|---|
| 5.40 | 0.10 | 16.37 | 213.79 | 7.88 |
| 7.38 | 0.07 | 11.98 | 470.25 | 17.33 |
| 8.56 | 0.07 | 10.33 | 430.26 | 15.86 |
| 8.93 | 0.08 | 9.91 | 563.71 | 20.78 |
| 9.14 | 0.07 | 9.67 | 392.66 | 14.47 |
| 10.03 | 0.08 | 8.82 | 375.08 | 13.82 |
| 10.73 | 0.13 | 8.25 | 332.70 | 12.26 |
| 11.71 | 0.12 | 7.56 | 840.50 | 30.98 |
| 13.69 | 0.17 | 6.47 | 335.68 | 12.37 |
| 15.08 | 0.18 | 5.88 | 653.88 | 24.10 |
| 16.04 | 0.33 | 5.52 | 105.31 | 3.88 |
| 16.85 | 0.08 | 5.26 | 920.36 | 33.92 |
| 17.85 | 0.13 | 4.97 | 2713.30 | 100.00 |
| 18.28 | 0.10 | 4.85 | 347.67 | 12.81 |
| 18.86 | 0.12 | 4.71 | 1897.24 | 69.92 |
| 20.05 | 0.20 | 4.43 | 1456.16 | 53.67 |
| 20.72 | 0.07 | 4.29 | 659.49 | 24.31 |
| 21.74 | 0.17 | 4.09 | 354.74 | 13.07 |
| 22.83 | 0.27 | 3.90 | 189.17 | 6.97 |
| 23.56 | 0.10 | 3.78 | 1152.90 | 42.49 |
| 24.03 | 0.20 | 3.70 | 645.49 | 23.79 |
| 25.45 | 0.20 | 3.50 | 217.43 | 8.01 |
| 26.23 | 0.10 | 3.40 | 366.63 | 13.51 |
| 27.62 | 0.23 | 3.23 | 654.84 | 24.13 |
| 28.58 | 0.23 | 3.12 | 253.96 | 9.36 |
| 29.85 | 0.27 | 2.99 | 254.72 | 9.39 |
| 32.10 | 0.20 | 2.79 | 233.50 | 8.61 |
| 33.37 | 0.33 | 2.69 | 165.44 | 6.10 |
| 35.47 | 0.27 | 2.53 | 105.15 | 3.88 |
| 37.02 | 0.40 | 2.43 | 122.14 | 4.50 |

Free base crystalline form VI: was prepared by heating free base crystalline form V to 150° C.

The omecamtiv mecarbil free base crystalline form VI was characterized by an XRPD pattern comprising peaks in Table 4.

TABLE 4

| Pos. [°2 Th.] | FWHM [°2 Th.] | d-spacing [Å] | Height [cts] | Rel. Int. [%] |
|---|---|---|---|---|
| 9.07 | 0.08 | 9.75 | 895.54 | 31.71 |
| 14.28 | 0.13 | 6.20 | 147.01 | 5.20 |
| 15.19 | 0.20 | 5.83 | 42.70 | 1.51 |
| 15.88 | 0.12 | 5.58 | 539.11 | 19.09 |
| 16.67 | 0.08 | 5.32 | 796.74 | 28.21 |
| 17.81 | 0.08 | 4.98 | 1094.93 | 38.77 |
| 18.18 | 0.17 | 4.88 | 2824.51 | 100.00 |
| 18.80 | 0.12 | 4.72 | 850.75 | 30.12 |
| 19.70 | 0.10 | 4.51 | 1045.62 | 37.02 |
| 20.23 | 0.13 | 4.39 | 185.58 | 6.57 |
| 20.89 | 0.10 | 4.25 | 1310.32 | 46.39 |
| 21.28 | 0.12 | 4.18 | 925.51 | 32.77 |
| 23.72 | 0.08 | 3.75 | 691.60 | 24.49 |
| 24.26 | 0.08 | 3.67 | 784.97 | 27.79 |
| 26.19 | 0.20 | 3.40 | 146.84 | 5.20 |
| 26.80 | 0.17 | 3.33 | 235.58 | 8.34 |
| 27.59 | 0.13 | 3.23 | 347.69 | 12.31 |
| 28.90 | 0.33 | 3.09 | 163.33 | 5.78 |
| 29.82 | 0.12 | 3.00 | 368.54 | 13.05 |

Free base crystalline form VII: was prepared during a solubility screen from water slurry. 10 mg of free base was placed in a vial and 50 µL aliquots for the first 300 µL, 1004 thereafter (up to 1 mL), of water was added to the vial. Between each addition the mixture was checked for dissolution and if no dissolution was apparent the mixture was heated to ca. 50° C. and checked again. This procedure was continued until dissolution was observed or until 100 volumes of solvent had been added. The solid was filtered and an XRPD collected.

The omecamtiv mecarbil free base crystalline form VII was characterized by an XRPD pattern comprising peaks in Table 5.

TABLE 5

| Pos. [°2 Th.] | FWHM [°2 Th.] | d-spacing [Å] | Height [cts] | Rel. Int. [%] |
|---|---|---|---|---|
| 4.37 | 0.08 | 20.24 | 4137.34 | 100.00 |
| 7.84 | 0.13 | 11.27 | 89.35 | 2.16 |
| 8.40 | 0.06 | 10.52 | 285.34 | 6.90 |
| 8.71 | 0.08 | 10.15 | 172.30 | 4.16 |
| 10.81 | 0.15 | 8.19 | 74.73 | 1.81 |
| 13.08 | 0.08 | 6.77 | 387.47 | 9.37 |
| 15.66 | 0.08 | 5.66 | 481.77 | 11.64 |
| 16.83 | 0.10 | 5.27 | 1596.66 | 38.59 |
| 18.92 | 0.10 | 4.69 | 1248.28 | 30.17 |
| 19.61 | 0.09 | 4.53 | 1696.18 | 41.00 |
| 20.32 | 0.05 | 4.37 | 584.96 | 14.14 |
| 20.49 | 0.10 | 4.33 | 961.99 | 23.25 |
| 21.61 | 0.08 | 4.11 | 319.30 | 7.72 |
| 22.26 | 0.10 | 3.99 | 1149.06 | 27.77 |
| 23.22 | 0.08 | 3.83 | 265.13 | 6.41 |
| 23.46 | 0.10 | 3.79 | 299.05 | 7.23 |
| 24.21 | 0.13 | 3.68 | 1205.74 | 29.14 |
| 25.41 | 0.05 | 3.51 | 1016.23 | 24.56 |
| 27.58 | 0.13 | 3.23 | 318.93 | 7.71 |
| 29.53 | 0.15 | 3.02 | 279.27 | 6.75 |
| 30.13 | 0.15 | 2.97 | 221.71 | 5.36 |
| 31.32 | 0.61 | 2.86 | 95.23 | 2.30 |

The XRPD peaks unique to each of the free base crystalline forms III-VII disclosed herein are shown in Table 6.

TABLE 6

| Free Base Crystalline Form | Peaks Unique to Each Form (KA1 °) | | | | | |
|---|---|---|---|---|---|---|
| Form III | 9.50 | 19.06 | 23.01 | | | |
| Form IV | 5.18 | 10.35 | 14.84 | 15.54 | 18.10 | 19.92 |
| Form V | 7.38 | 8.56 | 9.14 | 18.28 | | |
| Form VI | 9.07 | 16.67 | 18.18 | 19.70 | 20.89 | 21.28 |
| Form VII | 8.40 | 8.71 | 13.08 | 15.66 | 19.61 | |

Amorphous hydrochloride salt: An amorphous bis-hydrochloride salt was prepared by dissolving 0.505 g of bis-hydrochloride monohydrate salt Form A in 20 mL of water, flash frozen in liquid nitrogen and lyophilized. Chloride analysis gave a result of 14.6% Cl which is in agreement with a bis-hydrochloride. Thermal analysis indicates approximately a 7.9% weight loss during heating due to loss of water and a Tg around 149° C. Vapor sorption studies show that the amorphous form is hygroscopic and converts to the crystalline bis-hydrochloride monohydrate Form A.

Ethane Sulfonate crystalline salt: was prepared in a primary salt screen. A 2 mL aliquot of acetone was added to ~40 mg of free base. 1.05 equivalents of ethane sulfonate as a 1M solution in THF were added and the sample was temperature cycled for 3-5 days.

The omecamtiv mecarbil ethane sulfonate crystalline salt was characterized by an XRPD pattern comprising peaks in Table 7.

TABLE 7

| Pos. [°2 Th.] | FWHM [°2 Th.] | d-spacing [Å] | Height [cts] | Rel. Int. [%] |
|---|---|---|---|---|
| 8.61 | 0.10 | 10.27 | 1864.81 | 100.00 |
| 13.61 | 0.15 | 6.51 | 141.09 | 7.57 |
| 16.14 | 0.10 | 5.49 | 1152.97 | 61.83 |

TABLE 7-continued

| Pos. [°2 Th.] | FWHM [°2 Th.] | d-spacing [Å] | Height [cts] | Rel. Int. [%] |
|---|---|---|---|---|
| 16.76 | 0.13 | 5.29 | 825.27 | 44.26 |
| 16.97 | 0.08 | 5.22 | 914.05 | 49.02 |
| 17.23 | 0.13 | 5.15 | 1148.35 | 61.58 |
| 18.35 | 0.15 | 4.84 | 579.44 | 31.07 |
| 19.20 | 0.20 | 4.62 | 710.28 | 38.09 |
| 20.27 | 0.20 | 4.38 | 781.89 | 41.93 |
| 20.73 | 0.08 | 4.28 | 1275.35 | 68.39 |
| 20.96 | 0.10 | 4.24 | 1275.82 | 68.42 |
| 23.73 | 0.20 | 3.75 | 494.48 | 26.52 |
| 25.24 | 0.15 | 3.53 | 262.30 | 14.07 |
| 25.95 | 0.15 | 3.43 | 442.47 | 23.73 |
| 26.30 | 0.10 | 3.39 | 512.57 | 27.49 |
| 27.09 | 0.20 | 3.29 | 204.40 | 10.96 |
| 29.01 | 0.41 | 3.08 | 74.97 | 4.02 |

Bis-fumarate crystalline salt form A: was prepared by dissolving 1 equivalent of free base (4.104 g) and 2.1 equivalents of fumaric acid (as 84 mL in a 95% EtOH/water solution) in 20 mL of 90% THF in water then distilling under house vacuum at 50° C. An additional 92 mL of water and mono-fumarate Form A seed were added to induce precipitation.

The omecamtiv mecarbil bis-fumarate crystalline salt form A was characterized by an XRPD pattern comprising peaks in Table 8.

TABLE 8

| Pos. [°2 Th.] | FWHM [°2 Th.] | d-spacing [Å] | Height [cts] | Rel. Int. [%] |
|---|---|---|---|---|
| 5.64 | 0.18 | 15.67 | 1058.97 | 74.12 |
| 8.83 | 0.27 | 10.01 | 92.99 | 6.51 |
| 10.80 | 0.17 | 8.20 | 144.21 | 10.09 |
| 12.04 | 0.20 | 7.35 | 271.90 | 19.03 |
| 15.76 | 0.17 | 5.62 | 249.66 | 17.47 |
| 16.40 | 0.10 | 5.41 | 417.23 | 29.20 |
| 16.80 | 0.13 | 5.28 | 1428.74 | 100.00 |
| 17.94 | 0.20 | 4.94 | 167.95 | 11.76 |
| 18.32 | 0.13 | 4.84 | 247.68 | 17.34 |
| 19.38 | 0.17 | 4.58 | 130.62 | 9.14 |
| 19.87 | 0.13 | 4.47 | 159.85 | 11.19 |
| 20.61 | 0.27 | 4.31 | 198.11 | 13.87 |
| 21.55 | 0.13 | 4.12 | 445.40 | 31.17 |
| 21.87 | 0.13 | 4.06 | 589.24 | 41.24 |
| 22.03 | 0.13 | 4.04 | 583.89 | 40.87 |
| 22.88 | 0.13 | 3.89 | 300.01 | 21.00 |
| 23.61 | 0.10 | 3.77 | 1008.70 | 70.60 |
| 23.87 | 0.13 | 3.73 | 1042.62 | 72.97 |
| 25.07 | 0.27 | 3.55 | 109.91 | 7.69 |
| 26.01 | 0.18 | 3.43 | 795.76 | 55.70 |
| 27.20 | 0.27 | 3.28 | 900.61 | 63.04 |
| 27.86 | 0.23 | 3.20 | 317.54 | 22.23 |
| 29.55 | 0.27 | 3.02 | 61.88 | 4.33 |
| 31.04 | 0.20 | 2.88 | 103.03 | 7.21 |
| 32.73 | 0.27 | 2.74 | 145.12 | 10.16 |
| 35.00 | 0.20 | 2.56 | 80.10 | 5.61 |
| 36.01 | 0.27 | 2.49 | 62.22 | 4.35 |
| 36.54 | 0.23 | 2.46 | 138.74 | 9.71 |

Bis-fumarate crystalline salt form B: was prepared during DVS cycle of bis-fumarate Form A.

The omecamtiv mecarbil bis-fumarate crystalline salt form B was characterized by an XRPD pattern comprising peaks in Table 9.

TABLE 9

| Pos. [°2 Th.] | FWHM [°2 Th.] | d-spacing [Å] | Height [cts] | Rel. Int. [%] |
|---|---|---|---|---|
| 5.68 | 0.20 | 15.57 | 557.86 | 53.41 |
| 6.11 | 0.15 | 14.47 | 941.86 | 90.18 |
| 9.69 | 0.07 | 9.13 | 213.36 | 20.43 |
| 11.43 | 0.17 | 7.74 | 195.35 | 18.70 |
| 12.92 | 0.10 | 6.85 | 428.18 | 41.00 |
| 13.13 | 0.08 | 6.74 | 739.41 | 70.80 |
| 14.34 | 0.40 | 6.18 | 52.05 | 4.98 |
| 15.95 | 0.20 | 5.56 | 656.27 | 62.84 |
| 16.83 | 0.23 | 5.27 | 142.59 | 13.65 |
| 17.22 | 0.20 | 5.15 | 178.09 | 17.05 |
| 18.08 | 0.20 | 4.91 | 494.57 | 47.35 |
| 19.05 | 0.20 | 4.66 | 135.39 | 12.96 |
| 19.52 | 0.33 | 4.55 | 99.22 | 9.50 |
| 20.81 | 0.20 | 4.27 | 362.18 | 34.68 |
| 22.47 | 0.15 | 3.96 | 547.41 | 52.41 |
| 22.95 | 0.27 | 3.87 | 553.11 | 52.96 |
| 24.53 | 0.20 | 3.63 | 147.89 | 14.16 |
| 26.04 | 0.20 | 3.42 | 434.11 | 41.57 |
| 27.01 | 0.13 | 3.30 | 1044.39 | 100.00 |
| 28.43 | 0.13 | 3.14 | 313.18 | 29.99 |
| 31.37 | 0.27 | 2.85 | 59.28 | 5.68 |
| 32.32 | 0.23 | 2.77 | 49.90 | 4.78 |
| 34.89 | 0.40 | 2.57 | 65.58 | 6.28 |
| 35.89 | 0.23 | 2.50 | 54.73 | 5.24 |
| 37.16 | 0.20 | 2.42 | 68.51 | 6.56 |

Bis-fumarate crystalline salt form C: was prepared from slurry of bis-fumarate Forms A and B in 2 mL water at RT. Water solubility was determined to be 13.7 mg/mL (pH 3.1).

The omecamtiv mecarbil bis-fumarate crystalline salt form C was characterized by an XRPD pattern comprising peaks in Table 10.

TABLE 10

| Pos. [°2 Th.] | FWHM [°2 Th.] | d-spacing [Å] | Height [cts] | Rel. Int. [%] |
|---|---|---|---|---|
| 5.88 | 0.17 | 15.03 | 5167.95 | 100.00 |
| 10.38 | 0.54 | 8.53 | 75.90 | 1.47 |
| 10.70 | 0.10 | 8.27 | 162.04 | 3.14 |
| 11.56 | 0.12 | 7.65 | 325.84 | 6.30 |
| 12.74 | 0.10 | 6.95 | 1330.99 | 25.75 |
| 13.56 | 0.12 | 6.53 | 529.65 | 10.25 |
| 15.33 | 0.13 | 5.78 | 181.25 | 3.51 |
| 16.85 | 0.10 | 5.26 | 336.53 | 6.51 |
| 17.15 | 0.12 | 5.17 | 1259.92 | 24.38 |
| 17.63 | 0.10 | 5.03 | 864.50 | 16.73 |
| 18.79 | 0.12 | 4.72 | 557.14 | 10.78 |
| 19.52 | 0.12 | 4.55 | 229.88 | 4.45 |
| 20.29 | 0.12 | 4.38 | 906.12 | 17.53 |
| 20.60 | 0.12 | 4.31 | 510.74 | 9.88 |
| 20.86 | 0.10 | 4.26 | 460.43 | 8.91 |
| 21.47 | 0.07 | 4.14 | 668.33 | 12.93 |
| 21.77 | 0.08 | 4.08 | 697.87 | 13.50 |
| 22.21 | 0.13 | 4.00 | 865.69 | 16.75 |
| 22.92 | 0.13 | 3.88 | 864.48 | 16.73 |
| 23.58 | 0.13 | 3.77 | 792.02 | 15.33 |
| 24.15 | 0.07 | 3.68 | 600.60 | 11.62 |
| 24.55 | 0.13 | 3.63 | 373.42 | 7.23 |
| 25.41 | 0.17 | 3.51 | 1064.69 | 20.60 |
| 26.37 | 0.12 | 3.38 | 254.11 | 4.92 |
| 26.78 | 0.12 | 3.33 | 1601.63 | 30.99 |
| 26.86 | 0.06 | 3.33 | 1640.39 | 31.74 |
| 27.31 | 0.12 | 3.26 | 450.94 | 8.73 |
| 27.83 | 0.16 | 3.20 | 618.62 | 11.97 |
| 28.97 | 0.06 | 3.08 | 340.41 | 6.59 |
| 29.93 | 0.24 | 2.98 | 283.61 | 5.49 |
| 30.37 | 0.24 | 2.94 | 102.99 | 1.99 |
| 31.97 | 0.20 | 2.80 | 88.93 | 1.72 |
| 32.37 | 0.29 | 2.76 | 67.32 | 1.30 |
| 33.10 | 0.16 | 2.70 | 128.77 | 2.49 |
| 34.02 | 0.33 | 2.63 | 173.14 | 3.35 |
| 35.76 | 0.29 | 2.51 | 160.08 | 3.10 |

TABLE 10-continued

| Pos. [°2 Th.] | FWHM [°2 Th.] | d-spacing [Å] | Height [cts] | Rel. Int. [%] |
|---|---|---|---|---|
| 38.14 | 0.24 | 2.36 | 76.60 | 1.48 |
| 38.88 | 0.33 | 2.31 | 187.08 | 3.62 |
| 39.55 | 0.20 | 2.28 | 104.38 | 2.02 |

Mono-fumarate crystalline salt form D: was first prepared during a high throughput screen by adding 0.3 mL of a 0.05M solution of free base in methanol and 0.3 mL of a fumaric acid 0.05M solution in methanol to a glass plate then solvent was evaporated then 0.4 mL of solvent (water, 0.001 M HCl aq, acetone, acetonitrile or hexanes) was added and heated to 50° C. for 4 hours then evaporated.

The omecamtiv mecarbil mono-fumarate crystalline salt form D was characterized by an XRPD pattern comprising peaks in Table 11.

TABLE 11

| Pos. [°2 Th.] | FWHM [°2 Th.] | d-spacing [Å] | Height [cts] | Rel. Int. [%] |
|---|---|---|---|---|
| 8.01 | 0.09 | 11.04 | 102.83 | 59.94 |
| 12.11 | 0.11 | 7.31 | 72.99 | 42.55 |
| 12.67 | 0.13 | 6.99 | 50.43 | 29.40 |
| 14.46 | 0.13 | 6.12 | 83.35 | 48.59 |
| 15.20 | 0.19 | 5.83 | 55.38 | 32.28 |
| 16.01 | 0.19 | 5.54 | 50.34 | 29.34 |
| 16.57 | 0.11 | 5.35 | 76.69 | 44.71 |
| 17.04 | 0.14 | 5.20 | 32.05 | 18.69 |
| 17.63 | 0.16 | 5.03 | 37.88 | 22.08 |
| 18.48 | 0.16 | 4.80 | 16.35 | 9.53 |
| 20.02 | 0.11 | 4.43 | 34.71 | 20.23 |
| 20.51 | 0.22 | 4.33 | 31.27 | 18.23 |
| 21.75 | 0.16 | 4.09 | 37.60 | 21.92 |
| 22.86 | 0.19 | 3.89 | 18.19 | 10.60 |
| 24.25 | 0.13 | 3.67 | 171.54 | 100.00 |
| 24.97 | 0.19 | 3.57 | 82.03 | 47.82 |
| 25.84 | 0.13 | 3.45 | 41.01 | 23.91 |
| 26.17 | 0.16 | 3.41 | 74.19 | 43.25 |
| 27.10 | 0.13 | 3.29 | 37.05 | 21.60 |
| 27.97 | 0.19 | 3.19 | 21.24 | 12.38 |
| 28.61 | 0.19 | 3.12 | 11.11 | 6.48 |
| 29.21 | 0.16 | 3.06 | 37.43 | 21.82 |
| 30.69 | 0.25 | 2.91 | 10.74 | 6.26 |
| 34.70 | 0.50 | 2.59 | 7.97 | 4.64 |
| 37.41 | 0.19 | 2.40 | 11.12 | 6.48 |
| 38.48 | 0.38 | 2.34 | 6.46 | 3.77 |

The XRPD peaks unique to each of the fumarate crystalline salts forms A-D disclosed herein are shown in Table 12.

TABLE 12

| Fumarate Form | Peaks Unique to Each Form (°2Th.) | | | | |
|---|---|---|---|---|---|
| Form A | 5.64 | 15.76 | 22.03 | 23.87 | |
| Form B | 5.68 | 6.11 | 13.13 | 18.08 | 22.47 |
| Form C | 5.88 | 18.79 | 25.41 | 26.86 | |
| Form D | 8.01 | 15.20 | 20.02 | | |

Bis-Maleate crystalline salt form A: Procedure A: was first prepared during a high throughput screen by adding 0.2 mL of a 0.124M solution of free base in methanol and 0.2 mL of a maleic acid 0.25M solution in methanol to a glass plate then solvent was evaporated then 0.2 mL of solvent (water, 0.001 M HCl aq or acetone) was added and heated to 50° C. for 4 hours then evaporated. Salt was scaled up by adding 100 mg free base to an 8 mL vial and 5 mL methanol and gently heating to dissolve. Maleic acid (2 mL of a 0.25M solution in acetone) was added at room temperature. Precipitate was isolated by filtration.

Procedure B—bis-maleate crystalline salt form A was prepared by dissolving 3.011 g of free base (1 eq) and 1.828 g of maleic acid (solution in 8 mL MeOH; 2.1 eq) in 45 mL methanol at 60° C. then cooled to precipitate. Water solubility was determined to be 3.8 mg/mL (pH 3.7).

Procedure C—bis-maleate crystalline salt form A was also prepared in a primary salt screen. A 2 mL aliquot of 2-propanol, THF, acetonitrile, isopropyl acetate or acetone was added to ~40 mg of free base. 1.05 equivalents of maleic acid as a 1M solution in THF were added and the sample was temperature cycled for 3-5 days.

The omecamtiv mecarbil bis-maleate crystalline salt form A was characterized by an XRPD pattern comprising peaks in Table 13.

TABLE 13

| Pos. [°2 Th.] | FWHM [°2 Th.] | d-spacing [Å] | Height [cts] | Rel. Int. [%] |
|---|---|---|---|---|
| 3.32 | 0.82 | 26.60 | 267.10 | 3.31 |
| 4.99 | 0.05 | 17.71 | 482.89 | 5.98 |
| 6.60 | 0.08 | 13.38 | 216.56 | 2.68 |
| 6.95 | 0.41 | 12.72 | 56.27 | 0.70 |
| 7.25 | 0.08 | 12.19 | 198.55 | 2.46 |
| 9.17 | 0.15 | 9.64 | 73.48 | 0.91 |
| 9.97 | 0.08 | 8.87 | 7989.17 | 98.97 |
| 10.56 | 0.08 | 8.38 | 1761.58 | 21.82 |
| 12.96 | 0.09 | 6.83 | 311.81 | 3.86 |
| 13.25 | 0.09 | 6.68 | 1227.24 | 15.20 |
| 14.54 | 0.12 | 6.09 | 356.32 | 4.41 |
| 14.83 | 0.08 | 5.98 | 743.84 | 9.21 |
| 15.31 | 0.10 | 5.79 | 8072.29 | 100.00 |
| 15.53 | 0.09 | 5.71 | 2487.57 | 30.82 |
| 16.04 | 0.10 | 5.52 | 6086.12 | 75.40 |
| 16.38 | 0.10 | 5.41 | 2253.00 | 27.91 |
| 17.10 | 0.08 | 5.19 | 675.31 | 8.37 |
| 17.44 | 0.12 | 5.08 | 3071.51 | 38.05 |
| 17.70 | 0.13 | 5.01 | 2667.01 | 33.04 |
| 18.17 | 0.10 | 4.88 | 932.80 | 11.56 |
| 18.45 | 0.10 | 4.81 | 273.07 | 3.38 |
| 19.00 | 0.13 | 4.67 | 2099.18 | 26.00 |
| 19.33 | 0.08 | 4.59 | 392.68 | 4.86 |
| 20.13 | 0.14 | 4.41 | 1667.83 | 20.66 |
| 21.47 | 0.12 | 4.14 | 2989.90 | 37.04 |
| 21.83 | 0.08 | 4.07 | 1329.81 | 16.47 |
| 22.02 | 0.06 | 4.04 | 747.10 | 9.26 |
| 22.31 | 0.10 | 3.98 | 822.83 | 10.19 |
| 22.44 | 0.09 | 3.96 | 1010.70 | 12.52 |
| 23.02 | 0.10 | 3.86 | 347.42 | 4.30 |
| 23.15 | 0.10 | 3.84 | 372.20 | 4.61 |
| 23.58 | 0.13 | 3.77 | 194.06 | 2.40 |
| 24.38 | 0.06 | 3.65 | 1003.21 | 12.43 |
| 24.64 | 0.09 | 3.61 | 876.08 | 10.85 |
| 25.66 | 0.15 | 3.47 | 924.66 | 11.45 |
| 26.66 | 0.13 | 3.34 | 1042.71 | 12.92 |
| 26.96 | 0.13 | 3.31 | 4976.38 | 61.65 |
| 27.83 | 0.13 | 3.21 | 845.81 | 10.48 |
| 28.10 | 0.10 | 3.18 | 293.57 | 3.64 |
| 28.55 | 0.15 | 3.13 | 766.92 | 9.50 |
| 29.31 | 0.08 | 3.05 | 151.67 | 1.88 |
| 30.17 | 0.20 | 2.96 | 186.07 | 2.31 |
| 30.76 | 0.23 | 2.91 | 458.79 | 5.68 |
| 31.67 | 0.13 | 2.83 | 362.78 | 4.49 |
| 32.01 | 0.13 | 2.80 | 453.36 | 5.62 |
| 32.25 | 0.13 | 2.78 | 561.46 | 6.96 |
| 32.67 | 0.18 | 2.74 | 427.72 | 5.30 |
| 33.11 | 0.20 | 2.71 | 342.20 | 4.24 |
| 33.65 | 0.13 | 2.66 | 375.70 | 4.65 |
| 34.17 | 0.10 | 2.62 | 370.55 | 4.59 |
| 34.39 | 0.10 | 2.61 | 643.90 | 7.98 |
| 34.51 | 0.15 | 2.60 | 639.10 | 7.92 |

Bis-malonate crystalline salt: was prepared by dissolving 200.7 mg of free base (1 eq) and 525 μL of malonic acid in methanol (2.1 eq) in 5 mL methanol at 50° C. then 0.5 mL IPAc was added to precipitate then heat cycled twice 40° C./RT. Water solubility was determined to be greater than 62 mg/mL (pH 3.69).

The omecamtiv mecarbil bis-malonate crystalline salt was characterized by an XRPD pattern comprising peaks in Table 14.

TABLE 14

| Pos. [°2 Th.] | FWHM [°2 Th.] | d-spacing [Å] | Height [cts] | Rel. Int. [%] |
|---|---|---|---|---|
| 4.74 | 0.09 | 18.64 | 734.38 | 65.86 |
| 9.30 | 0.13 | 9.51 | 262.93 | 23.58 |
| 11.37 | 0.13 | 7.78 | 1115.14 | 100.00 |
| 13.73 | 0.13 | 6.45 | 154.92 | 13.89 |
| 14.25 | 0.11 | 6.22 | 902.82 | 80.96 |
| 15.13 | 0.16 | 5.86 | 567.42 | 50.88 |
| 15.69 | 0.11 | 5.65 | 94.13 | 8.44 |
| 16.45 | 0.13 | 5.39 | 438.97 | 39.36 |
| 16.83 | 0.13 | 5.27 | 165.27 | 14.82 |
| 18.08 | 0.13 | 4.91 | 552.17 | 49.52 |
| 18.29 | 0.11 | 4.85 | 855.08 | 76.68 |
| 18.88 | 0.16 | 4.70 | 287.13 | 25.75 |
| 19.54 | 0.13 | 4.54 | 232.73 | 20.87 |
| 20.14 | 0.08 | 4.41 | 819.11 | 73.45 |
| 20.77 | 0.11 | 4.28 | 300.42 | 26.94 |
| 21.21 | 0.25 | 4.19 | 192.92 | 17.30 |
| 23.32 | 0.16 | 3.81 | 218.40 | 19.58 |
| 23.87 | 0.13 | 3.73 | 766.34 | 68.72 |
| 24.67 | 0.13 | 3.61 | 193.04 | 17.31 |
| 25.72 | 0.22 | 3.46 | 82.90 | 7.43 |
| 26.51 | 0.22 | 3.36 | 211.46 | 18.96 |
| 27.59 | 0.13 | 3.23 | 520.24 | 46.65 |
| 27.78 | 0.08 | 3.21 | 805.51 | 72.23 |
| 28.01 | 0.20 | 3.19 | 630.55 | 56.54 |
| 28.90 | 0.28 | 3.09 | 273.00 | 24.48 |
| 29.68 | 0.22 | 3.01 | 33.94 | 3.04 |
| 30.18 | 0.22 | 2.96 | 51.90 | 4.65 |
| 33.70 | 0.22 | 2.66 | 96.86 | 8.69 |
| 34.19 | 0.19 | 2.62 | 54.63 | 4.90 |
| 35.52 | 0.22 | 2.53 | 39.53 | 3.54 |
| 36.82 | 0.19 | 2.44 | 42.45 | 3.81 |
| 37.62 | 0.63 | 2.39 | 36.76 | 3.30 |

Mesylate crystalline salt form A: was prepared by dissolving 200.7 mg of free base (1 eq) and 68.1 μL of methanesulfonic acid (2.1 eq) in 5 mL methanol at 50° C., 2 mL IPAc and 5 mL acetone were added to precipitate. Water solubility was determined to be greater than 72 mg/mL (pH 1.39).

The omecamtiv mecarbil mesylate crystalline salt form A was characterized by an XRPD pattern comprising peaks in Table 15.

TABLE 15

| Pos. [°2 Th.] | FWHM [°2 Th.] | d-spacing [Å] | Height [cts] | Rel. Int. [%] |
|---|---|---|---|---|
| 4.02 | 0.38 | 21.96 | 492.38 | 100.00 |
| 4.87 | 0.25 | 18.15 | 472.41 | 95.94 |
| 7.79 | 0.19 | 11.35 | 87.26 | 17.72 |
| 11.61 | 0.25 | 7.62 | 110.78 | 22.50 |
| 15.21 | 0.25 | 5.82 | 120.46 | 24.46 |
| 15.86 | 0.25 | 5.59 | 76.35 | 15.51 |
| 16.51 | 0.19 | 5.37 | 103.12 | 20.94 |
| 17.57 | 0.28 | 5.05 | 160.72 | 32.64 |
| 18.42 | 0.31 | 4.82 | 126.44 | 25.68 |
| 19.26 | 038 | 4.61 | 218.37 | 44.35 |
| 20.53 | 0.19 | 4.33 | 98.62 | 20.03 |
| 21.55 | 0.13 | 4.12 | 184.64 | 37.50 |
| 23.17 | 0.50 | 3.84 | 115.61 | 23.48 |
| 24.39 | 0.28 | 3.65 | 207.28 | 42.10 |
| 25.51 | 0.16 | 3.49 | 126.17 | 25.63 |
| 26.38 | 0.25 | 3.38 | 65.52 | 13.31 |

TABLE 15-continued

| Pos. [°2 Th.] | FWHM [°2 Th.] | d-spacing [Å] | Height [cts] | Rel. Int. [%] |
|---|---|---|---|---|
| 27.63 | 0.25 | 3.23 | 83.43 | 16.94 |
| 30.85 | 0.38 | 2.90 | 29.23 | 5.94 |

Bis-mesylate crystalline salt form B: was prepared in a primary salt screen. A 2 mL aliquot of 2-propanol was added to ~40 mg of free base. 1.05 equivalents of methanesulfonic acid as a 1M solution in THF were added and the sample was temperature cycled for 3-5 days then tert-butyl methyl ether was added as an antisolvent. Solubility in pH 1 and 4.5 buffers was determined to be greater than 23 mg/mL.

The omecamtiv mecarbil bis-mesylate crystalline salt form B was characterized by an XRPD pattern comprising peaks in Table 16.

TABLE 16

| Pos. [°2 Th.] | FWHM [°2 Th.] | d-spacing [Å] | Height [cts] | Rel. Int. [%] |
|---|---|---|---|---|
| 8.30 | 0.08 | 10.65 | 4139.68 | 77.69 |
| 8.94 | 0.06 | 9.89 | 358.87 | 6.73 |
| 9.59 | 0.08 | 9.22 | 222.95 | 4.18 |
| 10.78 | 0.08 | 8.21 | 360.97 | 6.77 |
| 11.15 | 0.05 | 7.94 | 127.57 | 2.39 |
| 11.66 | 0.09 | 7.59 | 724.49 | 13.60 |
| 12.15 | 0.09 | 7.28 | 3000.51 | 56.31 |
| 14.37 | 0.12 | 6.17 | 521.87 | 9.79 |
| 14.93 | 0.10 | 5.93 | 402.24 | 7.55 |
| 15.36 | 0.08 | 5.77 | 258.87 | 4.86 |
| 15.57 | 0.08 | 5.69 | 436.88 | 8.20 |
| 16.18 | 0.10 | 5.48 | 560.02 | 10.51 |
| 16.64 | 0.08 | 5.33 | 1864.30 | 34.99 |
| 16.81 | 0.08 | 5.27 | 744.70 | 13.98 |
| 17.07 | 0.06 | 5.19 | 2428.76 | 45.58 |
| 17.19 | 0.09 | 5.16 | 3783.32 | 71.00 |
| 17.41 | 0.10 | 5.09 | 2291.40 | 43.00 |
| 17.76 | 0.12 | 4.99 | 1630.15 | 30.59 |
| 19.24 | 0.09 | 4.61 | 757.57 | 14.22 |
| 19.82 | 0.10 | 4.48 | 1081.40 | 20.29 |
| 20.29 | 0.12 | 4.38 | 2158.58 | 40.51 |
| 20.66 | 0.14 | 4.30 | 1716.49 | 32.21 |
| 21.62 | 0.13 | 4.11 | 1236.28 | 23.20 |
| 22.04 | 0.13 | 4.03 | 739.53 | 13.88 |
| 22.39 | 0.15 | 3.97 | 5328.66 | 100.00 |
| 23.54 | 0.18 | 3.78 | 176.98 | 3.32 |
| 23.95 | 0.06 | 3.72 | 593.98 | 11.15 |
| 24.60 | 0.12 | 3.62 | 1334.05 | 25.04 |
| 25.02 | 0.13 | 3.56 | 2954.89 | 55.45 |
| 25.59 | 0.17 | 3.48 | 1527.25 | 28.66 |
| 25.89 | 0.12 | 3.44 | 581.20 | 10.91 |
| 26.14 | 0.18 | 3.41 | 329.04 | 6.17 |
| 26.49 | 0.13 | 3.36 | 171.39 | 3.22 |
| 27.14 | 0.12 | 3.29 | 637.23 | 11.96 |
| 27.35 | 0.08 | 3.26 | 1259.20 | 23.63 |
| 27.41 | 0.05 | 3.26 | 1229.76 | 23.08 |
| 27.89 | 0.19 | 3.20 | 181.37 | 3.40 |
| 28.86 | 0.09 | 3.09 | 126.53 | 2.37 |
| 29.45 | 0.16 | 3.03 | 536.88 | 10.08 |
| 29.89 | 0.25 | 2.99 | 142.78 | 2.68 |
| 31.11 | 0.31 | 2.87 | 220.88 | 4.15 |
| 32.47 | 0.25 | 2.76 | 129.04 | 2.42 |
| 33.10 | 0.19 | 2.70 | 166.58 | 3.13 |
| 33.51 | 0.25 | 2.67 | 417.91 | 7.84 |
| 34.56 | 0.16 | 2.59 | 235.62 | 4.42 |

The XRPD peaks unique to each of the mesylate crystalline salts forms A and B disclosed herein are shown in Table 17.

TABLE 17

| Mesylate Form | Peaks Unique to Each Form (°2Th.) | | | | | | | |
|---|---|---|---|---|---|---|---|---|
| Form A | 4.02 | 4.87 | 15.21 | 15.86 | 20.53 | 24.39 | | |
| Form B | 8.30 | 8.94 | 9.59 | 12.15 | 14.37 | 19.82 | 20.29 | 22.04 25.02 |

Bis-naphthalate-2-sulfonate crystalline salt: was prepared. For the primary (small scale) screen a 2 mL aliquot of 2-propanol, THF, acetonitrile, isopropyl acetate, acetone or toluene was added to 40 mg of free base, 1.05 equivalents of naphthalate-2-sulfonate sodium salt and 1.0 eq of 1M hydrochloric acid were added then temperature cycled for 3-5 days. The salt was analyzed by XRPD. For the secondary screen (scale-up) 1.05 eq of naphthalene-2-sulfonate and 2M hydrochloric acid in THF were added to 700 mg of free base in 7 mL of 2-propanol then temperature cycled (RT to 40 C) for 3 days, filtered, dried in vacuum oven at ambient temperature. The salt was analyzed by XRPD, IR, HPLC, 1H NMR, PLM, TG/DTA, DSC, DVS, VH-XRPD, stability studies, thermodynamic solubility studies, disproportionation studies and hydration studies. Solubility in pH 1 and 4.5 buffers was determined to be greater than 10 mg/mL.

The omecamtiv mecarbil bis-naphthalate-2-sulfonate crystalline salt was characterized by an XRPD pattern comprising peaks in Table 18.

TABLE 18

| Pos. [°2 Th.] | FWHM [°2 Th.] | d-spacing [Å] | Height [cts] | Rel. Int. [%] |
|---|---|---|---|---|
| 4.49 | 0.06 | 19.70 | 5776.56 | 100.00 |
| 6.25 | 0.08 | 14.14 | 572.59 | 9.91 |
| 6.65 | 0.20 | 13.29 | 561.77 | 9.73 |
| 8.95 | 0.10 | 9.88 | 138.06 | 2.39 |
| 9.72 | 0.15 | 9.10 | 54.78 | 0.95 |
| 13.44 | 0.08 | 6.59 | 367.63 | 6.36 |
| 14.39 | 0.10 | 6.16 | 341.11 | 5.91 |
| 14.92 | 0.12 | 5.94 | 904.43 | 15.66 |
| 15.51 | 0.20 | 5.71 | 276.65 | 4.79 |
| 16.28 | 0.08 | 5.44 | 918.98 | 15.91 |
| 17.02 | 0.20 | 5.21 | 280.34 | 4.85 |
| 18.20 | 0.10 | 4.87 | 1575.43 | 27.27 |
| 18.62 | 0.13 | 4.77 | 3005.63 | 52.03 |
| 18.90 | 0.12 | 4.69 | 792.38 | 13.72 |
| 19.53 | 0.15 | 4.54 | 806.67 | 13.96 |
| 20.82 | 0.26 | 4.27 | 664.39 | 11.50 |
| 21.38 | 0.06 | 4.16 | 1580.84 | 27.37 |
| 21.52 | 0.13 | 4.13 | 1906.58 | 33.01 |
| 22.02 | 0.18 | 4.04 | 410.81 | 7.11 |
| 22.43 | 0.15 | 3.96 | 364.89 | 6.32 |
| 22.80 | 0.23 | 3.90 | 479.37 | 8.30 |
| 24.40 | 0.10 | 3.65 | 608.59 | 10.54 |
| 25.16 | 0.09 | 3.54 | 424.12 | 7.34 |
| 26.11 | 0.10 | 3.41 | 2521.03 | 43.64 |
| 27.01 | 0.13 | 3.30 | 388.79 | 6.73 |
| 27.77 | 0.15 | 3.21 | 210.15 | 3.64 |
| 29.67 | 0.15 | 3.01 | 314.29 | 5.44 |
| 30.21 | 0.26 | 2.96 | 233.20 | 4.04 |
| 30.78 | 0.20 | 2.90 | 266.96 | 4.62 |
| 31.63 | 0.36 | 2.83 | 418.96 | 7.25 |
| 33.42 | 0.31 | 2.68 | 268.71 | 4.65 |
| 34.00 | 0.20 | 2.64 | 207.67 | 3.60 |

Mono-napadisylate crystalline salt: was prepared during a high throughput screen by adding 0.2 mL of a 0.124M solution of free base in methanol and 0.2 mL of a 1,5-naphthalene-disulfonic acid 0.25M solution in methanol to a glass plate then solvent was evaporated then 0.2 mL of solvent (acetonitrile or 0.001M HCl aq) was added and heated to 50° C. for 4 hours then evaporated. Salt was scaled up by adding 100 mg free base to an 8 mL Vial and 3 mL methanol and gently heating to dissolve. 1,5-naphthalene-disulfonic acid (2 mL of a 0.25 M solution) was added at room temperature. Solids were collected after evaporation and filtration. Water solubility was determined to be 0.3 mg/mL (pH 2.35).

The omecamtiv mecarbil mono-napadisylate crystalline salt was characterized by an XRPD pattern comprising peaks in Table 19.

TABLE 19

| Angle 2-Theta° | d value Angstrom | Intensity Count (Height) | Rel. Int. [%] |
|---|---|---|---|
| 6.671 | 13.251 | 82.2 | 6.4 |
| 7.052 | 12.535 | 171 | 13.2 |
| 10.837 | 8.1642 | 360 | 27.9 |
| 12.266 | 7.2159 | 516 | 39.9 |
| 13.409 | 6.6034 | 442 | 34.2 |
| 14.572 | 6.0789 | 460 | 35.6 |
| 15.144 | 5.8503 | 356 | 27.6 |
| 15.75 | 5.6266 | 753 | 58.3 |
| 16.466 | 5.3837 | 788 | 61 |
| 17.831 | 4.9745 | 1292 | 100 |
| 18.824 | 4.7141 | 469 | 36.3 |
| 19.938 | 4.4533 | 955 | 73.9 |
| 21.828 | 4.0716 | 829 | 64.2 |
| 22.868 | 3.8888 | 605 | 46.9 |
| 23.487 | 3.7877 | 477 | 36.9 |
| 24.339 | 3.6571 | 307 | 23.8 |
| 25.263 | 3.5253 | 393 | 30.5 |

Nicotinate crystalline salt: was prepared in a primary salt screen. A 2 mL aliquot of THF was added to ~40 mg of free base. 1.05 equivalents of nicotinic acid were added and the sample was temperature cycled for 3-5 days then evaporated.

The omecamtiv mecarbil nicotinate crystalline salt was characterized by an XRPD pattern comprising peaks in Table 20.

TABLE 20

| Pos, [°2 Th.] | FWHM [°2 Th.] | d-spacing [Å] | Height [cts] | Rel. Int. [%] |
|---|---|---|---|---|
| 3.69 | 0.05 | 23.96 | 4182.86 | 73.17 |
| 7.36 | 0.06 | 12.01 | 1796.70 | 31.43 |
| 8.55 | 0.08 | 10.34 | 3192.46 | 55.85 |
| 9.13 | 0.08 | 9.69 | 3381.54 | 59.16 |
| 10.01 | 0.08 | 8.84 | 1830.40 | 32.02 |
| 11.70 | 0.10 | 7.56 | 135.02 | 2.36 |
| 12.43 | 0.09 | 7.12 | 759.00 | 13.28 |
| 13.83 | 0.08 | 6.40 | 329.03 | 5.76 |
| 14.74 | 0.10 | 6.01 | 648.74 | 11.35 |
| 15.04 | 0.15 | 5.89 | 392.48 | 6.87 |
| 15.50 | 0.12 | 5.72 | 2090.66 | 36.57 |
| 16.70 | 0.09 | 5.31 | 3962.66 | 69.32 |
| 16.84 | 0.09 | 5.27 | 5013.53 | 87.70 |
| 17.62 | 0.10 | 5.03 | 2110.97 | 36.93 |
| 17.87 | 0.12 | 4.96 | 510.00 | 8.92 |
| 18.30 | 0.12 | 4.85 | 3434.06 | 60.07 |
| 18.58 | 0.13 | 4.78 | 1509.52 | 26.41 |
| 18.85 | 0.10 | 4.71 | 353.23 | 6.18 |
| 19.59 | 0.13 | 4.53 | 2097.05 | 36.69 |
| 19.99 | 0.15 | 4.44 | 5716.36 | 100.00 |
| 20.34 | 0.17 | 4.37 | 2282.98 | 39.94 |
| 20.76 | 0.15 | 4.28 | 2868.05 | 50.17 |
| 21.32 | 0.15 | 4.17 | 2273.73 | 39.78 |
| 22.03 | 0.14 | 4.03 | 1235.06 | 21.61 |
| 22.91 | 0.13 | 3.88 | 1620.93 | 28.36 |
| 23.43 | 0.14 | 3.80 | 3577.00 | 62.57 |
| 23.87 | 0.12 | 3.73 | 895.16 | 15.66 |
| 24.83 | 0.20 | 3.58 | 3276.98 | 57.33 |
| 24.92 | 0.05 | 3.58 | 2632.73 | 46.06 |
| 25.40 | 0.16 | 3.50 | 1715.21 | 30.01 |

TABLE 20-continued

| Pos, [°2 Th.] | FWHM [°2 Th.] | d-spacing [Å] | Height [cts] | Rel. Int. [%] |
|---|---|---|---|---|
| 25.95 | 0.23 | 3.43 | 2961.06 | 51.80 |
| 26.85 | 0.11 | 3.32 | 1483.29 | 25.95 |
| 26.94 | 0.09 | 3.31 | 1729.54 | 30.26 |
| 27.32 | 0.14 | 3.26 | 2177.84 | 38.10 |
| 28.01 | 0.19 | 3.18 | 1526.39 | 26.70 |
| 28.94 | 0.09 | 3.08 | 887.28 | 15.52 |
| 29.34 | 0.22 | 3.04 | 154.50 | 2.70 |
| 29.93 | 0.19 | 2.98 | 217.00 | 3.80 |
| 31.00 | 0.22 | 2.88 | 319.34 | 5.59 |
| 31.44 | 0.12 | 2.84 | 286.19 | 5.01 |
| 31.78 | 0.16 | 2.81 | 214.18 | 3.75 |
| 32.10 | 0.22 | 2.79 | 385.58 | 6.75 |
| 32.59 | 0.19 | 2.75 | 320.31 | 5.60 |
| 32.94 | 0.12 | 2.72 | 259.73 | 4.54 |
| 33.23 | 0.22 | 2.69 | 207.23 | 3.63 |
| 34.14 | 0.28 | 2.62 | 300.22 | 5.25 |
| 34.65 | 0.22 | 2.59 | 283.29 | 4.96 |

Oxalate crystalline salt form A: Procedure A—was prepared a high throughput screen by adding 0.3 mL of a 0.05M solution of free base in methanol and 0.3 mL of a oxalic acid 0.05M solution in methanol to a glass plate then solvent was evaporated then 0.4 mL of solvent (water, 0.001 M HCl aq, acetone, acetonitrile or hexanes) was added and heated to 50° C. for 4 hours then evaporated.

Procedure B—was prepared by dissolving 47 mg of free base in ~10 mL of methanol, then 145 µL of a 102 mg/mL solution of oxalic acid was added and sample was placed in a $N_2$ box. Solids were then slurried in water/ethanol at RT.

The omecamtiv mecarbil oxalate crystalline salt form A was characterized by an XRPD pattern comprising peaks in Table 21.

TABLE 21

| Pos. [°2Th.] | FWHM [°2 Th.] | d-spacing [Å] | Height [cts] | Rel. Int. [%] |
|---|---|---|---|---|
| 6.48 | 0.16 | 13.64 | 163.25 | 62.74 |
| 10.36 | 0.22 | 8.54 | 17.19 | 6.61 |
| 11.85 | 0.14 | 7.47 | 24.67 | 9.48 |
| 13.01 | 0.16 | 6.81 | 86.11 | 33.10 |
| 14.79 | 0.11 | 5.99 | 75.91 | 29.17 |
| 15.35 | 0.13 | 5.77 | 45.24 | 17.39 |
| 17.11 | 0.14 | 5.18 | 260.20 | 100.00 |
| 18.24 | 0.50 | 4.86 | 7.90 | 3.04 |
| 19.23 | 0.13 | 4.62 | 28.45 | 10.94 |
| 19.91 | 0.31 | 4.46 | 40.62 | 15.61 |
| 21.48 | 0.19 | 4.14 | 55.28 | 21.25 |
| 22.07 | 0.19 | 4.03 | 25.22 | 9.69 |
| 22.75 | 0.19 | 3.91 | 42.95 | 16.50 |
| 23.82 | 0.08 | 3.74 | 258.28 | 99.26 |
| 24.88 | 0.38 | 3.58 | 9.55 | 3.67 |
| 25.70 | 0.16 | 3.47 | 30.99 | 11.91 |
| 28.55 | 0.44 | 3.13 | 31.95 | 12.28 |
| 29.86 | 0.19 | 2.99 | 16.81 | 6.46 |
| 30.71 | 0.19 | 2.91 | 31.18 | 11.98 |
| 33.32 | 0.19 | 2.69 | 16.02 | 6.16 |

Oxalate crystalline salt form B: was prepared during vapor sorption analysis of oxalate crystalline salt form A.

The omecamtiv mecarbil oxalate crystalline salt form B was characterized by an XRPD pattern comprising peaks in Table 22.

TABLE 22

| Pos. [°2Th.] | FWHM [°2Th.] | d-spacing [Å] | Height [cts] | Rel. Int. [%] |
|---|---|---|---|---|
| 7.38 | 0.11 | 11.97 | 219.37 | 77.59 |
| 13.30 | 0.14 | 6.66 | 127.50 | 45.10 |
| 14.76 | 0.19 | 6.00 | 21.36 | 7.55 |
| 16.54 | 0.13 | 5.36 | 64.20 | 22.71 |
| 17.11 | 0.13 | 5.18 | 245.68 | 86.90 |
| 17.95 | 0.09 | 4.94 | 166.30 | 58.82 |
| 18.45 | 0.11 | 4.81 | 91.52 | 32.37 |
| 21.25 | 0.09 | 4.18 | 106.18 | 37.56 |
| 22.63 | 0.13 | 3.93 | 114.73 | 40.58 |
| 24.35 | 0.19 | 3.66 | 25.92 | 9.17 |
| 24.82 | 0.19 | 3.59 | 73.08 | 25.85 |
| 25.77 | 0.16 | 3.46 | 282.73 | 100.00 |
| 28.61 | 0.25 | 3.12 | 25.78 | 9.12 |
| 29.58 | 0.13 | 3.02 | 25.44 | 9.00 |
| 30.49 | 0.38 | 2.93 | 17.89 | 6.33 |
| 31.76 | 0.25 | 2.82 | 24.02 | 8.50 |
| 34.46 | 0.50 | 2.60 | 17.34 | 6.13 |
| 36.26 | 0.63 | 2.48 | 8.50 | 3.00 |
| 37.35 | 0.19 | 2.41 | 14.20 | 5.02 |

The XRPD peaks unique to each of the oxalate crystalline salt forms A and B disclosed herein are shown in Table 23.

TABLE 23

| Oxalate Form | Peaks Unique to Each Form ([°2Th.]) | | |
|---|---|---|---|
| Form A | 6.48 | 13.01 | 23.82 |
| Form B | 7.38 | 13.30 | 16.54 |

Salicylate crystalline salt: was prepared in a primary salt screen. A 2 mL aliquot of 2-propanol or toluene was added to ~40 mg of free base. 1.05 equivalents of salicylic acid as a 1M solution in THF were added and the sample was temperature cycled for 3-5 days then the 2-propanol was evaporated.

The omecamtiv mecarbil salicylate crystalline salt was characterized by an XRPD pattern comprising peaks in Table 24.

TABLE 24

| Pos. [°2Th.] | FWHM [°2Th.] | d-spacing [Å] | Height [cts] | Rel. Int. [%] |
|---|---|---|---|---|
| 8.36 | 0.06 | 10.58 | 5425.26 | 100.00 |
| 9.78 | 0.06 | 9.05 | 634.48 | 11.69 |
| 10.08 | 0.06 | 8.78 | 1112.62 | 20.51 |
| 10.37 | 0.05 | 8.53 | 164.07 | 3.02 |
| 11.30 | 0.06 | 7.83 | 1739.85 | 32.07 |
| 11.82 | 0.05 | 7.48 | 271.53 | 5.00 |
| 12.00 | 0.05 | 7.38 | 412.51 | 7.60 |
| 13.69 | 0.06 | 6.47 | 843.47 | 15.55 |
| 13.80 | 0.04 | 6.42 | 717.86 | 13.23 |
| 14.25 | 0.15 | 6.21 | 74.68 | 1.38 |
| 15.51 | 0.09 | 5.71 | 588.40 | 10.85 |
| 16.75 | 0.09 | 5.29 | 3941.54 | 72.65 |
| 17.56 | 0.06 | 5.05 | 2277.70 | 41.98 |
| 17.77 | 0.05 | 4.99 | 1649.96 | 30.41 |
| 17.86 | 0.08 | 4.97 | 2140.62 | 39.46 |
| 18.67 | 0.09 | 4.75 | 1989.60 | 36.67 |
| 19.11 | 0.08 | 4.64 | 1216.29 | 22.42 |
| 19.27 | 0.06 | 4.61 | 812.90 | 14.98 |
| 19.62 | 0.08 | 4.52 | 795.44 | 14.66 |
| 20.02 | 0.08 | 4.43 | 709.58 | 13.08 |
| 20.22 | 0.13 | 4.39 | 1916.47 | 35.33 |
| 20.79 | 0.08 | 4.27 | 721.20 | 13.29 |
| 21.07 | 0.13 | 4.22 | 1935.15 | 35.67 |
| 21.78 | 0.09 | 4.08 | 313.94 | 5.79 |
| 22.19 | 0.05 | 4.01 | 532.25 | 9.81 |
| 22.39 | 0.10 | 3.97 | 665.30 | 12.26 |
| 22.75 | 0.08 | 3.91 | 677.94 | 12.50 |

TABLE 24-continued

| Pos. [°2Th.] | FWHM [°2Th.] | d-spacing [Å] | Height [cts] | Rel. Int. [%] |
|---|---|---|---|---|
| 22.92 | 0.06 | 3.88 | 673.25 | 12.41 |
| 23.58 | 0.13 | 3.77 | 3464.58 | 63.86 |
| 24.10 | 0.10 | 3.69 | 257.32 | 4.74 |
| 24.99 | 0.10 | 3.56 | 457.77 | 8.44 |
| 25.23 | 0.09 | 3.53 | 1162.00 | 21.42 |
| 25.59 | 0.09 | 3.48 | 506.81 | 9.34 |
| 26.79 | 0.09 | 3.33 | 620.95 | 11.45 |
| 27.40 | 0.17 | 3.26 | 1709.43 | 31.51 |
| 27.78 | 0.15 | 3.21 | 231.91 | 4.27 |
| 28.21 | 0.18 | 3.16 | 2479.45 | 45.70 |
| 28.76 | 0.10 | 3.10 | 278.54 | 5.13 |
| 29.32 | 0.13 | 3.05 | 236.55 | 4.36 |
| 29.65 | 0.15 | 3.01 | 309.68 | 5.71 |
| 29.94 | 0.06 | 2.98 | 491.39 | 9.06 |
| 30.50 | 0.13 | 2.93 | 198.15 | 3.65 |
| 31.34 | 0.31 | 2.85 | 86.35 | 1.59 |
| 32.15 | 0.20 | 2.78 | 138.16 | 2.55 |
| 32.74 | 0.10 | 2.74 | 175.34 | 3.23 |
| 34 07 | 0.06 | 2.63 | 656.95 | 12.11 |

Hemi-succinate crystalline salt: as prepared during a high throughput screen by adding 0.3 mL of a 0.05M solution of free base in methanol and 0.3 mL of a succinic acid 0.05M solution in methanol to a glass plate then solvent was evaporated then 0.4 mL of solvent (water, 0.001 M HCl aq, acetone, acetonitrile or hexanes) was added and heated to 50° C. for 4 hours then evaporated. Water solubility was determined to be 7.4 mg/mL (pH 4.7).

The omecamtiv mecarbil hemi-succinate crystalline salt was characterized by an XRPD pattern comprising peaks in Table 25.

TABLE 25

| Angle 2-Theta° | d value Angstrom | Intensity Count (Height) | Rel. Int. [%] |
|---|---|---|---|
| 5.488 | 16.102 | 191 | 11.5 |
| 6.319 | 13.988 | 504 | 30.5 |
| 7.596 | 11.638 | 237 | 14.3 |
| 12.932 | 6.8459 | 437 | 26.4 |
| 14.092 | 6.2847 | 245 | 14.8 |
| 15.079 | 5.8756 | 361 | 21.8 |
| 16.971 | 5.2244 | 307 | 18.6 |
| 18.768 | 4.728 | 1654 | 100 |
| 19.318 | 4.5947 | 1074 | 64.9 |
| 20.495 | 4.3334 | 1229 | 74.3 |
| 21.244 | 4.1822 | 790 | 47.8 |
| 21.889 | 4.0604 | 849 | 51.4 |
| 23.492 | 3.7869 | 1651 | 99.8 |
| 24.228 | 3.6736 | 531 | 32.1 |
| 25.364 | 3.5116 | 488 | 29.5 |
| 26.671 | 3.3424 | 749 | 45.3 |
| 27.389 | 3.2563 | 636 | 38.5 |
| 28.316 | 3.1518 | 635 | 38.4 |

Bis-sulfate crystalline salt form A: Procedure A—prepared during a high throughput screen by adding 0.2 mL of a 0.124M solution of free base in methanol and 0.2 mL of a sulfuric acid 0.25M solution in methanol to a glass plate then solvent was evaporated then 0.2 mL of solvent (THF or 0.001M HCl aq) was added and heated to 50° C. for 4 hours then evaporated. Salt was scaled up by adding 100 mg free base to an 8 mL vial and 4 mL methanol and gently heating to dissolve. Sulphuric acid (2 mL of a 0.25 M solution) was added at room temperature. Solids were collected after evaporation to dryness.

Procedure B—prepared by dissolving 200.7 mg free base (1 eq) and 1.05 mL of 1M sulfuric acid (2.1 eq) in 5 mL methanol at 50° C. then cooled to precipitate.

Procedure C—formed when Form D was exposed to 40 C/75% RH storage conditions for 3 days. Water solubility was determined to be 16 mg/mL (pH 1.5).

The omecamtiv mecarbil bis-sulfate crystalline salt form A was characterized by an XRPD pattern comprising peaks in Table 26.

TABLE 26

| Pos. [°2Th.] | FWHM [°2Th.] | d-spacing [Å] | Height [cts] | Rel. Int. [%] |
|---|---|---|---|---|
| 5.39 | 0.05 | 16.40 | 803.64 | 14.66 |
| 7.55 | 0.06 | 11.71 | 915.17 | 16.70 |
| 8.33 | 0.05 | 10.62 | 247.72 | 4.52 |
| 10.13 | 0.08 | 8.73 | 62.00 | 1.13 |
| 14.35 | 0.09 | 6.17 | 3211.66 | 58.60 |
| 14.63 | 0.08 | 6.05 | 340.15 | 6.21 |
| 15.12 | 0.09 | 5.86 | 414.53 | 7.56 |
| 15.64 | 0.09 | 5.66 | 517.83 | 9.45 |
| 16.00 | 0.10 | 5.54 | 503.75 | 9.19 |
| 16.17 | 0.09 | 5.48 | 833.42 | 15.21 |
| 16.39 | 0.08 | 5.41 | 379.73 | 6.93 |
| 16.71 | 0.08 | 5.31 | 565.39 | 10.32 |
| 16.92 | 0.06 | 5.24 | 1727.49 | 31.52 |
| 17.07 | 0.08 | 5.19 | 1764.97 | 32.20 |
| 17.68 | 0.09 | 5.02 | 464.46 | 8.47 |
| 18.33 | 0.09 | 4.84 | 344.30 | 6.28 |
| 18.60 | 0.08 | 4.77 | 648.56 | 11.83 |
| 19.26 | 0.12 | 4.61 | 5480.54 | 100.00 |
| 19.75 | 0.10 | 4.50 | 350.13 | 6.39 |
| 20.22 | 0.08 | 4.39 | 1216.75 | 22.20 |
| 20.83 | 0.10 | 4.26 | 1272.51 | 23.22 |
| 21.03 | 0.08 | 4.23 | 507.32 | 9.26 |
| 21.38 | 0.09 | 4.16 | 1278.02 | 23.32 |
| 22.27 | 0.12 | 3.99 | 1717.52 | 31.34 |
| 22.77 | 0.09 | 3.90 | 602.87 | 11.00 |
| 23.14 | 0.13 | 3.84 | 1861.14 | 33.96 |
| 23.42 | 0.08 | 3.80 | 727.12 | 13.27 |
| 23.76 | 0.12 | 3.75 | 1376.36 | 25.11 |
| 24.32 | 0.12 | 3.66 | 1360.34 | 24.82 |
| 25.11 | 0.13 | 3.55 | 1608.13 | 29.34 |
| 25.48 | 0.41 | 3.50 | 169.13 | 3.09 |
| 25.74 | 0.13 | 3.46 | 2483.24 | 45.31 |
| 26.30 | 0.08 | 3.39 | 445.14 | 8.12 |
| 26.46 | 0.06 | 3.37 | 589.33 | 10.75 |
| 27.71 | 0.06 | 3.22 | 1509.03 | 27.53 |
| 28.15 | 0.08 | 3.17 | 1156.37 | 21.10 |
| 28.90 | 0.08 | 3.09 | 415.94 | 7.59 |
| 29.24 | 0.09 | 3.05 | 516.64 | 9.43 |
| 29.92 | 0.06 | 2.99 | 927.24 | 16.92 |
| 30.38 | 0.13 | 2.94 | 210.94 | 3.85 |
| 30.65 | 0.08 | 2.92 | 266.96 | 4.87 |
| 31.57 | 0.13 | 2.83 | 212.99 | 3.89 |
| 32.14 | 0.09 | 2.79 | 339.08 | 6.19 |
| 33.10 | 0.18 | 2.71 | 172.88 | 3.15 |
| 33.78 | 0.20 | 2.65 | 181.24 | 3.31 |
| 34.22 | 0.15 | 2.62 | 131.00 | 2.39 |

Bis-sulfate crystalline salt form B: was prepared by dissolving 150 mg free base in 20 mL of acetone and adding 22 µL of 17.6M sulfuric acid then sonicating. Isolated solids were slurried in water at RT. Water solubility was determined to by 9 mg/mL (pH 3.5).

The omecamtiv mecarbil bis-sulfate crystalline salt form B was characterized by an XRPD pattern comprising peaks in Table 27.

TABLE 27

| Pos. [°2Th.] | FWHM [°2Th.] | d-spacing [Å] | Height [cts] | Rel. Int. [%] |
|---|---|---|---|---|
| 10.67 | 0.19 | 8.29 | 12.89 | 6.12 |
| 11.72 | 0.19 | 7.55 | 160.31 | 76.09 |
| 12.17 | 0.19 | 7.27 | 80.11 | 38.02 |
| 12.93 | 0.13 | 6.85 | 43.21 | 20.51 |

TABLE 27-continued

| Pos. [°2Th.] | FWHM [°2Th.] | d-spacing [Å] | Height [cts] | Rel. Int. [%] |
|---|---|---|---|---|
| 14.57 | 0.22 | 6.08 | 17.85 | 8.47 |
| 17.79 | 0.13 | 4.99 | 30.92 | 14.67 |
| 18.39 | 0.11 | 4.82 | 82.79 | 39.29 |
| 18.76 | 0.09 | 4.73 | 32.73 | 15.54 |
| 19.84 | 0.22 | 4.47 | 101.51 | 48.18 |
| 20.48 | 0.11 | 4.34 | 124.27 | 58.98 |
| 21.34 | 0.25 | 4.16 | 11.41 | 5.41 |
| 21.90 | 0.25 | 4.06 | 10.23 | 4.86 |
| 23.60 | 0.17 | 3.77 | 210.68 | 100.00 |
| 24.23 | 0.13 | 3.67 | 35.79 | 16.99 |
| 25.13 | 0.16 | 3.54 | 44.10 | 20.93 |
| 25.63 | 0.19 | 3.48 | 98.90 | 46.94 |
| 29.30 | 0.31 | 3.05 | 29.96 | 14.22 |
| 30.12 | 0.13 | 2.97 | 47.50 | 22.55 |
| 30.98 | 0.19 | 2.89 | 15.83 | 7.51 |
| 31.48 | 0.19 | 2.84 | 18.11 | 8.60 |
| 31.94 | 0.19 | 2.80 | 13.68 | 6.49 |
| 36.02 | 0.25 | 2.49 | 10.23 | 4.86 |
| 36.85 | 0.50 | 2.44 | 7.64 | 3.63 |
| 38.16 | 0.25 | 2.36 | 11.73 | 5.57 |

Bis-sulfate crystalline salt form C: was prepared by heating bis-sulfate Form B on TGA.

The omecamtiv mecarbil bis-sulfate crystalline salt form C was characterized by an XRPD pattern comprising peaks in Table 28.

TABLE 28

| Pos. [°2Th.] | FWHM [°2Th.] | d-spacing [Å] | Height [cts] | Rel. Int. [%] |
|---|---|---|---|---|
| 8.20 | 0.19 | 10.79 | 30.31 | 4.27 |
| 10.39 | 0.13 | 8.51 | 179.40 | 25.28 |
| 10.72 | 0.09 | 8.25 | 226.72 | 31.94 |
| 10.98 | 0.13 | 8.06 | 252.05 | 35.51 |
| 11.49 | 0.22 | 7.70 | 136.57 | 19.24 |
| 12.17 | 0.19 | 7.27 | 132.34 | 18.65 |
| 12.52 | 0.16 | 7.07 | 159.11 | 22.42 |
| 12.99 | 0.22 | 6.82 | 238.57 | 33.61 |
| 13.56 | 0.22 | 6.53 | 122.29 | 17.23 |
| 15.98 | 0.25 | 5.55 | 37.67 | 5.31 |
| 16.74 | 0.19 | 5.30 | 135.94 | 19.15 |
| 17.11 | 0.16 | 5.18 | 296.18 | 41.73 |
| 17.43 | 0.22 | 5.09 | 332.88 | 46.90 |
| 18.04 | 0.31 | 4.92 | 107.59 | 15.16 |
| 19.60 | 0.14 | 4.53 | 249.29 | 35.12 |
| 20.94 | 0.22 | 4.24 | 215.86 | 30.41 |
| 21.53 | 0.22 | 4.13 | 109.98 | 15.50 |
| 22.47 | 0.31 | 3.96 | 100.45 | 14.15 |
| 23.09 | 0.28 | 3.85 | 136.51 | 19.23 |
| 23.98 | 0.31 | 3.71 | 58.62 | 8.26 |
| 24.76 | 0.19 | 3.60 | 230.19 | 32.43 |
| 25.25 | 0.31 | 3.53 | 709.74 | 100.00 |
| 25.87 | 0.16 | 3.44 | 263.23 | 37.09 |
| 26.51 | 0.19 | 3.36 | 179.86 | 25.34 |
| 27.63 | 0.76 | 3.23 | 91.65 | 12.91 |
| 29.33 | 0.50 | 3.04 | 30.11 | 4.24 |
| 32.14 | 0.38 | 2.79 | 44.36 | 6.25 |
| 33.91 | 0.38 | 2.64 | 17.82 | 2.51 |
| 35.27 | 0.38 | 2.55 | 15.44 | 2.18 |
| 39.25 | 0.25 | 2.30 | 22.20 | 3.13 |

Sulfate crystalline salt form D: was prepared in a primary salt screen. To prepare Form D a 2 mL aliquot of acetone was added to ~40 mg of free base. 1.05 equivalents of sulfuric acid as a 1M solution in THF were added and the sample was temperature cycled for 3-5 days.

The omecamtiv mecarbil sulfate crystalline salt form D was characterized by an XRPD pattern comprising peaks in Table 29.

TABLE 29

| Pos. [°2Th.] | FWHM [°2Th.] | d-spacing [Å] | Height [cts] | Rel. Int. [%] |
|---|---|---|---|---|
| 7.32 | 0.08 | 12.08 | 844.93 | 59.30 |
| 8.02 | 0.05 | 11.03 | 224.63 | 15.77 |
| 11.67 | 0.10 | 7.58 | 138.68 | 9.73 |
| 12.20 | 0.10 | 7.25 | 169.56 | 11.90 |
| 12.55 | 0.10 | 7.05 | 121.39 | 8.52 |
| 13.57 | 0.08 | 6.52 | 1067.44 | 74.92 |
| 14.54 | 0.10 | 6.09 | 805.82 | 56.56 |
| 16.29 | 0.08 | 5.44 | 758.59 | 53.24 |
| 16.41 | 0.08 | 5.40 | 705.84 | 49.54 |
| 16.91 | 0.15 | 5.24 | 520.14 | 36.51 |
| 17.36 | 0.20 | 5.11 | 373.69 | 26.23 |
| 18.70 | 0.06 | 4.74 | 783.62 | 55.00 |
| 20.44 | 0.15 | 4.34 | 1424.79 | 100.00 |
| 21.02 | 0.15 | 4.23 | 587.18 | 41.21 |
| 21.77 | 0.15 | 4.08 | 625.52 | 43.90 |
| 22.37 | 0.15 | 3.97 | 403.56 | 28.32 |
| 22.90 | 0.15 | 3.88 | 1136.86 | 79.79 |
| 23.72 | 0.15 | 3.75 | 749.74 | 52.62 |
| 24.28 | 0.08 | 3.67 | 771.24 | 54.13 |
| 25.14 | 0.13 | 3.54 | 490.08 | 34.40 |
| 25.88 | 0.10 | 3.44 | 399.16 | 28.02 |
| 26.58 | 0.09 | 3.35 | 808.90 | 56.77 |
| 27.25 | 0.15 | 3.27 | 783.97 | 55.02 |
| 28.10 | 0.15 | 3.18 | 200.02 | 14.04 |
| 29.43 | 0.18 | 3.04 | 218.32 | 15.32 |
| 30.45 | 0.41 | 2.94 | 99.72 | 7.00 |
| 33.15 | 0.31 | 2.70 | 89.81 | 6.30 |
| 33.88 | 0.15 | 2.65 | 121.18 | 8.51 |

The XRPD peaks unique to each of the sulfate crystalline salt forms A-D disclosed herein are shown in Table 30.

TABLE 30

| Sulfate Form | Peaks Unique to Each Form ([°2Th.]) | | | | |
|---|---|---|---|---|---|
| Form A | 5.39 | 7.55 | 14.35 | 19.26 | 20.22 |
| Form B | 11.72 | 20.48 | | | |
| Form C | 10.98 | 11.49 | 18.04 | 19.60 | |
| Form D | 7.32 | 8.02 | 20.44 | | |

2-Hydroxyethane sulfonate crystalline salt: was prepared in a primary salt screen. A 2 mL aliquot of THF, acetonitrile or isopropyl acetate was added to ~40 mg of free base. 1.05 equivalents of 2-hydroxyethane sulfonic acid as a solid and 1 equivalent of 1M hydrochloric acid were added and the sample was temperature cycled for 3-5 days.

The omecamtiv mecarbil 2-hydroxyethane sulfonate crystalline salt was characterized by an XRPD pattern comprising peaks in Table 31.

TABLE 31

| Pos. [°2Th.] | FWHM [°2Th.] | d-spacing [Å] | Height [cts] | Rel. Int. [%] |
|---|---|---|---|---|
| 6.26 | 0.08 | 14.13 | 219.45 | 9.02 |
| 6.69 | 0.18 | 13.21 | 374.53 | 15.39 |
| 9.95 | 0.06 | 8.89 | 2434.20 | 100.00 |
| 14.43 | 0.15 | 6.14 | 98.15 | 4.03 |
| 14.99 | 0.23 | 5.91 | 360.35 | 14.80 |
| 15.51 | 0.15 | 5.71 | 182.59 | 7.50 |
| 16.37 | 0.09 | 5.41 | 438.44 | 18.01 |
| 17.06 | 0.26 | 5.20 | 148.91 | 6.12 |
| 17.85 | 0.08 | 4.97 | 916.01 | 37.63 |
| 19.61 | 0.15 | 4.53 | 272.20 | 11.18 |
| 19.93 | 0.05 | 4.46 | 695.74 | 28.58 |
| 20.07 | 0.06 | 4.42 | 590.93 | 24.28 |
| 20.46 | 0.12 | 4.34 | 487.31 | 20.02 |
| 20.95 | 0.18 | 4.24 | 261.07 | 10.73 |
| 22.06 | 0.18 | 4.03 | 158.42 | 6.51 |
| 22.89 | 0.26 | 3.88 | 158.38 | 6.51 |

TABLE 31-continued

| Pos. [°2Th.] | FWHM [°2Th.] | d-spacing [Å] | Height [cts] | Rel. Int. [%] |
|---|---|---|---|---|
| 23.96 | 0.15 | 3.71 | 128.47 | 5.28 |
| 24.41 | 0.13 | 3.65 | 155.88 | 6.40 |
| 25.06 | 0.15 | 3.55 | 488.47 | 20.07 |
| 26.20 | 0.18 | 3.40 | 632.72 | 25.99 |
| 26.98 | 0.20 | 3.30 | 133.39 | 5.48 |
| 27.92 | 0.08 | 3.20 | 162.41 | 6.67 |
| 28.43 | 0.15 | 3.14 | 116.74 | 4.80 |
| 29.98 | 0.04 | 2.98 | 438.04 | 18.00 |
| 32.16 | 0.04 | 2.78 | 443.24 | 18.21 |
| 33.38 | 0.41 | 2.68 | 86.61 | 3.56 |
| 34.39 | 0.06 | 2.61 | 387.48 | 15.92 |

Bis-tartrate crystalline salt form A: was prepared by dissolving 200.7 mg (1 eq) of free base and 525 µL (30.02 g in 100 mL methanol, 2.1 eq) in 20 mL methanol and heat cycle 40° C./RT twice. Water solubility was determined to be >53 mg/mL (pH 3.28).

The omecamtiv mecarbil bis-tartrate crystalline salt form A was characterized by an XRPD pattern comprising peaks in Table 32.

TABLE 32

| Pos. [°2Th.] | FWHM [°2Th.] | d-spacing [Å] | Height [cts] | Rel. Int. [%] |
|---|---|---|---|---|
| 4.20 | 0.19 | 21.02 | 968.44 | 59.18 |
| 4.77 | 0.19 | 18.52 | 1062.98 | 64.96 |
| 7.49 | 0.16 | 11.80 | 715.72 | 43.74 |
| 7.67 | 0.09 | 11.52 | 629.63 | 38.48 |
| 8.22 | 0.19 | 10.75 | 793.41 | 48.48 |
| 8.43 | 0.09 | 10.49 | 699.24 | 42.73 |
| 9.49 | 0.19 | 9.32 | 377.23 | 23.05 |
| 11.18 | 0.25 | 7.91 | 193.33 | 11.81 |
| 11.88 | 0.31 | 7.45 | 208.48 | 12.74 |
| 13.05 | 0.22 | 6.79 | 590.85 | 36.11 |
| 13.26 | 0.13 | 6.68 | 608.71 | 37.20 |
| 14.98 | 0.11 | 5.92 | 1399.17 | 85.50 |
| 15.14 | 0.22 | 5.85 | 1490.06 | 91.05 |
| 16.42 | 0.35 | 5.40 | 437.01 | 26.70 |
| 17.34 | 0.08 | 5.11 | 983.61 | 60.11 |
| 17.47 | 0.14 | 5.08 | 1247.90 | 76.26 |
| 18.02 | 0.19 | 4.92 | 1121.36 | 68.52 |
| 18.23 | 0.16 | 4.87 | 911.65 | 55.71 |
| 18.72 | 0.13 | 4.74 | 441.84 | 27.00 |
| 19.20 | 0.16 | 4.62 | 370.82 | 22.66 |
| 21.19 | 0.11 | 4.19 | 1636.46 | 100.00 |
| 22.50 | 0.19 | 3.95 | 667.89 | 40.81 |
| 23.86 | 0.16 | 3.73 | 212.59 | 12.99 |
| 24.53 | 0.41 | 3.63 | 339.28 | 20.73 |
| 25.67 | 0.38 | 3.47 | 528.93 | 32.32 |
| 26.30 | 0.31 | 3.39 | 451.92 | 27.62 |
| 28.14 | 0.25 | 3.17 | 388.50 | 23.74 |
| 28.44 | 0.22 | 3.14 | 285.60 | 17.45 |
| 29.87 | 0.38 | 2.99 | 258.33 | 15.79 |
| 31.32 | 0.31 | 2.86 | 101.08 | 6.18 |
| 32.48 | 0.25 | 2.76 | 128.85 | 7.87 |
| 33.69 | 0.25 | 2.66 | 103.91 | 6.35 |
| 34.42 | 0.25 | 2.61 | 158.44 | 9.68 |
| 35.36 | 0.31 | 2.54 | 97.83 | 5.98 |
| 35.92 | 0.19 | 2.50 | 84.54 | 5.17 |
| 36.60 | 0.31 | 2.46 | 82.62 | 5.05 |
| 37.41 | 0.25 | 2.40 | 136.23 | 8.32 |
| 37.88 | 0.25 | 2.38 | 96.44 | 5.89 |

Bis-tartrate crystalline salt form B: was prepared by dissolving 1.004 g of omecamtiv mecarbil and 0.788 g L-tartaric acid (2.1 eq) in 50 mL of MeOH at 50° C. then cooling to precipitate.

The omecamtiv mecarbil bis-tartrate crystalline salt form B was characterized by an XRPD pattern comprising peaks in Table 33.

TABLE 33

| Pos. [°2Th.] | FWHM [°2Th.] | d-spacing [Å] | Height [cts] | Rel. Int. [%] |
|---|---|---|---|---|
| 3.77 | 0.17 | 23.43 | 971.26 | 100.00 |
| 4.72 | 0.27 | 18.74 | 635.71 | 65.45 |
| 5.69 | 0.27 | 15.52 | 516.33 | 53.16 |
| 6.95 | 0.27 | 12.73 | 358.34 | 36.89 |
| 9.34 | 0.27 | 9.46 | 200.35 | 20.63 |
| 10.07 | 0.23 | 8.78 | 434.70 | 44.76 |
| 11.18 | 0.54 | 7.92 | 167.11 | 17.21 |
| 12.63 | 0.20 | 7.01 | 158.00 | 16.27 |
| 15.18 | 0.20 | 5.84 | 190.67 | 19.63 |
| 17.69 | 0.17 | 5.01 | 282.08 | 29.04 |
| 22.35 | 0.20 | 3.98 | 177.49 | 18.27 |
| 25.46 | 0.40 | 3.50 | 62.01 | 6.38 |

Bis-tartrate crystalline salt form C: was prepared by slurry of bis-tartrate Form B in water.

The omecamtiv mecarbil bis-tartrate crystalline salt form C was characterized by an XRPD pattern comprising peaks in Table 34.

TABLE 34

| Pos. [°2Th.] | FWHM [°2Th.] | d-spacing [Å] | Height [cts] | Rel. Int. [%] |
|---|---|---|---|---|
| 3.57 | 0.13 | 24.73 | 920.53 | 89.99 |
| 3.86 | 0.15 | 22.88 | 1022.92 | 100.00 |
| 4.78 | 0.40 | 18.49 | 513.98 | 50.25 |
| 6.23 | 0.20 | 14.19 | 427.74 | 41.82 |
| 7.04 | 0.13 | 12.56 | 270.90 | 26.48 |
| 9.36 | 0.17 | 9.45 | 637.85 | 62.36 |
| 13.08 | 0.10 | 6.77 | 549.91 | 53.76 |
| 13.96 | 0.17 | 6.34 | 239.78 | 23.44 |
| 15.84 | 0.17 | 5.59 | 348.37 | 34.06 |
| 16.88 | 0.20 | 5.25 | 121.74 | 11.90 |
| 17.60 | 0.27 | 5.04 | 146.72 | 14.34 |
| 18.20 | 0.20 | 4.87 | 147.06 | 14.38 |
| 18.73 | 0.23 | 4.74 | 245.18 | 23.97 |
| 20.40 | 0.20 | 4.35 | 268.32 | 26.23 |
| 22.58 | 0.27 | 3.94 | 120.04 | 11.73 |
| 25.44 | 0.40 | 3.50 | 192.03 | 18.77 |
| 26.06 | 0.47 | 3.42 | 213.11 | 20.83 |
| 28.61 | 0.40 | 3.12 | 106.58 | 10.42 |

Mono-tartrate crystalline salt form D: was prepared by mixing 1.004 g of omecamtiv mecarbil and 0.375 g of L-tartaric acid (1 eq) in 10 mL of 5% $H_2O$ in THF at 50° C. then cooling to precipitate.

The omecamtiv mecarbil mono-tartrate crystalline salt form D was characterized by an XRPD pattern comprising peaks in Table 35.

TABLE 35

| Pos. [°2Th.] | FWHM [°2Th.] | d-spacing [Å] | Height [cts] | Rel. Int. [%] |
|---|---|---|---|---|
| 6.94 | 0.12 | 12.74 | 377.02 | 15.46 |
| 9.77 | 0.17 | 9.05 | 478.47 | 19.62 |
| 10.87 | 0.17 | 8.14 | 2097.98 | 86.02 |
| 12.74 | 0.13 | 6.95 | 204.81 | 8.40 |
| 13.04 | 0.13 | 6.79 | 144.17 | 5.91 |
| 13.79 | 0.15 | 6.42 | 871.83 | 35.75 |
| 14.54 | 0.20 | 6.09 | 418.22 | 17.15 |
| 14.86 | 0.13 | 5.96 | 315.83 | 12.95 |
| 15.40 | 0.18 | 5.75 | 2345.40 | 96.17 |
| 17.36 | 0.18 | 5.11 | 1127.77 | 46.24 |
| 17.74 | 0.17 | 5.00 | 512.38 | 21.01 |
| 18.58 | 0.12 | 4.78 | 598.49 | 24.54 |
| 18.87 | 0.17 | 4.70 | 693.22 | 28.42 |
| 19.25 | 0.17 | 4.61 | 322.02 | 13.20 |
| 20.71 | 0.13 | 4.29 | 293.45 | 12.03 |

TABLE 35-continued

| Pos. [°2Th.] | FWHM [°2Th.] | d-spacing [Å] | Height [cts] | Rel. Int. [%] |
|---|---|---|---|---|
| 21.78 | 0.17 | 4.08 | 1734.64 | 71.13 |
| 23.11 | 0.20 | 3.85 | 97.51 | 4.00 |
| 23.58 | 0.13 | 3.77 | 214.55 | 8.80 |
| 24.69 | 0.12 | 3.61 | 423.81 | 17.38 |
| 25.43 | 0.17 | 3.50 | 2438.82 | 100.00 |
| 26.24 | 0.20 | 3.40 | 529.42 | 21.71 |
| 26.50 | 0.13 | 3.36 | 437.75 | 17.95 |
| 26.99 | 0.27 | 3.30 | 259.96 | 10.66 |
| 28.58 | 0.27 | 3.12 | 73.70 | 3.02 |
| 29.43 | 0.27 | 3.03 | 100.12 | 4.11 |
| 30.40 | 0.13 | 2.94 | 161.38 | 6.62 |
| 32.74 | 0.27 | 2.74 | 127.69 | 5.24 |
| 34.76 | 0.17 | 2.58 | 210.18 | 8.62 |
| 35.46 | 0.17 | 2.53 | 118.22 | 4.85 |
| 36.31 | 0.20 | 2.47 | 191.26 | 7.84 |
| 37.01 | 0.13 | 2.43 | 138.71 | 5.69 |
| 37.64 | 0.27 | 2.39 | 131.07 | 5.37 |

The XRPD peaks unique to each of the tartrate crystalline salt forms A-D disclosed herein are shown in Table 36.

TABLE 36

| Tartrate Form | Peaks Unique to Each Form (°2Th.) | | | | | |
|---|---|---|---|---|---|---|
| Form A | 4.20 | 7.49 | 8.22 | 11.88 | 16.42 | 21.19 |
| Form B | 3.77 | 5.69 | 10.07 | | | |
| Form C | 3.57 | 6.23 | 15.84 | | | |
| Form D | 9.77 | 15.40 | | | | |

What is claimed:

1. An omecamtiv mecarbil free base crystalline form which is any one of the following forms:
   i) an omecamtiv mecarbil free base crystalline form III, characterized by an X-ray powder diffraction (XRPD) pattern comprising peaks at 9.50, 19.06, and 23.01±0.2° 2θ using Cu Kα radiation;
   ii) an omecamtiv mecarbil free base crystalline form IV, characterized by an X-ray powder diffraction (XRPD) pattern comprising peaks at 5.18, 10.35, 14.84, 15.54, 18.10, and 19.92±0.2° 2θ using Cu Kα radiation;
   iii) an omecamtiv mecarbil free base crystalline form V, characterized by an X-ray powder diffraction (XRPD) pattern comprising peaks at 7.38, 8.56, 9.14, and 18.28±0.2° 2θ using Cu Kα radiation;
   iv) an omecamtiv mecarbil free base crystalline form VI, characterized by an X-ray powder diffraction (XRPD) pattern comprising peaks at 9.07, 16.67, 18.18, 19.70, 20.89, and 21.28±0.2° 2θ using Cu Kα radiation; or
   v) an omecamtiv mecarbil free base crystalline form VII, characterized by an X-ray powder diffraction (XRPD) pattern comprising peaks at 8.40, 8.71, 13.08, 15.66, and 19.61±0.2° 2θ using Cu Kα radiation.

2. The omecamtiv mecarbil free base crystalline form of claim 1, wherein the crystalline form is omecamtiv mecarbil free base crystalline form III, characterized by an X-ray powder diffraction (XRPD) pattern comprising peaks at 9.50, 19.06, and 23.01±0.2° 2θ using Cu Kα radiation.

3. The omecamtiv mecarbil free base crystalline form III of claim 2, further characterized by XRPD pattern peaks at 14.27, 15.25, 16.10, 17.78, and 23.87±0.2° 2θ using Cu Kα radiation.

4. The omecamtiv mecarbil free base crystalline form III of claim 2, further characterized by XRPD pattern peaks at 7.91, 20.65, 28.11, 31.01, 31.95, and 32.34±0.2° 2θ using Cu Kα radiation.

5. The omecamtiv mecarbil free base crystalline form III of claim 2, having an XRPD pattern substantially as shown in FIG. 1.

6. The omecamtiv mecarbil free base crystalline form III of claim 2, having an endothermic transition at 175° C. to 190° C., as measured by differential scanning calorimetry.

7. The omecamtiv mecarbil free base crystalline form III of claim 6, wherein the endothermic transition is at 186° C.±3° C.

8. The omecamtiv mecarbil free base crystalline form III of claim 2, having a thermogravimetric analysis (TGA) substantially as shown in FIG. 3.

9. The omecamtiv mecarbil free base crystalline form of claim 5, wherein the crystalline form is omecamtiv mecarbil free base crystalline form IV, characterized by an X-ray powder diffraction (XRPD) pattern comprising peaks at 5.18, 10.35, 14.84, 15.54, 18.10, and 19.92±0.2° 2θ using Cu Kα radiation.

10. The omecamtiv mecarbil free base crystalline form IV of claim 9, further characterized by XRPD pattern peaks at 14.21, 20.62, 20.77, 22.86, 24.05, 24.36, 27.81, and 29.42±0.2° 2θ using Cu Kα radiation.

11. The omecamtiv mecarbil free base crystalline form IV of claim 9, further characterized by XRPD pattern peaks at 7.42, 7.70, 21.70, 22.40, 23.09, 25.20, 25.72, 27.40, 28.18, 28.63, 28.98, and 30.51±0.2° 2θ using Cu Kα radiation.

12. The omecamtiv mecarbil free base crystalline form IV of claim 9, having an XRPD pattern substantially as shown in FIG. 4.

13. The omecamtiv mecarbil free base crystalline form IV of claim 9, having an endothermic transition at 175° C. to about 190° C., as measured by differential scanning calorimetry.

14. The omecamtiv mecarbil free base crystalline form IV of claim 13, wherein the endothermic transition is at 185° C.±3° C.

15. The omecamtiv mecarbil free base crystalline form IV of claim 9, having a thermogravimetric analysis (TGA) as shown in FIG. 6.

16. The omecamtiv mecarbil free base crystalline form of claim 1, wherein the crystalline form is omecamtiv mecarbil free base crystalline form V, characterized by an X-ray powder diffraction (XRPD) pattern comprising peaks at 7.38, 8.56, 9.14, and 18.28±0.2° 2θ using Cu Kα radiation.

17. The omecamtiv mecarbil free base crystalline form V of claim 16, further characterized by XRPD pattern peaks at 8.93, 10.03, 10.73, 11.71, 13.69, 15.08, 16.85, 17.85, 18.86, 20.05, 20.72, 21.74, 23.56, 24.03, 26.23, and 27.62±0.2° 2θ using Cu Kα radiation.

18. The omecamtiv mecarbil free base crystalline form V of claim 16, further characterized by XRPD pattern peaks at 5.40, 16.04, 22.83, 25.45, 26.23, 27.62, 28.58, 29.85, 32.10, and 33.37±0.2° 2θ using Cu Kα radiation.

19. The omecamtiv mecarbil free base crystalline form V of claim 16, having an XRPD pattern substantially as shown in FIG. 7.

20. The omecamtiv mecarbil free base crystalline form V of claim 16, having an endothermic transition at 175° C. to 190° C., as measured by differential scanning calorimetry.

21. The omecamtiv mecarbil free base crystalline form V of claim 20, wherein the endothermic transition is at 185° C.±3° C.

22. The omecamtiv mecarbil free base crystalline form V of claim 16, having a thermogravimetric analysis (TGA) as shown in FIG. 9.

23. The omecamtiv mecarbil free base crystalline form of claim 1, wherein the crystalline form is omecamtiv mecarbil free base free base crystalline form VI, characterized by an X-ray powder diffraction (XRPD) pattern comprising peaks at 9.07, 16.67, 18.18, 19.70, 20.89, and 21.28±0.2° 2θ using Cu Kα radiation.

24. The omecamtiv mecarbil free base crystalline form VI of claim 23, further characterized by XRPD pattern peaks at 15.88, 17.81, 18.80, 23.72, 24.26, 26.80, 27.59, and 29.82±0.2° 2θ using Cu Kα radiation.

25. The omecamtiv mecarbil free base crystalline form VI of claim 23, further characterized by XRPD pattern peaks at 14.28, 20.23, 26.19, and 28.90±0.2° 2θ using Cu Kα radiation.

26. The omecamtiv mecarbil free base crystalline form VI of claim 23, having an XRPD pattern substantially as shown in FIG. 10.

27. The omecamtiv mecarbil free base crystalline form VI of claim 23, having an endothermic transition at 175° C. to 190° C., as measured by differential scanning calorimetry.

28. The omecamtiv mecarbil free base crystalline form VI of claim 27, wherein the endothermic transition is at 185° C.±3° C.

29. The omecamtiv mecarbil free base crystalline form of claim 1, wherein the crystalline form is omecamtiv mecarbil free base crystalline form VII, characterized by an X-ray powder diffraction (XRPD) pattern comprising peaks at 8.40, 8.71, 13.08, 15.66, and 19.61±0.2° 2θ using Cu Kα radiation.

30. The omecamtiv mecarbil free base crystalline form VII of claim 29, further characterized by XRPD pattern peaks at 4.37, 16.83, 18.92, 20.32, 20.49, 22.26, 24.21, and 25.41±0.2° 2θ using Cu Kα radiation.

31. The omecamtiv mecarbil free base crystalline form VII of claim 29, further characterized by XRPD pattern peaks at 7.84, 10.81, 21.61, 23.22, 23.46, 27.58, 29.53, 30.13, and 31.32±0.2° 2θ using Cu Kα radiation.

32. The omecamtiv mecarbil free base crystalline form VII of claim 29, having an XRPD pattern substantially as shown in FIG. 12.

* * * * *